United States Patent
Cady et al.

(10) Patent No.: US 11,572,595 B2
(45) Date of Patent: Feb. 7, 2023

(54) NON-REPLICATIVE TRANSDUCTION PARTICLES WITH ONE OR MORE NON-NATIVE TAIL FIBERS AND TRANSDUCTION PARTICLE-BASED REPORTER SYSTEMS

(71) Applicant: Roche Molecular Systems, Inc., Pleasanton, CA (US)

(72) Inventors: Kyle C. Cady, Santa Clara, CA (US); Colin Lam, Redwood City, CA (US); Jeffrey Alexander, Hayward, CA (US); Kristina Chu, Pleasanton, CA (US); Barbara Eckert, El Cerrito, CA (US); Dylan Goldman, San Jose, CA (US); Patrick Lin, San Jose, CA (US); Kalyani Mangipudi, Pleasanton, CA (US); Misha Mehta, Pleasanton, CA (US); Arrash Moghaddasi, Sunnyvale, CA (US); Hai Nguyen, San Jose, CA (US); Natacha Sorenson, Los Gatos, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 298 days.

(21) Appl. No.: 16/722,724

(22) Filed: Dec. 20, 2019

(65) Prior Publication Data

US 2020/0208226 A1    Jul. 2, 2020

Related U.S. Application Data

(60) Provisional application No. 62/926,989, filed on Oct. 28, 2019, provisional application No. 62/787,151, filed on Dec. 31, 2018.

(51) Int. Cl.
*C12Q 1/6897* (2018.01)
*C12N 1/20* (2006.01)
(Continued)

(52) U.S. Cl.
CPC ............ *C12Q 1/6897* (2013.01); *C12N 1/20* (2013.01); *C12N 15/70* (2013.01); *C12N 15/74* (2013.01);
(Continued)

(58) Field of Classification Search
None
See application file for complete search history.

(56) References Cited

U.S. PATENT DOCUMENTS

| | | | |
|---|---|---|---|
| 7,700,729 B2 | 4/2010 | Scholl et al. | |
| 7,732,586 B2 | 6/2010 | Martin, Jr. et al. | |

(Continued)

FOREIGN PATENT DOCUMENTS

WO    2016188998 A1    12/2016

OTHER PUBLICATIONS

Ando H. et al., "Engineering Modular Viral Scaffolds for Targeted Bacterial Population Editing", 2015, Cell Systems 1, 187-196.
(Continued)

*Primary Examiner* — Michelle S Horning
(74) *Attorney, Agent, or Firm* — David J. Chang

(57) ABSTRACT

The present invention relates to compositions comprising and methods of producing genetically engineered bacteriophages, bacteriophage-like particles and non-replicating transduction particles (NRTPs) that contain non-native tail fibers that display altered host specificity and/or reactivity. The present invention also relates to methods of using these bacteriophages and NRTPs for the development of novel diagnostics, therapeutics and/or research reagents for bacteria-related diseases.

2 Claims, 9 Drawing Sheets

Specification includes a Sequence Listing.

(51) Int. Cl.
| | |
|---|---|
| *C12N 15/70* | (2006.01) |
| *C12N 15/74* | (2006.01) |
| *C12Q 1/14* | (2006.01) |
| *C12Q 1/18* | (2006.01) |
| *C12Q 1/66* | (2006.01) |
| *C12Q 1/689* | (2018.01) |

(52) U.S. Cl.
CPC .................. *C12Q 1/14* (2013.01); *C12Q 1/18* (2013.01); *C12Q 1/66* (2013.01); *C12Q 1/689* (2013.01); *C12N 2795/10043* (2013.01); *C12N 2795/10152* (2013.01); *C12N 2795/10343* (2013.01); *C12N 2795/10352* (2013.01); *C12Y 113/12007* (2013.01); *G01N 2333/31* (2013.01)

(56) References Cited

U.S. PATENT DOCUMENTS

| | | | |
|---|---|---|---|
| 8,206,971 | B2 | 6/2012 | Scholl et al. |
| 8,445,639 | B2 | 5/2013 | Scholl et al. |
| 8,673,553 | B2 | 3/2014 | Scholl et al. |
| 9,388,453 | B2 * | 7/2016 | Rey .......................... C12N 1/20 |
| 9,617,522 | B2 | 4/2017 | Lu et al. |
| 2017/0306298 | A1 | 10/2017 | Fairhead et al. |
| 2017/0313991 | A1 | 11/2017 | Fairhead et al. |

OTHER PUBLICATIONS

Guidolin, A. et al., "Organization of the bacteriophage P1 tail-fibre operon", 1989, Gene, 76, 239-243.

Iida, S. "Bacteriophage PI Carries Two Related Sets of Genes Determining Its Host Range in the Invertible C Segment of Its Genome", 1984, Virology, 134, 421-434.

Lobocka, M.B. et al., "Genome of Bacteriophage P1", 2004, Journal of Bacteriology, 186 (21), 7032-7068.

Sandmeier H. et al., "DNA Inversion Regions Min of Plasmid p15B and Cin of Bacteriophage P1: Evolution of Bacteriophage Tail Fiber Genes", 1992, Journal of Bacteriology, 174 (12), 3936-3944.

Sandmeier H. "Acquisition and rearrangement of sequence motifs in the evolution of bacteriophage tail fibres", 1994, Molecular Microbiology, 12 (3), 343-50.

Scholl, D. et al., "An Engineered R-Type Pyocin Is a Highly Specific and Sensitive Bactericidal Agent for the Food-Borne Pathogen *Escherichia coli* O157:H7", 2009, Antimicrob. Agents Chemother., 53 (7), 3074-3080.

Williams, S.R. et al., "Retargeting R-Type Pyocins to Generate Novel Bactericidal Protein Complexes", 2008, Appl. Environ. Microbiol., 74 (12), 3868-3876.

Yehl, K. et al., "Engineering Phage Host-Range and Suppressing Bacterial Resistance through Phage Tail Fiber Mutagenesis", Cell, 179, 459-469.

Yosef, I. et al., "Extending the Host Range of Bacteriophage Particles for DNA Transduction", Molecular Cell, 66, 721-728.

International Search Report for International application No. PCT/EP2019/086888 dated Mar. 11, 2020.

Hiroki, A., et al., Engineering Modular Viral Scaffolds for Targeted Bacterial Population Editing, Cell Systems, Sep. 1, 2015, pp. 187-196, vol. 1, No. 3.

International Search Report dated Jul. 8, 2020 in Application No. PCT/EP2019/086888, 20 pages.

* cited by examiner

A)

P1 R, S_c-S_v and U (Native)

FUNCTIONAL

P1 R, Type 11 Kpn S_c-S_v and U (Plum)

FUNCTIONAL

P1 R, p15B S_c-S_v and U (Tangerine try 2)

FUNCTIONAL

P1 R and S_c, Type 11 Kpn S_v and U (Jazzberry)

FUNCTIONAL

P1 R, p15B S_c-S_v and U (Tangerine try 1)

PARTIAL FUNCTION

P1 R and S_c, Type 11 Kpn S_v and U (Thistle)

NOT FUNCTIONAL

B)

SEQUENCE LISTING

<160> NUMBER OF SEQ ID NOS: 117

<210> SEQ ID NO 1
<211> LENGTH: 3949
<212> TYPE: DNA
<213> ORGANISM: Artificial Sequence
<220> FEATURE:
<223> OTHER INFORMATION: Asparagus Tail Fiber

<400> SEQUENCE: 1

```
atgtctgacg tctcaacaaa cctctataag agtcagttgt tggactatta ctatcagcgg      60
cgcgctgaat cgtccattaa caaaggctct cgattttaa tcagcaaggc cgttttcggt     120
accagttcgc tggttactaa gaaggagat ggcacttatg agattggaga actgccaaag     180
```

```
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg ataacgaga acaagccaat cgccattatt     360
tgtgtccagg aagactcgct gtatgtgggc aaaacatata ccgcagttat ggccataaac    420
acgactacag cataaggata tgcttgatga atgacgttac agttgttaca tcggttactt    480
acccatcatc cgagtcgttg gctctggtgg ccgatgtgca ataccacgaa ccatatctgt    540
cagccgcgct aaaccgaaaa ttcaggggga ttgttgaccc gggatttat gccggtttct     600 tacctaagcc tggcggtggg atgaacctgt taattacctc agtggatggt gataaaaccg    660
caggcgcggc gtcggtggat attggtgaat tttaccaggt aactattcag caacgtaagg    720
atatttctct tgcacttagt gcaggcaaga aatatgcaat tgtgctgaag gaagatacc     780 tccttggaga agatacctac caggtgaata ccgcgtcaca tattcatgcg gctgaatttg    840
ttgccagaac ctataccgat tcatatcagt taggagatgg ggagctgctt gtttgtacgg    900
tgaatatccc tgctagtgta tctgccatta cccaggagat gattgataca tccgagcgta    960
tcaaccgctc gatcggcatt gatatttcag actctgtaac cagtaccaga agtgatgttg    1020
ctgcaagttc gctggcagtt aaaaaagcct acgatctggc gaaaagcaag tatacggcac    1080
aggatgcaag cacaacgcaa aagggattag ttcagctcag tagcgcaact aacagcgaca    1140
gcgaaacaat ggcggctacc cctaaagctg ttaagtctat aaaagatctg gctgatacca    1200
aagcgccaat agaaagcccg agtctgacag gaacgccaac cgcgccgacg gcagcgcaag    1260
gtacaaacag cacgcagatc gcaaatacag cctttgttaa ggcagctata actgcactta    1320
tcaacggtgc gcctggcaca ctggatacgc tgaaagaaat agcggctgcg atcaataacg    1380
acccgaatta cagcacaact atcaacaatg ccttggctct caaagcgcct ttggcaagcc    1440
ctgcattaac gggtgtccct actgcgccta cggctgcaca gggcacaaac aatacgcaga    1500
tcgctacgac tgcttacgta cgggctgcta tctctgcatt ggtcggctca tcacctgaag    1560
ctcttgatac cctgtatgag cttgcagcag cactgggcaa tgacccgaac tttgcgacaa    1620
caatgacaaa tgcgctggca gggaaacagc cacttgatgc aactttaacc gcgcttgctg    1680
gtcttgcgac aggcgcaaat aaattgccgt actttaccgg tacagacact gtttctcaga    1740
ctgacttaac gtcagttggt cgcgatattc tggccaaaac aagcattctt gctgttatcc    1800
aataccttgg tttaagagaa ctcggtacca gcggtgaaaa gatcccctg ttgagcacgg     1860 ctaacacatg gagtgcacgc cagactttca acggcgggat caccggggcg ctgacaggga    1920
acgccgatac cgcaacgaaa ttgaaaacag ccagaaacat taatggcgtc aggttcgatg    1980
gttctggtga cattaatatc aatactctgg tatcgcgcgg tcgcgtaacg gccctggagg    2040
cgaatgcaca gggaacatcc gggattcagc tgtatgaggc atacaacaat ggctacccctt   2100 cccctatgg caatgtgctt caccttaaag gtgccaccgc tgctggcgaa ggtgagttat     2160
tcattggctg gagtggcacg agcggtgccc atgcgcccgt acatatccgt tcgcggcggg    2220
atactgattc tgccaactgg tctgaatggg cgcaggtcta tgcgtcaaaa gattcaattc    2280
ccggcgtcaa tgccaagggg gatcaggata cctctggtaa tgcggctaca cgaccaagt    2340 tgcagacagc atgtactatc aacggcgtct cgtttgacgg ttctaaaaat attgagctaa    2400
cggcggaaga tttaaatcta caggaaacgg taaacaaggc tgataacgcg gttcaaaaga    2460
caggcgatac cttgtccggt ggacttactt ttgaaaacga ctcaatcctt gcctggattc    2520
ggaatactga ctgggcgaag attggttta aaaatgatgc cgacagcgat actgattcat    2580
```

```
acatgtggtt tgaaacaggc gacaacggca atgaatattt caaatggaga agcaaacaaa    2640
gtaccacaac aaaagacctg atgaatctta aatgggatgc tttgtctgtt cttgtcaatg    2700
ccattgtaaa tggcgaagtc atatcaaaat cagcaaacgg cctccgtatt gcttatggta    2760
attacggatt ctttattcgt aatgatggtt caaatacata cttcatgttg acaaactccg    2820
gtgacaacat ggggacttat aacggattaa ggccattatg gattaataac gctactggcg    2880
ctgtttcgat ggggcgtggt cttaatgttt caggggatac actttcagac cgttttgcta    2940
ttaacagcag taatggtatg tggattcaga tgcgcgataa caacgctatc tttgggaaaa    3000
atatagttaa cactgatagc gctcaggcgt tgcttcgcca gaatcacgcc gaccgcaaat    3060
ttatgattgg cggtctggga aataagcaat ttggcatcta catgattaat aactcaagga    3120
cagccaatgg caccgatggt caggcgtaca tggataataa cggaaactgg ttatgcggtg    3180
ctcaggtcat tccgggaaat tacgccaact ttgactcccg ctacgtgcgt gacgttcggc    3240
tgggaactca gtcactgact ggcggcttgt ctcgtgatta caaggcgcca tccggtcatg    3300
ttattacagg ttttcatacc aatggcgact gggaaatgca gggaggggat gacaaggttt    3360
atatccgtcc ggttcagaag aatatcaacg gtacctggta taatgtagcg agcgcctgat    3420
tatgatgcat ctgaaaaaca ttaagtcaga aaatccaaaa actaaagagc aatatcagct    3480
aacaaagaat tttgatgtta tctggttatg gtccgaagac gggaaaaact ggtatgaaga    3540
agtaaataac tttcaggacg acaccataaa gattgtatac gacgaaaata atattattgt    3600
tgccataacc aaagatgcct caacgcttaa tcccgaaggc tttagcgtcg ttgagattcc    3660
agatataaca gccaaccgcc gcgctgatga ttcaggaaag tggatgttta aggatggagc    3720
tgtagttaaa cggatttata cggcagacga acagcaacaa caagccgaat cacaaaaggc    3780
cgcattgctt tccgaagctg aatcagtcat ccagccgctg aacgcgctg  tcaggctgaa    3840 tatggcgacg gatgaggaac gcgcacgact ggagtcatgg gaacgctaca gtgttctggt    3900
cagccgtgtg gatacggcaa atcccgaatg gccacaaaag cctgaataa                3949
```

<210> SEQ ID NO 2
<211> LENGTH: 3161
<212> TYPE: DNA
<213> ORGANISM: Artificial Sequence
<220> FEATURE:
<223> OTHER INFORMATION: Banana Tail Fiber

<400> SEQUENCE: 2

```
atgtctgacg tctcaacaaa cctctataag agtcagttgt tggactatta ctatcagcgg      60
cgcgctgaat cgtccattaa caaaggctct cgattttttaa tcagcaaggc cgttttcggt     120
accagttcgc tggttactaa gaaggagat ggcacttatg agattggaga actgccaaag      180
gctttcgaac tggcagaact gaccagtcaa ttttgcacca tcaacctcgt cccaacctac      240
tcaggcggga taattactgt ccgaatggac cttgatcaaa gccagttgca ggaagggaaa      300 aactaccccat tcaacactct ggttgttctg ataacgaga acaagccaat cgccattatt      360
tgtgtccagg aagactcgct gtatgtgggc aaaacatata ccgcagttat ggccataaac      420
acgactacag cataaggata tgcttgatga atgacgttac agttgttaca tcggttactt      480
acccatcatc cgagtcgttg gctctggtgg ccgatgtgca ataccacgaa ccatatctgt      540
cagccgcgct aaaccgaaaa ttcaggggga ttgttgaccc gggattttat gccggtttct     600
tacctaagcc tggcggtggg atgaacctgt taattacctc agtggatggt gataaaaccg      660
```

```
caggcgcggc gtcggtggat attggtgaat tttaccaggt aactattcag caacgtaagg      720
atatttctct tgcacttagt gcaggcaaga aatatgcaat tgtgctgaag ggaagatacc      780
tccttggaga agatacctac caggtgaata ccgcgtcaca tattcatgcg gctgaatttg      840
ttgccagaac ctataccgat tcatatcagt taggagatgg ggagctgctt gtttgtacgg      900
tgaatatccc tgctagtgta tctgccatta cccaggagat gattgataca tccgagcgta      960
tcaaccgctc gatcggcatt gatatttcag actctgtaac cagtaccaga agtgatgttg     1020
ctgcaagttc gctggcagtt aaaaaagcct acgatctggc gaaaagcaag tatacggcac     1080
aggatgcaac cacagcaaga aaaggtatcg tccagctcag tagtgcaacc gacagtactt     1140
cggaggcgct ggcggcaacg ccgaaagccg ttaaggccgt gaatgacaac gctaacgggc     1200
gcgtaccatc agcgcgtaag gtaaacggca gggcgctggc ttcggatatc agcattacgg     1260
cgcaggatat tttcaacggg caggccgtgg caattggcaa cgccgccgac ctgaacgcct     1320
acaccacgcc gggactgtat taccagccag cgaacgcgca ggctcaaacc ggcaggaatt     1380
atccagaagc caacgccggt tcgctggaag tttataagca tgccggtatc acgcagattt     1440
accggattta taacagctcc cgctcgtaca ttcgcacgct ttacagcggg acgtggtcag     1500
cctgggttaa acagtatgat gcggccaata acccctcccc ggctgatatt aatgccgtga     1560
ataagggcgg cgatacaatg accgggggc ttaagattcg cgctgctgat gcgttgcgca     1620
tttacgatgc ggcatacggt atgatttttc gccgttcaga aaataatttt taccttatcc     1680
cgaccgcaaa agaccagggc gaagatggcg gtataagtgg actacgcccg ctttatatcg     1740
acctcaccaa cggcagagtg acgctgggta acggagcggt tgttaacggc ggtcttgggc     1800
tgggtgtagt cagcggcctt gggggaact ctattgccct gggggataat gacaccggct     1860
tcaaacagaa cggagatggt gtgctggatg tttatgctaa cagcaagcag gtaatgcgat     1920
tcctgaacag tggcataacg agttatatgc tcttcaacat gaatgcaggc gcatcagtaa     1980
gcagcactct cacctttaaa aacggtagcg gtatcacttc agagaaaact ggtgccaacc     2040
cccgaaacgg ccgaatttac tggggcggtg atgcgagtcg cggcaacagg atagagtttg     2100
cagatgatgc cggctggaaa gcttacattg agcgtcatcc ctcaaacggt gttcagttag     2160
tcgtaaatgg gcgaatcaat ggaagtattg tttattccag tggtgaagta ctggcaggag     2220
gagggagcgc acgctttgct gctgatggaa atatatttgg ctcaaaatgg ggcaatcaat     2280
ggcttgatgc ctatttaaaa aatacctatc agccaaaggg caattatacc ccggcaggtc     2340
aggcttatac aaaagtagag tctgacggac gttttcagcc taaagggagt tatacccccg     2400
cggggcaggc ttacacgaag gcggaaagcg atgcgcggta aacctcaaa aataccgcaa     2460 ccaaatcagc caatgccatg acgcataaag atgcttcaac aggtgttatg gaagtcgtta     2520
tgagtaatat caacgttcca aacaaaacaa atgttaacgt gacatttcct gcggcttttc     2580
caaatgcatg tgtaggggtt gtaattacat ataatggggc agggcatggg tctgcgatg      2640 attcggcaat ttatgttccg tcttattcac gtactggatg cacattatat gctcataacg     2700
ccgatggcaa atttatgcta attgctaaag gatattgaat gaggatttat tttagcccta     2760
gcgaaattgg tttttatcat gaatcagata acaagcttta tttactagcg ggtacttggc     2820
cgaatgattt acttgaaatt tcggagaagt ggttcctgta tctgttggaa ggtcaacaga     2880
aaggtaaggt aatcactgta aatgattacg atcagcctgt tcttgtagac ccgccaaccg     2940
ccactaaaga gcagctcctt gccgaggctg atgctcagaa ggaagcgctc atgaactctg     3000
ccagtgccgt aattgagcca ttgaaagatg ccgttgagtt gggtatgtca acagatgaag     3060
```

```
aggaaggttt actgttggca tggcagcaat atagggtgct gttgatgcgg gttgatacat    3120
cgcatgcacc agatatcgag tggcctgtat tgccagcatg a                       3161

<210> SEQ ID NO 3
<211> LENGTH: 3308
<212> TYPE: DNA
<213> ORGANISM: Artificial Sequence
<220> FEATURE:
<223> OTHER INFORMATION: Bittersweet Tail Fiber

<400> SEQUENCE: 3
atgtctgacg tctcaacaaa cctctataag agtcagttgt tggactatta ctatcagcgg      60
cgcgctgaat cgtccattaa caaaggctct cgatttttaa tcagcaaggc cgttttcggt     120
accagttcgc tggttactaa gaaggagat ggcacttatg agattggaga actgccaaag     180
gctttcgaac tggcagaact gaccagtcaa ttttgcacca tcaacctcgt cccaacctac     240
tcaggcggga taattactgt ccgaatggac cttgatcaaa gccagttgca ggaagggaaa     300
aactacccat tcaacactct ggttgttctg ataacgaga acaagccaat cgccattatt     360
tgtgtccagg aagactcgct gtatgtgggc aaaacatata ccgcagttat ggccataaac     420
acgactacag cataaggata tgcttgatga atgacgtcac cgttgttacg agtgttacct     480
acccctcgcc tgagtcatta gcgttagttg cagacgttca gtaccacgaa ccgtatcttt     540
cagcagctct taaccgtaaa ttccgcggaa ttgtcgatcc aggattttac gccgggttcc     600
tgcctaagcc tggcggcggc atgaatcttc tgattacgtc agtcgacggg gataaaactg     660
cgggagcggc atcggtagat atcggggaat tctaccaggt tacaattcaa catcgtaaag     720
acatttcgtt agcacttaac gctgggaaga aatacgccat tgtcttgaaa ggccgctatt     780
tgttaggtga agatacgtac caggtcaata cagcaagtca catccacgcc gctgaatttg     840
tcgcacgtac atataccgat tcctaccagc ttggggatgg tgagttactt gtgtgcaccg     900
tgaacattcc tgctggagtg tcaacgatca cgcaggagat gatcgatact tcagagcgta     960
ttaatcgcac gatcgggatt gatatttcag acagcgtcac ctcgactcgc tcagatgtcg    1020
cggcttcatc tcttgcagtg aaaaaggcct acgacctggc caagtcgaag tacacagctc    1080
aggacgcgag caccacccaa aagggtctgg tacagttatc atctgcgacg aattcaacat    1140
ccgaggttct tgcagcgaca cctaaagcgg taaaagccgc gtatgatctt gccaatggga    1200
aatacaccgc acaggacgcc acaactacac aaaagggtat tgtgcagttg tcgagtgaca    1260
ccaactcaac gtcggagaca ctggcggcca cgccgaaagc agtcaaagct gcatacgacc    1320
ttgcggctgg taaagcgccc tcatcccaca ctcaccccctg gaatcagatt actggtgtac    1380
ccaccgcaag cttaactgca aagggtatca ctcaattgag ttccgcgacc aacagcacca    1440
gtgaagtttt agctgctacc ccaaaggcag ttaaagccgc ttacgacttg gctaatggaa    1500
aatatacagc gcaggacgcg accactgcac aaaaaggaat tgtgcaactt cgagcgcaa    1560 cgaactccac aagtgaagtt ttggcagcta cgcctaaagc cgtcaaagcc gcgtatgatt    1620
tggcgaatgg taagtatact gcgcaagatg cgacgactac gcagaaaggt attgtccaac    1680
tgtcaagtga caccaacagc acgtcagaga ccttggctgc tacacctaaa gcagtgaaag    1740
ctgcctatga tcttgcggct gggaaagccc cgtcatcaca cacacatcca tggaaccaga    1800
ttacggtcgt acctacggcc tctttaactg cgaagggcat tacacaatta tcatccgcga    1860
ctaacagcac cagtgaggtt ttagctgcaa caccgaaagc agtgaaggca gcctacgatt    1920
```

| | |
|---|---|
| tggcgaacgg taaatatacg gctcaagatg cgaccaccgc gcaaaagggc attgtgcaac | 1980 |
| tgtcgtctgc aacaaattca acgtcggaag ttctggcagc aactccaaag gcagtgaaag | 2040 |
| ccgcctatga cttagcaaac ggtaaacagg ccgcggatgc gacgttaacg gcattggcgg | 2100 |
| ctcttgcaac tgcagcggac aagttaccgt atttcacggg cgttgaccgt gctgccctga | 2160 |
| cagcgttaac ctctgttggg cgtgccattt taggcaagac ctcgattcaa tctgttttag | 2220 |
| attaccttgg tttgggggaa ggctcagcat tgcctgttgg cgtacctgtt ccgtggccct | 2280 |
| cagccactcc gccaacgggg tggctgaaat gtaacggagc agcatttttct tctgaaaagt | 2340 |
| acccaaatct ggcaaaggct taccctacta ataaattgcc ggatttacgc ggtgaattta | 2400 |
| ttcgtggctg ggatgacgga cgtggtgtgg atgccgggcg acaattatta tcttcacagg | 2460 |
| gggatgcaat aagaaatatt gaggggttcg cagatggcgg gatcggcatg tcttttgatg | 2520 |
| caatcagagg ggcttttttac gatgcaggaa cacgatcagc gagaatgccg aataacacaa | 2580 |
| ctactataga caaaaccgat gaccttggat tcgacgcctc tcgtgtcgtg ccaacagcta | 2640 |
| atgaaaaccg tcctcgtaat attgccttta attatatcgt aagggcggca taaattatgg | 2700 |
| ataatgcgat attaaatagc gaacttatag ccatacaggc aggaaacatt atcgtttata | 2760 |
| actatgatgg tggtaatcgg gaatatattt ctgcatcaac tgaatatctt gctgttggcg | 2820 |
| ttggtattcc ggcaaattct tgttttggatg ctccaggctc acataaagca ggttatcgaa | 2880 |
| ttctccgttc agaggattta agttcatggg agtatgtgcc agatcatcgt ggcgaaactg | 2940 |
| tctatagcat tgacacaggg aatcccgaag aaatcacggt gttgggtgac tatccggaaa | 3000 |
| atacaaccac tatcgccccg ctaacaccat acgacaaatg ggatggagag aaatgggtgg | 3060 |
| ttgatactga ggctcaacat agtgcagctg tagaggcagc agaaacaaaa cgtcagtcat | 3120 |
| tgattgatac tgcgatggat tccattagtc tgattcagtt gaaattacgg gctggacgga | 3180 |
| agttgacgca ggcagaaacc acgcagctta actccgtgct agattatata gacgagctga | 3240 |
| acgcgatgga tttaaccacg gcaccagatc tcaactggcc tgaaaaacaa ctttctacag | 3300 |
| ccagttga | 3308 |

<210> SEQ ID NO 4
<211> LENGTH: 3272
<212> TYPE: DNA
<213> ORGANISM: Artificial Sequence
<220> FEATURE:
<223> OTHER INFORMATION: Cobalt Tail Fiber

<400> SEQUENCE: 4

| | |
|---|---|
| atgtctgacg tctcaacaaa cctctataag agtcagttgt tggactatta ctatcagcgg | 60 |
| cgcgctgaat cgtccattaa caaaggctct cgatttttaa tcagcaaggc cgttttcggt | 120 |
| accagttcgc tggttactaa gaaaggagat ggcacttatg agattggaga actgccaaag | 180 |
| gctttcgaac tggcagaact gaccagtcaa ttttgcacca tcaacctcgt cccaacctac | 240 |
| tcaggcggga taattactgt ccgaatggac cttgatcaaa gccagttgca ggaagggaaa | 300 |
| aactacccat tcaacactct ggttgttctg ataacgaga acaagccaat cgccattatt | 360 |
| tgtgtccagg aagactcgct gtatgtgggc aaaacatata ccgcagttat ggccataaac | 420 |
| acgactacag cataaggata tgcttgatga atgacgtcac cgttgttacg agtgttacct | 480 |
| accccctcgcc tgagtcatta gcgttagttg cagacgttca gtaccacgaa ccgtatcttt | 540 |
| cagcagctct taaccgtaaa ttccgcgaaa ttgtcgatcc aggattttac gccgggttcc | 600 |
| tgcctaagcc tggcggcggc atgaatcttc tgattacgtc agtcgacggg gataaaactg | 660 |

```
cgggagcggc atcggtagat atcggggaat tctaccaggt tacaattcaa catcgtaaag    720
acatttcgtt agcacttaac gctgggaaga aatacgccat tgtcttgaaa ggccgctatt    780
tgttaggtga agatacgtac caggtcaata cagcaagtca catccacgcc gctgaatttg    840
tcgcacgtac atataccgat tcctaccagc ttggggatgg tgagttactt gtgtgcaccg    900
tgaacattcc tgctggagtg tcaacgatca cgcaggagat gatcgatact tcagagcgta    960
ttaatcgcac gatcgggatt gatatttcag acagcgtcac ctcgactcgc tcagatgtcg   1020
cggcttcatc tcttgcagtg aaaaaggcct acgacctggc caagtcgaag tacacagctc   1080
aggacgcgag caccacccaa aagggtctgg tacagttatc atctgcgacg aattcaacat   1140
ccgaggttct tgcagcgaca cctaaagcgg taaaagccgc gtatgatctt gccaatggga   1200
aatacaccgc acaggacgcc acaactacac aaaagggtat tgtgcagttg tcgagtgaca   1260
ccaactcaac gtcggagaca ctggcggcca cgccgaaagc agtcaaagct gcatacgacc   1320
ttgcggctgg taaagcgccc tcatcccaca ctcacccctg gaatcagatt actggtgtac   1380
ccaccgcaag cttaactgca aagggtatca ctcaattgag ttccgcgacc aacagcacca   1440
gtgaagtttt agctgctacc ccaaaggcag ttaaagccgc ttacgacttg gctaatggaa   1500
aatatacagc gcaggacgcg accactgcac aaaaaggaat tgtgcaactt tcgagcgcaa   1560
cgaactccac aagtgaagtt ttggcagcta cgcctaaagc cgtcaaagcc gcgtatgatt   1620
tggcgaatgg taagtatact gcgcaagatg cgacgactac gcagaaaggt attgtccaac   1680
tgtcaagtga caccaacagc acgtcagaga ccttggctgc tacacctaaa gcagtgaaag   1740
ctgcctatga tcttgcggct gggaaagccc cgtcatcaca cacacatcca tggaaccaga   1800
ttacggtcgt acctcggcc tctttaactg cgaagggcat tacacaatta tcatccgcga   1860
ctaacagcac cagtgaggtt ttagctgcaa caccgaaagc agtgaaggca gcctacgatt   1920
tggcgaacgg taaatatacg gctcaagatg cgaccaccgc gcaaaagggc attgtgcaac   1980
tgtcgtctgc aacaaattca acgtcggaag ttctggcagc aactccaaag gcagtgaaag   2040
ccgcctatga cttagcaaac ggtaaacagg ccgcggatgc gacgttaacg gcattggcgg   2100
ctcttgcaac tgcagcggac aagttaccgt atttcacggg cgttgaccgt gctgccctga   2160
cagcgttaac ctctgttggg cgtgccattt taggcaagac ctcgattcaa tctgttttag   2220
attaccttgg tttaggggaa ggctctgcac tgcctgttgg tgtgcccgtt ccgtggccct   2280
tagaaacacc accaacgggc tggctaaaat gcaatggtgc agcatttcct tctgaaatgt   2340
atcccaaact ggcaaaagcc taccccacca ataaattacc ggatttacgc ggtgaattta   2400
tccgtggctg ggatgatggg cgcgggattg atgcgggacg aaccctgctt tcagggcagg   2460
atggtacaag tttttctcat tacgaggta atttcgacat tgggtctggt cattcaatca   2520
ataactatga ccaaattgtt tctaaccaac caggattttc ccgttttttca tttgcagggc   2580
cttcacgagg tgatggggtt aattatgtaa ccattcgtcc tcgtaacatt gcgtttaatt   2640
atatcgtaag ggcggcatga atggataatg cgatattaaa tagcgaactt atagccatac   2700
aggcaggaaa cattatcgtt tataactatg atggtggtaa tcgggaatat atttctgcat   2760
caactgaata tcttgctgtt ggcgttggta ttccggcaaa ttcttgtttg gatgctccag   2820
gctcacataa agcaggttat gcgattctcc gttcagagga tttaagttca tgggagtatg   2880
tgccagatca tcgtggcgaa actgtctata gcattgacac agggaatccc gaagaaatca   2940
cggtgttggg tgactatccg gaaaatacaa ccactatcgc cccgctaaca ccatacgaca   3000
```

```
aatgggatgg agagaaatgg gtggttgata ctgaggctca acatagtgca gctgtagagg    3060
cagcagaaac aaaacgtcag tcattgattg atactgcgat ggattccatt agtctgattc    3120
agttgaaatt acgggctgga cggaagttga cgcaggcaga aaccacgcag cttaactccg    3180
tgctagatta tatagacgag ctgaacgcga tggatttaac cacggcacca gatctcaact    3240
ggcctgaaaa acaactttct acagccagtt ga                                  3272

<210> SEQ ID NO 5
<211> LENGTH: 2183
<212> TYPE: DNA
<213> ORGANISM: Artificial Sequence
<220> FEATURE:
<223> OTHER INFORMATION: Cornflower Tail Fiber

<400> SEQUENCE: 5
atgtctgacg tctcaacaaa cctctataag agtcagttgt tggactatta ctatcagcgg     60
cgcgctgaat cgtccattaa caaaggctct cgatttttaa tcagcaaggc cgttttcggt    120
accagttcgc tggttactaa gaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg ataacgaga acaagccaat cgccattatt    360
tgtgtccagg aagactcgct gtatgtgggc aaaacatata ccgcagttat ggccataaac    420
acgactacag cataaggata tgcttgatga atgacgttac agttgttaca tcggttactt    480
acccatcatc cgagtcgttg gctctggtgg ccgatgtgca ataccacgaa ccatatctgt    540
cagccgcgct aaaccgaaaa ttcaggggga ttgttgaccc gggatttat gccggtttct    600 tacctaagcc tggcggtggg atgaacctgt taattacctc agtggatggt gataaaaccg    660
caggcgcggc gtcggtggat attggtgaat ttaccaggt aactattcag caacgtaagg    720
atatttctct tgcacttagt gcaggcaaga aatatgcaat tgtgctgaag gaagatacc    780 tccttggaga agataccta caggtgaata ccgcgtcaca tattcatgcg gctgaatttg    840
ttgccagaac ctataccgat tcatatcagt taggagatgg ggagctgctt gtttgtacgg    900
tgaatatccc tgctagtgta tctgccatta cccaggagat gattgataca tccgagcgta    960
tcaaccgctc gatcggcatt gatatttcag actctgtaac cagtaccaga agtgatgttg   1020
ctgcaagttc gctggcagtt aaaaaagcct acgatctggc gaaaagcaag gcggcgatag   1080
ccgggatggc gaaggcatcg gatcttaacg cactggcaaa actcacagga ggaaacaaac   1140
tcgacggctc gcaggttata accagcgata atgccggttt tattctcggt aagaactcag   1200
atctggctct gctcaaaaaa caggggcaag gcgggacaat tgccgttggc tcggaacac   1260 cgtttagggt tcagcgttca agagcgacca ctgtatcacc ggcagacacc tttgatgaca   1320
tcctcgttat tgatgccaac aaccgaacga cactacctgg cgcgctgact gccggcggcg   1380
acatcgacaa cacgacgaag gggttgctgt atacccaggc gattgagctg tcatttagca   1440
cgccatacat cgactttcat tttaactaca gcaccgacga cttcaccggg cggattatgg   1500
ccactgccgc cgatcaaatt agtgtacaag gtagtcattg gcgagttgac agggatcttc   1560
gtgttggtgg tatggcagat attgcagggt gggcgcaatg cggagtcgac ctctcggcca   1620
acaggacaga ctttggttcc cctgctattg gttcgttggt ttcaggcgga cgtattcgat   1680
ccagaatgct gggacgcggc ggtaacgttg acccctccgg ggcgtgggc ggtttctatg   1740 ttgaagagca cgtaggaacc gaacacagga ttatcatgta tatggacggc ttcggagaa   1800
```

```
ccgacgcatg gtcattccgc gcaggtgggg taatttccac gcccaagggc gacgtcatga    1860
cgaccggttc cgacgtgcga ctgaaaactg acttcacaca agcgcctgga aacgcctcag    1920
agcgcattga acgcttaggg gtgtgtgagt accggatgaa gggggaaacg cgccggaggc    1980
gtggttttat cgctcagcag gctgaaaaag ctgatgatct gtatactttc ctcggcatcg    2040
agcaggagat tgatggcgaa aaatttaagg tgatgaatgt ggattacacg gcaatcattg    2100
ctgacctggt tacggtggcg cagggtttac tggttaaaaa tcaggaactg gaaaggcgta    2160
tatctgtact ggagggatc tga                                              2183
```

<210> SEQ ID NO 6
<211> LENGTH: 3272
<212> TYPE: DNA
<213> ORGANISM: Artificial Sequence
<220> FEATURE:
<223> OTHER INFORMATION: Denim Tail Fiber

<400> SEQUENCE: 6

```
atgtctgacg tctcaacaaa cctctataag agtcagttgt tggactatta ctatcagcgg    60
cgcgctgaat cgtccattaa caaaggctct cgattttaa tcagcaaggc cgttttcggt    120
accagttcgc tggttactaa gaaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg gataacgaga acaagccaat cgccattatt    360
tgtgtccagg aagactcgct gtatgtgggc aaaacatata ccgcagttat ggccataaac    420
acgactacag cataaggata tgcttgatga atgacgtcac cgttgttacg agtgttacct    480 accccctcgcc tgagtcatta gcgttagttg cagacgttca gtaccacgaa ccgtatcttt    540
cagcagctct taaccgtaaa ttccgcggaa ttgtcgatcc aggatttac gccgggttcc    600 tgcctaagcc tggcggcggc atgaatcttc tgattacgtc agtcgacggg gataaaactg    660
cgggagcggc atcggtagat atcggggaat tctaccaggt tacaattcaa catcgtaaag    720
acatttcgtt agcacttaac gctgggaaga atacgccat tgtcttgaaa ggccgctatt    780
tgttaggtga agatacgtac caggtcaata cagcaagtca catccacgcc gctgaatttg    840
tcgcacgtac atataccgat tcctaccagc ttggggatgg tgagttactt gtgtgcaccg    900
tgaacattcc tgctggagtg tcaacgatca cgcaggagat gatcgatact tcagagcgta    960
ttaatcgcac gatcggggatt gatatttcag acagcgtcac ctcgactcgc tcagatgtcg    1020
cggcttcatc tcttgcagtg aaaaaggcct acgacctggc caagtcgaag tacacagctc    1080
aggacgcgag caccacccaa aagggtctgg tacagttatc atctgcgacg aattcaacat    1140
ccgaggttct tgcagcgaca cctaaagcgg taaaagccgc gtatgatctt gccaatggga    1200
aatacaccgc acaggacgcc acaactacac aaaaggtat tgtgcagttg tcgagtgaca    1260
ccaactcaac gtcggagaca ctggcggcca cgccgaaagc agtcaaagct gcatacgacc    1320
ttgcggctgg taaagcgccc tcatcccaca ctcacccctg gaatcagatt actggtgtac    1380
ccaccgcaag cttaactgca agggtatca ctcaattgag ttccgcgacc aacagcacca    1440
gtgaagtttt agctgctacc ccaaaggcag ttaaagccgc ttacgacttg gctaatggaa    1500
aatatacagc gcaggacgcg accactgcac aaaaaggaat tgtgcaactt cgagcgcaa    1560 cgaactccac aagtgaagtt ttggcagcta cgcctaaagc cgtcaaagcc gcgtatgatt    1620
```

-continued

| | |
|---|---|
| tggcgaatgg taagtatact gcgcaagatg cgacgactac gcagaaaggt attgtccaac | 1680 |
| tgtcaagtga caccaacagc acgtcagaga ccttggctgc tacacctaaa gcagtgaaag | 1740 |
| ctgcctatga tcttgcggct gggaaagccc cgtcatcaca cacacatcca tggaaccaga | 1800 |
| ttacggtcgt acctacggcc tcttaactg cgaagggcat tacacaatta tcatccgcga | 1860 |
| ctaacagcac cagtgaggtt ttagctgcaa caccgaaagc agtgaaggca gcctacgatt | 1920 |
| tggcgaacgg taaatatacg gctcaagatg cgaccaccgc gcaaaagggc attgtgcaac | 1980 |
| tgtcgtctgc aacaaattca acgtcggaag ttctggcagc aactccaaag gcagtgaaag | 2040 |
| ccgcctatga cttagcaaac ggtaaacagg ccgcggatgc gacgttaacg gcattggcgg | 2100 |
| ctcttgcaac tgcagcggac aagttaccgt atttcacggg cgttgaccgt gctgccctga | 2160 |
| cagcgttaac ctctgttggg cgtgccattt taggcaagac ctcgattcaa tctgttttag | 2220 |
| attaccttgg tttaggggaa ggctcggcgc tgcccgttgg tgtacctgtt ccatggccct | 2280 |
| ccgccacacc accaacgggg tggctgaaat gtaacggagc agcattttct tctgaaaagt | 2340 |
| acccaaatct ggcaaaggtt taccccacta ataaattgcc ggatctacgg ggcgaattta | 2400 |
| ttcgaggttg ggatgatgga cgaggtgtgg acaatgggcg agcattatta agcagccaag | 2460 |
| aggctacaaa cttttctcag cgtgccgaa atataggcga tggtgcaggg cacgcaatta | 2520 |
| attttcatga tggcatcgtc ggaaatcagc caggattttc acgatttaat ttcaccagta | 2580 |
| actctgtagg tgatggtata aattttgttg ctgtcaggcc gcgaaatatc gcatttaatt | 2640 |
| acatcgtaag ggcggcataa atggataatg cgatattaaa tagcgaactt atagccatac | 2700 |
| aggcaggaaa cattatcgtt tataactatg atggtggtaa tcgggaatat atttctgcat | 2760 |
| caactgaata tcttgctgtt ggcgttggta ttccggcaaa ttcttgtttg gatgctccag | 2820 |
| gctcacataa agcaggttat gcgattctcc gttcagagga tttaagttca tgggagtatg | 2880 |
| tgccagatca tcgtggcgaa actgtctata gcattgacac agggaatccc gaagaaatca | 2940 |
| cggtgttggg tgactatccg gaaaatacaa ccactatcgc cccgctaaca ccatacgaca | 3000 |
| aatgggatgg agagaaatgg gtggttgata ctgaggctca acatagtgca gctgtagagg | 3060 |
| cagcagaaac aaaacgtcag tcattgattg atactgcgat ggattccatt agtctgattc | 3120 |
| agttgaaatt acgggctgga cggaagttga cgcaggcaga aaccacgcag cttaactccg | 3180 |
| tgctagatta tatagacgag ctgaacgcga tggatttaac cacggcacca gatctcaact | 3240 |
| ggcctgaaaa acaactttct acagccagtt ga | 3272 |

<210> SEQ ID NO 7
<211> LENGTH: 3797
<212> TYPE: DNA
<213> ORGANISM: Artificial Sequence
<220> FEATURE:
<223> OTHER INFORMATION: Eggplant Tail Fiber

<400> SEQUENCE: 7

| | |
|---|---|
| atgtctgacg tctcaacaaa cctctataag agtcagttgt tggactatta ctatcagcgg | 60 |
| cgcgctgaat cgtccattaa caaaggctct cgatttttaa tcagcaaggc cgttttcggt | 120 |
| accagttcgc tggttactaa gaaaggagat ggcacttatg agattggaga actgccaaag | 180 |
| gctttcgaac tggcagaact gaccagtcaa ttttgcacca tcaacctcgt cccaacctac | 240 |
| tcaggcggga taattactgt ccgaatggac cttgatcaaa gccagttgca ggaagggaaa | 300 |
| aactacccat tcaacactct ggttgttctg ataacgaga acaagccaat cgccattatt | 360 |
| tgtgtccagg aagactcgct gtatgtgggc aaaacatata ccgcagttat ggccataaac | 420 |

```
acgactacag cataaggata tgcttgatgg gggctgataa aacgaacaac ataatgacac    480
tatcctctgg tgtctcacag cctttgcttg ctgatgttca atatttcgaa ctctatagta    540
gttcggctct taacagaaaa cttaaaaata ttgttttgcc tggcttttac tgtggatttg    600
aaccagttcc cggcacaggg ttgagtgttc gtataacttc tgaaaactca gaaggtaaag    660
gggctgcttc agtagatgta aataatgttc agatatccgt tcagcaaata gaagatgtga    720
ctgtctcggt aaaggctggg gctaccaaca ttattgtgct ggaagccaat tttgaacatg    780
gtgtaaaaac gacacaggta gatagcgcat cttctgtcag tgctgcaaga atttacgcgc    840
gtacggacaa tactattggg cagaatcaaa ttgaattatg tcgagttatc gtgcctaacg    900
gcgcaacggc tgtgactaaa gaatgattg tgcttaaata ccgggttaac cgtgctgttg    960
gtgtcgaatt ctctaatgaa ataagcagta cagaagaaag aaaagcggct acacctctgg   1020
ctgtcaaaac tctccatgat ttggttgata caaaagctcc gctcgatagt ccgcatctgt   1080
caggtacgcc gacttcgccg cacctgaacc cggtacaaa caacacacag atcgcaaatg   1140
cggcctttgt ctatgctgct ataaatgcgc ttatcaatgg tgctccggga acgatggaca   1200
cgctgaaaga aatagcggct gcgatcaata acgacccgaa tttcagcaca actatcaaca   1260
atgctctggc tcttaaagct cctttagcaa gtcctgcatt aacgggaata cctactgcgc   1320
ctaccgctgc acagggtacg aataacacgc agattgctac gaccgcttat gtaagagctg   1380
ccatatccgc attggttggt tcatcaccag aagctcttga taccctgaat gagcttgccg   1440
cagcacttgg taatgacccg aactttgcga caacaatgac aaatgcgctg gcaggcaaac   1500
agcctctgga tgcaacttta accgcgctcg ctggccttgc gactggtgca aacaaactgc   1560
cttatttcac cggtaaggat acggtagcgc agactgattt aacgtcagtc ggtcgcgata   1620
ttctggctaa acaagcaca ctggccgtta tccaatacct tggtttaaga gaactcggta   1680
ccagcggtga aaagatcccc ctgttgagca cggctaacac gtggagtgca cgccagactt   1740
tcaacggcgg gatcaccggg gcgctgacag ggaacgccga taccgcgacg aaattaaaaa   1800
cagccataaa cattaatggc gtcaggttcg atggttctac gaacatttcg ataccaacaa   1860
ttacgtctag aggacgcgtt actgcgctta ccggtacaac gcaaggtgct gctactggat   1920
tgcagatgta tgaggcatac aacaatggct acccttcccc ctatggcaat gtgcttcacc   1980
ttaaaggtgc caccgctgct ggcgaaggtg agttattcat tggctggagt ggcacaaatg   2040
gcgctcatgc acctgctttc attcgatcca aaagagatag cactgctgcg catggtccg    2100 agtgggcaca gatctatacg tcaaaagatt cagttcccgg cgtcaatgcc aaagggaatc   2160
aggacacctc tggtaatgcg gctacagcga ccaaattgca gatagcatgt actatcaacg   2220
gcgtctcgtt tgacggttct aaaaatattg agctaacggc ggaagattta aatctacagg   2280
aaacggtaaa caaggctgat aacgcggttc aaaagacagg cgataccttg tccggtggac   2340 ttactttga aaacgactca atccttgcct ggattcggaa tactgactgg gcgaagattg   2400 gtttttaaaaa tgatgccgac agcgatactg attcatacat gtggtttgag acaggcgaca   2460
acggcaatga atatttcaaa tggagaagca aacaaagtac cacaacaaaa gacctgatga   2520
atcttaaatg ggatgctttg tatgttcttg tcaatgccat tgtaaatggc gaagtcatat   2580
caaaatcagc aaacggccta cgtattgctt atggtaatta cggattcttt attcgtaatg   2640
atggttcaaa tacatacttc atgttgacaa actccggtga caacatgggg acttataacg   2700
gattaaggcc attatggatt aataacgcta ctggcgctgt ttcgatggga cgtggtctta   2760
```

```
atgtttcagg ggagacactt tcagaccgtt ttgctattaa cagcagtaat ggtatgtgga      2820
ttcagatgcg cgataacaac gctatctttg ggaaaaatat agttaacact gatagcgctc      2880
aggcgttact tcgccagaat cacgccgacc gaaagttcat gataggtgga ctggggaaca      2940
agcaatttgg catctacatg attaataact caaggacagc caatggcacc gatggtcagg      3000
cgtacatgga taataacggt aactggcttt gtggtgcgca agttattccc ggcaattatg      3060
gcaattttga ctcacgctat gtgagagatg tccgacttgg cacacgtgtt gttcaattga      3120
tggcgcgtgg tggtcgttat gaaaaagccg acacgcaat taccggatta agaatcattg      3180
gtgaagtaga tggcgatgat gaagccatct tcaggccaat acaaaaatac atcaatggca      3240
catggtataa cgtcgcacag gtgtaaatta tgcagcactt aaaaaatatc aggtcaggaa      3300
acccaaagac aaaagagcaa taccaattaa caaagaattt tgacgtaatc tggttgtggt      3360
ctgaagacgg aaaaaactgg tatgaggaag tgaaaaactt caaccagac accataaaga       3420 ttgtttacga tgaaaataat attattgtcg ccatcaccaa agatgcctcc acgcttaacc      3480
ctgaaggttt tagcgtcgtt gaggttcccg acataacagc caaccgccgc gctgatgatt      3540
caggaaagtg gatgtttaag gatggagctg tagttaaacg gatttatacg gcagacgaac      3600
agcaacaaca agccgaatca caaaaggccg cattgctttc cgaagctgaa tcagtcatcc      3660
agccgctgga acgcgctgtc aggctgaata tggcaacaga cgaggaacgc acacgactgg      3720
aagcatggga acgctacagt gttctggtca gccgtgtgga tacggcaaat cctgaatggc      3780
cacaaaagcc tgaataa                                                     3797

<210> SEQ ID NO 8
<211> LENGTH: 3938
<212> TYPE: DNA
<213> ORGANISM: Artificial Sequence
<220> FEATURE:
<223> OTHER INFORMATION: Fern Tail Fiber

<400> SEQUENCE: 8
atgtctgacg tctcaacaaa cctctataag agtcagttgt tggactatta ctatcagcgg       60
cgcgctgaat cgtccattaa caaaggctct cgattttaa tcagcaaggc cgttttcggt       120
accagttcgc tggttactaa gaaaggagat ggcacttatg agattggaga actgccaaag      180
gctttcgaac tggcagaact gaccagtcaa ttttgcacca tcaacctcgt cccaaccta      240 tcaggcggga taattactgt ccgaatggac cttgatcaaa gccagttgca ggaagggaaa      300
aactacccat tcaacactct ggttgttctg gataacgaga acaagccaat cgccattatt      360
tgtgtccagg aagactcgct gtatgtgggc aaaacatata ccgcagttat ggccataaac      420
acgactacag cataaggata tgcttgatga atgacgttac agttgttaca tcggttactt      480
acccatcatc cgagtcgttg gctctggtgg ccgatgtgca ataccacgaa ccatatctgt      540
cagccgcgct aaaccgaaaa ttcaggggga ttgttgaccc gggatttta gccggtttct       600 tacctaagcc tggcggtggg atgaacctgt taattacctc agtggatggt gataaaaccg      660
caggcgcggc gtcggtggat attggtgaat ttaccaggt aactattcag caacgtaagg       720
atatttctct tgcacttagt gcaggcaaga aatatgcaat tgtgctgaag gaagatacc       780 tccttggaga agataccta caggtgaata ccgcgtcaca tattcatgcg gctgaatttg      840
ttgccagaac ctataccgat tcatatcagt taggagatgg ggagctgctt gtttgtacgg      900
tgaatatccc tgctagtgta tctgccatta cccaggagat gattgataca tccgagcgta      960
tcaaccgctc gatcggcatt gatatttcag actctgtaac cagtaccaga agtgatgttg      1020
```

```
ctgcaagttc gctggcagtt aaaaaagcct acgatctggc gaaaagcaag tatacggcac    1080
aggatgcaag cacaacgcaa aagggattag ttcagctcag tagcgcaact aacagcgaca    1140
gcgaaacaat ggcggctacc cctaaagctg ttaagtctat aaaagatctg gctgatacca    1200
aagcgccaat agaaagcccg agtctgacag gaacgccaac cgcgccgacg gcagcgcaag    1260
gtacaaacag cacgcagatc gcaaatacag cctttgttaa ggcagctata actgcactta    1320
tcaacggtgc gcctggcaca ctggatacgc tgaaagaaat agcggctgcg atcaataacg    1380
acccgaatta cagcacaact atcaacaatg ccttggctct caaagcgcct ttggcaagcc    1440
ctgcattaac gggtgtccct actgcgccta cggctgcaca gggcacaaac aatacgcaga    1500
tcgctacgac tgcttacgta cgggctgcta tctctgcatt ggtcggctca tcacctgaag    1560
ctcttgatac cctgtatgag cttgcagcag cactgggcaa tgacccgaac tttgcgacaa    1620
caatgacaaa tgcgctggca gggaaacagc cacttgatgc aactttaacc gcgcttgctg    1680
gtcttgcgac aggcgcaaat aaattgccgt actttaccgg tacagacact gtttctcaga    1740
ctgacttaac gtcagttggt cgcgatattc tggccaaaac aagcattctt gctgttatcc    1800
aataccttgg tttaagagaa ctcggtacca gcggtgaaaa gatcccctg ttgagcacgg    1860 ctaacacatg gagtgcacgc cagactttca acggcgggat caccggggcg ctgacaggga    1920
acgccgatac cgcaacgaaa ttgaaaacag ccagaaacat taatggcgtc aggttcgatg    1980
gttctggtga cattaatatc aatactctgg tatcgcgcgg tcgcgtaacg gccctggagg    2040
cgaatgcaca gggaacatcc gggattcagc tgtatgaggc atacaacaat ggctaccctt    2100 cccctatgg caatgtgctt caccttaaag gtgccaccgc tgctggcgaa ggtgagttat    2160
tcattggctg gagtggcacg agcggtgccc atgcgcccgt acatatccgt tcgcggcggg    2220
atactgattc tgccaactgg tctgaatggg cgcaggtcta tacgtcaaaa gattcaattc    2280
ccggcgtcaa tgccaaaggg gatcaggata cctctggtaa tgcggctaca gcgaccaagt    2340
tgcagacagc atgtactatc aacggcgtct cgtttgacgg ttctaaaaat attgagctaa    2400
cggcggaaga tttaaatcta caggaaacgg taaacaaggc tggtaacgct gttcaaaaga    2460
caggcgatac cttgtccggt gggcttactt ttgaaaatga ctcaatcctt gcctggattc    2520
gaaatactga ctgggcgaag attggattta aaaatgatgc cgatggtgac actgattcat    2580
acatgtggtt tgaaacaggc gacaacggca atgaatattt caaatggaga agcaaacgag    2640
gcaccacaac aaaagacctg atgaatctta atgggatgc tttgtatgtt cttgtcaatg    2700
ccattgtaaa cggcgaagtc atatcaaaat cagcaaacgg cctacgtatt gcttatggta    2760
attacggatt cttattcgt aatgatggtt caaatacata cttcatgttg acaaactccg    2820
gtgacaacat ggggacttat aacggattaa ggccattatg gattaataac gctactggcg    2880
ctgtttcgat ggggcgtggc cttaatgttt caggggagac gcttcagacc gtttgctata    2940
acagcagtaa tggtatgtgg attcagatgc gcgataacaa cgctatcttt gggaaaaata    3000
tagttaacac tgatagcgct caggcgttgc ttcgccagaa tcacgctgac cgcaagttca    3060
tgataggtgg actggggaac aagcaatttg gcatctacat gattaataac tcaaggacag    3120
ccaatggcac cgatggtcag gcgtacatgg acaataacgg taactggctt tgcggtgcgc    3180
aaattattcc cggaaattat ggcaattttg actcacgcta tgtgagcgat gtccgacttg    3240
gcacacgtgt tgttcagact atgcaaaaag gcgtgatgta tgagaaatca ggtcatgcaa    3300
ttacggggct tggcattgtc ggtgaagttg atggcgatga tccggcagta ttcagaccaa    3360
```

| | |
|---|---|
| tacaaaaata catcaatggc acatggtata acgtcgcaca ggtgtaattt atgcagcatt | 3420 |
| taaaaaatat taagtctgga aatccaaaaa caaaagaaca atatcagcta acaaagaatt | 3480 |
| ttgatgttat ctggttatgg tccgaagacg aaaaaactg gtatgaggaa gtgaaaaact | 3540 |
| ttcagccaga cacaataaag attgtttacg atgcaaataa tattattgtc gccatcacca | 3600 |
| aagatgcctc cacgcttaac cctgaaggtt atagcgtcgt tgaggttcct gatattacag | 3660 |
| ctaatcgtcg tgctgatgat tccggtaagt ggatgtttaa ggacggagct gtggttaaac | 3720 |
| ggatttatac ggcagacgag caacaacaac aggccgaatc acaaaaggcc gcgttacttt | 3780 |
| ccgaagcaga aaacgttatt cagccactgg aacgcgctgt caggctgaat atggcgacgg | 3840 |
| atgaggaacg cgcacgactg gagtcatggg aacgctatag tgttctggtc agccgtgtgg | 3900 |
| atacggcaaa tcctgaatgg ccacaaaagc ctgaataa | 3938 |

<210> SEQ ID NO 9
<211> LENGTH: 3901
<212> TYPE: DNA
<213> ORGANISM: Artificial Sequence
<220> FEATURE:
<223> OTHER INFORMATION: Fuchsia Tail Fiber

<400> SEQUENCE: 9

| | |
|---|---|
| atgtctgacg tctcaacaaa cctctataag agtcagttgt tggactatta ctatcagcgg | 60 |
| cgcgctgaat cgtccattaa caaaggctct cgatttttaa tcagcaaggc cgttttcggt | 120 |
| accagttcgc tggttactaa gaaaggagat ggcacttatg agattggaga actgccaaag | 180 |
| gctttcgaac tggcagaact gaccagtcaa ttttgcacca tcaacctcgt cccaacctac | 240 |
| tcaggcggga taattactgt ccgaatggac cttgatcaaa gccagttgca ggaagggaaa | 300 |
| aactacccat tcaacactct ggttgttctg gataacgaga acaagccaat cgccattatt | 360 |
| tgtgtccagg aagactcgct gtatgtgggc aaaacatata ccgcagttat ggccataaac | 420 |
| acgactacag cataaggata tgcttgatga atgacgttac agttgttaca tcggttactt | 480 |
| acccatcatc cgagtcgttg gctctggtgg ccgatgtgca ataccacgaa ccatatctgt | 540 |
| cagccgcgct aaaccgaaaa ttcagggga ttgttgaccc gggatttta tccggtttct | 600 |
| tacctaagcc tggcggtggg atgaacctgt taattacctc agtggatggt gataaaaccg | 660 |
| caggcgcggc gtcggtggat attggtgaat tttaccaggt aactattcag caacgtaagg | 720 |
| atatttctct tgcacttagt gcaggcaaga aatatgcaat tgtgctgaag ggaagatacc | 780 |
| tccttggaga agatacctac caggtgaata ccgcgtcaca tattcatgcg ctgaatttg | 840 |
| ttgccagaac ctataccgat tcatatcagt taggagatgg ggagctgctt gtttgtacgg | 900 |
| tgaatatccc tgctagtgta tctgccatta cccaggagat gattgataca tccgagcgta | 960 |
| tcaaccgctc gatcggcatt gatatttcag actctgtaac cagtaccaga agtgatgttg | 1020 |
| ctgcaagttc gctggcagtt aaaaaagcct acgatctggc gaaaagcaag tatacggcac | 1080 |
| aggatgcaag cacaacgcaa aagggattag ttcagctcag tagcgcaact aacagcgaca | 1140 |
| gcgaaacaat ggcggctacc cctaaagctg ttaagtctat aaaagatctg gctgatacca | 1200 |
| aagcgccaat agaagcccg agtctgacag gaacgccaac cgccgacg gcagcgcaag | 1260 |
| gtacaaacag cacgcagatc gcaaatacag cctttgttaa ggcagctata actgcactta | 1320 |
| tcaacggtgc gcctggcaca ctggatacgt tgaaagaaat agcggctgcg atcaataacg | 1380 |
| acccgaatta cagcacaact atcaacaatg ccttggctct caaagcgcct ttggcaagcc | 1440 |
| ctgcattaac gggtgtccct actgcgccta cggctgcaca gggcacaaac aatacgcaga | 1500 |

```
tcgctacgac tgcttacgta cgggctgcta tctctgcatt ggtcggctca tcacctgaag   1560
ctcttgatac cctgtatgag cttgcagcag cactgggcaa tgacccgaac tttgcgacaa   1620
caatgacaaa tgcgctggca gggaaacagc cacttgatgc aactttaacc gcgcttgctg   1680
gtcttgcgac aggcgcaaat aaattgccgt actttaccgg tacagacact gtttctcaga   1740
ctgacttaac gtcagttggt cgcgatattc tggccaaaac aagcattctt gctgttatcc   1800
atggtttaag agaactcggt accagtggtg aaaagatccc cctgttgagt acggctaaca   1860
catggagtgc gcgccagact ttcaatggcg ggatcaccgg ggcgctgata gggaacgccg   1920
acaccgcgac gaaattgaaa acagccataa acattaatgg cgtcaggttc gatggttcgg   1980
ctgacattaa tatcaatact ctggtatcgc gtggtcgcgt aacggctctg ggggcgaatg   2040 cacagggac atccgggatt cagctgtatg aggcatacaa caatggctat ccttccccct   2100
atggcaatgt gcttcacctt aaaggtgcca ccgctgctgg cgaaggtgaa ttattcattg   2160
gctggagtgt ctcgagcggt gaccatgcgc ccgtacatat ccgttcgcgg cgtgatattg   2220
attctgccaa ctggtctgaa tgggcacagg tctatacgtc aaaagattca gttcccggcg   2280
ttaatgccaa agggaatcag gatacctctg gtaatgcggc tacagcgacc aaattgcaga   2340
cggcgtgtac tatcaacggt gtctcgtttg atggttctaa aaacattgag ctaacggcgg   2400
aagatttaaa tcttgagcaa accgtagaat tagccgcagg agcattgcag aaaaaccaga   2460
acggtgcaga tattccgaat aaagataaat tcatacaaaa cacaggggcc tgtcgtgcat   2520
ttagcggtca gactgatatc gatggttcac aaggtgaatg gtcgacagtt gcatttatct   2580
cgtggctgga gaataacgga gctttccgac atccatactg gatgtgtaaa gggtcatggt   2640
cctatgccag aaacagggtt attacggata ccggttgtgg aaatatctgc cttgccggag   2700
ccgtgattga ggttatggga acccgcggcg caatgaccat acgcgttacc acgccgagca   2760
cgtccagcgg tggcggaatc actaacgctc aattcactta tattaatcat ggtgatgctt   2820
acgctcctgg ctggcgacga gactacaaca cgaaaaacca gcagcctgca tttgctttag   2880
ggcaaacagg acgcagggtc gcaaatgata agctgttgg ctggaactgg aatagcggcg   2940
tttatgatgc agatatcagt ggcgcatcga cattaatcct ccactttaat atgaatgcgg   3000
ggagttgccc tgctgtacag ttccgcgtga attacagaaa tggcggtatc ttttatcgtt   3060
cagcgcgtga tggttatggc tttgaagcta actggtcaga gttttacacc acaacacgca   3120
aaccctctgc gggagatgtt ggtgcatata cgcaggcaga atgtaactca aggtttatta   3180
caggtattcg cctggcggt ctgtcatctg ttcagacatg gaatggtcct ggctggtctg   3240
acaggtcagg ttatgtcgtt actggttcag ttaacggaaa ccgtgatgaa ttaattgata   3300
caactcaggc aaggccaatt cagtattgca ttaatggaac gtggtataac gcggggagta   3360
tttaattatg atgcacttaa gaaatattac agctggcaac cctaaaacaa aagagcaata   3420
ccagctaacg aaacaattta acatcaaatg gctttataca gaggatgaaa aaactggta   3480 tgaggaacaa aagaatttcc agtatgatac gttgaaaatg gcctatgacc acaacggcgt   3540
tattatttgt attgaaaagg atgtttcagc aattaatcca gaaggcgcaa gcgtcgttga   3600
attacctgat attacagcaa atcgccgggc tgatatttct ggtaaatgga tgttcaaaga   3660
tggcgtagtg gtaaagcgaa cttataccga ggaagagcag aggcaacaag cggaaaatga   3720
aaagcaaagt ctgctacagc tcgtcaggga taaacccag ctatgggact cacagctacg   3780
gctgggtatc atttccgccg agaataagca gaaattaacc gagtggatgc tctttgcgca   3840
```

```
gaaagtcgaa tccacagaca cctccagcct accagtaaca tttcccgaac aacctgaatg    3900
a                                                                    3901
```

<210> SEQ ID NO 10
<211> LENGTH: 2713
<212> TYPE: DNA
<213> ORGANISM: Artificial Sequence
<220> FEATURE:
<223> OTHER INFORMATION: Fuzzy Tail Fiber

<400> SEQUENCE: 10

```
atgtctgacg tctcaacaaa cctctataag agtcagttgt tggactatta ctatcagcgg      60
cgcgctgaat cgtccattaa caaaggctct cgattttaa tcagcaaggc cgttttcggt     120
accagttcgc tggttactaa gaaggagat ggcacttatg agattggaga actgccaaag     180
gctttcgaac tggcagaact gaccagtcaa ttttgcacca tcaacctcgt cccaacctac     240
tcaggcggga taattactgt ccgaatggac cttgatcaaa gccagttgca ggaagggaaa     300
aactacccat caacactct ggttgttctg ataacgaga acaagccaat cgccattatt      360
tgtgtccagg aagactcgct gtatgtgggc aaaacatata ccgcagttat ggccataaac     420
acgactacag cataaggata tgcttgatga atgacgttac agttgttaca tcggttactt     480
acccatcatc cgagtcgttg gctctggtgg ccgatgtgca ataccacgaa ccatatctgt     540
cagccgcgct aaaccgaaaa ttcaggggga ttgttgaccc gggatttat gccggtttct      600 tacctaagcc tggcggtggg atgaacctgt taattacctc agtggatggt gataaaaccg     660
caggcgcggc gtcggtggat attggtgaat tttaccaggt aactattcag caacgtaagg     720
atatttctct tgcacttagt gcaggcaaga aatatgcaat tgtgctgaag ggaagatacc     780
tccttggaga agatacctac caggtgaata ccgcgtcaca tattcatgcg gctgaatttg     840
ttgccagaac ctataccgat tcatatcagt taggagatgg ggagctgctt gtttgtacgg     900
tgaatatccc tgctagtgta tctgccatta cccaggagat gattgataca tccgagcgta     960
tcaaccgctc gatcggcatt gatatttcag actctgtaac cagtaccaga agtgatgttg    1020
ctgcaagttc gctggcagtt aaaaaagcct acgatcggc gaaaagcaag aaaccggacg    1080
gaacaacggg gacggtaaaa tcgtgggcgc agttcctcag cgaatacagt tcccgccaga    1140
ctgctatcga tggcgcgatc acagcagcag ggaagaacgt tgccagaacg tcatcaacca    1200
acacgttcac gcagcctcag acattcagca atggcgtcac attcagcgcc acaataaccg    1260
ctgctgggca atactccgg aataacagcg gcacacaatt tacggcgatt gatgccggaa     1320
gtctggaaat cagcagcgat accacgccct atattgattt tcatcataaa ggtagcgtag    1380
cggattatac gcacaggatt atcacggaag acggtgcgct ggccgtctac cctggccttc    1440
gtgttcgcgg tggttttggt ctttatggcg tggggacggt ttacggtgat gcttattcgc    1500
agggatttat tgcgcgtctt aataatgatc caaacgcatc tattggagac attcttgctt    1560
ctccgcgttt cacggttcgg tttaactcac gaggcagtga cagtaacgta gacggcgggc    1620
agggggcaat gtggtttgaa gagcaggtgg gcaccaacca tcgccttgta ttaatggccg    1680
gcgggtttag tgccaacgtt cagtactggc aatttctggc agacggcagg atttatagta    1740
gccagaacgg aaacgttcaa tggcaaggaa catccgatgc acgcctgaag cacgatattg    1800
aaccaacaga tggccagttg tctgtcgaac gtatccgcaa gctggagttg gtcacgttcg    1860
tctataacga tgacgagcag aacaggacac ggcggggat tatcgctcag caggcacaga    1920
aagtggaccc gcagtacgtt aagcaggtga acacgtcata catgaggaac ggtgagcagg    1980
```

| | |
|---|---|
| taaacgacga tcgcctgcaa ttggataata acgtgatcat gatggacaca ctggcggcgg | 2040 |
| taaaagtact gcttgagcga gtagacgaac tagaggagcg attatcggca catgGataaa | 2100 |
| agaaggagat ataccatgga tgcaagaaac catgacgaga atagaactgt ctggagtcct | 2160 |
| gggtaaaacc tttgggaagg ttcattatcg tttaataaag aacatcaatg aagccggaga | 2220 |
| ggcattatct gcgacgatcc ctggatttga aaggttcatg atatccagtg aggagcgtgg | 2280 |
| attgacctat gcagtattta aagggaataa gaatatcggg catgatgatt taggattccc | 2340 |
| tgtaagtggc gaaattatcc gcatagtccc tgttatcatt ggcagtaaga aggcaggaat | 2400 |
| tctccaaaca atccttggtg cagttattgt tgcggcaagt gttgcctatg gttttttcac | 2460 |
| agaggattgg gctaatgccg cgtatggtat tcaagctggc ggcgccatga tgctcggcgg | 2520 |
| cgtcgttcag atgctctccc cacagccagc tggcctggca cgaaaagaat ccgctgacaa | 2580 |
| taaagcgtcc tacgcctttg ggggcgtgac gaacactgcc tctcagggat acccggtccc | 2640 |
| tttgctttat ggcaaacggc gaattggcgg cgccattata tctgccggta tttacgtaga | 2700 |
| agaccagcaa taa | 2713 |

```
<210> SEQ ID NO 11
<211> LENGTH: 3112
<212> TYPE: DNA
<213> ORGANISM: Artificial Sequence
<220> FEATURE:
<223> OTHER INFORMATION: Inchworm Tail Fiber

<400> SEQUENCE: 11
```

| | |
|---|---|
| atgtctgacg tctcaacaaa cctctataag agtcagttgt tggactatta ctatcagcgg | 60 |
| cgcgctgaat cgtccattaa caaaggctct cgattttaa tcagcaaggc cgttttcggt | 120 |
| accagttcgc tggttactaa gaaaggagat ggcacttatg agattggaga actgccaaag | 180 |
| gctttcgaac tggcagaact gaccagtcaa ttttgcacca tcaacctcgt cccaacctac | 240 |
| tcaggcggga taattactgt ccgaatggac cttgatcaaa gccagttgca ggaagggaaa | 300 |
| aactacccat tcaacactct ggttgttctg gataacgaga acaagccaat cgccattatt | 360 |
| tgtgtccagg aagactcgct gtatgtgggc aaaacatata ccgcagttat ggccataaac | 420 |
| acgactacag cataaggata tgcttgatga atgacgttac agttgttaca tcggttactt | 480 |
| acccatcatc cgagtcgttg gctctggtgg ccgatgtgca ataccacgaa ccatatctgt | 540 |
| cagccgcgct aaaccgaaaa ttcagggga ttgttgaccc gggatttat gccggtttct | 600 |
| tacctaagcc tggcggtggg atgaacctgt taattacctc agtggatggt gataaaaccg | 660 |
| caggcgcggc gtcggtggat attggtgaat tttaccaggt aactattcag caacgtaagg | 720 |
| atatttctct tgcacttagt gcaggcaaga aatatgcaat tgtgctgaag ggaagatacc | 780 |
| tccttggaga agatacctac caggtgaata ccgcgtcaca tattcatgcg gctgaatttg | 840 |
| ttgccagaac ctataccgat tcatatcagt taggagatgg ggagctgctt gtttgtacgg | 900 |
| tgaatatccc tgctagtgta tctgccatta cccaggagat gattgataca tccgagcgta | 960 |
| tcaaccgctc gatcggcatt gatatttcag actctgtaac cagtaccaga agtgatgttg | 1020 |
| ctgcaagttc gctggcagtt aaaaaagcct acgatctggc gaaaagcaag gtcgctgccg | 1080 |
| atttcaaggg ccgcaagatc ctggctggca atggcctgct cggtggggc gatctttctg | 1140 |
| ccgaccgcag cattggcctg gcgccttccg gcgtgacggc gggcagctat cgttcggtca | 1200 |
| cggtgaacgc caacggggtg gtcacccagg gcagcaatcc gaccaccctg gccggctatg | 1260 |

```
cgatcggaga tgcctatacc aaggccgata ccgacggaaa actggcgcag aaagcgaaca      1320
aggccaccac cctggccggc tatggcatca ccgatgcgct gcgagtcgat ggcaacgccg      1380
tgtcatccag caggctggcc gcaccgcgca gcctggcagc cagtggcgat gcctcctggt      1440
cggtgacctt cgacggcagt gccaatgttt ctgcgccgct gagtcttccc gctaccggtg      1500
tggcggcggg cagctatccg aaggtgaccg tggatacgaa gggaagggtg actgctggaa      1560
tggcgctggc ggcgacggac attcccgggc tggatgcgtc gaagctggtc agcggggtgc      1620
tggccgagca gcgtttgccg gtattcgcgc gcgggttggc tactgctgtc tcgaacagta      1680
gcgatccgaa caccgcgacc gtgccgttga tgctgaccaa tcatgcgaac ggacctgttg      1740
ccggacgata cttctacatc cagtcgatgt tctatccgga tcagaacggc aatgcttcgc      1800
agattgcaac gagctacaac gctacatccg agatgtatgt acgggtgtcc tacgcggcca      1860
accctagcat ccgggagtgg ttgccctggc agcgctgcga cattggaggt tccttcacca      1920
aagaggccga tggtgaactg cctggaggcg tcaacctgga ttcgatggtg acctcagggt      1980
ggtggagcca gagtttttact gcccaagctg ccagtggagc caactaccct atagttcggg      2040
ccggcctgct tcatgtgtac gccgcgagta gcaatttcat ctatcagacg tatcaagcct      2100
acgatggtga gagtttctat ttccggtgcc ggcattcaaa tacctggttt ccctggcgtc      2160
gcatgtggca tggcggagac ttcaaccccca gtgactatct gttgaagtcg gggttctatt      2220
ggaatgcgtt accggaaaaa cctgccactt ttccaccatc cgcacataac catgacgtcg      2280
gacagcttac ttcgggcatt ctcccctgg cacgtggcgg cgtcggttcg aatacggcag      2340
cgggagcacg tagcactatc ggagcagggg ttcctgcgac tgcttccctt ggggcgagcg      2400
gatggtggcg ggacaatgac actggcctca ttaggcaatg ggggcaggtc acttgccccg      2460
ccgatgccga tgcttcgatt acgttcccga ttccttttccc tacgctatgc ctcggcggat      2520
atgcgaatca gacgagtgct ttccatccgg gaacggatgc cagtacaggt ttccgtggag      2580
cgactaccac taccgcggtg attcgcaatg gctactttgc tcaggcggtt ctttcatggg      2640
aggcatttgg acgatgaagg gcgaatatta tttctctcca gccaggtgg cattctatcc      2700 ggcctccttg cgagaggttt atgaatacgc aggctgctgg ccagtcgatg gcgagtgggt      2760
cagcgcagag ctacatgaac aactgatgaa cgaacaggcg gcaggccgag caatcagttc      2820
cgacgtgaat gggaacccag tagccgatcga gcgccctccg ctttcccgtc agcaacgtag      2880
cacccatgag cggagatggc gggatagtca gctgttggcg accgacggcc tagttgttcg      2940
ccatcgagat caattggaaa ccggaaagga aacgacctta ctccctgtcc ataccatga      3000 actcatgtcg tacagagcca gcttacggga ttggccggaa gagcctttat ttcccgacag      3060
tggcggacgc ccgtccgtac cagattggct cagacgttat gtcaccccct ga            3112
```

<210> SEQ ID NO 12
<211> LENGTH: 3350
<212> TYPE: DNA
<213> ORGANISM: Artificial Sequence
<220> FEATURE:
<223> OTHER INFORMATION: Indian Tail Fiber

<400> SEQUENCE: 12

```
atgtctgacg tctcaacaaa cctctataag agtcagttgt tggactatta ctatcagcgg        60
cgcgctgaat cgtccattaa caaaggctct cgatttttaa tcagcaaggc cgttttcggt       120
accagttcgc tggttactaa gaaagggagat ggcacttatg agattggaga actgccaaag       180
gctttcgaac tggcagaact gaccagtcaa ttttgcacca tcaacctcgt cccaacctac       240
```

-continued

```
tcaggcggga taattactgt ccgaatggac cttgatcaaa gccagttgca ggaagggaaa    300
aactacccat tcaacactct ggttgttctg gataacgaga caagccaat cgccattatt    360 tgtgtccagg aagactcgct gtatgtgggc aaaacatata ccgcagttat ggccataaac    420
acgactacag cataaggata tgcttgatga atgacgtcac cgttgttacg agtgttacct    480 accctcgcc tgagtcatta gcgttagttg cagacgttca gtaccacgaa ccgtatcttt    540
cagcagctct taaccgtaaa ttccgcggaa ttgtcgatcc aggattttac gccgggttcc    600
tgcctaagcc tggcggcggc atgaatcttc tgattacgtc agtcgacggg gataaaactg    660
cgggagcggc atcggtagat atcggggaat tctaccaggt tacaattcaa catcgtaaag    720
acatttcgtt agcacttaac gctgggaaga aatacgccat tgtcttgaaa ggccgctatt    780
tgttaggtga agatacgtac caggtcaata cagcaagtca catccacgcc gctgaatttg    840
tcgcacgtac atataccgat tcctaccagc ttggggatgg tgagttactt gtgtgcaccg    900
tgaacattcc tgctggagtg tcaacgatca cgcaggagat gatcgatact tcagagcgta    960
ttaatcgcac gatcgggatt gatatttcag acagcgtcac ctcgactcgc tcagatgtcg    1020
cggcttcatc tcttgcagtg aaaaaggcct acgacctggc caagtcgaag tacacagctc    1080
aggacgcgag caccacccaa aagggtctgg tacagttatc atctgcgacg aattcaacat    1140
ccgaggttct tgcagcgaca cctaaagcgg taaaagccgc gtatgatctt gccaatggga    1200
aatacaccgc acaggacgcc acaactacac aaaagggtat tgtgcagttg tcgagtgaca    1260
ccaactcaac gtcggagaca ctggcggcca cgccgaaagc agtcaaagct gcatacgacc    1320
ttgcggctgg taaagcgccc tcatcccaca ctcacccctg gaatcagatt actggtgtac    1380
ccaccgcaag cttaactgca aagggtatca ctcaattgag ttccgcgacc aacagcacca    1440
gtgaagtttt agctgctacc ccaaaggcag ttaaagccgc ttacgacttg gctaatggaa    1500
aatatacagc gcaggacgcg accactgcac aaaaaggaat tgtgcaactt tcgagcgcaa    1560
cgaactccac aagtgaagtt ttggcagcta cgcctaaagc cgtcaaagcc gcgtatgatt    1620
tggcgaatgg taagtatact gcgcaagatg cgacgactac gcagaaaggt attgtccaac    1680
tgtcaagtga caccaacagc acgtcagaga ccttggctgc tacacctaaa gcagtgaaag    1740
ctgcctatga tcttgcggct gggaaagccc cgtcatcaca cacacatcca tggaaccaga    1800
ttacggtcgt acctacggcc tctttaactg cgaagggcat tacacaatta tcatccgcga    1860
ctaacagcac cagtgaggtt ttagctgcaa caccgaaagc agtgaaggca gcctacgatt    1920
tggcgaacgg taaatatacg gctcaagatg cgaccaccgc gcaaaagggc attgtgcaac    1980
tgtcgtctgc aacaaattca acgtcggaag ttctggcagc aactccaaag gcagtgaaag    2040
ccgcctatga cttagcaaac ggtaaacagg ccgcggatgc gacgttaacg gcattggcgg    2100
ctcttgcaac tgcagcggac aagttaccgt atttcacggg cgttgaccgt gctgccctga    2160
cagcgttaac ctctgttggg cgtgccattt aggcaagac ctcgattcaa tctgttttag    2220
attaccttgg tttgggggaa ggctctgcac tgcctgttgg tgtgcccgtt ccgtggccct    2280
tagaaacacc accaacgggc tggctaaaat gcaatggtgc agcatttct tctgaaatgt    2340 atcccaaact ggcaaaagcc taccccacca ataaattacc ggatttacgc ggtgaattta    2400
tccgtggctg ggatgatggg cgcggggtgg atgctggccg cgctttgctt aattggcagc    2460
cacacacaat tttggaccat gcacactata tggaattatg acaggggac ggactcgccg    2520 caggaagtgc acgggaaggc gtaaatccag gaatactagc tacatacggt gacgggggaa    2580
```

```
tagttaaaac ggacgaaccc ggtcataagg tgccttcctc actacgagct attagctctc    2640
gtagtgttaa acgttatggt gaaattagtg gaaatgtagg tacagaaact cgccctcgca    2700
acgttgcatt taattacatc gtaagggcgg cataaattat ggataatgcg atattaaata    2760
gcgaacttat agccatacag gcaggaaaca ttatcgttta taactatgat ggtggtaatc    2820
gggaatatat ttctgcatca actgaatatc ttgctgttgg cgttggtatt ccggcaaatt    2880
cttgtttgga tgctccaggc tcacataaag caggttatgc gattctccgt tcagaggatt    2940
taagttcatg ggagtatgtg ccagatcatc gtggcgaaac tgtctatagc attgacacag    3000
ggaatcccga agaaatcacg gtgttgggtg actatccgga aaatacaacc actatcgccc    3060
cgctaacacc atacgacaaa tgggatggag agaaatgggt ggttgatact gaggctcaac    3120
atagtgcagc tgtagaggca gcagaaacaa aacgtcagtc attgattgat actgcgatgg    3180
attccattag tctgattcag ttgaaattac gggctggacg gaagttgacg caggcagaaa    3240
ccacgcagct taactccgtg ctagattata tagacgagct gaacgcgatg gatttaacca    3300
cggcaccaga tctcaactgg cctgaaaaac aactttctac agccagttga              3350
```

<210> SEQ ID NO 13
<211> LENGTH: 3311
<212> TYPE: DNA
<213> ORGANISM: Artificial Sequence
<220> FEATURE:
<223> OTHER INFORMATION: Indigo Tail Fiber

<400> SEQUENCE: 13

```
atgtctgacg tctcaacaaa cctctataag agtcagttgt tggactatta ctatcagcgg      60
cgcgctgaat cgtccattaa caaaggctct cgatttttaa tcagcaaggc cgttttcggt     120
accagttcgc tggttactaa gaaggagat ggcacttatg agattggaga actgccaaag      180
gctttcgaac tggcagaact gaccagtcaa ttttgcacca tcaacctcgt cccaacctac     240
tcaggcggga taattactgt ccgaatggac cttgatcaaa gccagttgca ggaagggaaa     300
aactacccat tcaacactct ggttgttctg ataacgaga acaagccaat cgccattatt      360
tgtgtccagg aagactcgct gtatgtgggc aaaacatata ccgcagttat ggccataaac     420
acgactacag cataaggata tgcttgatga atgacgtcac cgttgttacg agtgttacct     480 accccctcgcc tgagtcatta gcgttagttg cagacgttca gtaccacgaa ccgtatcttt    540
cagcagctct taaccgtaaa ttccgcggaa ttgtcgatcc aggattttac gccgggttcc     600
tgcctaagcc tggcggcggc atgaatcttc tgattacgtc agtcgacggg gataaaactg     660
cgggagcggc atcggtagat atcggggaat tctaccaggt tacaattcaa catcgtaaag    720
acatttcgtt agcacttaac gctgggaaga aatacgccat tgtcttgaaa ggccgctatt     780
tgttaggtga agatacgtac caggtcaata cagcaagtca catccacgcc gctgaatttg    840
tcgcacgtac atataccgat tcctaccagc ttggggatgg tgagttactt gtgtgcaccg     900
tgaacattcc tgctggagtg tcaacgatca cgcaggagat gatcgatact tcagagcgta    960
ttaatcgcac gatcgggatt gatattcag acagcgtcac ctcgactcgc tcagatgtcg     1020
cggcttcatc tcttgcagtg aaaaaggcct acgacctggc caagtcgaag tacacagctc   1080
aggacgcgag caccacccaa aagggtctgg tacagttatc atctgcgacg aattcaacat     1140
ccgaggttct tgcagcgaca cctaaagcgg taaaagccgc gtatgatctt gccaatggga     1200
aatacaccgc acaggacgcc acaactacac aaaagggtat tgtgcagttg tcgagtgaca    1260
ccaactcaac gtcggagaca ctggcggcca cgccgaaagc agtcaaagct gcatacgacc   1320
```

```
ttgcggctgg taaagcgccc tcatcccaca ctcacccctg gaatcagatt actggtgtac    1380
ccaccgcaag cttaactgca aagggtatca ctcaattgag ttccgcgacc aacagcacca    1440
gtgaagtttt agctgctacc ccaaaggcag ttaaagccgc ttacgacttg gctaatggaa    1500
aatatacagc gcaggacgcg accactgcac aaaaaggaat tgtgcaactt tcgagcgcaa    1560
cgaactccac aagtgaagtt ttggcagcta cgcctaaagc cgtcaaagcc gcgtatgatt    1620
tggcgaatgg taagtatact gcgcaagatg cgacgactac gcagaaaggt attgtccaac    1680
tgtcaagtga caccaacagc acgtcagaga ccttggctgc tacacctaaa gcagtgaaag    1740
ctgcctatga tcttgcggct gggaaagccc cgtcatcaca cacacatcca tggaaccaga    1800
ttacggtcgt acctacggcc tctttaactg cgaagggcat tacacaatta tcatccgcga    1860
ctaacagcac cagtgaggtt ttagctgcaa caccgaaagc agtgaaggca gcctacgatt    1920
tggcgaacgg taaatatacg gctcaagatg cgaccaccgc gcaaaagggc attgtgcaac    1980
tgtcgtctgc aacaaattca acgtcggaag ttctggcagc aactccaaag gcagtgaaag    2040
ccgcctatga cttagcaaac ggtaaacagg ccgcggatgc gacgttaacg gcattggcgg    2100
ctcttgcaac tgcagcggac aagttaccgt atttcacggg cgttgaccgt gctgccctga    2160
cagcgttaac ctctgttggg cgtgccattt taggcaagac ctcgattcaa tctgttttag    2220
attaccttgg tttaggggaa ggctcggcgc tgcccgttgg tgtgcccgtt ccgtggccct    2280
tagaaacacc accaacgggc tggctaaaat gcaatggtgc agcattttct tctgaaaagt    2340
acccaaatct ggcaaaggct taccctacta ataaattgcc ggatttacgc ggtgaattta    2400
ttcgtggctg ggatgacggg cgggggattg actctggccg taatttatta tctgcacaga    2460
atgatgcaat tcagaatatt gttggttctt tcgggcgtac tcagcttttt agagatgtac    2520
ttagttcagg gccatttagt caacatggcc aagtattatc tacaggccta aaggaaacgg    2580
aaattattga gggttatggc tcttataact ggacattcga cgcctctcgc tcagttcgta    2640
cagcatctga aacccgcccc cgtaatattg catttaatta catcgtaagg gcggcataaa    2700
tggataatgc gatattaaat agcgaactta tagccataca ggcaggaaac attatcgttt    2760
ataactatga tggtggtaat cgggaatata tttctgcatc aactgaatat cttgctgttg    2820
gcgttggtat tccggcaaat tcttgttttgg atgctccagg ctcacataaa gcaggttatg    2880
cgattctccg ttcagaggat ttaagttcat gggagtatgt gccagatcat cgtggcgaaa    2940
ctgtctatag cattgacaca gggaatcccg aagaaatcac ggtgttgggt gactatccgg    3000
aaaatacaac cactatcgcc ccgctaacac catacgacaa atgggatgga gagaaatggg    3060
tggttgatac tgaggctcaa catagtgcag ctgtagaggc agcagaaaca aaacgtcagt    3120
cattgattga tactgcgatg gattccatta gtctgattca gttgaaatta cgggctggac    3180
ggaagttgac gcaggcagaa accacgcagc ttaactccgt gctagattat atagacgagc    3240
tgaacgcgat ggatttaacc acggcaccag atctcaactg gcctgaaaaa caactttcta    3300
cagccagttg a                                                         3311
```

<210> SEQ ID NO 14
<211> LENGTH: 4610
<212> TYPE: DNA
<213> ORGANISM: Artificial Sequence
<220> FEATURE:
<223> OTHER INFORMATION: Jazzberry Tail Fiber

<400> SEQUENCE: 14

```
atgtctgacg tctcaacaaa cctctataag agtcagttgt tggactatta ctatcagcgg      60
cgcgctgaat cgtccattaa caaaggctct cgattttaa tcagcaaggc cgttttcggt      120
accagttcgc tggttactaa gaaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg gataacgaga acaagccaat cgccattatt    360
tgtgtccagg aagactcgct gtatgtgggc aaaacatata ccgcagttat ggccataaac    420
acgactacag cataaggata tgcttgatga atgacgttac agttgttaca tcggttactt    480
acccatcatc cgagtcgttg gctctggtgg ccgatgtgca ataccacgaa ccatatctgt    540
cagccgcgct aaaccgaaaa ttcaggggga ttgttgaccc gggatttat gccggtttct    600 tacctaagcc tggcggtggg atgaacctgt taattacctc agtggatggt gataaaaccg    660
caggcgcggc gtcggtggat attggtgaat tttaccaggt aactattcag caacgtaagg    720
atatttctct tgcacttagt gcaggcaaga aatatgcaat tgtgctgaag ggaagatacc    780
tccttggaga agatacctac caggtgaata ccgcgtcaca tattcatgcg gctgaatttg    840
ttgccagaac ctataccgat tcatatcagt taggagatgg ggagctgctt gtttgtacgg    900
tgaatatccc tgctagtgta tctgccatta cccaggagat gattgataca tccgagcgta    960
tcaaccgctc gatcggcatt gatatttcag actctgtaac cagtaccaga agtgatgttg   1020
ctgcaagttc gctggcagtt aaaaaagcct acgatctggc gaaaagcaag tatacggcac   1080
aggatgcaag cacaacgcaa aagggattag ttcagctcag tagcgcaact aacagcgaca   1140
gcgaaacaat ggcggctacc cctaaagctg ttaagtctat aaaagatctg gctgatacca   1200
aagcgccaat agaaagcccg agtctgacag gaacgccaac cgcgccgacg gcagcgcaag   1260
gtacaaacag cacgcagatc gcaaatacag cctttgttaa ggcagctata actgcactta   1320
tcaacggtgc gcctggcaca ctggatacgc tgaaagaaat agcggctgcg atcaataacg   1380
acccgaatta cagcacaact atcaacaatg ccttggctct caaagcgcct ttggcaagcc   1440
ctgcattaac gggtgtccct actgcgccta cggctgcaca gggcacaaac aatacgcaga   1500
tcgctacgac tgcttacgta cgggctgcta tctctgcatt ggtcggctca tcacctgaag   1560
ctcttgatac cctgtatgag cttgcagcag cactgggcaa tgacccgaac tttgcgacaa   1620
caatgacaaa tgcgctggca gggaaacagc cacttgatgc aactttaacc gcgcttgctg   1680
gtcttgcgac aggcgcaaat aaattgccgt actttaccgg tacagacact gtttctcaga   1740
ctgacttaac gtcagttggt cgcgatattc tggccaaaac aagcattctt gctgttatcc   1800
aataccttgg tttaagagaa ctcggcacaa gcggtgaaaa gatcccctg ttgagcacgg    1860 ctaacacatg gagtgcacgc cagacttta acggcgggat caccggggcg ctgacaggga   1920
acgccgatac cgcgacgaag ttgaaaacag cacggaagat taacaacgtt tcatttgatg   1980
gttcggcaga cataacgctg acacctgaga accttggcgt caccagtctg acgtttgaga   2040
aaaacaacgg tgaaatgcct attgatgctg acctaaatac tttcggtccc gttgaggctt   2100
atcttggtgt ctggtccaaa gcaacatcca ccaacgcaac actggagaaa atttcccgg   2160 aagataatgc tgtcggtgtg cttgaggtat ttgctgccgg aaattttgca ggtacgcaac    2220
gctttaccac gagagacggc aatgtataca tacgcagact cgccaataag tggaatggct   2280
ctgatggtcc gtgggcata tggcgtcaca ctcaatcagc tacccgccct ttgagtacga    2340
ctatagacct gaatacgctt ggagccgccg aacatcttgg tttatggcgt aacagtagct   2400
```

```
cggctatagc ttcatatgaa cgcaattatc cagaggaagg cggctttgct caggggtgc    2460
ttgagatcct cgaaggcggg aattatgaaa gaacgcaacg ttataccact cgccgcggaa    2520
atatgtatgt ccgctgcctt gcggcaagct gggatgcatc aaatccgcag tgggaaccgt    2580
ggttaaaagt cggtcatcag tcagagagtc gttattacga aggtgattta aatgttctaa    2640
ccgaccccgg tatttacagt gttacaggaa aggcaacaaa cggtccgatg ctggacaccg    2700
ttggcgcgac actactttggg atactggaag taatcagacg ttttgatggt gtgtctgtct    2760
ggcagcgtta cacaaccaca gggaaatcag aaaccacaca gggacgcact tttgagcgcg    2820
tctacgccgg gagcaaatgg accgaatggc gagaagtata taactccttt tcgttgcctc    2880
tgaatctggg catcggtggc gcagtggcaa aactatccag tctggactgg cagacctacg    2940
attttgtgcc gggcagtctg ataaccgtgc ggcttgataa catgaccaac attcccgacg    3000
gtatggactg gggcgtcatt gatggcaacc tgataaacat cgcagttggt ccgagtgatg    3060
attccggtac ggggcgctca atgcatgtat ggcgcagcac tgtaagtaaa gcgaactacc    3120
gcttttttat ggtgcgtatt tcaggaaatc cgggaagccg cacgatcaca gcaagacgag    3180
taccaatcat tgacgaagcc cagacatggg gcgcgaaaca gacattcagt gctggccttt    3240
ctggtgaact gtccggcaat gcggcgacag caacaaagct gaaaacagcc cgtaaaatta    3300
ataacgtttc gtttgatggt tccggggata ttgaggtcct tcctgttggt gttccgctgc    3360
cgtggccatc agatactgtg ccgtctggtt acgccctgat gcagggacag acttttgaca    3420
aatctgcata cccgaaactt gcagccgctt atccgtcagg cgtgatcccg gatatgcgtg    3480
gctggacaat caagggcaaa cccgccagtg gtcgggacgt attgtctctg gaacaggatg    3540
gcattaaatc gcacacccac agcgccagcg catccaatac ggatttgggt acgaaaacca    3600
catcttcgtt tgattacggt actaaatcaa cgaataacac aggtgcacat acccacaatg    3660
tatctggtac tgcaaatagt gctggcgcac atactcatac cgtgccatta aggagaccaa    3720
acagtggcgg tatgaatttc gactggctgg atggtgcatc aagtggcacg gtggtgggga    3780
atggaactgt gccttcttct ggcgcacata cccactcagt atcaggcacc gctacaagtg    3840
ctggggcaca tgcacacact gttggtattg gcgctcatac gcactctgtt gcgattggtt    3900
cacatggaca taccatcacc gttaacgctg ctggcaacgc ggaaaacacc gttaaaaaca    3960
tcgcatttaa ttatattgtg aggcttgcat aaatggcatt cagaatgagt gaacaatcac    4020
gtactgtaaa aatttataac ctgctggccg gaactaatga gtttattggt gaaggtgacg    4080
catatattcc acctcataca gggctgccag ctaattctac agatatcgcc ccaccggaaa    4140
ttcctgctgg ctttgtggca gtttttaaca gtgaaaatga atcgtggaat attgttgaag    4200
accatcgtgg taaaacggtc tatgacgtgg catcgggga cgcgttgttt atttctgaac    4260
ccggaccgct accagagaat gtcacctggt tgtcgccagc aggggaatat cagaagtggg    4320
acggcgtatc ctgggtgaag gatgaggaag cagaaaaact gtttcggata cgggaagcgg    4380
aagagaaaaa ggcaaggttg atccaggagg caacagataa catcgcaatt ctgcaggatg    4440
cagttaatct tgaaatagca acaaacgagg aaaattcaca actggattcc tggagaaaat    4500
acagagtatt agtgagtaga attgacacca gtacagctcc ggtatcgta tggccagagc    4560
tgatgaatca gggttatgtg cgggaggacg agcagataac ttcagactga              4610
```

<210> SEQ ID NO 15
<211> LENGTH: 6917
<212> TYPE: DNA

<213> ORGANISM: Artificial Sequence
<220> FEATURE:
<223> OTHER INFORMATION: Jazzberry-Shamrock Tail Fiber

<400> SEQUENCE: 15

```
atgtctgacg tctcaacaaa cctctataag agtcagttgt tggactatta ctatcagcgg      60
cgcgctgaat cgtccattaa caaaggctct cgattttttaa tcagcaaggc cgttttcggt     120
accagttcgc tggttactaa gaaaggagat ggcacttatg agattggaga actgccaaag     180
gctttcgaac tggcagaact gaccagtcaa ttttgcacca tcaacctcgt cccaacctac     240
tcaggcggga taattactgt ccgaatggac cttgatcaaa gccagttgca ggaagggaaa     300
aactacccat tcaacactct ggttgttctg ataacgaga  acaagccaat cgccattatt     360
tgtgtccagg aagactcgct gtatgtgggc aaaacatata ccgcagttat ggccataaac     420
acgactacag cataaggata tgcttgatga atgacgttac agttgttaca tcggttactt     480
acccatcatc cgagtcgttg gctctggtgg ccgatgtgca ataccacgaa ccatatctgt     540
cagccgcgct aaaccgaaaa ttcagggga  ttgttgaccc gggattttat gccggtttct     600
tacctaagcc tggcggtggg atgaacctgt taattacctc agtggatggt gataaaaccg     660
caggcgcggc gtcggtggat attggtgaat tttaccaggt aactattcag caacgtaagg     720
atatttctct tgcacttagt gcaggcaaga aatatgcaat tgtgctgaag gaagatacc     780
tccttggaga agatacctac caggtgaata ccgcgtcaca tattcatgcg gctgaatttg     840
ttgccagaac ctataccgat tcatatcagt taggagatgg ggagctgctt gtttgtacgg     900
tgaatatccc tgctagtgta tctgccatta cccaggagat gattgataca tccgagcgta     960
tcaaccgctc gatcggcatt gatatttcag actctgtaac cagtaccaga agtgatgttg    1020
ctgcaagttc gctggcagtt aaaaaagcct acgatctggc gaaaagcaag tatacggcac    1080
aggatgcaag cacaacgcaa aagggattag ttcagctcag tagcgcaact aacagcgaca    1140
gcgaaacaat ggcggctacc cctaaagctg ttaagtctat aaaagatctg gctgatacca    1200
aagcgccaat agaaagcccg agtctgacag gaacgccaac cgcgccgacg gcagcgcaag    1260
gtacaaacag cacgcagatc gcaaatacag cctttgttaa ggcagctata actgcactta    1320
tcaacggtgc gcctggcaca ctggatacgc tgaaagaaat agcggctgcg atcaataacg    1380
acccgaatta cagcacaact atcaacaatg ccttggctct caaagcgcct ttggcaagcc    1440
ctgcattaac gggtgtccct actgcgccta cggctgcaca gggcacaaac aatacgcaga    1500
tcgctacgac tgcttacgta cgggctgcta tctctgcatt ggtcggctca tcacctgaag    1560
ctcttgatac cctgtatgag cttgcagcag cactgggcaa tgacccgaac tttgcgacaa    1620
caatgacaaa tgcgctggca gggaaacagc cacttgatgc aactttaacc gcgcttgctg    1680
gtcttgcgac aggcgcaaat aaattgccgt actttaccgg tacagacact gtttctcaga    1740
ctgacttaac gtcagttggt cgcgatattc tggccaaaac aagcattctt gctgttatcc    1800
aataccttgg tttaagagaa ctcggcacaa gcggtgaaaa gatcccctg  ttgagcacgg    1860
ctaacacatg gagtgcacgc cagactttta acggcgggat caccggggcg ctgacaggga    1920
acgccgatac cgcgacgaag ttgaaaacag cacggaagat taacaacgtt tcatttgatg    1980
gttcggcaga cataacgctg acacctgaga accttggcgt caccagtctg acgtttgaga    2040
aaaacaacgg tgaaatgcct attgatgctg acctaaatac tttcggtccc gttgaggctt    2100
atcttggtgt ctggtccaaa gcaacatcca ccaacgcaac actggagaaa aatttcccgg    2160
aagataatgc tgtcggtgtg cttgaggtat ttgctgccgg aaattttgca ggtacgcaac    2220
```

```
gctttaccac gagagacggc aatgtataca tacgcagact cgccaataag tggaatggct   2280
ctgatggtcc gtggggcata tggcgtcaca ctcaatcagc tacccgccct ttgagtacga   2340
ctatagacct gaatacgctt ggagccgccg aacatcttgg tttatggcgt aacagtagct   2400
cggctatagc ttcatatgaa cgcaattatc cagaggaagg cggctttgct caggggtgc    2460 ttgagatcct cgaaggcggg aattatggaa gaacgcaacg ttataccact cgccgcggaa   2520
atatgtatgt ccgctgcctt gcggcaagct gggatgcatc aaatccgcag tgggaaccgt   2580
ggttaaaagt cggtcatcag tcagagagtc gttattacga aggtgattta aatgttctaa   2640
ccgaccccgg tatttacagt gttacaggaa aggcaacaaa cggtccgatg ctggacaccg   2700
ttggcgcgac actacttggg atactggaag taatcagacg ttttgatggt gtgtctgtct   2760
ggcagcgtta cacaaccaca gggaaatcag aaaccacaca gggacgcact tttgagcgcg   2820
tctacgccgg gagcaaatgg accgaatggc gagaagtata taactccttt tcgttgcctc   2880
tgaatctggg catcggtggc gcagtggcaa aactatccag tctggactgg cagacctacg   2940
attttgtgcc gggcagtctg ataaccgtgc ggcttgataa catgaccaac attcccgacg   3000
gtatggactg gggcgtcatt gatggcaacc tgataaacat cgcagttggt ccgagtgatg   3060
attccggtac ggggcgctca atgcatgtat ggcgcagcac tgtaagtaaa gcgaactacc   3120
gcttttttat ggtgcgtatt tcaggaaatc cgggaagccg cacgatcaca gcaagacgag   3180
taccaatcat tgacgaagcc cagacatggg gcgcgaaaca gacattcagt gctggccttt   3240
ctggtgaact gtccggcaat gcggcgacag caacaaagct gaaaacagcc cgtaaaatta   3300
ataacgtttc gtttgatggt tccggggata ttgaggtcct tcctgttggt gttccgctgc   3360
cgtggccatc agatactgtg ccgtctggtt acgccctgat gcaggacag acttttgaca    3420 aatctgcata cccgaaactt gcagccgctt atccgtcagg cgtgatcccg gatatgcgtg   3480
gctggacaat caagggcaaa cccgccagtg gtcgggacgt attgtctctg aacaggatg    3540 gcattaaatc gcacacccac agcgccagcg catccaatac ggatttgggt acgaaaacca   3600
catcttcgtt tgattacggt actaaatcaa cgaataacac aggtgcacat acccacaatg   3660
tatctggtac tgcaaatagt gctggcgcac atactcatac cgtgccatta aggagaccaa   3720
acagtggcgg tatgaatttc gactggctgg atggtgcatc aagtggcacg gtggtgggga   3780
atggaactgt gccttcttct ggcgcacata cccactcagt atcaggcacc gctacaagtg   3840
ctggggcaca tgcacacact gttggtattg gcgctcatac gcactctgtt gcgattggtt   3900 cacatgggaca taccatcacc gttaacgctg ctggcaacgc ggaaaacacc gttaaaaaca   3960
tcgcatttaa ttatattgtg aggcttgcat aaatggcatt cagaatgagt gaacaatcac   4020
gtactgtaaa aatttataac ctgctggccg gaactaatga gttattggt gaaggtgacg     4080 catatattcc acctcataca gggctgccag ctaattctac agatatcgcc ccaccggaaa   4140
ttcctgctgg ctttgtggca gtttttaaca gtgaaaatga atcgtggaat attgttgaag   4200
accatcgtgg taaaacggtc tatgacgtgg catcggggga cgcgttgttt atttctgaac   4260
ccggaccgct accagagaat gtcacctggt tgtcgccagc aggggaatat cagaagtggg   4320
acggcgtatc ctgggtgaag gatgaggaag cagaaaaact gtttcggata cgggaagcgg   4380
aagagaaaaa ggcaaggttg atccaggagg caacagataa catcgcaatt ctgcaggatg   4440
cagttaatct tgaaatagca acaaacgagg aaaattcaca actggattcc tggagaaaat   4500
acagagtatt agtgagtaga attgacacca gtacagctcc ggatatcgta tggccagagc   4560
```

```
tgatgaatca gggttatgtg cgggaggacg agcagataac ttcagactga gacaaggccc    4620
gatagcgggc cttaatttcg cgttggccga ttcattaatg cagctgcaaa aaaccccctca   4680
agacccgttt agaggcccca aggggttatg ctagttattg ctcagcggtg gcagcagctt    4740
attcaggctt ttgtggccat tcaggatttg ccgtatccac acggctgacc agaacactgt    4800
agcgttccca tgactccagt cgtgcgtgtt cctcatccgt cgccatattc agcctgacag    4860
cgcgttccag cggctggatg actgattcag cttcggaaag taacgcggcc ttttgtgatt    4920
cggcctgttg ctgctgttcg tctgctgtat aagtcctcct gaccaccgct ccgtccttaa    4980
acatccactt ccctgaatca tcggcacgac ggttagctgt tatatcgggg atttcaacga    5040
cgctaaaacc ttcaggatta agcgtggagg catctttagt gacggcgaca ataatattat    5100
tttcgtcgta aacaatcttt attgtatccg gctgaaagtt cttcacttcc tcataccagt    5160
ttttcccgtc ttcagcgtaa agccagatga ctccgtgctt ctttgttaac tcatactgct    5220
ccagtgtttt agcattaccc gcttttatgt tctttaagtg catcatatta aacgctcgct    5280
acattatacc atgtgccatt tatatacttt tgaacgggtc tgtaataaac gccagctata    5340
ttatcggcag agttttttgcc tgtatcctga acattaatac cagacaatac atgacctgaa   5400
gggcactgga aattccatgt ttgccagtta ttcacaccat aatattgctg tgagccaagc    5460
cggacatctt tcacatatct ggagtcaaaa ttgccataat tgccgggaat aacttgcgca    5520
ccacaaagcc agttaccgtt attatccatg tacgcctgac catcggtgcc attggctgtc    5580
cttgagttat taatcatgta gatgccaaat tgcttatttc ccagaccgcc aatcataaat    5640
ttgcggtcgg catggtcctg acggagcaaa gcctgagcac catcagtgga taccgcatta    5700
cgtcccaaaa taacattctg gtcacgcata tgaatccaca tgccggtact actgttaatt    5760
gcaaaacggt ttgcaaatat atcccctgta acatcaagac catgccccat gcttatccgg    5820
ccagttctga gattaagcgt aaaggggcgt agtggcccta tattaccatt ttccccttca    5880
ttctctcgtg tagggatgat atgcaggcat tcttcagaac gacgaaaaat ggcaccaaaa    5940
gatgaattaa atatcctcag tgcattgact gtcgatattt tcacttcact gctgaaaagg    6000
gcttcaacaa gaacagacaa agcattccat ttaagattca tcaggtcttt aggccgggtg    6060
ccaatgatgc ggtgtctcca tttgaaatat tcattgccgt tgttgcctgt ttcaaaccac    6120
atgtaggaat cggtgtctgc atccgaatta tttttaaaac caatcttcgc ccagtcagta    6180
ttccgaatcc aggcaaggat tgagtcgttt tcaaaagtaa gtccaccgga caaggtatcg    6240
cctgtctttt gaaccgcgtt atcagccttg tttaccgttt cctgtagatt taaatcttcc    6300
gccgttagct caatattttt agaaccgtca aacgagacgc cgttgatagt acatgctgtc    6360
tgcaacttgg tcgctgtagc cgcattacca gaggtatcct gatccccttt ggcattgacg    6420
ccgggaattg aatcttttga cgtatagacc tgcgcccatt cagaccagtt ggcagaatca    6480
gtatcccgcc gcgaacggat atgtacgggc gcatggcgac cgctcgtgcc actccagcca    6540
atgaataact caccttcgcc agcagcggtg gcacctttaa ggtgaagcac attgccatag    6600
ggggaagggt agccattgtt gtatgcctca tacagctgaa tcccggatgt tcctgtgca    6660
ttcgcctcca gggccgttac gcgaccgcgc gataccagag tattgatatt aatgtcacca    6720
gaaccatcga acctgacgcc attaatgttt ctggctgttt tcaatttcgt tgcggtatcg    6780
gcgttccctg tcagcgcccc ggtgatcccg ccgttgaaag tctggcgtgc actccatgtg    6840
ttagccgtgc tcaacagggg gatctttttca ccgctggtac cgagttctct taaaccaagg   6900
tattggataa cagcaag                                                   6917
```

<210> SEQ ID NO 16
<211> LENGTH: 3907
<212> TYPE: DNA
<213> ORGANISM: Artificial Sequence
<220> FEATURE:
<223> OTHER INFORMATION: Jungle Tail Fiber

<400> SEQUENCE: 16

```
atgtctgacg tctcaacaaa cctctataag agtcagttgt tggactatta ctatcagcgg      60
cgcgctgaat cgtccattaa caaaggctct cgattttaa tcagcaaggc cgttttcggt     120
accagttcgc tggttactaa gaaggagat ggcacttatg agattggaga actgccaaag     180
gctttcgaac tggcagaact gaccagtcaa ttttgcacca tcaacctcgt cccaacctac     240
tcaggcggga taattactgt ccgaatggac cttgatcaaa gccagttgca ggaagggaaa     300
aactacccat tcaacactct ggttgttctg ataacgaga acaagccaat cgccattatt     360
tgtgtccagg aagactcgct gtatgtgggc aaaacatata ccgcagttat ggccataaac     420
acgactacag cataaggata tgcttgatga atgacgttac agttgttaca tcggttactt     480
acccatcatc cgagtcgttg gctctggtgg ccgatgtgca ataccacgaa ccatatctgt     540
cagccgcgct aaaccgaaaa ttcaggggga ttgttgaccc gggatttat gccggtttct     600 tacctaagcc tggcggtggg atgaacctgt taattacctc agtggatggt gataaaaccg     660
caggcgcggc gtcggtggat attggtgaat ttaccaggt aactattcag caacgtaagg     720
atatttctct tgcacttagt gcaggcaaga aatatgcaat tgtgctgaag gaagatacc     780 tccttggaga agatacctac caggtgaata ccgcgtcaca tattcatgcg gctgaatttg     840
ttgccagaac ctataccgat tcatatcagt taggagatgg ggagctgctt gtttgtacgg     900
tgaatatccc tgctagtgta tctgccatta cccaggagat gattgataca tccgagcgta     960
tcaaccgctc gatcggcatt gatatttcag actctgtaac cagtaccaga agtgatgttg    1020
ctgcaagttc gctggcagtt aaaaaagcct acgatctggc gaaaagcaag tatacggcac    1080
aggatgcaag cacaacgcaa aagggattag ttcagctcag tagcgcaact aacagcgaca    1140
gcgaaacaat ggcggctacc cctaaagctg ttaagtctat aaaagatctg gctgatacca    1200
aagcgccaat agaaagcccg agtctgacag gaacgccaac cgcgccgacg gcagcgcaag    1260
gtacaaacag cacgcagatc gcaaatacag cctttgttaa ggcagctata actgcactta    1320
tcaacggtgc gcctggcaca ctggatacgc tgaaagaaat agcggctgcg atcaataacg    1380
acccgaatta cagcacaact atcaacaatg ccttggctct caaagcgcct ttggcaagcc    1440
ctgcattaac gggtgtccct actgcgccta cggctgcaca gggcacaaac aatacgcaga    1500
tcgctacgac tgcttacgta cgggctgcta tctctgcatt ggtcggctca tcacctgaag    1560
ctcttgatac cctgtatgag cttgcagcag cactgggcaa tgacccgaac tttgcgacaa    1620
caatgacaaa tgcgctggca gggaaacagc cacttgatgc aactttaacc gcgcttgctg    1680
gtcttgcgac aggcgcaaat aaattgccgt actttaccgg tacagacact gtttctcaga    1740
ctgacttaac gtcagttggt cgcgatattc tggccaaaac aagcattctt gctgttatcc    1800 aatccttgg tttaagagaa ctcggtacca gcggtgaaaa gatcccctg ttgagcacgg    1860 ctaacacatg gagtgcacgc cagactttca cggcgggat caccggggcg ctgacaggga    1920
acgccgatac cgcaacgaaa ttgaaaacag ccagaaacat taatgcgtc aggttcgatg    1980 gttctggtga cattaatatc aatactctgg tatcgcgcgg tcgcgtaacg gccctggagg    2040
```

-continued

```
cgaatgcaca gggaacatcc gggattcagc tgtatgaggc atacaacaat ggctacccttt    2100 cccctatgg caatgtgctt caccttaaag gtgccaccgc tgctggcgaa ggtgagttat     2160
tcattggctg gagtggcacg agcggtgccc atgcgcccgt acatatccgt tcgcggcggg    2220
atactgattc tgccaactgg tctgaatggg cgcaggtcta tacgtcaaaa gattcaattc    2280
ccggcgtcaa tgccaaaggg gatcaggata cctctggtaa tgcggctaca gcgaccaagt    2340
tgcagacagc atgtactatc aacggtgtct cgtttgatgg ttctaaaaat attgagctaa    2400
cggctgaaaa tttaaatctt gagcgaacag tagaattagc cgctgggtca ttgcagaaaa    2460
atcagaacgg cgcggatatt cctggaaaag ataccttcac aaaaaatatt ggtgcatgtc    2520
gcgcttatag cgcatggctg aatattggtg gcgatagtca ggtctggaca accgcacaat    2580
ttatttcgtg gctggagagt caggggggcat ttaaccatcc ttactggatg tgcaaaggct    2640
catgggctta tgcaaacaat aaggtcatta cagatacagg ttgcggaaat atttgtcttg    2700
caggtgctgt ggtggaagtt attggcactc gcggcgcaat gaccatacgc gttactacgc    2760
cgagtacgtc cagcggcggc ggaatcacta acgctcaatt cacttatatt aatcatggtg    2820
atgcttatgc tcctggctgg cgacgagact acaacacgaa aaaccagcag cctgcatttg    2880
ctttaggaca aacaggaagc actgtcgaaa tgataaagc tgttggctgg aactggaata    2940
gcggggtcta taacgcaaat attggtggcg catcgacatt aatcctccac ttcaatatga    3000
atacggggag ttgccctgcc gtacagttcc gtgtgaatta caggaacggc ggtattttt     3060 atcgttcagc gcgtgatggt tacggattcg aagctgactg gtcagaaatt tacaccacaa    3120
cacgtaagcc atcagcggga gatgttggtg catatacgca ggcagaatgt aactcaaggt    3180
ttattacagg tattcgtctt ggcggtctgt catctgttca gacatggaat ggtcccggct    3240
ggtctgacag gtcaggttat gtcgttacgg gttcagttaa cggaaaccgt gatgaattaa    3300
ttgatacaac tcaggcaagg ccaattcagt attgcattaa tggaacgtgg tataacgcgg    3360
ggagtattta attatgatgc acttaaaaaa tattactgct ggcaaccta aaacaaaaga    3420 gcaataccag ctaacgaaac aatttaacat caaatggctt tatacagagg atgggaaaaa    3480
ctggtatgag gaacaaaaga actttcagcc tgatacgttg aaaatggtct atgaccacaa    3540
cggcgttatt atttgtattg aaaaggatgt ttcagcaatt aatccagaag gcgcaaacgt    3600
cgttgaggtt cctgatatta cagcaaatcg ccgggctgat atttcgggta atggatgtt    3660 caaagatggt gtagtgataa agcgaactta taccgaggaa gagcagaggc aacaagcgga    3720
aaatgaaaag caaagcctgc tacagctcgt cagggataaa acacagctat gggactcaca    3780
gctacggctg gcatcatttt ccgacgagaa taaacaaaaa ttaacagagt ggatgctcta    3840
cgcgcagaag gtcgaatcca cagacacctc cagcctgcca gtaacgtttc cagaacaacc    3900
agaatga                                                              3907
```

<210> SEQ ID NO 17
<211> LENGTH: 3167
<212> TYPE: DNA
<213> ORGANISM: Artificial Sequence
<220> FEATURE:
<223> OTHER INFORMATION: Mango Tail Fiber

<400> SEQUENCE: 17

```
atgtctgacg tctcaacaaa cctctataag agtcagttgt tggactatta ctatcagcgg      60
cgcgctgaat cgtccattaa caaaggctct cgatttttaa tcagcaaggc cgttttcggt     120
accagttcgc tggttactaa gaaaggagat ggcacttatg agattggaga actgccaaag    180
```

```
gctttcgaac tggcagaact gaccagtcaa ttttgcacca tcaacctcgt cccaacctac      240
tcaggcggga taattactgt ccgaatggac cttgatcaaa gccagttgca ggaagggaaa      300
aactacccat tcaacactct ggttgttctg gataacgaga acaagccaat cgccattatt      360
tgtgtccagg aagactcgct gtatgtgggc aaaacatata ccgcagttat ggccataaac      420
acgactacag cataaggata tgcttgatga atgacgttac agttgttaca tcggttactt      480
acccatcatc cgagtcgttg gctctggtgg ccgatgtgca ataccacgaa ccatatctgt      540
cagccgcgct aaaccgaaaa ttcagggga ttgttgaccc gggattttat gccggtttct       600
tacctaagcc tggcggtggg atgaacctgt taattacctc agtggatggt gataaaaccg      660
caggcgcggc gtcggtggat attggtgaat ttaccaggt aactattcag caacgtaagg       720
atatttctct tgcacttagt gcaggcaaga aatatgcaat tgtgctgaag gaagatacc       780 tccttggaga agatacctac caggtgaata ccgcgtcaca tattcatgcg gctgaatttg      840
ttgccagaac ctataccgat tcatatcagt taggagatgg ggagctgctt gtttgtacgg      900
tgaatatccc tgctagtgta tctgccatta cccaggagat gattgataca tccgagcgta      960
tcaaccgctc gatcggcatt gatatttcag actctgtaac cagtaccaga agtgatgttg     1020
ctgcaagttc gctggcagtt aaaaaagcct acgatctggc gaaaagcaag tatacggcac     1080
aggatgcaac cacggcgcgt aaggggatcg ttcagctgag tagcgccact gacagcgtgt     1140
ctgaggtgct ggcggcaacg ccgaaggcgg tgaagactgc gtatgatctg gcgaacgcca     1200
agtacactgc ggtggatgcc actcggcgcg gtaaggggct tgtccagctc agcagtgcga     1260
ttgacagtgt gtcggagatg ctggcagcga cgccgaaggc ggttaaatcc gcaaacgaca     1320
acgctactgc agccaatata aatgccagtg agcgagttag taaagccggt gacagtatga     1380
ccggaacatt aaatcaggac gctgtagcac aggccaccta caacttaacg gcactttcca     1440
acgccacgac aggcaataaa aattatcttc gtaaaatgcg cggcggagcg acggacacta     1500
tctggcatga aaccgttcag gggggcgaat accgtctggc gacaggcagt accgattcgc     1560
aggaggagct ggcgattagc actaataccg gcctgagagt gagaggtaat ttaacctcac     1620
aacttggcgg attttattca gggaatacga aaaaattctc tttttattca tcaaatacct     1680
ctgacaagaa tgcagctctg cgcctctggg gaaatgtaga ccgcccatct gtagtcgaac     1740
tgggggatga caccggctac cattttact ctcagcgaaa taaagatggc tcgctattgc      1800
ttcaggcaaa cggcgccgga caatttagcg gttatttacg ttcaaacgga gaagtacaat     1860
ccatttccgc aaatagttat cggattgcat atggaaacta cgggtgtttc tggcgcaacg     1920
acggtaataa tctttatctg atgctgacga ataaggcga tgcttacgga aactacaatt      1980
cattgcgtcc attacgggtt agcctggaaa ccggggcatt acaatctgag acaccattta     2040
ctgtaggcaa caccattttc gctacgaagg aaattacagc gggttatgcc ggtgcacttg     2100
catgggcaga acagtacaaa acaaaagcag ctttttttaa ctcatattcg acaaccggtg     2160
cgagtgaata ccatccagct ttaaaacaac aggcaagcat tgccggtgtc aattcatggg     2220
ctttttcaat ggggtctctt gtcgctgata ccgctctttc atggcatttg cacatgaaag     2280
gcagtggcgg tcaggatgtc aattataaat gggataccag tggtaatttt agcgcgccag     2340
gccagctcat tcccggaagt tttgctaatt tcgactcccg ttattatacc aaagggcaaa     2400
gcgatgcggt ttatatggca aaaaccggag catacacaaa agccgaaagc gatgctcgtt     2460
ataatctgaa aaacacggcc agtagggctg caagcggttg ggagaaagac aacactacag     2520
```

| | |
|---|---|
| gaattatgaa gcagtgggggg attgcaacac gtacagcgga ctctacacgg ataaccttcc | 2580 |
| caactgcgtt tccaactact tgcgtcagcg tgcagctaac actgctttat accaatgggt | 2640 |
| tccatgatca gaatatttat gttcaaaatc ctgatgcttc aggttttacc tacattgctg | 2700 |
| gtagtggtga agtcaaagtg tatttcgaag cgagaggtta ttaaatggga tatgtttatt | 2760 |
| gtcacgctac gggcgctttt tataatgatg ctctggtggc agactaccgt tccgccggtt | 2820 |
| cgtggccgga taattatgta actgtgctgg atgacgatta tgaatcattg atggcagggc | 2880 |
| aggctgttgg gaaaatgatt gtttctgata ataatggtta tcctgttctg acggaaccac | 2940 |
| cggaaccgac acacgaagaa caagtaaatc aggcatcgtc acaaaaatta tttttgatga | 3000 |
| aaacggcgaa tgaaattatt actccgctcg aggatgcagt cgagctcgga attgccaccg | 3060 |
| atgaagaagc ggccacgctg ctactctgga agcgttaccg cgtattgtta aacagactgg | 3120 |
| atctcagcaa agccccagat attcaatggc cagaacgccc ggcctga | 3167 |

<210> SEQ ID NO 18
<211> LENGTH: 3323
<212> TYPE: DNA
<213> ORGANISM: Artificial Sequence
<220> FEATURE:
<223> OTHER INFORMATION: Maroon Tail Fiber

<400> SEQUENCE: 18

| | |
|---|---|
| atgtctgacg tctcaacaaa cctctataag agtcagttgt tggactatta ctatcagcgg | 60 |
| cgcgctgaat cgtccattaa caaaggctct cgattttaa tcagcaaggc cgttttcggt | 120 |
| accagttcgc tggttactaa gaaggagat ggcacttatg agattggaga actgccaaag | 180 |
| gctttcgaac tggcagaact gaccagtcaa ttttgcacca tcaacctcgt cccaacctac | 240 |
| tcaggcggga taattactgt ccgaatggac cttgatcaaa gccagttgca ggaagggaaa | 300 |
| aactacccat tcaacactct ggttgttctg ataacgaga acaagccaat cgccattatt | 360 |
| tgtgtccagg aagactcgct gtatgtgggc aaaacatata ccgcagttat ggccataaac | 420 |
| acgactacag cataaggata tgcttgatga atgacgtcac cgttgttacg agtgttacct | 480 |
| accccctcgcc tgagtcatta gcgttagttg cagacgttca gtaccacgaa ccgtatcttt | 540 |
| cagcagctct taaccgtaaa ttccgcggaa ttgtcgatcc aggattttac gccgggttcc | 600 |
| tgcctaagcc tggcggcggc atgaatcttc tgattacgtc agtcgacggg gataaaactg | 660 |
| cgggagcggc atcggtagat atcggggaat tctaccaggt tacaattcaa catcgtaaag | 720 |
| acatttcgtt agcacttaac gctgggaaga aatacgccat tgtcttgaaa ggccgctatt | 780 |
| tgttaggtga agatacgtac caggtcaata cagcaagtca catccacgcc gctgaatttg | 840 |
| tcgcacgtac atataccgat tcctaccagc ttggggatgg tgagttactt gtgtgcaccg | 900 |
| tgaacattcc tgctggagtg tcaacgatca cgcaggagat gatcgatact tcagagcgta | 960 |
| ttaatcgcac gatcgggatt gatatttcag acagcgtcac ctcgactcgc tcagatgtcg | 1020 |
| cggcttcatc tcttgcagtg aaaaaggcct acgacctggc caagtcgaag tacacagctc | 1080 |
| aggacgcgag caccacccaa aagggtctgg tacagttatc atctgcgacg aattcaacat | 1140 |
| ccgaggttct tgcagcgaca cctaaagcgg taaaagccgc gtatgatctt gccaatggga | 1200 |
| aatacaccgc acaggacgcc acaactacac aaaagggtat tgtgcagttg tcgagtgaca | 1260 |
| ccaactcaac gtcggagaca ctggcggcca cgccgaaagc agtcaaagct gcatacgacc | 1320 |
| ttgcggctgg taaagcgccc tcatcccaca ctcacccctg gaatcagatt actggtgtac | 1380 |
| ccaccgcaag cttaactgca aagggtatca ctcaattgag ttccgcgacc aacagcacca | 1440 |

```
gtgaagtttt agctgctacc ccaaaggcag ttaaagccgc ttacgacttg gctaatggaa    1500
aatatacagc gcaggacgcg accactgcac aaaaaggaat tgtgcaactt tcgagcgcaa    1560
cgaactccac aagtgaagtt ttggcagcta cgcctaaagc cgtcaaagcc gcgtatgatt    1620
tggcgaatgg taagtatact gcgcaagatg cgacgactac gcagaaaggt attgtccaac    1680
tgtcaagtga caccaacagc acgtcagaga ccttggctgc tacacctaaa gcagtgaaag    1740
ctgcctatga tcttgcggct gggaaagccc cgtcatcaca cacacatcca tggaaccaga    1800
ttacggtcgt acctacggcc tctttaactg cgaagggcat tacacaatta tcatccgcga    1860
ctaacagcac cagtgaggtt ttagctgcaa caccgaaagc agtgaaggca gcctacgatt    1920
tggcgaacgg taaatatacg gctcaagatg cgaccaccgc gcaaaagggc attgtgcaac    1980
tgtcgtctgc aacaaattca acgtcggaag ttctggcagc aactccaaag gcagtgaaag    2040
ccgcctatga cttagcaaac ggtaaacagg ccgcggatgc gacgttaacg gcattggcgg    2100
ctcttgcaac tgcagcggac aagttaccgt atttcacggg cgttgaccgt gctgccctga    2160
cagcgttaac ctctgttggg cgtgccattt taggcaagac ctcgattcaa tctgttttag    2220
attaccttgg tttaggggaa ggctcggcgc tgcccgttgg tgtacctgtt ccatggccct    2280
ccgccacacc accaacgggg tggctgaaat gtaacggagc agcatttttct tctgaaatgt    2340 atcccaaact ggcaaaggcc taccccacca ataaattacc ggatttacgg ggagaattta    2400
ttcgcggctg ggatgatggg cgcggggtgg atgcgggacg tgctttattg agcattcaga    2460
caggaatgct ggaaaagcac cgacatattg ttgtagccaa tgatggttac gacacaaaag    2520
atgaatggga gctggcgaca attttcaaaa aaacatacac acaaggacgg gggcttgatg    2580
cctcaaatac aggagggaat tgattccat caccgacact tcattctcga gggagtattg    2640
gtaatactgg cgggagtgaa acccgtccac gaaatatcgc atttaattac atcgtaaggg    2700
cggcataaat tatggataat gcgatattaa atagcgaact tatagccata caggcaggaa    2760
acattatcgt ttataactat gatggtggta atcgggaata tatttctgca tcaactgaat    2820
atcttgctgt tggcgttggt attccggcaa attcttgttt ggatgctcca ggctcacata    2880
aagcaggtta tgcgattctc cgttcagagg atttaagttc atgggagtat gtgccagatc    2940
atcgtggcga aactgtctat agcattgaca cagggaatcc cgaagaaatc acggtgttgg    3000
gtgactatcc ggaaaataca accactatcg ccccgctaac accatacgac aaatgggatg    3060
gagagaaatg ggtggttgat actgaggctc aacatagtgc agctgtagag gcagcagaaa    3120
caaaacgtca gtcattgatt gatactgcga tggattccat tagtctgatt cagttgaaat    3180
tacgggctgg acggaagttg acgcaggcag aaaccacgca gcttaactcc gtgctagatt    3240
atatagacga gctgaacgcg atggatttaa ccacggcacc agatctcaac tggcctgaaa    3300
aacaactttc tacagccagt tga                                           3323
```

<210> SEQ ID NO 19
<211> LENGTH: 3760
<212> TYPE: DNA
<213> ORGANISM: Artificial Sequence
<220> FEATURE:
<223> OTHER INFORMATION: Mulberry Tail Fiber

<400> SEQUENCE: 19

```
atgtctgacg tctcaacaaa cctctataag agtcagttgt tggactatta ctatcagcgg     60
cgcgctgaat cgtccattaa caaaggctct cgattttttaa tcagcaaggc cgttttcggt    120
```

```
accagttcgc tggttactaa gaaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg gataacgaga acaagccaat cgccattatt    360
tgtgtccagg aagactcgct gtatgtgggc aaaacatata ccgcagttat ggccataaac    420
acgactacag cataaggata tgcttgatgg gggctgataa aacgaacaac ataatgacac    480
tatcctctgg tgtctcacag cctttgcttg ctgatgttca atatttcgaa ctctatagta    540
gttcggctct taacagaaaa cttaaaaata ttgttttgcc tggcttttac tgtggatttg    600
aaccagttcc cggcacaggg ttgagtgttc gtataacttc tgaaaactca gaaggtaaag    660
gggctgcttc agtagatgta aataatgttc agatatccgt tcagcaaata gaagatgtga    720
ctgtctcggt aaaggctggg gctaccaaca ttattgtgct ggaagccaat tttgaacatg    780
gtgtaaaaac gacacaggta gatagcgcat cttctgtcag tgctgcaaga atttacgcgc    840
gtacggacaa tactattggg cagaatcaaa ttgaattatg tcgagttatc gtgcctaacg    900
gcgcaacggc tgtgactaaa gaaatgattg tgcttaaata ccgggttaac cgtgctgttg    960
gtgtcgaatt ctctaatgaa ataagcagta cagaagaaag aaaagcggct acacctctgg   1020
ctgtcaaaac tctccatgat ttggttgata caaaagctcc gctcgatagt ccgcatctgt   1080
caggtacgcc gacttcgccg acacctgaac ccggtacaaa caacacacag atcgcaaatg   1140
cggcctttgt ctatgctgct ataaatgcgc ttatcaatgg tgctccggga acgatggaca   1200
cgctgaaaga aatagcggct gcgatcaata acgacccgaa tttcagcaca actatcaaca   1260
atgctctggc tcttaaagct cctttagcaa gtcctgcatt aacgggaata cctactgcgc   1320
ctaccgctgc acagggtacg aataacacgc agattgctac gaccgcttat gtaagagctg   1380
ccatatccgc attggttggt tcatcaccag aagctcttga taccctgaat gagcttgccg   1440
cagcacttgg taatgacccg aactttgcga caacaatgac aaatgcgctg gcaggcaaac   1500
agcctctgga tgcaacttta accgcgctcg ctggccttgc gactggtgca aacaaactgc   1560
cttatttcac cggtaaggat acggtagcgc agactgattt aacgtcagtc ggtcgcgata   1620
ttctggctaa aacaagcaca ctggccgtta tccaatacct tggtttaaga gaactcggta   1680
ccagtggtga aaagatcccc ctgttgagta cggctaacac atggagtgcg cgccagactt   1740
tcaatggcgg gatcaccggg gcgctgatag ggaacgccga caccgcgacg aaattgaaaa   1800
cagccataaa cattaatggc gtcaggttcg atggttcggc tgacattaat atcaatactc   1860
tggtatcgcg tggtcgcgta acggctctgg gggcgaatgc acaggggaca tccgggattc   1920
agctgtatga ggcatacaac aatggctatc cttcccccta tggcaatgtg cttcacctta   1980
aaggtgccac cgctgctggc gaaggtgaat tattcattgg ctggagtgtc tcgagcggtg   2040
accatgcgcc cgtacatatc cgttcgcggc gtgatattga ttctgccaac tggtctgaat   2100
gggcacaggt ctatacgtca aaagattcag ttcccggcgt taatgccaaa gggaatcagg   2160
atacctctgg taatgcggct acagcgacca aattgcagac ggcgtgtact atcaacggtg   2220
tctcgtttga tggttctaaa acattgagc taacggcgga agatttaaat cttgagcaaa   2280
ccgtagaatt agccgcagga gcattgcaga aaaaccagaa cggtgcagat attccgaata   2340
aagataaatt catacaaaac acaggggcct gtcgtgcatt tagcggtcag actgatatcg   2400
atggttcaca aggtgaatgg tcgacagttg catttatctc gtggctggag aataacggag   2460 cttccgaca tccatactgg atgtgtaaag ggtcatggtc ctatgccaga aacagggtta   2520
```

-continued

```
ttacggatac cggttgtgga aatatctgcc ttgccggagc cgtgattgag gttatgggaa    2580
cccgcggcgc aatgaccata cgcgttacca cgccagcgac gtccagcggt ggcggaatca    2640
ctaacgctca attcacttat attaatcatg gtgatgctta cgctcctggc tggcgacgag    2700
actacaaaac gaaaaaccag cagcctgcat ttgctttagg gcaaacagga cgcagggtcg    2760
caaatgataa agctgttggc tggaactgga atagcggcgt ttatgatgca gatatcagtg    2820
gcgcatcgac attaatcctc cactttaata tgaatgcggg gagttgccct gctgtacagt    2880
tccgcgtgaa ttacagaaat ggcggtatct tttatcgttc agcgcgtgat ggttatggct    2940
ttgaagctaa ctggtcagag ttttacacca caacacgcaa accctctgcg ggagatgttg    3000
gtgcatatac gcaggcagaa tgtaactcaa ggtttattac aggtattcgc cttggcggtc    3060
tgtcatctgt tcagacatgg aatggtcctg gctggtctga caggtcaggt tatgtcgtta    3120
ctggttcagt taacggaaac cgtgatgaat taattgatac aactcaggca aggccaattc    3180
agtattgcat taatggaacg tggtataacg cggggagtat ttaattatga tgcacttaag    3240
aaatattaca gctggcaacc ctaaaacaaa agagcaatac cagctaacga aacaatttaa    3300
catcaaatgg ctttatacag aggatggaaa aaactggtat gaggaacaaa agaatttcca    3360
gtatgatacg ttgaaaatgg cctatgacca aacggcgtt attatttgta ttgaaaagga    3420
tgtttcagca attaatccag aaggcgcaag cgtcgttgaa ttacctgata ttacagcaaa    3480
tcgccgggct gatatttctg gtaaatggat gttcaaagat ggcgtagtgg taaagcgaac    3540
ttataccgag gaagagcaga ggcaacaagc ggaaaatgaa aagcaaagtc tgctacagct    3600
cgtcagggat aaaacccagc tatgggactc acagctacgg ctgggtatca tttccgccga    3660
gaataagcag aaattaaccg agtggatgct ctttgcgcag aaagtcgaat ccacagacac    3720
ctccagccta ccagtaacat ttcccgaaca acctgaatga                          3760
```

<210> SEQ ID NO 20
<211> LENGTH: 3951
<212> TYPE: DNA
<213> ORGANISM: Bacteriophage P1
<220> FEATURE:
<221> NAME/KEY: misc_feature
<223> OTHER INFORMATION: P1 S' tail fiber gene

<400> SEQUENCE: 20

```
atgtctgacg tctcaacaaa cctctataag agtcagttgt tggactatta ctatcagcgg      60
cgcgctgaat cgtccattaa caaaggctct cgattttaa tcagcaaggc cgttttcggt     120
accagttcgc tggttactaa gaaaggagat ggcacttatg agattggaga actgccaaag     180
gctttcgaac tggcagaact gaccagtcaa ttttgcacca tcaacctcgt cccaacctac     240
tcaggcggga taattactgt ccgaatggac cttgatcaaa gccagttgca ggaagggaaa     300
aactacccat tcaacactct ggttgttctg gataacgaga acaagccaat cgccattatt     360
tgtgtccagg aagactcgct gtatgtgggc aaaacatata ccgcagttat ggccataaac     420
acgactacag cataaggata tgcttgatga atgacgttac agttgttaca tcggttactt     480
acccatcatc cgagtcgttg gctctggtgg ccgatgtgca ataccacgaa ccatatctgt     540
cagccgcgct aaaccgaaaa tcaggggga ttgttgaccc gggatttat gccggtttct     600 tacctaagcc tggcggtggg atgaacctgt taattacctc agtggatggt gataaaaccg     660
caggcgcggc gtcggtggat attggtgaat ttaccaggt aactattcag caacgtaagg     720
atatttctct tgcacttagt gcaggcaaga aatatgcaat tgtgctgaag ggaagatacc     780
```

```
tccttggaga agatacctac caggtgaata ccgcgtcaca tattcatgcg gctgaatttg      840
ttgccagaac ctataccgat tcatatcagt taggagatgg ggagctgctt gtttgtacgg      900
tgaatatccc tgctagtgta tctgccatta cccaggagat gattgataca tccgagcgta      960
tcaaccgctc gatcggcatt gatatttcag actctgtaac cagtaccaga agtgatgttg     1020
ctgcaagttc gctggcagtt aaaaaagcct acgatctggc gaaaagcaag tatacggcac     1080
aggatgcaag cacaacgcaa aagggattag ttcagctcag tagcgcaact aacagcgaca     1140
gcgaaacaat ggcggctacc cctaaagctg ttaagtctat aaaagatctg gctgatacca     1200
aagcgccaat agaaagcccg agtctgacag gaacgccaac cgcgccgacg gcagcgcaag     1260
gtacaaacag cacgcagatc gcaaatacag cctttgttaa ggcagctata actgcactta     1320
tcaacggtgc gcctggcaca ctggatacgc tgaaagaaat agcggctgcg atcaataacg     1380
acccgaatta cagcacaact atcaacaatg ccttggctct caaagcgcct ttggcaagcc     1440
ctgcattaac gggtgtccct actgcgccta cggctgcaca gggcacaaac aatacgcaga     1500
tcgctacgac tgcttacgta cgggctgcta tctctgcatt ggtcggctca tcacctgaag     1560
ctcttgatac cctgtatgag cttgcagcag cactgggcaa tgacccgaac tttgcgacaa     1620
caatgacaaa tgcgctggca gggaaacagc cacttgatgc aactttaacc gcgcttgctg     1680
gtcttgcgac aggcgcaaat aaattgccgt actttaccgg tacagacact gtttctcaga     1740
ctgacttaac gtcagttggt cgcgatattc tggccaaaac aagcattctt gctgttatcc     1800
aataccttgg tttaagagaa ctcggtacca gcggtgaaaa gatccccctg ttgagcacgg     1860
ctaacacatg gagtgcacgc cagactttca acggcgggat caccggggcg ctgacaggga     1920
acgccgatac cgcaacgaaa ttgaaaacag ccagaaacat taatggcgtc aggttcgatg     1980
gttctggtga cattaatatc aatactctgg tatcgcgcgg tcgcgtaacg gccctggagg     2040
cgaatgcaca gggaacatcc gggattcagc tgtatgaggc atacaacaat ggctacccctt    2100 cccctatgg caatgtgctt caccttaaag gtgccaccgc tgctggcgaa ggtgagttat     2160
tcattggctg gagtggcacg agcggtgccc atgcgcccgt acatatccgt tcgcggcggg     2220
atactgattc tgccaactgg tctgaatggg cgcaggtcta tacgtcaaaa gattcaattc     2280
ccggcgtcaa tgccaaaggg gatcaggata cctctggtaa tgcggctaca gcgaccaagt     2340
tgcagacagc atgtactatc aacggtgtct cgtttgatgt ttctaaaaat attgagctaa     2400
cggctgaaaa tttaaatctt gagcgaacag tagaattagc cgctgggtca ttgcagaaaa     2460
atcagaacgc cgcggatatt cctggaaaag ataccttcac aaaaaatatt ggtgcatgtc     2520
gcgcttttca cagttctatt agtacaggtg cagggaactg gacaacggca caattgattg     2580
aatggctgga ttctcaaggg gcattcaatc acccatactg gatgtgcaaa tgttcatggt     2640
cgtacggcaa taataaaatt ataaccgata ctggctgtgg aactattcat cttgcaggtt     2700
gcgttattga ggttatgggt aataaaggtg ccatgaccat ccgtgtaaca acaccaagca     2760
cttccagcgg tggcggaatc actaacgctc aattcactta tattaatcat ggtgatgctt     2820
acgctcctgg ctggcgacga gactacaaca cgaaaaacct gcaacctgca tttgctttag     2880
ggcagacagg aaacagggtt gcaaatgata aagctgttgg ctggaactgg aatagcggtg     2940
tttatgatgc agacctaaaa ggcgcatcaa cattaattct tcatttcaat atgaacgcgg     3000
gtagctgccc ggctgtacaa ttacgcgtga attataagaa cggcggtatt tattatcgtt     3060
cagcgcgtga tggttatgga tttgaggctg actggtcaga gttttacacc acaacccgca     3120
```

```
aaccctctgc gggggatgtt ggtgcatata cgcaggcaga atgtaactca aggtttatta    3180
caggtattcg cctgggcggt ctgtcatctg tccagacatg gaatggcccc ggctggtctg    3240
acaggtcagg ttatgtcgtt acgggttcag ttaacgggaa ccgtgatgaa ttaattgata    3300
caacacaggc aaggccaatt cagtattgca ttaatgggac gtggtataac gcggggagta    3360
tttaattatg atgcacttaa gaaatattac agctggcaac cctaaaacaa aagagcaata    3420
ccagctaacg aaacaattta acatcaaatg gctttataca gaggatggaa aaaactggta    3480
tgaggaacaa aagaatttcc agtatgatac gttgaaaatg gcctatgacc acaacggcgt    3540
tattatttgt attgaaaagg atgtttcagc aattaatcca gaaggcgcaa gcgtcgttga    3600
attacctgat attacagcaa atcgccgggc tgatatttct ggtaaatgga tgttcaaaga    3660
tggcgtagtg gtaaagcgaa cttataccga ggaagagcag aggcaacaag cggaaaatga    3720
aaagcaaagt ctgctacagc tcgtcaggga taaaacccag ctatgggact cacagctacg    3780
gctgggtatc atttccgccg agaataagca gaaattaacc gagtggatgc tctttgcgca    3840
gaaagtcgaa tccacagaca cctccagcct accagtaaca tttcccgaac aacctgaatg    3900
agacaaggcc cgatagcggg ccttaatttt ctctcggctt gaacgaattg t             3951
```

<210> SEQ ID NO 21
<211> LENGTH: 8085
<212> TYPE: DNA
<213> ORGANISM: Artificial Sequence
<220> FEATURE:
<223> OTHER INFORMATION: P1S-P1S'-Shamrock Tail Fiber

<400> SEQUENCE: 21

```
cgaatggacc ttgatcaaag ccagttgcag gaagggaaaa actacccatt caacactctg      60
gttgttctgg ataacgagaa caagccaatc gccattattt gtgtccagga agactcgctg     120
tatgtgggca aaacatatac cgcagttatg gccataaaca cgactacagc ataaggatat     180
gcttgatgaa tgacgttaca gttgttacat cggttactta cccatcatcc gagtcgttgg     240
ctctggtggc cgatgtgcaa taccacgaac catatctgtc agccgcgcta aaccgaaaat     300
tcagggggat tgttgacccg ggattttatg ccggtttctt acctaagcct ggcggtggga     360
tgaacctgtt aattacctca gtggatggtg ataaaaccgc aggcgcggcg tcggtggata     420
ttggtgaatt ttaccaggta actattcagc aacgtaagga tatttctctt gcacttagtg     480
caggcaagaa atatgcaatt gtgctgaagg gaagataccct ccttggagaa gatacctacc     540
aggtgaatac cgcgtcacat attcatgcgg ctgaatttgt tgccagaacc tataccgatt     600
catatcagtt aggagatggg gagctgcttg tttgtacggt gaatatccct gctagtgtat     660
ctgccattac ccaggagatg attgatacat ccgagcgtat caaccgctcg atcggcattg     720
atatttcaga ctctgtaacc agtaccagaa gtgatgttgc tgcaagttcg ctggcagtta     780
aaaaagccta cgatctggcg aaaagcaagt atacggcaca ggatgcaagc acaacgcaaa     840
agggattagt tcagctcagt agcgcaacta acagcgacag cgaaacaatg gcggctaccc     900
ctaaagctgt taagtctata aaagatctgg ctgataccaa agcgccaata gaaagcccga     960
gtctgacaga aacgccaacc gcgccgacgg cagcgcaagg tacaaacagc acgcagatcg    1020
caaatacagc ctttgttaag gcagctataa ctgcacttat caacggtgcg cctggcacac    1080
tggatacgct gaaagaaata gcggctgcga tcaataacga cccgaattac agcacaacta    1140
tcaacaatgc cttggctctc aaagcgcctt ggcaagccc tgcattaacg ggtgtcccta    1200
ctgcgcctac ggctgcacag ggcacaaaca atacgcagat cgctacgact gcttacgtac    1260
```

```
gggctgctat ctctgcattg gtcggctcat cacctgaagc tcttgatacc ctgtatgagc    1320
ttgcagcagc actgggcaat gacccgaact ttgcgacaac aatgacaaat gcgctggcag    1380
ggaaacagcc acttgatgca actttaaccg cgcttgctgg tcttgcgaca ggcgcaaata    1440
aattgccgta ctttaccggt acagacactg tttctcagac tgacttaacg tcagttggtc    1500
gcgatattct ggccaaaaca agcattcttg ctgttatcca ataccttggt ttaagagaac    1560
tcggtaccag cggtgaaaag atcccccctgt tgagcacggc taacacatgg agtgcacgcc    1620
agactttcaa cggcgggatc accggggcgc tgacagggaa cgccgatacc gcaacgaaat    1680
tgaaaacagc cagaaacatt aatggcgtca ggttcgatgg ttctggtgac attaatatca    1740
atactctggt atcgcgcggt cgcgtaacgg ccctggaggc gaatgcacag gaacatccg    1800 ggattcagct gtatgaggca tacaacaatg gctacccttc cccctatggc aatgtgcttc    1860
accttaaagg tgccaccgct gctggcgaag gtgagttatt cattggctgg agtggcacga    1920
gcggtgccca tgcgcccgta catatccgtt cgcggcggga tactgattct gccaactggt    1980
ctgaatgggc gcaggtctat acgtcaaaag attcaattcc cggcgtcaat gccaaggggg    2040
atcaggatac ctctggtaat gcggctacag cgaccaagtt gcagacagca tgtactatca    2100
acggcgtctc gtttgacggt tctaaaaata ttgagctaac ggcggaagat ttaaatctac    2160
aggaaacggt aaacaaggct gataacgcgg ttcaaaagac aggcgatacc ttgtccggtg    2220
gacttacttt tgaaaacgac tcaatccttg cctggattcg gaatactgac tgggcgaaga    2280
ttggttttaa aaatgatgcc gacagcgata ctgattcata catgtggttt gaaacaggcg    2340
acaacggcaa tgaatatttc aaatggagaa gcaaacaaag taccacaaca aaagacctga    2400
tgaatcttaa atgggatgct ttgtatgttc ttgtcaatgc cattgtaaat ggcgaagtca    2460
tatcaaaatc agcaaacggc ctacgtattg cttatggtaa ttacggattc tttattcgta    2520
atgatggttc aaatacatac ttcatgttga caaactccgg tgacaacatg gggacttata    2580
acggattaag gccattatgg attaataacg ctactggcgc tgtttcgatg gggcgtggcc    2640
ttaatgtttc aggggagaca cttttcagacc gttttgctat taacagcagt aatggtatgt    2700
ggattcagat gcgcgataac aacgctatct ttgggaaaaa tatagttaac actgatagca    2760
ctcaggcgtt acttcgccag aatcacgccg accgaaagtt catgataggt ggactgggga    2820
acaagcaatt tggcatctac atgattaata actcaaggac agccaatggc accgatggtc    2880
aggcgtacat ggacaataac ggtaactggc tttgcggtgc gcaaattatt cccggaaatt    2940
atggcaattt tgactcacgc tatgtgagag atgtccgact tggcacacgt gttgttcaat    3000
tgatggcgcg tggagggcgt tatgaaagag ccggacacgc acttaccgga ttaaggatta    3060
ttggtgaagt tgatgcgat gatgacgcta tcttcaggcc gatacaaaaa tacatcaatg    3120
gcatatggta taacgtcgca caggtgtaaa ttatgcagca cttaaaaaat atcaggtcag    3180
gaaacccaaa gacaaagag caataccaat taacaaagaa ttttgacgta atctggttgt    3240
ggtctgaaga cggaaaaaac tggtatgagg aagtgaaaaa ctttcaacca gacaccataa    3300
agattgttta cgatgaaaat aatattattg tcgccatcac caaagatgcc tccacgctta    3360
accctgaagg ttttagcgtc gttgaggttc ccgacataac agccaaccgc cgcgctgatg    3420
attcaggaaa gtggatgttt aaggatggag ctgtagttaa acggatttat acggcagacg    3480
aacagcaaca acaagccgaa tcacaaaagg ccgcattgct ttccgaagct gaatcagtca    3540
tccagccgct ggaacgcgct gtcaggctga atatggcaac agacgaggaa cgcacacgac    3600
```

```
tggaagcatg ggaacgctac agtgttctgg tcagccgtgt ggatacggca atcctgaat    3660
ggccacaaaa gcctgaataa aaattaaggc ccgctatcgg ccttgtctc attcaggttg    3720
ttcgggaaat gttactggta ggctggaggt gtctgtggat tcgactttct gcgcaaagag   3780
catccactcg gttaatttct gcttattctc ggcggaaatg atacccagcc gtagctgtga   3840
gtcccatagc tgggttttat ccctgacgag ctgtagcaga ctttgctttt catttccgc    3900
ttgttgcctc tgctcttcct cggtataagt tcgctttacc actacgccat ctttgaacat   3960
ccatttacca gaaatatcag cccggcgatt tgctgtaata tcaggtaatt caacgacgct   4020
tgcgccttct ggattaattg ctgaaacatc cttttcaata caaataataa cgccgttgtg   4080
gtcataggcc attttcaacg tatcatactg gaaattcttt tgttcctcat accagttttt   4140
tccatcctct gtataaagcc atttgatgtt aaattgtttc gttagctggt attgctcttt   4200
tgttttaggg ttgccagctg taatatttct taagtgcatc ataattaaat actccccgcg   4260
ttataccacg tcccattaat gcaatactga attggccttg cctgtgttgt atcaattaat   4320
tcatcacggt tcccgttaac tgaacccgta acgacataac ctgacctgtc agaccagccg   4380
gggccattcc atgtctggac agatgacaga ccgcccaggc gaatacctgt aataaaccct   4440
gagttacatt ctgcctgcgt atatgcacca acatcccccg cagagggttt gcgggttgtg   4500
gtgtaaaact ctgaccagtc agcctcaaat ccataaccat cacgcgctga acgataataa   4560
ataccgccgt tcttataatt cacgcgtaat tgtacagccg ggcagctacc cgcgttcata   4620
ttgaaatgaa gaattaatgt tgatgcgcct tttaggtctg catcataaac accgctattc   4680
cagttccagc caacagcttt atcatttgca accctgtttc ctgtctgccc taaagcaaat   4740
gcaggttgca ggttttttcgt gttgtagtct cgtcgccagc caggagcgta agcatcacca   4800
tgattaatat aagtgaattg agcgttagtg attccgccac cgctggaagt gcttggtgtt   4860
gttacacgga tggtcatggc acctttatta cccataacct caataacgca acctgcaaga   4920
tgaatagttc cacagccagt atcggttata attttattat tgccgtacga ccatgaacat   4980
ttgcacatcc agtatgggtg attgaatgcc ccttgagaat ccagccattc aatcaattgt   5040
gccgttgtcc agttccctgc acctgtacta atagaactgt gaaaagcgcg acatgccacca  5100
atattttttg tgaaggtatc ttttccagga atatccgcgc cgttctgatt tttctgcaat   5160
gacccagcgg ctaattctac tgttcgctca agatttaaat tttcagccgt tagctcaata   5220
tttttagaac catcaaacga gacaccgttg atagtacatg ctgtctgcaa cttggtcgct   5280
gtagccgcat taccagaggt atcctgatcc cctttggcat tgacgccggg aattgaatct   5340
tttgacgtat agacctgcgc ccattcagac cagttggcag aatcagtatc cgccgcgaa    5400
cggatatgta cgggcgcatg ggcaccgctc gtgccactcc agccaatgaa taactcacct   5460
tcgccagcag cggtggcacc tttaaggtga agcacattgc catagggga agggtagcca    5520
ttgttgtatg cctcatacag ctgaatcccg gatgttccct gtgcattcgc ctccagggcc   5580
gttacgcgac cgcgcgatac cagagtattg atattaatgt caccagaacc atcgaacctg   5640
acgccattaa tgtttctggc tgttttcaat ttcgttgcgg tatcggcgtt ccctgtcagc   5700
gccccggtga tcccgccgtt gaaagtctgg cgtgcactcc atgtgttagc cgtgctcaac   5760
aggggggatct tttcaccgct ggtaccgagt tctcttaaac caaggtttag gattgacgcg   5820
ttggccgatt cattaatgca gctgcaaaaa acccctcaag acccgtttag aggcccaag    5880
gggttatgct agtattgct cagcggtggc agcagcttat tcaggctttt gtggccattc    5940
aggatttgcc gtatccacac ggctgaccag aacactgtag cgttcccatg actccagtcg   6000
```

-continued

```
tgcgtgttcc tcatccgtcg ccatattcag cctgacagcg cgttccagcg gctggatgac    6060
tgattcagct tcggaaagta acgcggcctt ttgtgattcg gcctgttgct gctgttcgtc    6120
tgctgtataa gtcctcctga ccaccgctcc gtccttaaac atccacttcc ctgaatcatc    6180
ggcacgacgg ttagctgtta tatcggggat ttcaacgacg ctaaaacctt caggattaag    6240
cgtggaggca tctttagtga cggcgacaat aatattattt tcgtcgtaaa caatctttat    6300
tgtatccggc tgaaagttct tcacttcctc ataccagttt ttcccgtctt cagcgtaaag    6360
ccagatgact ccgtgcttct ttgttaactc atactgctcc agtgttttag cattacccgc    6420
ttttatgttc tttaagtgca tcatattaaa cgctcgctac attataccat gtgccattta    6480
tatacttttg aacgggtctg taataaacgc cagctatatt atcggcagag ttttttgcctg    6540 tatcctgaac attaatacca gacaatacat gacctgaagg gcactggaaa ttccatgttt    6600
gccagttatt cacaccataa tattgctgtg agccaagccg gacatctttc acatatctgg    6660
agtcaaaatt gccataattg ccgggaataa cttgcgcacc acaaagccag ttaccgttat    6720
tatccatgta cgcctgacca tcggtgccat tggctgtcct tgagttatta atcatgtaga    6780
tgccaaattg cttatttccc agaccgccaa tcataaattt gcggtcggca tggtcctgac    6840
ggagcaaagc ctgagcacca tcagtggata ccgcattacg tcccaaaata acattctggt    6900
cacgcatatg aatccacatg ccggtactac tgttaattgc aaaacggttt gcaaatatat    6960
cccctgtaac atcaagacca tgccccatgc ttatccggcc agttctgaga ttaagcgtaa    7020
aggggcgtag tggcccctata ttaccatttt ccccttcatt ctctcgtgta gggatgatat    7080
gcaggcattc ttcagaacga cgaaaaatgg caccaaaaga tgaattaaat atcctcagtg    7140
cattgactgt cgatattttc acttcactgc tgaaaagggc ttcaacaaga acagacaaag    7200
cattccattt aagattcatc aggtctttag gccgggtgcc aatgatgcgg tgtctccatt    7260
tgaaatattc attgccgttg ttgcctgttt caaaccacat gtaggaatcg gtgtctgcat    7320
ccgaattatt tttaaaacca atcttcgccc agtcagtatt ccgaatccag gcaaggattg    7380
agtcgttttc aaaagtaagt ccaccggaca aggtatcgcc tgtcttttga accgcgttat    7440
cagccttgtt taccgtttcc tgtagattta aatcttccgc cgttagctca atattttag    7500 aaccgtcaaa cgagacgccg ttgatagtac atgctgtctg caacttggtc gctgtagccg    7560
cattaccaga ggtatcctga tcccctttgg cattgacgcc gggaattgaa tcttttgacg    7620
tatagacctg cgcccattca gaccagttgg cagaatcagt atcccgccgc gaacggatat    7680
gtacgggcgc atgggcaccg ctcgtgccac tccagccaat gaataactca ccttcgccag    7740
cagcggtggc acctttaagg tgaagcacat tgccataggg ggaagggtag ccattgttgt    7800
atgcctcata cagctgaatc ccggatgttc cctgtgcatt cgcctccagg gccgttacgc    7860
gaccgcgcga taccagagta ttgatattaa tgtcaccaga accatcgaac ctgacgccat    7920
taatgtttct ggctgttttc aatttcgttg cggtatcggc gttccctgtc agcgccccgg    7980
tgatcccgcc gttgaaagtc tggcgtgcac tccatgtgtt agccgtgctc aacaggggga    8040
tcttttcacc gctggtaccg agttctctta aaccaaggta ttgga                    8085
```

<210> SEQ ID NO 22
<211> LENGTH: 3212
<212> TYPE: DNA
<213> ORGANISM: Artificial Sequence
<220> FEATURE:
<223> OTHER INFORMATION: Pine Tail Fiber

<400> SEQUENCE: 22

```
atgtctgacg tctcaacaaa cctctataag agtcagttgt tggactatta ctatcagcgg      60
cgcgctgaat cgtccattaa caaaggctct cgattttttaa tcagcaaggc cgttttcggt    120
accagttcgc tggttactaa gaaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg ataacgaga acaagccaat cgccattatt     360
tgtgtccagg aagactcgct gtatgtgggc aaaacatata ccgcagttat ggccataaac    420
acgactacag cataaggata tgcttgatga atgacgttac agttgttaca tcggttactt    480
acccatcatc cgagtcgttg gctctggtgg ccgatgtgca ataccacgaa ccatatctgt    540
cagccgcgct aaaccgaaaa ttcagggga ttgttgaccc gggatttat gccggtttct      600
tacctaagcc tggcggtggg atgaacctgt taattacctc agtggatggt gataaaaccg    660
caggcgcggc gtcggtggat attggtgaat tttaccaggt aactattcag caacgtaagg    720
atatttctct tgcacttagt gcaggcaaga aatatgcaat tgtgctgaag gaagatacc     780
tccttggaga agatacctac caggtgaata ccgcgtcaca tattcatgcg gctgaatttg    840
ttgccagaac ctataccgat tcatatcagt taggagatgg ggagctgctt gtttgtacgg    900
tgaatatccc tgctagtgta tctgccatta cccaggagat gattgataca tccgagcgta    960
tcaaccgctc gatcggcatt gatatttcag actctgtaac cagtaccaga agtgatgttg   1020
ctgcaagttc gctggcagtt aaaaaagcct acgatctggc gaaaagcaag tatacggcac   1080
aggatgcaag cacaacgcaa aagggattag ttcagctcag tagcgcaact aacagcgaca   1140
gcgaaacaat ggcggctacc cctaaagctg ttaagtctat aaaagatctg gctgatacca   1200
aagcgccaat agaaagcccg agtctgacag gaacgccaac cgcgccgacg gcagcgcaag   1260
gtacaaacag cacgcagatc gcaaatacag cctttgttaa ggcagctata actgcactta   1320
tcaacggtgc gcctggcaca ctggatacgc tgaaagaaat agcggctgcg atcaataacg   1380
acccgaatta cagcacaact atcaacaatg ccttggctct caaagcgcct ttgaacagcc   1440
ctgcactgac cggaacgcca acgacgccaa ctgcgcgaca gggaacgaat aatactcaga   1500
tcgcaaacac ggctttcgtt atggccgcga ttgccgccct tgtagactcg tcgcctgacg   1560
cactgaatac gctgaacgag ctggcggcgg cgctgggcaa tgacccgaat tttgctacca   1620
ccatgactaa tgcgcttgcg ggtaagcaac cgaaagatgc taccctgacg gcgctggcgg   1680
ggcttgctac tgcggcagac aggtttccgt attttacggg gaatgatgtt gccagcctgg   1740
cgaccctgac aaaagtcggg cgggatattc tggctaaatc gaccgttgcc gccgttatcg   1800
aatatctcgg tttacaggaa acggtaaacc gagccgggaa cgccgtgcaa aaaatggcg    1860
ataccttgtc cggtggactt acttttgaaa acgactcaat ccttgcctgg attcgaaata   1920
ctgactgggc gaagattgga tttaaaaatg atgccgatgg tgacactgat tcatacatgt   1980
ggtttgaaac gggggataac ggcaatgaat atttcaaatg gagaagccgc cagagtacca   2040
caacaaaaga cctgatgacg ttgaaatggg atgcactaaa tattcttgtt aatgccgtca   2100
ttaatggctg ttttggagtt ggtacgacga atgcactagg tggtagctct attgttcttg   2160
gtgataatga taccggattt aaacagaatg gagacggtat tcttgatgtt tatgctaaca   2220
gtcagcgtgt attccgtttt cagaatggag tggctattgc tttaaaaat attcaggcag   2280
gtgatagtaa aaagttctcg ctatccagct ctaatacatc cacgaagaat attacctta   2340
```

-continued

```
atttatgggg tgcttccacc cgtccagtgg ttgcagagtt aggcgatgag gccggatggc    2400
atttctatag ccagcgaaat acagataact cggtaatatt tgctgttaac ggtcagatgc    2460
aacccagcaa ctggggaaat tttgattccc gctatgtgaa agatgttcgc ctgggtacgc    2520
gagttgttca attgatggcg cgaggtggtc gttatgaaaa agccggacac acgattaccg    2580
gattaagaat cattggtgaa gtagatggcg atgatgaagc catcttcagg ccgatacaaa    2640
aatacatcaa tggcacatgg tataacgttg cgcaggtgta agttatgcag catttaaaga    2700
acattaagtc aggtaatcca aaaacaaaag agcaatatca gctaacaaag aattttgatg    2760
ttatctggtt atggtccgaa gacggaaaaa actggtatga ggaagtgaag aactttcagc    2820
cagacacaat aaagattgtt tacgatgaaa ataatattat tgtcgctatc accagagatg    2880
cttcaacgct taatcctgaa ggttttagcg ttgttgaggt tcctgatatt acctccaacc    2940
gacgtgctga cgactcaggt aaatggatgt ttaaggatgg tgctgtggtt aaacggattt    3000
atacggcaga tgaacagcaa caacaggcag aatcacaaaa ggccgcgtta ctttccgaag    3060
cggaaaacgt tattcagcca ctggaacgcg ctgtcaggct gaatatggcg acggatgagg    3120
aacgtgcacg actggagtca tgggaacgtt acagcgttct ggtcagccgt gtggatcctg    3180
caaatcctga atggccggaa atgccgcaat aa                                  3212
```

<210> SEQ ID NO 23
<211> LENGTH: 4609
<212> TYPE: DNA
<213> ORGANISM: Artificial Sequence
<220> FEATURE:
<223> OTHER INFORMATION: Plum Tail Fiber

<400> SEQUENCE: 23

```
atgtctgacg tctcaacaaa cctctataag agtcagttgt tggactatta ctatcagcgg     60
cgcgctgaat cgtccattaa caaaggctct cgatttttaa tcagcaaggc cgttttcggt    120
accagttcgc tggttactaa gaaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg gataacgaga acaagccaat cgccattatt    360
tgtgtccagg aagactcgct gtatgtgggc aaaaacatata ccgcagttat ggccataaac    420
acgactacag cataaggata tgcttgatga atgacgttac agttgttaca tcagttactt    480
acccatcgcc tgagtcactg gctctggtgg ctgatgtgca ataccacgaa ccatatctgt    540
cagccgcgct aaaccgaaaa ttcagggggaa ttgttgaccc tggattttat gcaggtttcc    600
tgccgaagcc tggtggtggg atgaacctgt taatcacctc agtggatggt gataaaactg    660
ctggcgctgc gtcagtggat attggtgaat ctaccaggt aactattcag caccgtaagg    720
atatttctct tgcacttagt gcaggcaaga aatatgcaat tgtgctgaag gaagatacc    780 tccttggaga ggatacctat caggttaata ccgcgtcaca tattcatgcg gctgaatttg    840
ttgccagaac ctataccgat tcatatcagt taggagatgg ggagctgctt gtttgtacgg    900
tgaatatccc tgctggcgta tcagccatta cccaggagat gattgataca tccgagcgta    960
ttaaccgcac gatcggcatt gatatttcag actctgtaac cagtagcaga agtgatgttg    1020
ctgcaagttc gctggcagtt aaaaaagcct acgatctggc gaaaagcaag tatcggcgc    1080 aggatgcaag cacaacgcaa aagggattag ttcagctcag tagcgaaact aacagcgaca    1140
```

```
gcgaaacaat ggcggctacc cctaaagcca ttaagtctgt aaaagatctt gctgatacca    1200
aagcgccaat agaaagcccg agtctgacag aaacgccaac cgcgccgacg gcagcgcaag    1260
gtacaaatag cacgcagatc gcaaatacag cctttgttaa ggcagctata acggcactta    1320
tcaacggtgc acctggcaca ctggatacgc ttaaagaaat agctgctgcg atcaataacg    1380
acccgaattt cagcacaact atcaacaatg ctctggctct taaagctcct ttagcaagtc    1440
ctgcattaac gggaatacct actgcgccaa ccgctgcaca gggtacgaat aacacgcaga    1500
ttgctacgac cgcttatgta agagctgcca tatccgcatt ggttggttca tcaccagaag    1560
ctcttgatac cctgaatgag cttgccgcag cacttggtaa tgacccgaac tttgcgacaa    1620
caatgacaaa tgcgctggca ggcaaacagc ctctggatgc aactttaacc gcgcttgcgg    1680
gtcttgctac aggcgcaaat aaattgccgt actttaccgg tacagacact gtttctcaga    1740
ctgacttaac gtcagtcggt cgcgatattc tggccaaaac aagcgtcctt gctgttatcc    1800
aataccttgg tttaagagaa ctcggcacaa gcggtgaaaa gatcccctg ttgagcacgg     1860 ctaacacatg gagtgcacgc cagactttta acggcgggat caccggggcg ctgacaggga    1920
acgccgatac cgcgacgaag ttgaaaaacag cacggaagat taacaacgtt tcatttgatg    1980
gttcggcaga cataacgctg acacctgaga accttggcgt caccagtctg acgtttgaga    2040
aaaacaacgg tgaaatgcct attgatgctg acctaaatac tttcggtccc gttgaggctt    2100
atcttggtgt ctggtccaaa gcaacatcca ccaacgcaac actggagaaa aatttcccgg    2160
aagataatgc tgtcggtgtg cttgaggtat ttgctgccgg aaattttgca ggtacgcaac    2220
gctttaccac gagagacggc aatgtataca tacgcagact cgccaataag tggaatggct    2280
ctgatggtcc gtggggcata tggcgtcaca ctcaatcagc tacccgccct ttgagtacga    2340
ctatagacct gaatacgctt ggagccgccg aacatcttgg tttatggcgt aacagtagct    2400
cggctatagc ttcatatgaa cgcaattatc agaggaagg cggcttgct caggggtgc      2460 ttgagatcct cgaaggcggg aattatgaa gaacgcaacg ttataccact cgccgcggaa    2520
atatgtatgt ccgctgcctt gcggcaagct gggatgcatc aaatccgcag tgggaaccgt    2580
ggttaaaagt cggtcatcag tcagagagtc gttattacga aggtgattta aatgttctaa    2640
ccgaccccgg tatttacagt gttacaggaa aggcaacaaa cggtccgatg ctggacaccg    2700
ttggcgcgac actacttggg atactggaag taatcagacg ttttgatggt gtgtctgtct    2760
ggcagcgtta cacaaccaca gggaaatcag aaaccacaca gggacgcact tttgagcgcg    2820
tctacgccgg gagcaaatgg accgaatggc gagaagtata taactccttt tcgttgcctc    2880
tgaatctggg catcggtggc gcagtggcaa aactatccag tctggactgg cagacctacg    2940
attttgtgcc gggcagtctg ataaccgtgc ggcttgataa catgaccaac attcccgacg    3000
gtatggactg gggcgtcatt gatggcaacc tgataaacat cgcagttggt ccgagtgatg    3060
attccggtac ggggcgctca atgcatgtat ggcgcagcac tgtaagtaaa gcgaactacc    3120
gcttttttat ggtgcgtatt tcaggaaatc cgggaagccg cacgatcaca gcaagacgag    3180
taccaatcat tgacgaagcc cagacatggg gcgcgaaaca gacattcagt gctggccttt    3240
ctggtgaact gtccggcaat gcggcgacag caacaaagct gaaaacagcc cgtaaaatta    3300
ataacgtttc gtttgatggt tccggggata ttgaggtcct tcctgttggt gttccgctgc    3360
cgtggccatc agatactgtg ccgtctggtt acgccctgat gcaggacag acttttgaca    3420 aatctgcata cccgaaactt gcagccgctt atccgtcagg cgtgatcccg gatatgcgtg    3480
gctggacaat caagggcaaa cccgccagtg gtcgggacgt attgtctctg aacaggatg    3540
```

```
gcattaaatc gcacacccac agcgccagcg catccaatac ggatttgggt acgaaaacca    3600
catcttcgtt tgattacggt actaaatcaa cgaataacac aggtgcacat acccacaatg    3660
tatctggtac tgcaaatagt gctggcgcac atactcatac cgtgccatta aggagaccaa    3720
acagtggcgg tatgaatttc gactggctgg atggtgcatc aagtggcacg gtggtgggga    3780
atggaactgt gccttcttct ggcgcacata cccactcagt atcaggcacc gctacaagtg    3840
ctggggcaca tgcacacact gttggtattg gcgctcatac gcactctgtt gcgattggtt    3900
cacatggaca taccatcacc gttaacgctg ctggcaacgc ggaaaacacc gttaaaaaca    3960
tcgcatttaa ttatattgtg aggcttgcat aatggcattc agaatgagtg aacaatcacg    4020
tactgtaaaa atttataacc tgctggccgg aactaatgag tttattggtg aaggtgacgc    4080
atatattcca cctcatacag ggctgccagc taattctaca gatatcgccc caccggaaat    4140
tcctgctggc tttgtggcag tttttaacag tgaaaatgaa tcgtggaata ttgttgaaga    4200
ccatcgtggt aaaacggtct atgacgtggc atcgggggac gcgttgttta tttctgaacc    4260
cggaccgcta ccagagaatg tcacctggtt gtcgccagca ggggaatatc agaagtggga    4320
cggcgtatcc tgggtgaagg atgaggaagc agaaaaactg tttcggatac gggaagcgga    4380
agagaaaaag gcaaggttga tccaggaggc aacagataac atcgcaattc tgcaggatgc    4440
agttaatctt gaaatagcaa caaacgagga aaattcacaa ctggattcct ggagaaaata    4500
cagagtatta gtgagtagaa ttgacaccag tacagctccg gatatcgtat ggccagagct    4560
gatgaatcag ggttatgtgc gggaggacga gcagataact tcagactga               4609

<210> SEQ ID NO 24
<211> LENGTH: 4723
<212> TYPE: DNA
<213> ORGANISM: Artificial Sequence
<220> FEATURE:
<223> OTHER INFORMATION: Queen Tail Fiber
<220> FEATURE:
<221> NAME/KEY: misc_feature
<222> LOCATION: (2370)..(2370)
<223> OTHER INFORMATION: n is a, c, g, or t
<220> FEATURE:
<221> NAME/KEY: misc_feature
<222> LOCATION: (2385)..(2385)
<223> OTHER INFORMATION: n is a, c, g, or t
<220> FEATURE:
<221> NAME/KEY: misc_feature
<222> LOCATION: (2431)..(2431)
<223> OTHER INFORMATION: n is a, c, g, or t

<400> SEQUENCE: 24
atgtctgacg tctcaacaaa cctctataag agtcagttgt tggactatta ctatcagcgg      60
cgcgctgaat cgtccattaa caaaggctct cgatttttaa tcagcaaggc cgttttcggt     120
accagttcgc tggttactaa gaaggagatg gcacttatg agattggaga actgccaaag      180
gctttcgaac tggcagaact gaccagtcaa ttttgcacca tcaacctcgt cccaacctac     240
tcaggcggga taattactgt ccgaatggac cttgatcaaa gccagttgca ggaagggaaa     300
aactacccat tcaacactct ggttgttctg gataacgaga acaagccaat cgccattatt     360
tgtgtccagg aagactcgct gtatgtgggc aaaacatata ccgcagttat ggccataaac     420
acgactacag cataaggata tgcttgatga atgacgttac agttgttaca tcggttactt     480
acccatcatc cgagtcgttg gctctggtgg ccgatgtgca ataccacgaa ccatatctgt     540
cagccgcgct aaaccgaaaa ttcagggga ttgttgaccc gggatttat gccggtttct      600
```

```
tacctaagcc tggcggtggg atgaacctgt taattacctc agtggatggt gataaaaccg    660
caggcgcggc gtcggtggat attggtgaat tttaccaggt aactattcag caacgtaagg    720
atatttctct tgcacttagt gcaggcaaga aatatgcaat tgtgctgaag ggaagatacc    780
tccttggaga agatacctac caggtgaata ccgcgtcaca tattcatgcg gctgaatttg    840
ttgccagaac ctataccgat tcatatcagt taggagatgg ggagctgctt gtttgtacgg    900
tgaatatccc tgctagtgta tctgccatta cccaggagat gattgataca tccgagcgta    960
tcaaccgctc gatcggcatt gatatttcag actctgtaac cagtaccaga agtgatgttg   1020
ctgcaagttc gctggcagtt aaaaaagcct acgatctggc gaaaagcaag tatacggcac   1080
aggatgcaag cacaacgcaa aagggattag ttcagctcag tagcgcaact aacagcgaca   1140
gcgaaacaat ggcggctacc cctaaagctg ttaagtctat aaaagatctg gctgatacca   1200
aagcgccaat agaaagcccg agtctgacag gaacgccaac cgcgccgacg gcagcgcaag   1260
gtacaaacag cacgcagatc gcaaatacag cctttgttaa ggcagctata actgcactta   1320
tcaacggtgc gcctggcaca ctggatacgc tgaaagaaat agcggctgcg atcaataacg   1380
acccgaatta cagcacaact atcaacaatg ccttggctct caaagcgcct ttggcaagcc   1440
ctgcattaac gggtgtccct actgcgccta cggctgcaca gggcacaaac aatacgcaga   1500
tcgctacgac tgcttacgta cgggctgcta tctctgcatt ggtcggctca tcacctgaag   1560
ctcttgatac cctgtatgag cttgcagcag cactgggcaa tgacccgaac tttgcgacaa   1620
caatgacaaa tgcgctggca gggaaacagc cacttgatgc aactttaacc gcgcttgctg   1680
gtcttgcgac aggcgcaaat aaattgccgt actttaccgg tacagacact gtttctcaga   1740
ctgacttaac gtcagttggt cgcgatattc tggccaaaac aagcattctt gctgttatcc   1800
aataccttgg tttaagagaa ctcggtacca gcggtgaaaa gatcccectg ttgagcacgg   1860 ctaacacatg gagtgcacgc cagactttca acggcgggat caccggggcg ctgacaggga   1920
acgccgatac cgcaacgaaa ttgaaaacaa aaaggtcgct tcaagttgac ctccaaagtg   1980
ataacgccat cgactttgat ggttcatcaa atgctcttct gggcataaaa ggtatttac    2040 caattactca tggggatta ggtgcatcca gcgtctctgg agggcgtact aatcttggat    2100
taggtgttgc ggacatcccc caatttaagg gtatcaatct tgttaactca acagactctg   2160
atttagcggc gtcagggatt gtaagtggtt atctgaataa ttcagctggg gtacagagga   2220
gtcgtttcag aatttattca gagataagga gtgacaaccg ctcatggctg acgttacatc   2280
tacaatctga taccaacacc aataaatatg ccggattaga cattgacggt aattttctga   2340
ttaccggtga tagcaaatgc cgagcattan aaccaactga tgtancgtta acaagaaaaa   2400
atattgatgt ttacagcaaa gccgaagtag nccttaaaaa agggatgaaa ttcaccagag   2460
tcaatgctcc ttctggagct gaagagggta aattctatcc tgtagtcatc aagagatctg   2520
caacgagcaa tggtgaactt gcttctcggg ttattatttc cactgcgccg cgccaagctg   2580
cacatcgcat gaacaactgc gaattcaatg gttttgtgat gcctgctggt tggagtgaca   2640
gagggcggta cgcatacggg atgttctggc aatatcagga tgcagaacgg gcgattcatt   2700
ctattgcgat gagcaataaa gacgatgaag ttagctcagt tttttatatt gaaggcggag   2760
catttccagt atgcgttctt gtggaggagg ggctttctgt tgttgtccct acaacggatt   2820
atrttgttgg acaaaccaca tacaaatggg gggcaaccaa ccctaaagct gaatgtatag   2880
ctgccgacat aattattgat tttagcaatg gtcgtggttt ctatagctct ggaaacctca   2940
atggtaatgc tgcaacagca actaaattac agaccgccag aacaatcaac ggagtaacct   3000
```

```
tcgatggcac tactgatatt tcgttgacac cagagaacat tggcgcgctg tcactatccg    3060
gaggcacatt attaggaggt ctgacagctc ctttacttac cactaaaagc gatcttattt    3120
ttagtagcca tacaagccgt catatccgct ttacatatac gaaaaatgac ggcacaacac    3180
taactgatgg gtacatattt aaagatggtg tcgataaccc taacagacga ccaggtatcc    3240
ggataaattg tgctgcgccg aatgamgtgc tcrcgtcagt tgttgacgat gcaaaaatgt    3300
atctgcgacg tttccgctcc agcacaggtg caagcatatg gcatgaaaca atagagaata    3360
acgtttatcg cttatgcaca ggaacaactg acgctcagga agagttagtc ttgaggactg    3420
gttcctatgc gaaattcgct ggcgagatta tttccaaatc ggcgaatggt cttcgtattg    3480
cctatggcaa ctatggattc tttatccgaa cgatggttc aagcacatac ttcatgttga     3540
ccgcctcggg tgacaatctt ggaacatgga atagtttaag accgcttacc attaacaacg    3600
ctaacggggc tgtttcaatc ggtaatggac tcaatgtaac tggcgatata agaaccaatg    3660
catgggtata tgcaaacaga ttttctgtta atagcagctc aggttcttgg attagtatgc    3720
gagatcaaaa tgttattttt ggtcttaata aggtatcaac cagttccgcc caggcattat    3780
taagacaaga ccatgctgac agaaagttct ttattggtgg tcttggtaat agtcaattcg    3840
gcttttacat gattaacaac tcaagaacat caaatggtac agatggccag gcatttcttg    3900
atagcagtgg taacttccag tgcggcgggc aaatacttcc aactaactat agtaattttg    3960
actcgcgcta cacattaaaa acggcttgtg tgacaagcgt aagaatggga tctgctgcca    4020
gttataaacc atcaagcaat ggtgtttcct ggactcagaa tctaggaagc ggactggtta    4080
tgacaggtat tattgttcaa gaaacaggag gtaattcagc cgacaatatc ggcgggattt    4140
attatcgacc ggttcagtat tgtatcaacg gtacatggta cacagcagca tcagtataat    4200
gagagagcat atgaataact ttaaaaattt cgcaccatat acgcctggtg aagataaaag    4260
agagcttgtt gatgcaggag ttttattcct gttggatgaa aatggtaacg actggtatga    4320
atgtcaaaag ttattttcgg aatgtacaaa ggtaattgcg tatgatagca acaatatcgt    4380
tgtcagcatt acagatgacg cctcaaccct ttggcccata ggattatctg tagcagaagt    4440
ggatagttta cctgaagatg tagatatcaa cggtggttgg gtgtttagag acaactctgt    4500
tgttaaacgc atatattctg atacggagtt acaacagcaa gctgaatcaa aaaaggctgc    4560
cttactttca catgccgaat cagttattgt aactcttgag cgggcggtta aattgaatat    4620
ggcaacagat gaggaacgag ctaaactgga agcatgggag cgttatagcg tgttggttta    4680
tcgcgtagat acagctaaac cagaatggcc agaagaaccg tag                      4723

<210> SEQ ID NO 25
<211> LENGTH: 3908
<212> TYPE: DNA
<213> ORGANISM: Artificial Sequence
<220> FEATURE:
<223> OTHER INFORMATION: Razzmatazz Tail Fiber

<400> SEQUENCE: 25
atgtctgacg tctcaacaaa cctctataag agtcagttgt tggactatta ctatcagcgg      60
cgcgctgaat cgtccattaa caaaggctct cgattttaa tcagcaaggc cgttttcggt      120
accagttcgc tggttactaa gaaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
```

```
aactacccat tcaacactct ggttgttctg gataacgaga caagccaat cgccattatt      360 tgtgtccagg aagactcgct gtatgtgggc aaaacatata ccgcagttat ggccataaac      420
acgactacag cataaggata tgcttgatga atgacgttac agttgtcaca tcggttactt      480
acccatcacc cgagtcgttg gctctggtgg ctgatgtgca ataccacgaa ccatatctgt      540
cagccgcgct aaaccgaaaa ttcaggggga ttgttgaccc gggattttat gccggtttct      600
tacctaagcc tggcggtggg atgaacctgt taatcacctc agtggatggt gataaaaccg      660
caggcgcggc gtcggtggat attggtgaat tctaccaggt aactattcag caacgtaagg      720
atatttctct tgcacttagt gcaggcaaga aatatgcaat tgtgctgaag gaagatacc       780 tccttggaga agatacctat caggtgaata ccgcgtcaca tattcatgcg gctgaatttg      840
ttgccagaac ctataccgat tcatatcagt taggagatgg ggagctgctt gtttgtacgg      900
tgaatatccc tgctggtgta tctgccatta cccaggagat gattgataca tccgagcgta      960
tcaaccgcac gatcggcatt gatatttcag actctgtaac cagtaccaga agtgatgttg     1020
ctgcaagttc gctggcagtt aaaaaagcct acgatctggc gaaaagcaag tatcggcgc      1080 aggatgcaag cataacgcaa aagggattag ttcagctcag tagcgcaact aacagcgaca     1140
gcgaaacaat ggcggctacc cctaaagctg ttaagtctat aaaagatctg gctgatacca     1200
aagcgccaat agaaagcccg agtctgacag gaacgccaag cgcgccgacg gcagcgcaag     1260
gtacaaacag cacgcagata gcaaatacag cctttgttaa ggcagctata actgcactta     1320
tcaacggtgc acctggcaca ctggatacac ttaaagaaat agctgctgcg atcaataacg     1380
acccgaattt cagcacaact gtcaacaatg ctctggccct taaagcgcct ttagcaagtc     1440
ctgcattaac gggaatacct actgcgccta ccgctgcaca gggtacgaat aacacgcaga     1500
ttgctacgac cgcttatgta agagctgcca tatccgcact ggtcggctca tcacctgaag     1560
ctcttgatac cctgaatgag cttgcagcag cactgggcaa tgacccgaac tttgcgacaa     1620
caatgacaaa tgcgctggca gggaaacagc cacttgatgc aactttaacc gcgcttgctg     1680
gtcttgcgac agacgcaaat aaattgccgt actttaccgg tacagacact gtttctcaga     1740
ctgacttaac gtcagtcggt cgcgatattc tggccaaaac aagcgttctt gctgttatcc     1800
aataccttgg tttaagagaa ctcggtacca gtggtgaaaa gatcccctg ttgagcacgg      1860 ctaacacatg gagtgcacgc cagactttta acggcgggat caccggggcg ctgacaggga     1920
acgccgacac cgcgacgaaa ttaaaaacag ccataaacat taatggcgtc agattcgatg     1980
gttctacgaa catttcgata ccaacaatta cgtctagagg acgcgttact gcgcttaccg     2040
gtacaacgca aggtgctgct actggattgc agatgtatga ggcatacaac aatggttatc     2100
cgacgactta cgggaatgta cttcacctga agggagctgc atccactggt gaaggcgagt     2160
tgctcattgg ctggagtggc acaaatggcg ctcatgcacc agctttcatt cgatccaaaa     2220
gagatagcac tgctgcggca tggtccgaat gggcacagat ctatacgtca aaagattccg     2280
ttcccggcgt aataccaaa gggaatcagg acacctctgg taatgcggct acagcgacca      2340
aattgcagac ggcgtgtact atcaacggtg tctcgtttga cggttctaaa aatattgagc     2400
taacggcgga agatttaaat cttgagcaaa ctgtagaatt agccgcagga gcattacaga     2460
aaaaccagaa cggcgcagat attccgggaa agatacctt caccaaaaat attggtgcct      2520
gccgcgcata tagcgcatgg ctgaatattg tgtgcgatag tcaggtctgg acaaccgcgc     2580 aatttattc gtggctggag agtcagggag catttaacca tccttactgg atgtgcaaag      2640
gctcatgggc ttatgcaaat aataaggtca ttacagatac aggttgcgga aatatttgtc     2700
```

```
ttgcaggtgc tgtggtggaa gttattggca ctcgcggcgc aatgaccata cgcgttacta   2760
cgccgagcac gtccagcggt ggcggaatta ctaacgctca attcacttat attaatcatg   2820
gtgatgctta tgctcctggc tggcgaagag actacaacac gaaaaaccag cagcctgcat   2880
ttgctttagg gcaaacagga agcagggttg caaatgataa agctgttggc tggaactgga   2940
atagcggcgt ttatgatgca gatatcagtg gcgcatcgac attaatcctc cacttcaata   3000
tgaatgcggg gagttgccct gctgtacagt tccgcgtgaa ttataagaac ggcggtatct   3060
tttatcgttc agcgcgtgat ggttatggct ttgaagctaa ctggtcagag ttttacacca   3120
caacccgcaa accctctgcg ggggatgttg gtgcatatac gcaggcagaa tgtaactcaa   3180
ggtttattac aggtattcgc ctaggcggtc tgtcatctgt tcagacatgg aatggtcccg   3240
gctggtctga caggtcaggt tatgtcgtta caggttcagt taacgaaaac cgtgatgaat   3300
taattgatac aactcaggca aggccaattc agtattgcat taatgggacg tggtataacg   3360
cggggagtat ttaaatgatg cacttaaaaa acattactgc tggcaaccct aaaacaaaag   3420
agcaatacca gctaacgaaa caatttaaca tcaaatggct ttatacagag gatgggaaaa   3480
actggtatga ggaacaaaag aactttcagc ctgatacgtt gaaaatggtc tatgaccaca   3540
acgacgttat tatttgtatt gaaaaggatg tttcagcaat taatccagaa ggcgcaagcg   3600
tcgttgaggt tcctgatatt acagcaaatc gccgggctga tatttcgggt aaatagatgt   3660
tcaaagatgg cgtagtgata aagcgaactt ataccgagga ggaacaaagg cagcaggcag   3720
agaatgaaaa acaaagcctg ttgcaacttg tcagggataa aacccagcta tgggactcac   3780
agctacggct gggcatcatt tccgacgaga ataaacaaaa attaactgag tggatgctct   3840
atgcgcagaa agtcgaatct acagacacct ccagcctgcc agtaacattt cccgaacaac   3900
ctgaatga                                                            3908
```

<210> SEQ ID NO 26
<211> LENGTH: 3683
<212> TYPE: DNA
<213> ORGANISM: Artificial Sequence
<220> FEATURE:
<223> OTHER INFORMATION: Salmon Tail Fiber

<400> SEQUENCE: 26

```
atgtctgacg tctcaacaaa cctctataag agtcagttgt tggactatta ctatcagcgg    60
cgcgctgaat cgtccattaa caaaggctct cgattttttaa tcagcaaggc cgttttcggt   120
accagttcgc tggttactaa gaaggagat ggcacttatg agattggaga actgccaaag   180
gctttcgaac tggcagaact gaccagtcaa ttttgcacca tcaacctcgt cccaacctac   240
tcaggcggga taattactgt ccgaatggac cttgatcaaa gccagttgca ggaagggaaa   300
aactacccat tcaacactct ggttgttctg ataacgaga acaagccaat cgccattatt   360
tgtgtccagg aagactcgct gtatgtgggc aaaacatata ccgcagttat ggccataaac   420
acgactacag cataaggata tgcttgatga atgacgttac agttgttaca tcggttactt   480
acccatcatc cgagtcgttg gctctggtgg ccgatgtgca ataccacgaa ccatatctgt   540
cagccgcgct aaaccgaaaa ttcagggga ttgttgaccc gggatttat gccggtttct   600 tacctaagcc tggcggtggg atgaacctgt taattacctc agtggatggt gataaaaccg   660
caggcgcggc gtcggtggat attggtgaat tttaccaggt aactattcag caacgtaagg   720
atatttctct tgcacttagt gcaggcaaga aatatgcaat tgtgctgaag ggaagatacc   780
```

-continued

```
tccttggaga agatacctac caggtgaata ccgcgtcaca tattcatgcg gctgaatttg    840
ttgccagaac ctataccgat tcatatcagt taggagatgg ggagctgctt gtttgtacgg    900
tgaatatccc tgctagtgta tctgccatta cccaggagat gattgataca tccgagcgta    960
tcaaccgctc gatcggcatt gatatttcag actctgtaac cagtaccaga agtgatgttg   1020
ctgcaagttc gctggcagtt aaaaaagcct acgatctggc gaaaagcaag tatacggcac   1080
aggatgcaag cacaacgcaa aagggattag ttcagctcag tagcgcaact aacagcgaca   1140
gcgaaacaat ggcggctacc cctaaagctg ttaagtctat aaaagatctg gctgatacca   1200
aagcgccaat agaaagcccg agtctgacag gaacgccaac cgcgccgacg gcagcgcaag   1260
gtacaaacag cacgcagatc gcaaatacag cctttgttaa ggcagctata actgcactta   1320
tcaacggtgc gcctggcaca ctggatacgc tgaaagaaat agcggctgcg atcaataacg   1380
acccgaatta cagcacaact atcaacaatg ccttggctct caaagcgcct ttggcaagcc   1440
ctgcattaac gggtgtccct actgcgccta cggctgcaca gggcacaaac aatacgcaga   1500
tcgctacgac tgcttacgta cgggctgcta tctctgcatt ggtcggctca tcacctgaag   1560
ctcttgatac cctgtatgag cttgcagcag cactgggcaa tgacccgaac tttgcgacaa   1620
caatgacaaa tgcgctggca gggaaacagc cacttgatgc aactttaacc gcgcttgctg   1680
gtcttgcgac aggcgcaaat aaattgccgt actttaccgg tacagacact gtttctcaga   1740
ctgacttaac gtcagttggt cgcgatattc tggccaaaac aagcattctt gctgttatcc   1800
aataccttgg tttaagagaa ctcggtacca gcggtgaaaa gatcccctg ttgagcacgg   1860 ctaacacatg gagtgcgcgc cagactttca acggagggat caccggggca ctgacaggga   1920
acgccgacac cgcgacgaaa ttgaaaacag cacgcactat tggcggtgtg gcatttgatg   1980
gtactgcgaa tattaattta cctggtgtta acgttgcggg taatcagaat acatccggta   2040
acgcggctac agcgaccaag ttgcagacag catgtactat caacggcgtc tcgtttgatg   2100
gttctaaaaa tattgagcta acggcggaag atttaaatct acaggaattt attaataaag   2160
caaataatgc cgttcagcgt tcaggcgata tcttgtccgg cggacttact tttgaaaacg   2220
actcaatcct tgcctggatt cgaaatactg actgggcaaa gattggattt aaaaatgatg   2280
ccgacagcga cacagattca tacatgtggt ttgaaacagg cgacaacggc aatgaatatt   2340
tcaaatggag aagcaaacaa agcaccacaa caaaagacct gatgaatctt aaatgggatg   2400 cttttgtctgt tcttgttaaa gccctttttca gcagtgaagt aaaaatatcg acagtcaatg   2460
cactgaggat atttaattca tcttttggtg ccattttcg ccgttctgaa gaatgcctgc    2520
atatcatccc tacacgagag aatgaggggg aaaatggtga tatagggcca ctacgtccct   2580
ttacgcttaa tctcagaact ggccgcataa ctatggggca tggtctggat gttacaggag   2640
atataacaac taacgcctgg gtgtatgcaa acaggtttgc tattaatagt ggctcaacct   2700
catggattga tatgcgaaac cagaatgtca tttttggtag aaacgcagta tcaacaagtt   2760
ctgcgcaggc tttgttaaga caagaccatg cagaacgcaa attttttgtc ggtggacttg   2820
gtaactacca gtttggtttt tacatgatta ataactcaag gacagccaat ggcaccgatg   2880
gtcaggcgta catggataat aacggtaact ggctttgtgg ctcgcaagtt attcctggca   2940
actatggcaa ttttgattcc agatatgtga gagatgttcg cctgggtacg cgagttgttc   3000
aattgatggc gcgtggtggt cgttatgaaa aagccggaca cgcaattacc ggattaagaa   3060
tcattggtga agtagatggc gatgatgaag ccatcttcag gccaatacaa aaatacatca   3120
atggcacatg gtataacgtc gcacaggtgt aaatgatgca gcatttaaaa aatattaagt   3180
```

```
ctggaaatcc taaaacgaaa gaacaatatc agctaacaaa gaattttgat gttatctggt    3240
tatggtccga agacgataaa aactggtatg aggaagtgaa aaactttcag ccagacacaa    3300
taaagattgt ttacgatgca aataatatta ttgtcgccat cactaaagat gcctccacgc    3360
ttaaccctga aggttttagc gtcgttgagg ttcctgatat tacagccaac cgccgcgctg    3420
atgattcagg aaagtggatg tttaaggatg gagctgtagt taaacggatt tatacggcag    3480
acgaacagca acaacaggcc gaatcacaaa aggccgcatt gctttccgaa gctgaatcag    3540
tcatccagcc gctggaacgc gctgtcaggc tgaatatggc aacagacgag gaacgcacac    3600
gactggaagc atgggaacgc tacagtgttc tggtcagccg tgtggatacg gcaaatcctg    3660
aatggccaca aaagcctgaa taa                                            3683
```

<210> SEQ ID NO 27
<211> LENGTH: 3301
<212> TYPE: DNA
<213> ORGANISM: Artificial Sequence
<220> FEATURE:
<223> OTHER INFORMATION: Scarlet Tail Fiber

<400> SEQUENCE: 27

```
atgtctgacg tctcaacaaa cctctataag agtcagttgt tggactatta ctatcagcgg      60
cgcgctgaat cgtccattaa caaaggctct cgatttttaa tcagcaaggc cgttttcggt     120
accagttcgc tggttactaa gaaaggagat ggcacttatg agattggaga actgccaaag     180
gctttcgaac tggcagaact gaccagtcaa ttttgcacca tcaacctcgt cccaaccctac    240 tcaggcggga taattactgt ccgaatggac cttgatcaaa gccagttgca ggaagggaaa     300
aactacccat tcaacactct ggttgttctg gataacgaga acaagccaat cgccattatt     360
tgtgtccagg aagactcgct gtatgtgggc aaaacatata ccgcagttat ggccataaac     420
acgactacag cataaggata tgcttgatga atgacgtcac cgttgttacg agtgttacct     480 accccctcgcc tgagtcatta gcgttagttg cagacgttca gtaccacgaa ccgtatcttt    540
cagcagctct taaccgtaaa ttccgcggaa ttgtcgatcc aggattttac gccgggttcc     600
tgcctaagcc tggcggcggc atgaatcttc tgattacgtc agtcgacggg gataaaactg     660
cgggagcggc atcggtagat atcggggaat tctaccaggt tacaattcaa catcgtaaag     720
acatttcgtt agcacttaac gctgggaaga atacgccat tgtcttgaaa ggccgctatt      780
tgttaggtga agatacgtac caggtcaata cagcaagtca catccacgcc gctgaatttg     840
tcgcacgtac atataccgat tcctaccagc ttggggatgg tgagttactt gtgtgcaccg     900
tgaacattcc tgctggagtg tcaacgatca cgcaggagat gatcgatact tcagagcgta     960
ttaatcgcac gatcgggatt gatatttcag acagcgtcac ctcgactcgc tcagatgtcg    1020
cggcttcatc tcttgcagtg aaaaaggcct acgacctggc caagtcgaag tacacagctc    1080
aggacgcgag caccacccaa aagggtctgg tacagttatc atctgcgacg aattcaacat    1140
ccgaggttct tgcagcgaca cctaaagcgg taaaagccgc gtatgatctt gccaatggga    1200
aatacaccgc acaggacgcc acaactcacc aaaagggtat tgtgcagttg tcgagtgaca    1260
ccaactcaac gtcggagaca ctgcggcca cgccgaaagc agtcaaagct gcatacgacc     1320
ttgcggctgg taaagcgccc tcatcccaca ctcacccctg gaatcagatt actggtgtac    1380
ccaccgcaag cttaactgca aagggtatca ctcaattgag ttccgcgacc aacagcacca    1440
gtgaagtttt agctgctacc ccaaaggcag ttaaagccgc ttacgacttg gctaatggaa    1500
```

| | |
|---|---|
| aatatacagc gcaggacgcg accactgcac aaaaaggaat tgtgcaactt tcgagcgcaa | 1560 |
| cgaactccac aagtgaagtt ttggcagcta cgcctaaagc cgtcaaagcc gcgtatgatt | 1620 |
| tggcgaatgg taagtatact gcgcaagatg cgacgactac gcagaaaggt attgtccaac | 1680 |
| tgtcaagtga caccaacagc acgtcagaga ccttggctgc tacacctaaa gcagtgaaag | 1740 |
| ctgcctatga tcttgcggct gggaaagccc cgtcatcaca cacacatcca tggaaccaga | 1800 |
| ttacggtcgt acctacggcc tctttaactg cgaagggcat tacacaatta tcatccgcga | 1860 |
| ctaacagcac cagtgaggtt ttagctgcaa caccgaaagc agtgaaggca gcctacgatt | 1920 |
| tggcgaacgg taaatatacg gctcaagatg cgaccaccgc gcaaaagggc attgtgcaac | 1980 |
| tgtcgtctgc aacaaattca acgtcggaag ttctggcagc aactccaaag gcagtgaaag | 2040 |
| ccgcctatga cttagcaaac ggtaaacagg ccgcggatgc gacgttaacg gcattggcgg | 2100 |
| ctcttgcaac tgcagcggac aagttaccgt atttcacggg cgttgaccgt gctgccctga | 2160 |
| cagcgttaac ctctgttggg cgtgccattt taggcaagac ctcgattcaa tctgttttag | 2220 |
| attaccttgg tttgggggaa ggctctgcac tgcctgttgg tgtgcccgtt ccgtggccct | 2280 |
| tagaaacacc accaacgggc tggctaaaat gcaatggtgc agcattttct tctgaaatgt | 2340 |
| atcccaaact ggcaaaggcc taccccacca ataaattacc ggatttacgc ggtgagttta | 2400 |
| tccgtggttg ggatgatggg cgaggtgtgg atgcgggaag ggtcatctta agcatacagg | 2460 |
| ggtggttaac aggaagtcat tatcataata ttcggtcatg ggacgcgtgg gataacacgg | 2520 |
| tattggtgcc aaatgacaga ggggggggata gtctgttgtc gacagataac gccgtccggc | 2580 |
| aaggagcgat taatggtaaa tttaccagtc aatacagaac ggagttatct gggggggaatg | 2640 |
| aaacccgccc acgtaacatt gccttcaatt atattgtgag agcagcataa tggataatgc | 2700 |
| gatattaaat agcgaactta tagccataca ggcaggaaac attatcgttt ataactatga | 2760 |
| tggtggtaat cgggaatata tttctgcatc aactgaatat cttgctgttg gcgttggtat | 2820 |
| tccggcaaat tcttgtttgg atgctccagg ctcacataaa gcaggttatg cgattctccg | 2880 |
| ttcagaggat ttaagttcat gggagtatgt gccagatcat cgtggcgaaa ctgtctatag | 2940 |
| cattgacaca gggaatcccg aagaaatcac ggtgttgggt gactatccgg aaaatacaac | 3000 |
| cactatcgcc ccgctaacac catcgacaa atgggatgga gagaaatggg tggttgatac | 3060 |
| tgaggctcaa catagtgcag ctgtagaggc agcagaaaca aaacgtcagt cattgattga | 3120 |
| tactgcgatg gattccatta gtctgattca gttgaaatta cgggctggac ggaagttgac | 3180 |
| gcaggcagaa accacgcagc ttaactccgt gctagattat atagacgagc tgaacgcgat | 3240 |
| ggatttaacc acggcaccag atctcaactg gcctgaaaaa caactttcta cagccagttg | 3300 |
| a | 3301 |

<210> SEQ ID NO 28
<211> LENGTH: 3965
<212> TYPE: DNA
<213> ORGANISM: Artificial Sequence
<220> FEATURE:
<223> OTHER INFORMATION: Shamrock Tail Fiber

<400> SEQUENCE: 28

| | |
|---|---|
| atgtctgacg tctcaacaaa cctctataag agtcagttgt tggactatta ctatcagcgg | 60 |
| cgcgctgaat cgtccattaa caaaggctct cgattttaa tcagcaaggc cgttttcggt | 120 |
| accagttcgc tggttactaa gaaagggagat ggcacttatg agattggaga actgccaaag | 180 |
| gctttcgaac tggcagaact gaccagtcaa ttttgcacca tcaacctcgt cccaacctac | 240 |

```
tcaggcggga taattactgt ccgaatggac cttgatcaaa gccagttgca ggaagggaaa    300
aactacccat tcaacactct ggttgttctg gataacgaga caagccaat cgccattatt    360 tgtgtccagg aagactcgct gtatgtgggc aaaacatata ccgcagttat ggccataaac    420
acgactacag cataaggata tgcttgatga atgacgttac agttgttaca tcggttactt    480
acccatcatc cgagtcgttg gctctggtgg ccgatgtgca ataccacgaa ccatatctgt    540
cagccgcgct aaaccgaaaa ttcagggga ttgttgaccc gggatttat gccgtttct    600 tacctaagcc tggcggtggg atgaacctgt taattacctc agtggatggt gataaaaccg    660
caggcgcggc gtcggtggat attggtgaat tttaccaggt aactattcag caacgtaagg    720
atatttctct tgcacttagt gcaggcaaga aatatgcaat tgtgctgaag ggaagatacc    780
tccttggaga agatacctac caggtgaata ccgcgtcaca tattcatgcg gctgaatttg    840
ttgccagaac ctataccgat tcatatcagt taggagatgg ggagctgctt gtttgtacgg    900
tgaatatccc tgctagtgta tctgccatta cccaggagat gattgataca tccgagcgta    960
tcaaccgctc gatcggcatt gatatttcag actctgtaac cagtaccaga agtgatgttg   1020
ctgcaagttc gctggcagtt aaaaaagcct acgatctggc gaaaagcaag tatacggcac   1080
aggatgcaag cacaacgcaa aagggattag ttcagctcag tagcgcaact aacagcgaca   1140
gcgaaacaat ggcggctacc cctaaagctg ttaagtctat aaaagatctg ctgatacca   1200 aagcgccaat agaaagcccg agtctgacag gaacgccaac cgcgccgacg gcagcgcaag   1260
gtacaaacag cacgcagatc gcaaatacag cctttgttaa ggcagctata actgcactta   1320
tcaacggtgc gcctggcaca ctggatacgc tgaaagaaat agcggctgcg atcaataacg   1380
acccgaatta cagcacaact atcaacaatg ccttggctct caaagcgcct ttggcaagcc   1440
ctgcattaac gggtgtccct actgcgccta cggctgcaca gggcacaaac aatacgcaga   1500
tcgctacgac tgcttacgta cgggctgcta tctctgcatt ggtcggctca tcacctgaag   1560
ctcttgatac cctgtatgag cttgcagcag cactgggcaa tgacccgaac tttgcgacaa   1620
caatgacaaa tgcgctggca gggaaacagc cacttgatgc aactttaacc gcgcttgctg   1680
gtcttgcgac aggcgcaaat aaattgccgt actttaccgg tacagacact gtttctcaga   1740
ctgacttaac gtcagttggt cgcgatattc tggccaaaac aagcattctt gctgttatcc   1800
aataccttgg tttaagagaa ctcggtacca gcggtgaaaa gatcccctg ttgagcacgg   1860 ctaacacatg gagtgcacgc cagactttca acggcgggat caccggggcg ctgacaggga   1920
acgccgatac cgcaacgaaa ttgaaaacag ccagaaacat taatgcgtc aggttcgatg   1980 gttctggtga cattaatatc aatactctgg tatcgcgcgg tcgcgtaacg gccctggagg   2040
cgaatgcaca gggaacatcc gggattcagc tgtatgaggc atacaacaat ggctaccctt   2100 cccctatgg caatgtgctt caccttaaag gtgccaccgc tgctggcgaa ggtgagttat   2160
tcattggctg gagtggcacg agcggtgccc atgcgcccgt acatatccgt tcgcggcggg   2220
atactgattc tgccaactgg tctgaatggg cgcaggtcta tacgtcaaaa gattcaattc   2280
ccggcgtcaa tgccaaaggg gatcaggata cctctggtaa tgcggctaca gcgaccaagt   2340
tgcagacagc atgtactatc aacggcgtct cgtttgacgg ttctaaaaat attgagctaa   2400
cggcggaaga tttaaatcta caggaaacgg taaacaaggc tgataacgcg gttcaaaaga   2460
caggcgatac cttgtccggt ggacttactt ttgaaaacga ctcaatcctt gcctggattc   2520
ggaatactga ctgggcgaag attggttta aaaataattc ggatgcagac accgattcct   2580
```

| | |
|---|---|
| acatgtggtt tgaaacaggc aacaacggca atgaatattt caaatggaga caccgcatca | 2640 |
| ttggcacccg gcctaaagac ctgatgaatc ttaaatggaa tgctttgtct gttcttgttg | 2700 |
| aagccctttt cagcagtgaa gtgaaaatat cgacagtcaa tgcactgagg atatttaatt | 2760 |
| catcttttgg tgccattttt cgtcgttctg aagaatgcct gcatatcatc cctacacgag | 2820 |
| agaatgaagg ggaaaatggt aatatagggc cactacgccc ctttacgctt aatctcagaa | 2880 |
| ctggccggat aagcatgggg catggtcttg atgttacagg ggatatattt gcaaaccgtt | 2940 |
| ttgcaattaa cagtagtacc ggcatgtgga ttcatatgcg tgaccagaat gttattttgg | 3000 |
| gacgtaatgc ggtatccact gatggtgctc aggctttgct ccgtcaggac catgccgacc | 3060 |
| gcaaatttat gattggcggt ctgggaaata agcaatttgg catctacatg attaataact | 3120 |
| caaggacagc caatggcacc gatggtcagg cgtacatgga taataacggt aactggcttt | 3180 |
| gtggtgcgca agttattccc ggcaattatg gcaattttga ctccagatat gtgaaagatg | 3240 |
| tccggcttgg ctcacagcaa tattatggtg tgaataactg gcaaacatgg aatttccagt | 3300 |
| gcccttcagg tcatgtattg tctggtatta atgttcagga tacaggcaaa aactctgccg | 3360 |
| ataatatagc tggcgtttat tacagacccg ttcaaaagta tataaatggc acatggtata | 3420 |
| atgtagcgag cgtttaaatg atgcacttaa agaacataaa agcgggtaat gctaaaacac | 3480 |
| tggagcagta tgagttaaca aagaagcacg gagtcatctg gctttacgct gaagacggga | 3540 |
| aaaactggta tgaggaagtg aagaactttc agccggatac aataaagatt gtttacgacg | 3600 |
| aaaataatat tattgtcgcc gtcactaaag atgcctccac gcttaatcct gaaggtttta | 3660 |
| gcgtcgttga aatccccgat ataacagcta accgtcgtgc cgatgattca gggaagtgga | 3720 |
| tgtttaagga cggagcggtg gtcaggagga cttatacagc agacgaacag cagcaacagg | 3780 |
| ccgaatcaca aaaggccgcg ttactttccg aagctgaatc agtcatccag ccgctggaac | 3840 |
| gcgctgtcag gctgaatatg gcgacggatg aggaacacgc acgactggag tcatgggaac | 3900 |
| gctacagtgt tctggtcagc cgtgtggata cggcaaatcc tgaatggcca caaaagcctg | 3960 |
| aataa | 3965 |

<210> SEQ ID NO 29
<211> LENGTH: 3344
<212> TYPE: DNA
<213> ORGANISM: Artificial Sequence
<220> FEATURE:
<223> OTHER INFORMATION: Sunset Tail Fiber

<400> SEQUENCE: 29

| | |
|---|---|
| atgtctgacg tctcaacaaa cctctataag agtcagttgt tggactatta ctatcagcgg | 60 |
| cgcgctgaat cgtccattaa caaaggctct cgattttttaa tcagcaaggc cgttttcggt | 120 |
| accagttcgc tggttactaa gaaaggagat ggcacttatg agattggaga actgccaaag | 180 |
| gctttcgaac tggcagaact gaccagtcaa ttttgcacca tcaacctcgt cccaacctac | 240 |
| tcaggcggga taattactgt ccgaatggac cttgatcaaa gccagttgca ggaagggaaa | 300 |
| aactacccat tcaacactct ggttgttctg ataacgagag acaagccaat cgccattatt | 360 |
| tgtgtccagg aagactcgct gtatgtgggc aaaacatata ccgcagttat ggccataaac | 420 |
| acgactacag cataaggata tgcttgatga atgacgtcac cgttgttacg agtgttacct | 480 |
| accccctcgc ctgagtcatta gcgttagttg cagacgttca gtaccacgaa ccgtatcttt | 540 |
| cagcagctct taaccgtaaa ttccgcggaa ttgtcgatcc aggattttac gccgggttcc | 600 |
| tgcctaagcc tggcggcggc atgaatcttc tgattacgtc agtcgacggg gataaaactg | 660 |

```
cgggagcggc atcggtagat atcggggaat tctaccaggt tacaattcaa catcgtaaag    720
acatttcgtt agcacttaac gctgggaaga aatacgccat tgtcttgaaa ggccgctatt    780
tgttaggtga agatacgtac caggtcaata cagcaagtca catccacgcc gctgaatttg    840
tcgcacgtac atataccgat tcctaccagc ttggggatgg tgagttactt gtgtgcaccg    900
tgaacattcc tgctggagtg tcaacgatca cgcaggagat gatcgatact tcagagcgta    960
ttaatcgcac gatcgggatt gatatttcag acagcgtcac ctcgactcgc tcagatgtcg   1020
cggcttcatc tcttgcagtg aaaaaggcct acgacctggc caagtcgaag tacacagctc   1080
aggacgcgag caccacccaa aagggtctgg tacagttatc atctgcgacg aattcaacat   1140
ccgaggttct tgcagcgaca cctaaagcgg taaaagccgc gtatgatctt gccaatggga   1200
aatacaccgc acaggacgcc acaactacac aaaagggtat tgtgcagttg tcgagtgaca   1260
ccaactcaac gtcggagaca ctggcggcca cgccgaaagc agtcaaagct gcatacgacc   1320
ttgcggctgg taaagcgccc tcatcccaca ctcacccctg gaatcagatt actggtgtac   1380
ccaccgcaag cttaactgca aagggtatca ctcaattgag ttccgcgacc aacagcacca   1440
gtgaagtttt agctgctacc ccaaaggcag ttaaagccgc ttacgacttg gctaatggaa   1500
aatatacagc gcaggacgcg accactgcac aaaaaggaat tgtgcaactt tcgagcgcaa   1560
cgaactccac aagtgaagtt ttggcagcta cgcctaaagc cgtcaaagcc gcgtatgatt   1620
tggcgaatgg taagtatact gcgcaagatg cgacgactac gcagaaaggt attgtccaac   1680
tgtcaagtga caccaacagc acgtcagaga ccttggctgc tacacctaaa gcagtgaaag   1740
ctgcctatga tcttgcggct gggaaagccc cgtcatcaca cacacatcca tggaaccaga   1800
ttacggtcgt acctacggcc tctttaactg cgaagggcat tacacaatta tcatccgcga   1860
ctaacagcac cagtgaggtt ttagctgcaa caccgaaagc agtgaaggca gcctacgatt   1920
tggcgaacgg taaatatacg gctcaagatg cgaccaccgc gcaaaagggc attgtgcaac   1980
tgtcgtctgc aacaaattca acgtcggaag ttctggcagc aactccaaag gcagtgaaag   2040
ccgcctatga cttagcaaac ggtaaacagg ccgcggatgc gacgttaacg gcattggcgg   2100
ctcttgcaac tgcagcggac aagttaccgt atttcacggg cgttgaccgt gctgccctga   2160
cagcgttaac ctctgttggg cgtgccattt taggcaagac ctcgattcaa tctgttttag   2220
attaccttgg tttaggggaa ggctcggcgc tgcccgttgg tgtgcctgtt ccgtggccct   2280
cagccacacc gccaacgggg tggctgaaat gcaatggtgc agcatttttct tctgaaaagt   2340 acccaaatct ggcaaaggtt tacccaacgt taaaattacc tgatttacgc ggtgagttta   2400
tccgtggctg ggatgatggg cgagggattg actctggtcg ctctatttta agcgagcaag   2460
gatatgcaac ggaggatcat gctcacggat taccgtcaaa atcaaccgta gcaactgacc   2520
gctcaattaa tttctacttt gacgaggcat gggctactag tggtaatacg ggagttatca   2580 gatggggaa cacaagcgat gcaggattgc cagcccctaa ttatggaact tttaaaacat   2640
ataaacagtc cgtagctaat ttaggtactg ctggcttaga aacccgccct cgtaatattg   2700
catttaatta tattgtgagg gcggattaaa ttatggataa tgcgatatta aatagcgaac   2760
ttatagccat acaggcagga acattatcg tttataacta tgatggtggt aatcgggaat   2820
atatttctgc atcaactgaa tatcttgctg ttggcgttgg tattccggca aattcttgtt   2880
tggatgctcc aggctcacat aaagcaggtt atgcgattct ccgttcagag gatttaagtt   2940
catgggagta tgtgccagat catcgtggcg aaactgtcta tagcattgac acagggaatc   3000
```

| | |
|---|---|
| ccgaagaaat cacggtgttg ggtgactatc cggaaaatac aaccactatc gccccgctaa | 3060 |
| caccatacga caaatgggat ggagagaaat gggtggttga tactgaggct caacatagtg | 3120 |
| cagctgtaga ggcagcagaa acaaaacgtc agtcattgat tgatactgcg atggattcca | 3180 |
| ttagtctgat tcagttgaaa ttacgggctg gacggaagtt gacgcaggca gaaaccacgc | 3240 |
| agcttaactc cgtgctagat tatatagacg agctgaacgc gatggattta accacggcac | 3300 |
| cagatctcaa ctggcctgaa aaacaacttt ctacagccag ttga | 3344 |

```
<210> SEQ ID NO 30
<211> LENGTH: 3350
<212> TYPE: DNA
<213> ORGANISM: Artificial Sequence
<220> FEATURE:
<223> OTHER INFORMATION: Tangerine Tail Fiber

<400> SEQUENCE: 30
```

| | |
|---|---|
| atgtctgacg tctcaacaaa cctctataag agtcagttgt tggactatta ctatcagcgg | 60 |
| cgcgctgaat cgtccattaa caaaggctct cgattttaa tcagcaaggc cgttttcggt | 120 |
| accagttcgc tggttactaa gaaaggagat ggcacttatg agattggaga actgccaaag | 180 |
| gctttcgaac tggcagaact gaccagtcaa ttttgcacca tcaacctcgt cccaacctac | 240 |
| tcaggcggga taattactgt ccgaatggac cttgatcaaa gccagttgca ggaagggaaa | 300 |
| aactacccat tcaacactct ggttgttctg ataacgaga caagccaat cgccattatt | 360 |
| tgtgtccagg aagactcgct gtatgtgggc aaaacatata ccgcagttat ggccataaac | 420 |
| acgactacag cataaggata tgcttgatga atgacgtcac cgttgttacg agtgttacct | 480 |
| accccctcgcc tgagtcatta gcgttagttg cagacgttca gtaccacgaa ccgtatcttt | 540 |
| cagcagctct taaccgtaaa ttccgcggaa ttgtcgatcc aggattttac gccgggttcc | 600 |
| tgcctaagcc tggcggcggc atgaatcttc tgattacgtc agtcgacggg gataaaactg | 660 |
| cgggagcggc atcggtagat atcggggaat tctaccaggt tacaattcaa catcgtaaag | 720 |
| acatttcgtt agcacttaac gctgggaaga aatacgccat tgtcttgaaa ggccgctatt | 780 |
| tgttaggtga agatacgtac caggtcaata cagcaagtca catccacgcc gctgaatttg | 840 |
| tcgcacgtac atataccgat tcctaccagc ttggggatgg tgagttactt gtgtgcaccg | 900 |
| tgaacattcc tgctggagtg tcaacgatca cgcaggagat gatcgatact tcagagcgta | 960 |
| ttaatcgcac gatcgggatt gatatttcag acagcgtcac ctcgactcgc tcagatgtcg | 1020 |
| cggcttcatc tcttgcagtg aaaaaggcct acgacctggc caagtcgaag tacacagctc | 1080 |
| aggacgcgag caccacccaa aagggtctgg tacagttatc atctgcgacg aattcaacat | 1140 |
| ccgaggttct tgcagcgaca cctaaagcgg taaaagccgc gtatgatctt gccaatggga | 1200 |
| aatacaccgc acaggacgcc acaactacac aaaagggtat tgtgcagttg tcgagtgaca | 1260 |
| ccaactcaac gtcggagaca ctggcggcca cgccgaaagc agtcaaagct gcatacgacc | 1320 |
| tgcggctgg taaagcgccc tcatcccaca ctcacccctg gaatcagatt actggtgtac | 1380 |
| ccaccgcaag cttaactgca agggtatca ctcaattgag ttccgcgacc aacagcacca | 1440 |
| gtgaagtttt agctgctacc ccaaaggcag ttaaagccgc ttacgacttg gctaatggaa | 1500 |
| aatatacagc gcaggacgcg accactgcac aaaaaggaat tgtgcaactt tcgagcgcaa | 1560 |
| cgaactccac aagtgaagtt ttggcagcta cgcctaaagc cgtcaaagcc gcgtatgatt | 1620 |
| tggcgaatgg taagtatact gcgcaagatg cgacgactac gcagaaaggt attgtccaac | 1680 |
| tgtcaagtga caccaacagc acgtcagaga ccttggctgc tacacctaaa gcagtgaaag | 1740 |

```
ctgcctatga tcttgcggct gggaaagccc cgtcatcaca cacacatcca tggaaccaga   1800
ttacggtcgt acctacggcc tctttaactg cgaagggcat tacacaatta tcatccgcga   1860
ctaacagcac cagtgaggtt ttagctgcaa caccgaaagc agtgaaggca gcctacgatt   1920
tggcgaacgg taaatatacg gctcaagatg cgaccaccgc gcaaaagggc attgtgcaac   1980
tgtcgtctgc aacaaattca acgtcggaag ttctggcagc aactccaaag gcagtgaaag   2040
ccgcctatga cttagcaaac ggtaaacagg ccgcggatgc gacgttaacg gcattggcgg   2100
ctcttgcaac tgcagcggac aagttaccgt atttcacggg cgttgaccgt gctgccctga   2160
cagcgttaac ctctgttggg cgtgccattt taggcaagac ctcgattcaa tctgttttag   2220
attaccttgg tttaggggaa ggctcggcgc tgcccgttgg tgtgcctgtt ccgtggccct   2280
ccgccacacc accaacgggg tggctgaaat gtaacggagc agcattttct tctgaaaagt   2340
acccaaatct ggcaaaggtt tacccaacgt taaaattacc tgatttacgc ggtgagttta   2400
tccgtggttg ggatgattcg agagggattg atacagggcg ttcattgcta agtggtcaga   2460
ctgcaacatt tattcgtaca gctttgcagg attattacgg tgtcgatctg actactaatg   2520
tcaaagtagg tatcgcttat gctactgctg attctgttat aactgttgga aaccctgcta   2580
atcctaaagc aggagataat agcgattatg ttccagcatc atcagataac tccataacag   2640
gcactcaaag gacggcagag gataatttta ccggggcatg gatatcaatg cgcccccgca   2700
acgttgcttt taattacatt gtaagggcca cataaattat ggataatgcg atattaaata   2760
gcgaacttat agccatacag gcaggaaaca ttatcgttta taactatgat ggtggtaatc   2820
gggaatatat ttctgcatca actgaatatc ttgctgttgg cgttggtatt ccggcaaatt   2880
cttgtttgga tgctccaggc tcacataaag caggttatgc gattctccgt tcagaggatt   2940
taagttcatg ggagtatgtg ccagatcatc gtggcgaaac tgtctatagc attgacacag   3000
ggaatcccga agaaatcacg gtgttgggtg actatccgga aaatacaacc actatcgccc   3060
cgctaacacc atacgacaaa tgggatggag agaaatgggt ggttgatact gaggctcaac   3120
atagtgcagc tgtagaggca gcagaaacaa aacgtcagtc attgattgat actgcgatgg   3180
attccattag tctgattcag ttgaaattac gggctggacg gaagttgacg caggcagaaa   3240
ccacgcagct taactccgtg ctagattata tagacgagct gaacgcgatg gatttaacca   3300
cggcaccaga tctcaactgg cctgaaaaac aactttctac agccagttga              3350
```

<210> SEQ ID NO 31
<211> LENGTH: 4520
<212> TYPE: DNA
<213> ORGANISM: Artificial Sequence
<220> FEATURE:
<223> OTHER INFORMATION: Thistle Tail Fiber

<400> SEQUENCE: 31

```
atgtctgacg tctcaacaaa cctctataag agtcagttgt tggactatta ctatcagcgg     60
cgcgctgaat cgtccattaa caaaggctct cgatttttaa tcagcaaggc cgttttcggt    120
accagttcgc tggttactaa gaaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg gataacgaga caagccaat cgccattatt    360 tgtgtccagg aagactcgct gtatgtgggc aaaacatata ccgcagttat ggccataaac    420
```

-continued

```
acgactacag cataaggata tgcttgatga atgacgttac agttgttaca tcggttactt    480
acccatcatc cgagtcgttg gctctggtgg ccgatgtgca ataccacgaa ccatatctgt    540
cagccgcgct aaaccgaaaa ttcaggggga ttgttgaccc gggatttat gccggtttct     600 tacctaagcc tggcggtggg atgaacctgt taattacctc agtggatggt gataaaaccg    660
caggcgcggc gtcggtggat attggtgaat tttaccaggt aactattcag caacgtaagg    720
atatttctct tgcacttagt gcaggcaaga aatatgcaat tgtgctgaag gaagatacc     780 tccttggaga agatacctac caggtgaata ccgcgtcaca tattcatgcg gctgaatttg    840
ttgccagaac ctataccgat tcatatcagt taggagatgg ggagctgctt gtttgtacgg    900
tgaatatccc tgctagtgta tctgccatta cccaggagat gattgataca tccgagcgta    960
tcaaccgctc gatcggcatt gatatttcag actctgtaac cagtaccaga agtgatgttg   1020
ctgcaagttc gctggcagtt aaaaaagcct acgatctggc gaaaagcaag tatacggcac   1080
aggatgcaag cacaacgcaa aagggattag ttcagctcag tagcgcaact aacagcgaca   1140
gcgaaacaat ggcggctacc cctaaagctg ttaagtctat aaaagatctg gctgatacca   1200
aagcgccaat agaaagcccg agtctgacag gaacgccaac cgcgccgacg gcagcgcaag   1260
gtacaaacag cacgcagatc gcaaatacag cctttgttaa ggcagctata actgcactta   1320
tcaacggtgc gcctggcaca ctggatacgt gaaagaaat agcggctgcg atcaataacg    1380
acccgaatta cagcacaact atcaacaatg ccttggctct caaagcgcct ttggcaagcc   1440
ctgcattaac gggtgtccct actgcgccta cggctgcaca gggcacaaac aatacgcaga   1500
tcgctacgac tgcttacgta cgggctgcta tctctgcatt ggtcggctca tcacctgaag   1560
ctcttgatac cctgtatgag cttgcagcag cactgggcaa tgacccgaac tttgcgacaa   1620
caatgacaaa tgcgctggca gggaaacagc cacttgatgc aactttaacc gcgcttgctg   1680
gtcttgcgac aggcgcaaat aaattgccgt actttaccgg tacagacact gtttctcaga   1740
ctgacttaac gtcagttggt cgcgatattc tggccaaaac aagcattctt gctgttatcc   1800
aataccttgg tttaagagaa ctcggcacaa gcggtgaaaa gatccccctg ttgagcacgg   1860
ctaacacatg gagtgcacgc cagactttta acggcgggat caccggggcg ctgacaggga   1920
acgccgatac cgcgacgaag ttgaaaacag cacggaagat taacaacgtt tcatttgatg   1980
gttcggcaga cataacgctg acacctgaga accttggcgt caccagtctg acgtttgaga   2040
aaaacaacgg tgaaatgcct attgatgctg acctaaatac tttcggtccc gttgaggctt   2100
atcttggtgt ctggtccaaa gcaacatcca ccaacgcaac actggagaaa atttcccgg    2160 aagataatgc tgtcggtgtg cttgaggtat ttgctgccgg aaattttgca ggtacgcaac   2220
gctttaccac gagagacggc aatgtataca tacgcagact cgccaataag tggaatggct   2280
ctgatggtcc gtggggcata tggcgtcaca ctcaatcagc tacccgccct ttgagtacga   2340
ctatagacct gaatacgctt ggagccgccg aacatcttgg tttatggcgt aacagtagct   2400
cggctatagc ttcatatgaa cgcaattatc agaggaagg cggcttttgct caggggggtgc   2460 ttgagatcct cgaaggcggg aattatggaa gaacgcaacg ttataccact cgccgcggaa   2520
atatgtatgt ccgctgcctt gcggcaagct gggatgcatc aaatccgcag tgggaaccgt   2580
ggttaaaagt cggtcatcag tcagagagtc gttattacga aggtgattta aatgttctaa   2640
ccgaccccgg tatttacagt gttacaggaa aggcaacaaa cggtccgatg ctggacaccg   2700
ttggcgcgac actacttggg atactggaag taatcagacg ttttgatggt gtgtctgtct   2760
ggcagcgtta cacaaccaca gggaaatcag aaaccacaca gggacgcact tttgagcgcg   2820
```

```
tctacgccgg gagcaaatgg accgaatggc gagaagtata taactccttt tcgttgcctc      2880
tgaatctggg catcggtggc gcagtggcaa actatccag tctggactgg cagacctacg      2940
attttgtgcc gggcagtctg ataaccgtgc ggcttgataa catgaccaac attcccgacg      3000
gtatggactg gggcgtcatt gatggcaacc tgataaacat cgcagttggt ccgagtgatg      3060
attccggtac ggggcgctca atgcatgtat ggcgcagcac tgtaagtaaa gcgaactacc      3120
gcttttttat ggtgcgtatt tcaggaaatc cggaagccg cacgatcaca gcaagacgag       3180
taccaatcat tgacgaagcc cagacatggg gcgcgaaaca gacattcagt gctggccttt      3240
ctggtgaact gtccggcaat gcggcgacag caacaaagct gaaaacagcc cgtaaaatta      3300
ataacgtttc gtttgatggt tccggggata ttgaggtcct tcctgttggt gttccgctgc      3360
cgtggccatc agatactgtg ccgtctggtt acgccctgat gcagggacag acttttgaca      3420
aatctgcata cccgaaactt gcagccgctt atccgtcagg cgtgatcccg gatatgcgtg      3480
gctggacaat caagggcaaa cccgccagtg gtcgggacg attgtctctg aacaggatg       3540 gcattaaatc gcacacccac agcgccagcg catccaatac ggatttgggt acgaaaacca      3600
catcttcgtt tgattacggt actaaatcaa cgaataacac aggtgcacat acccacaatg      3660
tatctggtac tgcaaatagt gctggcgcac atactcatac cgtgccatta aggagaccaa      3720
acagtggcgg tatgaatttc gactggctgg atggtgcatc aagtggcacg gtggtgggga      3780
atggaactgt gccttcttct ggcgcacata cccactcagt atcaggcacc gctacaagtg      3840
ctggggcaca tgcacacact gttggtattg gcgctcatac gcactctgtt gcgattggtt      3900
cacatggaca taccatcacc gttaacgctg ctggcaacgc ggaaaacacc gttaaaaaca      3960
tcgcatttaa ttatattgtg aggcttgcat aaatgcagca cttaaaaaat atcaggtcag      4020
gaaacccaaa gacaaagag caataccaat taacaagaa ttttgacgta atctggttgt        4080
ggtctgaaga cggaaaaac tggtatgagg aagtgaaaaa cttcaacca gacaccataa        4140 agattgttta cgatgaaaat aatattattg tcgccatcac caaagatgcc tccacgctta      4200
accctgaagg ttttagcgtc gttgaggttc ccgacataac agccaaccgc cgcgctgatg      4260
attcaggaaa gtggatgttt aaggatggag ctgtagttaa acggatttat acggcagacg      4320
aacagcaaca acaagccgaa tcacaaaagg ccgcattgct ttccgaagct gaatcagtca      4380
tccagccgct ggaacgcgct gtcaggctga atatggcaac agacgaggaa cgcacacgac      4440
tggaagcatg ggaacgctac agtgttctgg tcagccgtgt ggatacggca atcctgaat       4500 ggccacaaaa gcctgaataa                                                  4520
```

<210> SEQ ID NO 32
<211> LENGTH: 2132
<212> TYPE: DNA
<213> ORGANISM: Artificial Sequence
<220> FEATURE:
<223> OTHER INFORMATION: Tropical_pNS88 Tail Fiber

<400> SEQUENCE: 32

```
atgtctgacg tctcaacaaa cctctataag agtcagttgt tggactatta ctatcagcgg       60
cgcgctgaat cgtccattaa caaaggctct cgatttttaa tcagcaaggc cgttttcggt      120
accagttcgc tggttactaa gaaaggagat ggcacttatg agattggaga actgccaaag      180
gctttcgaac tggcagaact gaccagtcaa ttttgcacca tcaacctcgt cccaacctac      240
tcaggcggga taattactgt ccgaatggac cttgatcaaa gccagttgca ggaagggaaa      300
```

| | |
|---|---|
| aactacccat tcaacactct ggttgttctg ataacgaga acaagccaat cgccattatt | 360 |
| tgtgtccagg aagactcgct gtatgtgggc aaaacatata ccgcagttat ggccataaac | 420 |
| acgactacag cataaggata tgcttgatga atgacgttac agttgttaca tcggttactt | 480 |
| acccatcatc cgagtcgttg gctctggtgg ccgatgtgca ataccacgaa ccatatctgt | 540 |
| cagccgcgct aaaccgaaaa ttcaggggga ttgttgaccc gggatttat gccggtttct | 600 |
| tacctaagcc tggcggtggg atgaacctgt taattacctc agtggatggt gataaaaccg | 660 |
| caggcgcggc gtcggtggat attggtgaat tttaccaggt aactattcag caacgtaagg | 720 |
| atatttctct tgcacttagt gcaggcaaga aatatgcaat tgtgctgaag gaagatacc | 780 |
| tccttggaga agatacctac caggtgaata ccgcgtcaca tattcatgcg gctgaatttg | 840 |
| ttgccagaac ctataccgat tcatatcagt taggagatgg ggagctgctt gtttgtacgg | 900 |
| tgaatatccc tgctagtgta tctgccatta cccaggagat gattgataca tccgagcgta | 960 |
| tcaaccgctc gatcggcatt gatatttcag actctgtaac cagtaccaga agtgatgttg | 1020 |
| ctgcaagttc gctggcagtt aaaaaagcct acgatctggc gaaaagcaag tatacggcac | 1080 |
| aggatgcact catcaaagag tacgacgaga acattggcgc gtgggagacg ttcgccacca | 1140 |
| cctcagcaaa ccagagcatc acagttacca tcaatggcac ccccgtgact atccccggca | 1200 |
| tcggtaagct ggcacagaaa gggaccaacg gtgctctccc gattgaccag ggcgggactg | 1260 |
| gtgcaacgaa cgctgcagat gttcgcacaa acctcggttt aggagacagc gtcacagcca | 1320 |
| acttcggaag cctcgaaatt ggagcgaaaa atgcctcttc tgcaagcttc gttgatttcc | 1380 |
| attttcttgg cactaatgac tatgacgcgc gcatcctgtg tggtggtaat tcgaatggag | 1440 |
| ggatggggaa aggtgatttc actttctatg ctggaaaata cactttatc ggtgacagtt | 1500 |
| ttgagtttcg aaatcctatc acctgccaga acagcataac tgcttcaggg agcattagcg | 1560 |
| caggcggctc actaagagcc gtaacgtcat caaacgtatg ggcctccagc gatacacaga | 1620 |
| acgctcacgt gtggttttac ggtgcgggag gtattgaatc acgagggta atctatgcgc | 1680 |
| ccagggaagg taccatccgg ctcaggcctg ataataatga taatggtgga gcaaatggct | 1740 |
| atagcttctc tttcggagct gatggcaggt ttacctgtat ttctgtgaac cagacttcgg | 1800 |
| atgagcgagt gaagttcgac aaagagcccg tcagtaacgc tctggagaag atttgttccc | 1860 |
| tgacgggtta tacattcggc atccaactga ctgaatcgga atcggtgcac agcgcaggca | 1920 |
| tcatagctca ggatttggaa aaagtgttgc ccgttgctgt aagttctggc gggaccggca | 1980 |
| ctacaccgac cggagaagag attaacgatc taaaaaccgt ggactacagt gcgatgagcg | 2040 |
| ccttgtatgt tgaggccatg aaggagctgg ccaaccgggt aaaaagtata gagagtgagt | 2100 |
| ttgccgaact caaagcccga tccgcgatat ag | 2132 |

<210> SEQ ID NO 33
<211> LENGTH: 2117
<212> TYPE: DNA
<213> ORGANISM: Artificial Sequence
<220> FEATURE:
<223> OTHER INFORMATION: Tropical_pNS92 Tail Fiber

<400> SEQUENCE: 33

| | |
|---|---|
| atgtctgacg tctcaacaaa cctctataag agtcagttgt tggactatta ctatcagcgg | 60 |
| cgcgctgaat cgtccattaa caaaggctct cgatttttaa tcagcaaggc cgttttcggt | 120 |
| accagttcgc tggttactaa gaaaggagat ggcacttatg agattggaga actgccaaag | 180 |
| gctttcgaac tggcagaact gaccagtcaa ttttgcacca tcaacctcgt cccaacctac | 240 |

```
tcaggcggga taattactgt ccgaatggac cttgatcaaa gccagttgca ggaagggaaa      300
aactacccat tcaacactct ggttgttctg gataacgaga caagccaat cgccattatt       360
tgtgtccagg aagactcgct gtatgtgggc aaaacatata ccgcagttat ggccataaac      420
acgactacag cataaggata tgcttgatga atgacgttac agttgttaca tcggttactt      480
acccatcatc cgagtcgttg gctctggtgg ccgatgtgca ataccacgaa ccatatctgt      540
cagccgcgct aaaccgaaaa ttcagggga ttgttgaccc gggattttat gccgtttct        600
tacctaagcc tggcggtggg atgaacctgt taattacctc agtggatggt gataaaaccg      660
caggcgcggc gtcggtggat attggtgaat tttaccaggt aactattcag caacgtaagg      720
atatttctct tgcacttagt gcaggcaaga aatatgcaat tgtgctgaag ggaagatacc      780
tccttggaga agatacctac caggtgaata ccgcgtcaca tattcatgcg gctgaatttg      840
ttgccagaac ctataccgat tcatatcagt taggagatgg ggagctgctt gtttgtacgg      900
tgaatatccc tgctagtgta tctgccatta cccaggagat gattgataca tccgagcgta      960
tcaaccgctc gatcggcatt gatatttcag actctgtaac cagtaccaga agtgatgttg     1020
ctgcaagttc gctggcagtt aaaaaagcct acgatctggc gaaaagcaag tatacggcac     1080
aggatgcaga cgagaacatt ggcgcgtggg agacgttcgc caccacctca gcaaaccaga     1140
gcatcacagt taccatcaat ggcacccccg tgactatccc cggcatcggt aagctggcac     1200
agaaagggac caacggtgct ctcccgattg accagggcgg gactggtgca acgaacgctg     1260
cagatgttcg cacaaacctc ggtttaggag acagcgtcac agccaacttc ggaagcctcg     1320
aaattggagc gaaaaatgcc tcttctgcaa gcttcgttga tttccatttt cttggcacta     1380
atgactatga cgcgcgcatc ctgtgtggtg gtaattcgaa tggagggatg gggaaaggtg     1440
atttcacttt ctatgctgga aaatacactt ttatcggtga cagttttgag tttcgaaatc     1500
ctatcacctg ccagaacagc ataactgctt cagggagcat tagcgcaggc ggctcactaa     1560
gagccgtaac gtcatcaaac gtatgggcct ccagcgatac acagaacgct cacgtgtggt     1620
tttacggtgc gggaggtatt gaatcacgag gggtaatcta tgcgcccagg gaaggtacca     1680
tccggctcag gcctgataat aatgataatg gtggagcaaa tggctatagc ttctctttcg     1740
gagctgatgg caggtttacc tgtatttctg tgaaccagac ttcggatgag cgagtgaagt     1800
tcgacaaaga gcccgtcagt aacgctctgg agaagatttg ttccctgacg ggttatacat     1860
tcggcatcca actgactgaa tcggaatcgg tgcacagcgc aggcatcata gctcaggatt     1920
tggaaaaagt gttgcccgtt gctgtaagtt ctggcggac cggcactaca ccgaccggag     1980
aagagattaa cgatctaaaa accgtggact acagtgcgat gagcgccttg tatgttgagg     2040
ccatgaagga gctggccaac cgggtaaaaa gtatagagag tgagtttgcc gaactcaaag     2100
cccgatccgc gatatag                                                    2117
```

<210> SEQ ID NO 34
<211> LENGTH: 3908
<212> TYPE: DNA
<213> ORGANISM: Artificial Sequence
<220> FEATURE:
<223> OTHER INFORMATION: Violet Tail Fiber

<400> SEQUENCE: 34

```
atgtctgacg tctcaacaaa cctctataag agtcagttgt tggactatta ctatcagcgg       60
cgcgctgaat cgtccattaa caaaggctct cgattttaa tcagcaaggc cgttttcggt       120
```

```
accagttcgc tggttactaa gaaaggagat ggcacttatg agattggaga actgccaaag    180
gctttcgaac tggcagaact gaccagtcaa ttttgcacca tcaacctcgt cccaacctac    240
tcaggcggga taattactgt ccgaatggac cttgatcaaa gccagttgca ggaagggaaa    300
aactacccat tcaacactct ggttgttctg gataacgaga acaagccaat cgccattatt    360
tgtgtccagg aagactcgct gtatgtgggc aaaacatata ccgcagttat ggccataaac    420
acgactacag cataaggata tgcttgatga atgacgttac agttgtcaca tcggttactt    480
acccatcacc cgagtcgttg gctctggtgg ctgatgtgca ataccacgaa ccatatctgt    540
cagccgcgct aaaccgaaaa ttcaggggga ttgttgaccc gggatttat gccggtttct     600 tacctaagcc tggcggtggg atgaacctgt taatcacctc agtggatggt gataaaaccg    660
caggcgcggc gtcggtggat attggtgaat tctaccaggt aactattcag caacgtaagg    720
atatttctct tgcacttagt gcaggcaaga aatatgcaat tgtgctgaag ggaagatacc    780
tccttggaga agatacctat caggtgaata ccgcgtcaca tattcatgcg gctgaatttg    840
ttgccagaac ctataccgat tcatatcagt taggagatgg ggagctgctt gtttgtacgg    900
tgaatatccc tgctggtgta tctgccatta cccaggagat gattgataca tccgagcgta    960
tcaaccgcac gatcggcatt gatatttcag actctgtaac cagtaccaga agtgatgttg   1020
ctgcaagttc gctggcagtt aaaaaagcct acgatctggc gaaaagcaag tatacggcgc   1080
aggatgcaag cataacgcaa aagggattag ttcagctcag tagcgcaact aacagcgaca   1140
gcgaaacaat ggcggctacc cctaaagctg ttaagtctat aaaagatctg gctgatacca   1200
aagcgccaat agaaagcccg agtctgacag gaacgccaag cgcgccgacg gcagcgcaag   1260
gtacaaacag cacgcagata gcaaatacag cctttgttaa ggcagctata actgcactta   1320
tcaacggtgc acctggcaca ctggatacac ttaaagaaat agctgctgcg atcaataacg   1380
acccgaattt cagcacaact gtcaacaatg ctctggccct taaagcgcct ttagcaagtc   1440
ctgcattaac gggaataccc actgcgccta ccgctgcaca gggtacgaat aacacgcaga   1500
ttgctacgac cgcttatgta agagctgcca tatccgcatt ggttggttca tcaccagaag   1560
ctcttgatac cctgaatgag cttgccgcag cacttggtaa tgacccgaac tttgcgacaa   1620
caatgacaaa tgcgctggca ggcaaacagc ctctggatgc aactttaacc gcgctcgctg   1680
gccttgcgac tggtgcaaac aaactgcctt atttcaccgg taaggatacg gtagcgcaga   1740
ctgatttaac gtcagtcggt cgcgatattc tggccaaaac aagcgttctt gctgttatcc   1800
aataccttgg tttaagagaa ctcggtacca gtggtgaaaa gatccccctg ttgagcacgg   1860
ctaacacatg gagtgcacgc cagacttta acggcgggat caccggggcg ctgacaggga    1920
acgccgacac cgcgacgaaa ttaaaaacag ccataaacat taatggcgtc agattcgatg   1980
gttctacgaa catttcgata ccaacaatta cgtctagagg acgcgttact gcgcttaccg   2040
gtacaacgca aggtgctgct actgcgattgc agatgtatga ggcatacaac aatggttatc   2100
cgacgactta cggaaatgta cttcacctga agggagctgc atccactggt gaaggcgagt   2160
tgctcattgg ctggagtggc acaaatggcg ctcatgcacc agctttcatt cgatccaaaa   2220
gagatatcac tgctgcggca tggtccgaat gggcacagat ctatacgtca aaagattccg   2280
ttcccggcgt taataccaaa gggaatcagg acacctctgg taatgcggct acagcgacca   2340
aattgcagac ggcgtgtact atcaacggtg tctcgtttga cggttctaaa aatattgagc   2400
taacggcggc agatttaaat cttgagcaaa ctgtagaatt agccgcagga gcattacaga   2460
aaaaccagaa cggcgcagat attccgggaa aagataccctt taccaaaaat attggtgcct   2520
```

```
gccgcgcata tagcgcatgg ctgaatattg gtggcgatag tcaggtctgg acaaccgcgc    2580
aatttatttc gtggctggag agtcaggag catttaacca tccttactgg atgtgcaaag     2640
gctcatgggc ttatgcaaat aataaggtca ttacagatac aggttgcgga aatatttgtc    2700
ttgcaggtgc tgtggtggaa gttattggca ctcgcgcgc aatgaccata cgcgttacta     2760
cgccgagcac gtccagcggt ggcggaatta ctaacgctca attcacttat attaatcatg    2820
gtgatgctta tgctcctggc tggcgaagag actacaacac gaaaaaccag cagcctgcat    2880
ttgctttagg gcaaacagga agcagggttg caaatgataa agctgttggc tggaactgga    2940
atagcggcgt ttatgatgca gatatcagtg gcgcatcgac attaatcctc cacttcaata    3000
tgaatgcggg gagttgccct gctgtacagt tccgcgtgaa ttataagaac ggcggtatct    3060
tttatcgttc agcgcgtgat ggttatggct ttgaagctaa ctggtcagag ttttacacca    3120
caacccgcaa accctctgcg ggggatgttg gtgcatatac gcaggcagaa tgtaactcaa    3180
ggtttattac aggtattcgc ctgggcggtc tgtcatctgt tcagacatgg aatggtcccg    3240
gctggtctga caggtcaggt tatgtcgtta caggttcagt taacggaaac cgtgatgaat    3300
taattgatac aactcaggca aggccaattc agtattgcat taatgggacg tggtataacg    3360
cggggagtat ttaaatgatg cacttaaaaa acattactgc tggcaaccct aaaacaaaag    3420
agcaatacca gctaacgaaa caatttaaca tcaaatggct ttatacagag gatgggaaaa    3480
actggtatga ggaacaaaag aactttcagc ctgatacgtt gaaaatggtc tatgaccaca    3540
acgacgttat tatttgtatt gaaaaggatg tttcagcaat taatccagaa ggcgcaagcg    3600
tcgttgaggt tcctgatatt acagcaaatc gccgggctga tatttcgggt aaatggatgt    3660
tcaaagatgg cgtagtgata aagcgaactt ataccgagga ggaacaaagg cagcaggcag    3720
agaatgaaaa acaaagcctg ttgcaacttg tcagggataa aacccagcta tgggactcac    3780
agctacggct gggcatcatt tccgacgaga ataaacaaaa attaactgag tggatgctct    3840
atgcgcagaa agtcgaatct acagacacct ccagcctgcc agtaacattt cccgaacaac    3900
ctgaatga                                                            3908
```

<210> SEQ ID NO 35
<211> LENGTH: 990
<212> TYPE: PRT
<213> ORGANISM: Artificial Sequence
<220> FEATURE:
<223> OTHER INFORMATION: Asparagus Tail Fiber

<400> SEQUENCE: 35

```
Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110
```

```
Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
        260                 265                 270

Thr Asn Ser Thr Gln Ile Ala Asn Thr Ala Phe Val Lys Ala Ala Ile
    275                 280                 285

Thr Ala Leu Ile Asn Gly Ala Pro Gly Thr Leu Asp Thr Leu Lys Glu
290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
                325                 330                 335

Val Pro Thr Ala Pro Thr Ala Ala Gln Gly Thr Asn Asn Thr Gln Ile
        340                 345                 350

Ala Thr Thr Ala Tyr Val Arg Ala Ala Ile Ser Ala Leu Val Gly Ser
    355                 360                 365

Ser Pro Glu Ala Leu Asp Thr Leu Tyr Glu Leu Ala Ala Ala Leu Gly
370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
                420                 425                 430

Asp Leu Thr Ser Val Gly Arg Asp Ile Leu Ala Lys Thr Ser Ile Leu
            435                 440                 445

Ala Val Ile Gln Tyr Leu Gly Leu Arg Glu Leu Gly Thr Ser Gly Glu
    450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
                485                 490                 495

Thr Lys Leu Lys Thr Ala Arg Asn Ile Asn Gly Val Arg Phe Asp Gly
            500                 505                 510

Ser Gly Asp Ile Asn Ile Asn Thr Leu Val Ser Arg Gly Arg Val Thr
        515                 520                 525
```

```
Ala Leu Glu Ala Asn Ala Gln Gly Thr Ser Gly Ile Gln Leu Tyr Glu
            530                 535                 540

Ala Tyr Asn Asn Gly Tyr Pro Ser Pro Tyr Gly Asn Val Leu His Leu
545                 550                 555                 560

Lys Gly Ala Thr Ala Ala Gly Glu Gly Glu Leu Phe Ile Gly Trp Ser
                565                 570                 575

Gly Thr Ser Gly Ala His Ala Pro Val His Ile Arg Ser Arg Arg Asp
            580                 585                 590

Thr Asp Ser Ala Asn Trp Ser Glu Trp Ala Gln Val Tyr Thr Ser Lys
            595                 600                 605

Asp Ser Ile Pro Gly Val Asn Ala Lys Gly Asp Gln Asp Thr Ser Gly
            610                 615                 620

Asn Ala Ala Thr Ala Thr Lys Leu Gln Thr Ala Cys Thr Ile Asn Gly
625                 630                 635                 640

Val Ser Phe Asp Gly Ser Lys Asn Ile Glu Leu Thr Ala Glu Asp Leu
                645                 650                 655

Asn Leu Gln Glu Thr Val Asn Lys Ala Asp Asn Ala Val Gln Lys Thr
            660                 665                 670

Gly Asp Thr Leu Ser Gly Gly Leu Thr Phe Glu Asn Asp Ser Ile Leu
            675                 680                 685

Ala Trp Ile Arg Asn Thr Asp Trp Ala Lys Ile Gly Phe Lys Asn Asp
690                 695                 700

Ala Asp Ser Asp Thr Asp Ser Tyr Met Trp Phe Glu Thr Gly Asp Asn
705                 710                 715                 720

Gly Asn Glu Tyr Phe Lys Trp Arg Ser Lys Gln Ser Thr Thr Thr Lys
                725                 730                 735

Asp Leu Met Asn Leu Lys Trp Asp Ala Leu Ser Val Leu Val Asn Ala
            740                 745                 750

Ile Val Asn Gly Glu Val Ile Ser Lys Ser Ala Asn Gly Leu Arg Ile
            755                 760                 765

Ala Tyr Gly Asn Tyr Gly Phe Phe Ile Arg Asn Asp Gly Ser Asn Thr
770                 775                 780

Tyr Phe Met Leu Thr Asn Ser Gly Asp Asn Met Gly Thr Tyr Asn Gly
785                 790                 795                 800

Leu Arg Pro Leu Trp Ile Asn Asn Ala Thr Gly Ala Val Ser Met Gly
                805                 810                 815

Arg Gly Leu Asn Val Ser Gly Asp Thr Leu Ser Asp Arg Phe Ala Ile
            820                 825                 830

Asn Ser Ser Asn Gly Met Trp Ile Gln Met Arg Asp Asn Asn Ala Ile
            835                 840                 845

Phe Gly Lys Asn Ile Val Asn Thr Asp Ser Ala Gln Ala Leu Leu Arg
850                 855                 860

Gln Asn His Ala Asp Arg Lys Phe Met Ile Gly Gly Leu Gly Asn Lys
865                 870                 875                 880

Gln Phe Gly Ile Tyr Met Ile Asn Asn Ser Arg Thr Ala Asn Gly Thr
                885                 890                 895

Asp Gly Gln Ala Tyr Met Asp Asn Asn Gly Asn Trp Leu Cys Gly Ala
            900                 905                 910

Gln Val Ile Pro Gly Asn Tyr Ala Asn Phe Asp Ser Arg Tyr Val Arg
            915                 920                 925

Asp Val Arg Leu Gly Thr Gln Ser Leu Thr Gly Gly Leu Ser Arg Asp
            930                 935                 940

Tyr Lys Ala Pro Ser Gly His Val Ile Thr Gly Phe His Thr Asn Gly
```

-continued

```
              945                 950                 955                 960

Asp Trp Glu Met Gln Gly Gly Asp Asp Lys Val Tyr Ile Arg Pro Val
                    965                 970                 975

Gln Lys Asn Ile Asn Gly Thr Trp Tyr Asn Val Ala Ser Ala
                    980                 985                 990

<210> SEQ ID NO 36
<211> LENGTH: 763
<212> TYPE: PRT
<213> ORGANISM: Artificial Sequence
<220> FEATURE:
<223> OTHER INFORMATION: Banana Tail Fiber

<400> SEQUENCE: 36

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
                20                  25                  30

Ala Ala Leu Asn Arg Lys Phe Arg Gly Ile Val Asp Pro Gly Phe Tyr
            35                  40                  45

Ala Gly Phe Leu Pro Lys Pro Gly Gly Met Asn Leu Leu Ile Thr
        50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Thr Thr Ala Arg Lys Gly Ile Val Gln Leu
    210                 215                 220

Ser Ser Ala Thr Asp Ser Thr Ser Glu Ala Leu Ala Ala Thr Pro Lys
225                 230                 235                 240

Ala Val Lys Ala Val Asn Asp Asn Ala Asn Gly Arg Val Pro Ser Ala
                245                 250                 255

Arg Lys Val Asn Gly Arg Ala Leu Ala Ser Asp Ile Ser Ile Thr Ala
            260                 265                 270

Gln Asp Ile Phe Asn Gly Gln Ala Val Ala Ile Gly Asn Ala Ala Asp
        275                 280                 285

Leu Asn Ala Tyr Thr Thr Pro Gly Leu Tyr Tyr Gln Pro Ala Asn Ala
    290                 295                 300

Gln Ala Gln Thr Gly Arg Asn Tyr Pro Glu Ala Asn Ala Gly Ser Leu
305                 310                 315                 320

Glu Val Tyr Lys His Ala Gly Ile Thr Gln Ile Tyr Arg Ile Tyr Asn
```

```
              325                 330                 335
Ser Ser Arg Ser Tyr Ile Arg Thr Leu Tyr Ser Gly Thr Trp Ser Ala
              340                 345                 350
Trp Val Lys Gln Tyr Asp Ala Ala Asn Lys Pro Ser Pro Ala Asp Ile
              355                 360                 365
Asn Ala Val Asn Lys Gly Gly Asp Thr Met Thr Gly Gly Leu Lys Ile
              370                 375                 380
Arg Ala Ala Asp Ala Leu Arg Ile Tyr Asp Ala Ala Tyr Gly Met Ile
385                 390                 395                 400
Phe Arg Arg Ser Glu Asn Asn Phe Tyr Leu Ile Pro Thr Ala Lys Asp
                  405                 410                 415
Gln Gly Glu Asp Gly Gly Ile Ser Gly Leu Arg Pro Leu Tyr Ile Asp
                  420                 425                 430
Leu Thr Asn Gly Arg Val Thr Leu Gly Asn Gly Ala Val Val Asn Gly
                  435                 440                 445
Gly Leu Gly Leu Gly Val Val Ser Gly Leu Gly Asn Ser Ile Ala
450                 455                 460
Leu Gly Asp Asn Asp Thr Gly Phe Lys Gln Asn Gly Asp Gly Val Leu
465                 470                 475                 480
Asp Val Tyr Ala Asn Ser Lys Gln Val Met Arg Phe Leu Asn Ser Gly
                  485                 490                 495
Ile Thr Ser Tyr Met Leu Phe Asn Met Asn Ala Gly Ala Ser Val Ser
                  500                 505                 510
Ser Thr Leu Thr Phe Lys Asn Gly Ser Gly Ile Thr Ser Glu Lys Thr
                  515                 520                 525
Gly Ala Asn Pro Arg Asn Gly Arg Ile Tyr Trp Gly Gly Asp Ala Ser
                  530                 535                 540
Arg Gly Asn Arg Ile Glu Phe Ala Asp Asp Ala Gly Trp Lys Ala Tyr
545                 550                 555                 560
Ile Glu Arg His Pro Ser Asn Gly Val Gln Leu Val Val Asn Gly Arg
                  565                 570                 575
Ile Asn Gly Ser Ile Val Tyr Ser Ser Gly Glu Val Leu Ala Gly Gly
                  580                 585                 590
Gly Ser Ala Arg Phe Ala Ala Asp Gly Asn Ile Phe Gly Ser Lys Trp
                  595                 600                 605
Gly Asn Gln Trp Leu Asp Ala Tyr Leu Lys Asn Thr Tyr Gln Pro Lys
                  610                 615                 620
Gly Asn Tyr Thr Pro Ala Gly Gln Ala Tyr Thr Lys Val Glu Ser Asp
625                 630                 635                 640
Gly Arg Phe Gln Pro Lys Gly Ser Tyr Thr Pro Ala Gly Gln Ala Tyr
                  645                 650                 655
Thr Lys Ala Glu Ser Asp Ala Arg Tyr Asn Leu Lys Asn Thr Ala Thr
                  660                 665                 670
Lys Ser Ala Asn Ala Met Thr His Lys Asp Ala Ser Thr Gly Val Met
                  675                 680                 685
Glu Val Val Met Ser Asn Ile Asn Val Pro Asn Lys Thr Asn Val Asn
                  690                 695                 700
Val Thr Phe Pro Ala Ala Phe Pro Asn Ala Cys Val Gly Val Val Ile
705                 710                 715                 720
Thr Tyr Asn Gly Ala Gly His Gly Ser Gly Asp Asp Ser Ala Ile Tyr
                  725                 730                 735
Val Pro Ser Tyr Ser Arg Thr Gly Cys Thr Leu Tyr Ala His Asn Ala
                  740                 745                 750
```

```
Asp Gly Lys Phe Met Leu Ile Ala Lys Gly Tyr
            755                 760

<210> SEQ ID NO 37
<211> LENGTH: 748
<212> TYPE: PRT
<213> ORGANISM: Artificial Sequence
<220> FEATURE:
<223> OTHER INFORMATION: Bittersweet Tail Fiber

<400> SEQUENCE: 37

Met Asn Asp Val Thr Val Val Thr Ser Val Thr Tyr Pro Ser Pro Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln His Arg Lys Asp Ile Ser Leu Ala
                85                  90                  95

Leu Asn Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Gly Val Ser Thr
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Thr Ser Glu Val Leu Ala Ala Thr Pro Lys
225                 230                 235                 240

Ala Val Lys Ala Ala Tyr Asp Leu Ala Asn Gly Lys Tyr Thr Ala Gln
                245                 250                 255

Asp Ala Thr Thr Thr Gln Lys Gly Ile Val Gln Leu Ser Ser Asp Thr
            260                 265                 270

Asn Ser Thr Ser Glu Thr Leu Ala Ala Thr Pro Lys Ala Val Lys Ala
        275                 280                 285

Ala Tyr Asp Leu Ala Ala Gly Lys Ala Pro Ser Ser His Thr His Pro
    290                 295                 300

Trp Asn Gln Ile Thr Gly Val Pro Thr Ala Ser Leu Thr Ala Lys Gly
305                 310                 315                 320

Ile Thr Gln Leu Ser Ser Ala Thr Asn Ser Thr Ser Glu Val Leu Ala
                325                 330                 335

Ala Thr Pro Lys Ala Val Lys Ala Ala Tyr Asp Leu Ala Asn Gly Lys
            340                 345                 350
```

```
Tyr Thr Ala Gln Asp Ala Thr Thr Ala Gln Lys Gly Ile Val Gln Leu
            355                 360                 365

Ser Ser Ala Thr Asn Ser Thr Ser Glu Val Leu Ala Ala Thr Pro Lys
        370                 375                 380

Ala Val Lys Ala Ala Tyr Asp Leu Ala Asn Gly Lys Tyr Thr Ala Gln
385                 390                 395                 400

Asp Ala Thr Thr Gln Lys Gly Ile Val Gln Leu Ser Ser Asp Thr
                405                 410                 415

Asn Ser Thr Ser Glu Thr Leu Ala Ala Thr Pro Lys Ala Val Lys Ala
            420                 425                 430

Ala Tyr Asp Leu Ala Ala Gly Lys Ala Pro Ser Ser His Thr His Pro
            435                 440                 445

Trp Asn Gln Ile Thr Val Val Pro Thr Ala Ser Leu Thr Ala Lys Gly
        450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
                485                 490                 495

Tyr Thr Ala Gln Asp Ala Thr Thr Ala Gln Lys Gly Ile Val Gln Leu
            500                 505                 510

Ser Ser Ala Thr Asn Ser Thr Ser Glu Val Leu Ala Ala Thr Pro Lys
        515                 520                 525

Ala Val Lys Ala Ala Tyr Asp Leu Ala Asn Gly Lys Gln Ala Ala Asp
        530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
                565                 570                 575

Val Gly Arg Ala Ile Leu Gly Lys Thr Ser Ile Gln Ser Val Leu Asp
            580                 585                 590

Tyr Leu Gly Leu Gly Glu Gly Ser Ala Leu Pro Val Gly Val Pro Val
        595                 600                 605

Pro Trp Pro Ser Ala Thr Pro Pro Thr Gly Trp Leu Lys Cys Asn Gly
        610                 615                 620

Ala Ala Phe Ser Ser Glu Lys Tyr Pro Asn Leu Ala Lys Ala Tyr Pro
625                 630                 635                 640

Thr Asn Lys Leu Pro Asp Leu Arg Gly Glu Phe Ile Arg Gly Trp Asp
                645                 650                 655

Asp Gly Arg Gly Val Asp Ala Gly Arg Gln Leu Leu Ser Ser Gln Gly
            660                 665                 670

Asp Ala Ile Arg Asn Ile Glu Gly Phe Ala Asp Gly Ile Gly Met
            675                 680                 685

Ser Phe Asp Ala Ile Arg Gly Ala Phe Tyr Asp Ala Gly Thr Arg Ser
        690                 695                 700

Ala Arg Met Pro Asn Asn Thr Thr Thr Ile Asp Lys Thr Asp Asp Leu
705                 710                 715                 720

Gly Phe Asp Ala Ser Arg Val Val Pro Thr Ala Asn Glu Asn Arg Pro
                725                 730                 735

Arg Asn Ile Ala Phe Asn Tyr Ile Val Arg Ala Ala
            740                 745

<210> SEQ ID NO 38
<211> LENGTH: 737
```

-continued

```
<212> TYPE: PRT
<213> ORGANISM: Artificial Sequence
<220> FEATURE:
<223> OTHER INFORMATION: Cobalt Tail Fiber

<400> SEQUENCE: 38
```

Met Asn Asp Val Thr Val Val Thr Ser Val Thr Tyr Pro Ser Pro Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln His Arg Lys Asp Ile Ser Leu Ala
                85                  90                  95

Leu Asn Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Gly Val Ser Thr
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Gln Lys Gly Leu Val Gln Leu
    210                 215                 220

Ser Ser Ala Thr Asn Ser Thr Ser Glu Val Leu Ala Ala Thr Pro Lys
225                 230                 235                 240

Ala Val Lys Ala Ala Tyr Asp Leu Ala Asn Gly Lys Tyr Thr Ala Gln
                245                 250                 255

Asp Ala Thr Thr Thr Gln Lys Gly Ile Val Gln Leu Ser Ser Asp Thr
            260                 265                 270

Asn Ser Thr Ser Glu Thr Leu Ala Ala Thr Pro Lys Ala Val Lys Ala
        275                 280                 285

Ala Tyr Asp Leu Ala Ala Gly Lys Ala Pro Ser Ser His Thr His Pro
    290                 295                 300

Trp Asn Gln Ile Thr Gly Val Pro Thr Ala Ser Leu Thr Ala Lys Gly
305                 310                 315                 320

Ile Thr Gln Leu Ser Ser Ala Thr Asn Ser Thr Ser Glu Val Leu Ala
                325                 330                 335

Ala Thr Pro Lys Ala Val Lys Ala Ala Tyr Asp Leu Ala Asn Gly Lys
            340                 345                 350

Tyr Thr Ala Gln Asp Ala Thr Thr Ala Gln Lys Gly Ile Val Gln Leu
        355                 360                 365

Ser Ser Ala Thr Asn Ser Thr Ser Glu Val Leu Ala Ala Thr Pro Lys
    370                 375                 380

```
Ala Val Lys Ala Ala Tyr Asp Leu Ala Asn Gly Lys Tyr Thr Ala Gln
385                 390                 395                 400

Asp Ala Thr Thr Thr Gln Lys Gly Ile Val Gln Leu Ser Ser Asp Thr
            405                 410                 415

Asn Ser Thr Ser Glu Thr Leu Ala Ala Thr Pro Lys Ala Val Lys Ala
        420                 425                 430

Ala Tyr Asp Leu Ala Ala Gly Lys Ala Pro Ser Ser His Thr His Pro
        435                 440                 445

Trp Asn Gln Ile Thr Val Val Pro Thr Ala Ser Leu Thr Ala Lys Gly
    450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
                485                 490                 495

Tyr Thr Ala Gln Asp Ala Thr Thr Ala Gln Lys Gly Ile Val Gln Leu
            500                 505                 510

Ser Ser Ala Thr Asn Ser Thr Ser Glu Val Leu Ala Ala Thr Pro Lys
            515                 520                 525

Ala Val Lys Ala Ala Tyr Asp Leu Ala Asn Gly Lys Gln Ala Ala Asp
530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
                565                 570                 575

Val Gly Arg Ala Ile Leu Gly Lys Thr Ser Ile Gln Ser Val Leu Asp
            580                 585                 590

Tyr Leu Gly Leu Gly Glu Gly Ser Ala Leu Pro Val Gly Val Pro Val
            595                 600                 605

Pro Trp Pro Leu Glu Thr Pro Pro Thr Gly Trp Leu Lys Cys Asn Gly
    610                 615                 620

Ala Ala Phe Ser Ser Glu Met Tyr Pro Lys Leu Ala Lys Ala Tyr Pro
625                 630                 635                 640

Thr Asn Lys Leu Pro Asp Leu Arg Gly Glu Phe Ile Arg Gly Trp Asp
                645                 650                 655

Asp Gly Arg Gly Ile Asp Ala Gly Arg Thr Leu Leu Ser Gln Asp
            660                 665                 670

Gly Thr Ser Phe Ser His Tyr Gly Asn Phe Asp Ile Gly Ser Gly
            675                 680                 685

His Ser Ile Asn Asn Tyr Asp Gln Ile Val Ser Asn Gln Pro Gly Phe
    690                 695                 700

Ser Arg Phe Ser Phe Ala Gly Pro Ser Arg Gly Asp Gly Val Asn Tyr
705                 710                 715                 720

Val Thr Ile Arg Pro Arg Asn Ile Ala Phe Asn Tyr Ile Val Arg Ala
                725                 730                 735

Ala
```

<210> SEQ ID NO 39
<211> LENGTH: 578
<212> TYPE: PRT
<213> ORGANISM: Artificial Sequence
<220> FEATURE:
<223> OTHER INFORMATION: Cornflower Tail Fiber

<400> SEQUENCE: 39

Met Asn Asp Val Thr Val Val Thr Ser Val Thr Tyr Pro Ser Ser Glu

-continued

```
1               5                   10                  15
Ser Leu Ala Leu Val Ala Asp Val Gln Tyr His Glu Pro Tyr Leu Ser
            20                  25                  30
Ala Ala Leu Asn Arg Lys Phe Arg Gly Ile Val Asp Pro Gly Phe Tyr
            35                  40                  45
Ala Gly Phe Leu Pro Lys Pro Gly Gly Met Asn Leu Leu Ile Thr
            50                  55                  60
Ser Val Asp Gly Asp Lys Thr Ala Gly Ala Ser Val Asp Ile Gly
65                  70                  75                  80
Glu Phe Tyr Gln Val Thr Ile Gln Gln Arg Lys Asp Ile Ser Leu Ala
                85                  90                  95
Leu Ser Ala Gly Lys Lys Tyr Ala Ile Val Leu Lys Gly Arg Tyr Leu
            100                 105                 110
Leu Gly Glu Asp Thr Tyr Gln Val Asn Thr Ala Ser His Ile His Ala
            115                 120                 125
Ala Glu Phe Val Ala Arg Thr Tyr Thr Asp Ser Tyr Gln Leu Gly Asp
            130                 135                 140
Gly Glu Leu Leu Val Cys Thr Val Asn Ile Pro Ala Ser Val Ser Ala
145                 150                 155                 160
Ile Thr Gln Glu Met Ile Asp Thr Ser Glu Arg Ile Asn Arg Ser Ile
                165                 170                 175
Gly Ile Asp Ile Ser Asp Ser Val Thr Ser Thr Arg Ser Asp Val Ala
            180                 185                 190
Ala Ser Ser Leu Ala Val Lys Lys Ala Tyr Asp Leu Ala Lys Ser Lys
            195                 200                 205
Ala Ala Ile Ala Gly Met Ala Lys Ala Ser Asp Leu Asn Ala Leu Ala
            210                 215                 220
Lys Leu Thr Gly Gly Asn Lys Leu Asp Gly Ser Gln Val Ile Thr Ser
225                 230                 235                 240
Asp Asn Ala Gly Phe Ile Leu Gly Lys Asn Ser Asp Leu Ala Leu Leu
                245                 250                 255
Lys Lys Gln Gly Gln Gly Gly Thr Ile Ala Val Gly Ser Gly Thr Pro
            260                 265                 270
Phe Arg Val Gln Arg Ser Arg Ala Thr Thr Val Ser Pro Ala Asp Thr
            275                 280                 285
Phe Asp Asp Ile Leu Val Ile Asp Ala Asn Asn Arg Thr Thr Leu Pro
            290                 295                 300
Gly Ala Leu Thr Ala Gly Gly Asp Ile Asp Asn Thr Thr Lys Gly Leu
305                 310                 315                 320
Leu Tyr Thr Gln Ala Ile Glu Leu Ser Phe Ser Thr Pro Tyr Ile Asp
                325                 330                 335
Phe His Phe Asn Tyr Ser Thr Asp Phe Thr Gly Arg Ile Met Ala
            340                 345                 350
Thr Ala Ala Asp Gln Ile Ser Val Gln Gly Ser His Trp Arg Val Asp
            355                 360                 365
Arg Asp Leu Arg Val Gly Gly Met Ala Asp Ile Ala Gly Trp Ala Gln
            370                 375                 380
Cys Gly Val Asp Leu Ser Ala Asn Arg Thr Asp Phe Gly Ser Pro Ala
385                 390                 395                 400
Ile Gly Ser Leu Val Ser Gly Arg Ile Arg Ser Arg Met Leu Gly
                405                 410                 415
Arg Gly Gly Asn Val Asp Pro Ser Gly Ala Trp Gly Gly Phe Tyr Val
            420                 425                 430
```

-continued

```
Glu Glu His Val Gly Thr Glu His Arg Ile Ile Met Tyr Met Asp Gly
            435                 440                 445

Phe Gly Arg Thr Asp Ala Trp Ser Phe Arg Ala Gly Gly Val Ile Ser
    450                 455                 460

Thr Pro Lys Gly Asp Val Met Thr Thr Gly Ser Asp Val Arg Leu Lys
465                 470                 475                 480

Thr Asp Phe Thr Gln Ala Pro Gly Asn Ala Ser Glu Arg Ile Glu Arg
                485                 490                 495

Leu Gly Val Cys Glu Tyr Arg Met Lys Gly Glu Thr Arg Arg Arg Arg
            500                 505                 510

Gly Phe Ile Ala Gln Gln Ala Glu Lys Ala Asp Asp Leu Tyr Thr Phe
        515                 520                 525

Leu Gly Ile Glu Gln Glu Ile Asp Gly Glu Lys Phe Lys Val Met Asn
    530                 535                 540

Val Asp Tyr Thr Ala Ile Ile Ala Asp Leu Val Thr Val Ala Gln Gly
545                 550                 555                 560

Leu Leu Val Lys Asn Gln Glu Leu Glu Arg Ile Ser Val Leu Glu
                565                 570                 575

Gly Ile
```

<210> SEQ ID NO 40
<211> LENGTH: 737
<212> TYPE: PRT
<213> ORGANISM: Artificial Sequence
<220> FEATURE:
<223> OTHER INFORMATION: Denim Tail Fiber

<400> SEQUENCE: 40

```
Met Asn Asp Val Thr Val Thr Ser Val Thr Tyr Pro Ser Pro Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln His Arg Lys Asp Ile Ser Leu Ala
                85                  90                  95

Leu Asn Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Gly Val Ser Thr
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205
```

Tyr Thr Ala Gln Asp Ala Ser Thr Thr Gln Lys Gly Leu Val Gln Leu
210                 215                 220

Ser Ser Ala Thr Asn Ser Thr Ser Glu Val Leu Ala Ala Thr Pro Lys
225                 230                 235                 240

Ala Val Lys Ala Ala Tyr Asp Leu Ala Asn Gly Lys Tyr Thr Ala Gln
            245                 250                 255

Asp Ala Thr Thr Thr Gln Lys Gly Ile Val Gln Leu Ser Ser Asp Thr
            260                 265                 270

Asn Ser Thr Ser Glu Thr Leu Ala Ala Thr Pro Lys Ala Val Lys Ala
            275                 280                 285

Ala Tyr Asp Leu Ala Ala Gly Lys Ala Pro Ser Ser His Thr His Pro
290                 295                 300

Trp Asn Gln Ile Thr Gly Val Pro Thr Ala Ser Leu Thr Ala Lys Gly
305                 310                 315                 320

Ile Thr Gln Leu Ser Ser Ala Thr Asn Ser Thr Ser Glu Val Leu Ala
            325                 330                 335

Ala Thr Pro Lys Ala Val Lys Ala Ala Tyr Asp Leu Ala Asn Gly Lys
            340                 345                 350

Tyr Thr Ala Gln Asp Ala Thr Thr Ala Gln Lys Gly Ile Val Gln Leu
            355                 360                 365

Ser Ser Ala Thr Asn Ser Thr Ser Glu Val Leu Ala Ala Thr Pro Lys
370                 375                 380

Ala Val Lys Ala Ala Tyr Asp Leu Ala Asn Gly Lys Tyr Thr Ala Gln
385                 390                 395                 400

Asp Ala Thr Thr Thr Gln Lys Gly Ile Val Gln Leu Ser Ser Asp Thr
            405                 410                 415

Asn Ser Thr Ser Glu Thr Leu Ala Ala Thr Pro Lys Ala Val Lys Ala
            420                 425                 430

Ala Tyr Asp Leu Ala Ala Gly Lys Ala Pro Ser Ser His Thr His Pro
            435                 440                 445

Trp Asn Gln Ile Thr Val Val Pro Thr Ala Ser Leu Thr Ala Lys Gly
            450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
            485                 490                 495

Tyr Thr Ala Gln Asp Ala Thr Ala Gln Lys Gly Ile Val Gln Leu
            500                 505                 510

Ser Ser Ala Thr Asn Ser Thr Ser Glu Val Leu Ala Ala Thr Pro Lys
            515                 520                 525

Ala Val Lys Ala Ala Tyr Asp Leu Ala Asn Gly Lys Gln Ala Ala Asp
            530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
            565                 570                 575

Val Gly Arg Ala Ile Leu Gly Lys Thr Ser Ile Gln Ser Val Leu Asp
            580                 585                 590

Tyr Leu Gly Leu Gly Glu Gly Ser Ala Leu Pro Val Gly Val Pro Val
            595                 600                 605

Pro Trp Pro Ser Ala Thr Pro Pro Thr Gly Trp Leu Lys Cys Asn Gly
            610                 615                 620

Ala Ala Phe Ser Ser Glu Lys Tyr Pro Asn Leu Ala Lys Val Tyr Pro

```
                625                 630                 635                 640
Thr Asn Lys Leu Pro Asp Leu Arg Gly Glu Phe Ile Arg Gly Trp Asp
                    645                 650                 655

Asp Gly Arg Gly Val Asp Asn Gly Arg Ala Leu Leu Ser Ser Gln Glu
                    660                 665                 670

Ala Thr Asn Phe Ser Gln Arg Ala Gly Asn Ile Gly Asp Gly Ala Gly
                    675                 680                 685

His Ala Ile Asn Phe His Asp Gly Ile Val Gly Asn Gln Pro Gly Phe
                    690                 695                 700

Ser Arg Phe Asn Phe Thr Ser Asn Ser Val Gly Asp Gly Ile Asn Phe
705                 710                 715                 720

Val Ala Val Arg Pro Arg Asn Ile Ala Phe Asn Tyr Ile Val Arg Ala
                    725                 730                 735

Ala

<210> SEQ ID NO 41
<211> LENGTH: 939
<212> TYPE: PRT
<213> ORGANISM: Artificial Sequence
<220> FEATURE:
<223> OTHER INFORMATION: Eggplant Tail Fiber

<400> SEQUENCE: 41

Met Gly Ala Asp Lys Thr Asn Asn Ile Met Thr Leu Ser Ser Gly Val
1               5                   10                  15

Ser Gln Pro Leu Leu Ala Asp Val Gln Tyr Phe Glu Leu Tyr Ser Ser
                20                  25                  30

Ser Ala Leu Asn Arg Lys Leu Lys Asn Ile Val Leu Pro Gly Phe Tyr
                35                  40                  45

Cys Gly Phe Glu Pro Val Pro Gly Thr Gly Leu Ser Val Arg Ile Thr
        50                  55                  60

Ser Glu Asn Ser Glu Gly Lys Gly Ala Ala Ser Val Asp Val Asn Asn
65                  70                  75                  80

Val Gln Ile Ser Val Gln Gln Ile Glu Asp Val Thr Val Ser Val Lys
                85                  90                  95

Ala Gly Ala Thr Asn Ile Ile Val Leu Glu Ala Asn Phe Glu His Gly
                100                 105                 110

Val Lys Thr Thr Gln Val Asp Ser Ala Ser Ser Val Ser Ala Ala Arg
                115                 120                 125

Ile Tyr Ala Arg Thr Asp Asn Thr Ile Gly Gln Asn Gln Ile Glu Leu
        130                 135                 140

Cys Arg Val Ile Val Pro Asn Gly Ala Thr Ala Val Thr Lys Glu Met
145                 150                 155                 160

Ile Val Leu Lys Tyr Arg Val Asn Arg Ala Val Gly Val Glu Phe Ser
                165                 170                 175

Asn Glu Ile Ser Ser Thr Glu Glu Arg Lys Ala Ala Thr Pro Leu Ala
                180                 185                 190

Val Lys Thr Leu His Asp Leu Val Asp Thr Lys Ala Pro Leu Asp Ser
                195                 200                 205

Pro His Leu Ser Gly Thr Pro Thr Ser Pro Thr Pro Glu Pro Gly Thr
        210                 215                 220

Asn Asn Thr Gln Ile Ala Asn Ala Ala Phe Val Tyr Ala Ala Ile Asn
225                 230                 235                 240

Ala Leu Ile Asn Gly Ala Pro Gly Thr Met Asp Thr Leu Lys Glu Ile
                245                 250                 255
```

```
Ala Ala Ala Ile Asn Asn Asp Pro Asn Phe Ser Thr Ile Asn Asn
            260             265             270

Ala Leu Ala Leu Lys Ala Pro Leu Ala Ser Pro Ala Leu Thr Gly Ile
        275             280             285

Pro Thr Ala Pro Thr Ala Ala Gln Gly Thr Asn Asn Thr Gln Ile Ala
    290             295             300

Thr Thr Ala Tyr Val Arg Ala Ala Ile Ser Ala Leu Val Gly Ser Ser
305             310             315             320

Pro Glu Ala Leu Asp Thr Leu Asn Glu Leu Ala Ala Ala Leu Gly Asn
                325             330             335

Asp Pro Asn Phe Ala Thr Thr Met Thr Asn Ala Leu Ala Gly Lys Gln
            340             345             350

Pro Leu Asp Ala Thr Leu Thr Ala Leu Ala Gly Leu Ala Thr Gly Ala
        355             360             365

Asn Lys Leu Pro Tyr Phe Thr Gly Lys Asp Thr Val Ala Gln Thr Asp
    370             375             380

Leu Thr Ser Val Gly Arg Asp Ile Leu Ala Lys Thr Ser Thr Leu Ala
385             390             395             400

Val Ile Gln Tyr Leu Gly Leu Arg Glu Leu Gly Thr Ser Gly Glu Lys
                405             410             415

Ile Pro Leu Leu Ser Thr Ala Asn Thr Trp Ser Ala Arg Gln Thr Phe
            420             425             430

Asn Gly Gly Ile Thr Gly Ala Leu Thr Gly Asn Ala Asp Thr Ala Thr
        435             440             445

Lys Leu Lys Thr Ala Ile Asn Ile Asn Gly Val Arg Phe Asp Gly Ser
    450             455             460

Thr Asn Ile Ser Ile Pro Thr Ile Thr Ser Arg Gly Arg Val Thr Ala
465             470             475             480

Leu Thr Gly Thr Thr Gln Gly Ala Ala Thr Gly Leu Gln Met Tyr Glu
                485             490             495

Ala Tyr Asn Asn Gly Tyr Pro Ser Pro Tyr Gly Asn Val Leu His Leu
            500             505             510

Lys Gly Ala Thr Ala Ala Gly Glu Gly Glu Leu Phe Ile Gly Trp Ser
        515             520             525

Gly Thr Asn Gly Ala His Ala Pro Ala Phe Ile Arg Ser Lys Arg Asp
    530             535             540

Ser Thr Ala Ala Ala Trp Ser Glu Trp Ala Gln Ile Tyr Thr Ser Lys
545             550             555             560

Asp Ser Val Pro Gly Val Asn Ala Lys Gly Asn Gln Asp Thr Ser Gly
                565             570             575

Asn Ala Ala Thr Ala Thr Lys Leu Gln Ile Ala Cys Thr Ile Asn Gly
            580             585             590

Val Ser Phe Asp Gly Ser Lys Asn Ile Glu Leu Thr Ala Glu Asp Leu
        595             600             605

Asn Leu Gln Glu Thr Val Asn Lys Ala Asp Asn Ala Val Gln Lys Thr
    610             615             620

Gly Asp Thr Leu Ser Gly Gly Leu Thr Phe Glu Asn Asp Ser Ile Leu
625             630             635             640

Ala Trp Ile Arg Asn Thr Asp Trp Ala Lys Ile Gly Phe Lys Asn Asp
                645             650             655

Ala Asp Ser Asp Thr Asp Ser Tyr Met Trp Phe Glu Thr Gly Asp Asn
            660             665             670
```

```
Gly Asn Glu Tyr Phe Lys Trp Arg Ser Lys Gln Ser Thr Thr Lys
            675                 680                 685

Asp Leu Met Asn Leu Lys Trp Asp Ala Leu Tyr Val Leu Val Asn Ala
690                 695                 700

Ile Val Asn Gly Glu Val Ile Ser Lys Ser Ala Asn Gly Leu Arg Ile
705                 710                 715                 720

Ala Tyr Gly Asn Tyr Gly Phe Phe Ile Arg Asn Asp Gly Ser Asn Thr
                725                 730                 735

Tyr Phe Met Leu Thr Asn Ser Gly Asp Asn Met Gly Thr Tyr Asn Gly
            740                 745                 750

Leu Arg Pro Leu Trp Ile Asn Asn Ala Thr Gly Ala Val Ser Met Gly
            755                 760                 765

Arg Gly Leu Asn Val Ser Gly Glu Thr Leu Ser Asp Arg Phe Ala Ile
    770                 775                 780

Asn Ser Ser Asn Gly Met Trp Ile Gln Met Arg Asp Asn Asn Ala Ile
785                 790                 795                 800

Phe Gly Lys Asn Ile Val Asn Thr Asp Ser Ala Gln Ala Leu Leu Arg
                805                 810                 815

Gln Asn His Ala Asp Arg Lys Phe Met Ile Gly Gly Leu Gly Asn Lys
            820                 825                 830

Gln Phe Gly Ile Tyr Met Ile Asn Asn Ser Arg Thr Ala Asn Gly Thr
            835                 840                 845

Asp Gly Gln Ala Tyr Met Asp Asn Asn Gly Asn Trp Leu Cys Gly Ala
    850                 855                 860

Gln Val Ile Pro Gly Asn Tyr Gly Asn Phe Asp Ser Arg Tyr Val Arg
865                 870                 875                 880

Asp Val Arg Leu Gly Thr Arg Val Val Gln Leu Met Ala Arg Gly Gly
                885                 890                 895

Arg Tyr Glu Lys Ala Gly His Ala Ile Thr Gly Leu Arg Ile Ile Gly
            900                 905                 910

Glu Val Asp Gly Asp Glu Ala Ile Phe Arg Pro Ile Gln Lys Tyr
            915                 920                 925

Ile Asn Gly Thr Trp Tyr Asn Val Ala Gln Val
    930                 935
```

<210> SEQ ID NO 42
<211> LENGTH: 986
<212> TYPE: PRT
<213> ORGANISM: Artificial Sequence
<220> FEATURE:
<223> OTHER INFORMATION: Fern Tail Fiber

<400> SEQUENCE: 42

```
Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln Gln Arg Lys Asp Ile Ser Leu Ala
                85                  90                  95
```

```
Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
            115                 120                 125

Ala Glu Phe Val Ala Arg Thr Tyr Thr Asp Ser Tyr Gln Leu Gly Asp
        130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Gln Lys Gly Leu Val Gln Leu
        210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
        290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
                325                 330                 335

Val Pro Thr Ala Pro Thr Ala Ala Gln Gly Thr Asn Asn Thr Gln Ile
            340                 345                 350

Ala Thr Thr Ala Tyr Val Arg Ala Ala Ile Ser Ala Leu Val Gly Ser
        355                 360                 365

Ser Pro Glu Ala Leu Asp Thr Leu Tyr Glu Leu Ala Ala Ala Leu Gly
        370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
            420                 425                 430

Asp Leu Thr Ser Val Gly Arg Asp Ile Leu Ala Lys Thr Ser Ile Leu
        435                 440                 445

Ala Val Ile Gln Tyr Leu Gly Leu Arg Glu Leu Gly Thr Ser Gly Glu
        450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
                485                 490                 495

Thr Lys Leu Lys Thr Ala Arg Asn Ile Asn Gly Val Arg Phe Asp Gly
            500                 505                 510

Ser Gly Asp Ile Asn Ile Asn Thr Leu Val Ser Arg Gly Arg Val Thr
```

```
          515                 520                 525
Ala Leu Glu Ala Asn Ala Gln Gly Thr Ser Gly Ile Gln Leu Tyr Glu
    530                 535                 540

Ala Tyr Asn Asn Gly Tyr Pro Ser Pro Tyr Gly Asn Val Leu His Leu
545                 550                 555                 560

Lys Gly Ala Thr Ala Gly Glu Gly Glu Leu Phe Ile Gly Trp Ser
                565                 570                 575

Gly Thr Ser Gly Ala His Ala Pro Val His Ile Arg Ser Arg Arg Asp
                580                 585                 590

Thr Asp Ser Ala Asn Trp Ser Glu Trp Ala Gln Val Tyr Thr Ser Lys
            595                 600                 605

Asp Ser Ile Pro Gly Val Asn Ala Lys Gly Asp Gln Asp Thr Ser Gly
        610                 615                 620

Asn Ala Ala Thr Ala Thr Lys Leu Gln Thr Ala Cys Thr Ile Asn Gly
625                 630                 635                 640

Val Ser Phe Asp Gly Ser Lys Asn Ile Glu Leu Thr Ala Glu Asp Leu
                645                 650                 655

Asn Leu Gln Glu Thr Val Asn Lys Ala Gly Asn Ala Val Gln Lys Thr
            660                 665                 670

Gly Asp Thr Leu Ser Gly Gly Leu Thr Phe Glu Asn Asp Ser Ile Leu
        675                 680                 685

Ala Trp Ile Arg Asn Thr Asp Trp Ala Lys Ile Gly Phe Lys Asn Asp
690                 695                 700

Ala Asp Gly Asp Thr Asp Ser Tyr Met Trp Phe Glu Thr Gly Asp Asn
705                 710                 715                 720

Gly Asn Glu Tyr Phe Lys Trp Arg Ser Lys Arg Gly Thr Thr Thr Lys
                725                 730                 735

Asp Leu Met Asn Leu Lys Trp Asp Ala Leu Tyr Val Leu Val Asn Ala
            740                 745                 750

Ile Val Asn Gly Glu Val Ile Ser Lys Ser Ala Asn Gly Leu Arg Ile
        755                 760                 765

Ala Tyr Gly Asn Tyr Gly Phe Phe Ile Arg Asn Asp Gly Ser Asn Thr
770                 775                 780

Tyr Phe Met Leu Thr Asn Ser Gly Asp Asn Met Gly Thr Tyr Asn Gly
785                 790                 795                 800

Leu Arg Pro Leu Trp Ile Asn Asn Ala Thr Gly Ala Val Ser Met Gly
                805                 810                 815

Arg Gly Leu Asn Val Ser Gly Glu Thr Leu Gln Thr Val Cys Tyr Asn
            820                 825                 830

Ser Ser Asn Gly Met Trp Ile Gln Met Arg Asp Asn Asn Ala Ile Phe
        835                 840                 845

Gly Lys Asn Ile Val Asn Thr Asp Ser Ala Gln Ala Leu Leu Arg Gln
    850                 855                 860

Asn His Ala Asp Arg Lys Phe Met Ile Gly Gly Leu Gly Asn Lys Gln
865                 870                 875                 880

Phe Gly Ile Tyr Met Ile Asn Asn Ser Arg Thr Ala Asn Gly Thr Asp
                885                 890                 895

Gly Gln Ala Tyr Met Asp Asn Asn Gly Asn Trp Leu Cys Gly Ala Gln
            900                 905                 910

Ile Ile Pro Gly Asn Tyr Gly Asn Phe Asp Ser Arg Tyr Val Ser Asp
        915                 920                 925

Val Arg Leu Gly Thr Arg Val Val Gln Thr Met Gln Lys Gly Val Met
    930                 935                 940
```

-continued

```
Tyr Glu Lys Ser Gly His Ala Ile Thr Gly Leu Gly Ile Val Gly Glu
945                 950                 955                 960

Val Asp Gly Asp Pro Ala Val Phe Arg Pro Ile Gln Lys Tyr Ile
            965                 970                 975

Asn Gly Thr Trp Tyr Asn Val Ala Gln Val
            980                 985

<210> SEQ ID NO 43
<211> LENGTH: 972
<212> TYPE: PRT
<213> ORGANISM: Artificial Sequence
<220> FEATURE:
<223> OTHER INFORMATION: Fuchsia Tail Fiber

<400> SEQUENCE: 43

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
    290                 295                 300

Ile Ala Ala Ala Ile Asn Asn Asp Pro Asn Tyr Ser Thr Thr Ile Asn
305                 310                 315                 320
```

```
Asn Ala Leu Ala Leu Lys Ala Pro Leu Ala Ser Pro Ala Leu Thr Gly
                325                 330                 335

Val Pro Thr Ala Pro Thr Ala Ala Gln Gly Thr Asn Asn Thr Gln Ile
            340                 345                 350

Ala Thr Thr Ala Tyr Val Arg Ala Ala Ile Ser Ala Leu Val Gly Ser
        355                 360                 365

Ser Pro Glu Ala Leu Asp Thr Leu Tyr Glu Leu Ala Ala Ala Leu Gly
    370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
            420                 425                 430

Asp Leu Thr Ser Val Gly Arg Asp Ile Leu Ala Lys Thr Ser Ile Leu
        435                 440                 445

Ala Val Ile His Gly Leu Arg Glu Leu Gly Thr Ser Gly Glu Lys Ile
    450                 455                 460

Pro Leu Leu Ser Thr Ala Asn Thr Trp Ser Ala Arg Gln Thr Phe Asn
465                 470                 475                 480

Gly Gly Ile Thr Gly Ala Leu Ile Gly Asn Ala Asp Thr Ala Thr Lys
                485                 490                 495

Leu Lys Thr Ala Ile Asn Ile Asn Gly Val Arg Phe Asp Gly Ser Ala
            500                 505                 510

Asp Ile Asn Ile Asn Thr Leu Val Ser Arg Gly Arg Val Thr Ala Leu
        515                 520                 525

Gly Ala Asn Ala Gln Gly Thr Ser Gly Ile Gln Leu Tyr Glu Ala Tyr
    530                 535                 540

Asn Asn Gly Tyr Pro Ser Pro Tyr Gly Asn Val Leu His Leu Lys Gly
545                 550                 555                 560

Ala Thr Ala Ala Gly Glu Gly Glu Leu Phe Ile Gly Trp Ser Val Ser
                565                 570                 575

Ser Gly Asp His Ala Pro Val His Ile Arg Ser Arg Arg Asp Ile Asp
            580                 585                 590

Ser Ala Asn Trp Ser Glu Trp Ala Gln Val Tyr Thr Ser Lys Asp Ser
        595                 600                 605

Val Pro Gly Val Asn Ala Lys Gly Asn Gln Asp Thr Ser Gly Asn Ala
    610                 615                 620

Ala Thr Ala Thr Lys Leu Gln Thr Ala Cys Thr Ile Asn Gly Val Ser
625                 630                 635                 640

Phe Asp Gly Ser Lys Asn Ile Glu Leu Thr Ala Glu Asp Leu Asn Leu
                645                 650                 655

Glu Gln Thr Val Glu Leu Ala Ala Gly Ala Leu Gln Lys Asn Gln Asn
            660                 665                 670

Gly Ala Asp Ile Pro Asn Lys Asp Lys Phe Ile Gln Asn Thr Gly Ala
        675                 680                 685

Cys Arg Ala Phe Ser Gly Gln Thr Asp Ile Asp Gly Ser Gln Gly Glu
    690                 695                 700

Trp Ser Thr Val Ala Phe Ile Ser Trp Leu Glu Asn Asn Gly Ala Phe
705                 710                 715                 720

Arg His Pro Tyr Trp Met Cys Lys Gly Ser Trp Ser Tyr Ala Arg Asn
                725                 730                 735
```

```
Arg Val Ile Thr Asp Thr Gly Cys Gly Asn Ile Cys Leu Ala Gly Ala
            740                 745                 750

Val Ile Glu Val Met Gly Thr Arg Gly Ala Met Thr Ile Arg Val Thr
        755                 760                 765

Thr Pro Ser Thr Ser Ser Gly Gly Ile Thr Asn Ala Gln Phe Thr
    770                 775                 780

Tyr Ile Asn His Gly Asp Ala Tyr Ala Pro Gly Trp Arg Asp Tyr
785                 790                 795                 800

Asn Thr Lys Asn Gln Gln Pro Ala Phe Ala Leu Gly Gln Thr Gly Arg
                805                 810                 815

Arg Val Ala Asn Asp Lys Ala Val Gly Trp Asn Trp Asn Ser Gly Val
            820                 825                 830

Tyr Asp Ala Asp Ile Ser Gly Ala Ser Thr Leu Ile Leu His Phe Asn
            835                 840                 845

Met Asn Ala Gly Ser Cys Pro Ala Val Gln Phe Arg Val Asn Tyr Arg
    850                 855                 860

Asn Gly Gly Ile Phe Tyr Arg Ser Ala Arg Asp Gly Tyr Gly Phe Glu
865                 870                 875                 880

Ala Asn Trp Ser Glu Phe Tyr Thr Thr Thr Arg Lys Pro Ser Ala Gly
                885                 890                 895

Asp Val Gly Ala Tyr Thr Gln Ala Glu Cys Asn Ser Arg Phe Ile Thr
            900                 905                 910

Gly Ile Arg Leu Gly Gly Leu Ser Ser Val Gln Thr Trp Asn Gly Pro
            915                 920                 925

Gly Trp Ser Asp Arg Ser Gly Tyr Val Val Thr Gly Ser Val Asn Gly
    930                 935                 940

Asn Arg Asp Glu Leu Ile Asp Thr Thr Gln Ala Arg Pro Ile Gln Tyr
945                 950                 955                 960

Cys Ile Asn Gly Thr Trp Tyr Asn Ala Gly Ser Ile
            965                 970

<210> SEQ ID NO 44
<211> LENGTH: 550
<212> TYPE: PRT
<213> ORGANISM: Artificial Sequence
<220> FEATURE:
<223> OTHER INFORMATION: Fuzzy Tail Fiber

<400> SEQUENCE: 44

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ala Ser Val Asp Ile Gly
65              70                  75                  80

Glu Phe Tyr Gln Val Thr Ile Gln Gln Arg Lys Asp Ile Ser Leu Ala
            85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125
```

```
Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
                180                 185                 190

Ala Ser Ser Leu Ala Val Lys Lys Ala Tyr Asp Leu Ala Lys Ser Lys
            195                 200                 205

Lys Pro Asp Gly Thr Thr Gly Thr Val Lys Ser Trp Ala Gln Phe Leu
    210                 215                 220

Ser Glu Tyr Ser Ser Arg Gln Thr Ala Ile Asp Gly Ala Ile Thr Ala
225                 230                 235                 240

Ala Gly Lys Asn Val Ala Arg Thr Ser Ser Thr Asn Thr Phe Thr Gln
                245                 250                 255

Pro Gln Thr Phe Ser Asn Gly Val Thr Phe Ser Ala Thr Ile Thr Ala
                260                 265                 270

Ala Gly Gln Ile Leu Arg Asn Asn Ser Gly Thr Gln Phe Thr Ala Ile
            275                 280                 285

Asp Ala Gly Ser Leu Glu Ile Ser Ser Asp Thr Thr Pro Tyr Ile Asp
    290                 295                 300

Phe His His Lys Gly Ser Val Ala Asp Tyr Thr His Arg Ile Ile Thr
305                 310                 315                 320

Glu Asp Gly Ala Leu Ala Val Tyr Pro Gly Leu Arg Val Arg Gly Gly
                325                 330                 335

Phe Gly Leu Tyr Gly Val Gly Thr Val Tyr Gly Asp Ala Tyr Ser Gln
                340                 345                 350

Gly Phe Ile Ala Arg Leu Asn Asn Asp Pro Asn Ala Ser Ile Gly Asp
            355                 360                 365

Ile Leu Ala Ser Pro Arg Phe Thr Val Arg Phe Asn Ser Arg Gly Ser
    370                 375                 380

Asp Ser Asn Val Asp Gly Gly Gln Gly Ala Met Trp Phe Glu Glu Gln
385                 390                 395                 400

Val Gly Thr Asn His Arg Leu Val Leu Met Ala Gly Gly Phe Ser Ala
                405                 410                 415

Asn Val Gln Tyr Trp Gln Phe Leu Ala Asp Gly Arg Ile Tyr Ser Ser
                420                 425                 430

Gln Asn Gly Asn Val Gln Trp Gln Gly Thr Ser Asp Ala Arg Leu Lys
            435                 440                 445

His Asp Ile Glu Pro Thr Asp Gly Gln Leu Ser Val Glu Arg Ile Arg
    450                 455                 460

Lys Leu Glu Leu Val Thr Phe Val Tyr Asn Asp Asp Glu Gln Asn Arg
465                 470                 475                 480

Thr Arg Arg Gly Ile Ile Ala Gln Gln Ala Gln Lys Val Asp Pro Gln
                485                 490                 495

Tyr Val Lys Gln Val Asn Thr Ser Tyr Met Arg Asn Gly Glu Gln Val
                500                 505                 510

Asn Asp Asp Arg Leu Gln Leu Asp Asn Asn Val Ile Met Met Asp Thr
            515                 520                 525

Leu Ala Ala Val Lys Val Leu Leu Glu Arg Val Asp Glu Leu Glu Glu
    530                 535                 540

Arg Leu Ser Ala His Gly
```

545                     550

<210> SEQ ID NO 45
<211> LENGTH: 736
<212> TYPE: PRT
<213> ORGANISM: Artificial Sequence
<220> FEATURE:
<223> OTHER INFORMATION: Inchworm Tail Fiber

<400> SEQUENCE: 45

Met Asn Asp Val Thr Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Val Ala Ala Asp Phe Lys Gly Arg Lys Ile Leu Ala Gly Asn Gly Leu
    210                 215                 220

Leu Gly Gly Gly Asp Leu Ser Ala Asp Arg Ser Ile Gly Leu Ala Pro
225                 230                 235                 240

Ser Gly Val Thr Ala Gly Ser Tyr Arg Ser Val Thr Val Asn Ala Asn
                245                 250                 255

Gly Val Val Thr Gln Gly Ser Asn Pro Thr Thr Leu Ala Gly Tyr Ala
            260                 265                 270

Ile Gly Asp Ala Tyr Thr Lys Ala Asp Thr Asp Gly Lys Leu Ala Gln
        275                 280                 285

Lys Ala Asn Lys Ala Thr Thr Leu Ala Gly Tyr Gly Ile Thr Asp Ala
    290                 295                 300

Leu Arg Val Asp Gly Asn Ala Val Ser Ser Arg Leu Ala Ala Pro
305                 310                 315                 320

Arg Ser Leu Ala Ala Ser Gly Asp Ala Ser Trp Ser Val Thr Phe Asp
                325                 330                 335

Gly Ser Ala Asn Val Ser Ala Pro Leu Ser Leu Ser Ala Thr Gly Val
            340                 345                 350

Ala Ala Gly Ser Tyr Pro Lys Val Thr Val Asp Thr Lys Gly Arg Val 355                 360                 365
Thr Ala Gly Met Ala Leu Ala Ala Thr Asp Ile Pro Gly Leu Asp Ala
            370                 375                 380
Ser Lys Leu Val Ser Gly Val Leu Ala Glu Gln Arg Leu Pro Val Phe
385                 390                 395                 400
Ala Arg Gly Leu Ala Thr Ala Val Ser Asn Ser Ser Asp Pro Asn Thr
                405                 410                 415
Ala Thr Val Pro Leu Met Leu Thr Asn His Ala Asn Gly Pro Val Ala
            420                 425                 430
Gly Arg Tyr Phe Tyr Ile Gln Ser Met Phe Tyr Pro Asp Gln Asn Gly
                435                 440                 445
Asn Ala Ser Gln Ile Ala Thr Ser Tyr Asn Ala Thr Ser Glu Met Tyr
            450                 455                 460
Val Arg Val Ser Tyr Ala Ala Asn Pro Ser Ile Arg Glu Trp Leu Pro
465                 470                 475                 480
Trp Gln Arg Cys Asp Ile Gly Gly Ser Phe Thr Lys Glu Ala Asp Gly
                485                 490                 495
Glu Leu Pro Gly Gly Val Asn Leu Asp Ser Met Val Thr Ser Gly Trp
            500                 505                 510
Trp Ser Gln Ser Phe Thr Ala Gln Ala Ala Ser Gly Ala Asn Tyr Pro
            515                 520                 525
Ile Val Arg Ala Gly Leu Leu His Val Tyr Ala Ala Ser Ser Asn Phe
            530                 535                 540
Ile Tyr Gln Thr Tyr Gln Ala Tyr Asp Gly Glu Ser Phe Tyr Phe Arg
545                 550                 555                 560
Cys Arg His Ser Asn Thr Trp Phe Pro Trp Arg Arg Met Trp His Gly
                565                 570                 575
Gly Asp Phe Asn Pro Ser Asp Tyr Leu Leu Lys Ser Gly Phe Tyr Trp
            580                 585                 590
Asn Ala Leu Pro Gly Lys Pro Ala Thr Phe Pro Pro Ser Ala His Asn
            595                 600                 605
His Asp Val Gly Gln Leu Thr Ser Gly Ile Leu Pro Leu Ala Arg Gly
            610                 615                 620
Gly Val Gly Ser Asn Thr Ala Ala Gly Ala Arg Ser Thr Ile Gly Ala
625                 630                 635                 640
Gly Val Pro Ala Thr Ala Ser Leu Gly Ala Ser Gly Trp Trp Arg Asp
                645                 650                 655
Asn Asp Thr Gly Leu Ile Arg Gln Trp Gly Gln Val Thr Cys Pro Ala
            660                 665                 670
Asp Ala Asp Ala Ser Ile Thr Phe Pro Ile Pro Phe Pro Thr Leu Cys
            675                 680                 685
Leu Gly Gly Tyr Ala Asn Gln Thr Ser Ala Phe His Pro Gly Thr Asp
            690                 695                 700
Ala Ser Thr Gly Phe Arg Gly Ala Thr Thr Thr Ala Val Ile Arg
705                 710                 715                 720
Asn Gly Tyr Phe Ala Gln Ala Val Leu Ser Trp Glu Ala Phe Gly Arg
                725                 730                 735

<210> SEQ ID NO 46
<211> LENGTH: 762
<212> TYPE: PRT
<213> ORGANISM: Artificial Sequence
<220> FEATURE:
<223> OTHER INFORMATION: Indian Tail Fiber

```
<400> SEQUENCE: 46

Met Asn Asp Val Thr Val Val Thr Ser Val Thr Tyr Pro Ser Pro Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln His Arg Lys Asp Ile Ser Leu Ala
                85                  90                  95

Leu Asn Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Gly Val Ser Thr
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Thr Ser Glu Val Leu Ala Ala Thr Pro Lys
225                 230                 235                 240

Ala Val Lys Ala Ala Tyr Asp Leu Ala Asn Gly Lys Tyr Thr Ala Gln
                245                 250                 255

Asp Ala Thr Thr Thr Gln Lys Gly Ile Val Gln Leu Ser Ser Asp Thr
            260                 265                 270

Asn Ser Thr Ser Glu Thr Leu Ala Ala Thr Pro Lys Ala Val Lys Ala
        275                 280                 285

Ala Tyr Asp Leu Ala Ala Gly Lys Ala Pro Ser Ser His Thr His Pro
    290                 295                 300

Trp Asn Gln Ile Thr Gly Val Pro Thr Ala Ser Leu Thr Ala Lys Gly
305                 310                 315                 320

Ile Thr Gln Leu Ser Ser Ala Thr Asn Ser Thr Ser Glu Val Leu Ala
                325                 330                 335

Ala Thr Pro Lys Ala Val Lys Ala Ala Tyr Asp Leu Ala Asn Gly Lys
            340                 345                 350

Tyr Thr Ala Gln Asp Ala Thr Ala Gln Lys Gly Ile Val Gln Leu
    355                 360                 365

Ser Ser Ala Thr Asn Ser Thr Ser Glu Val Leu Ala Ala Thr Pro Lys
370                 375                 380

Ala Val Lys Ala Ala Tyr Asp Leu Ala Asn Gly Lys Tyr Thr Ala Gln
                385                 390                 395                 400

Asp Ala Thr Thr Thr Gln Lys Gly Ile Val Gln Leu Ser Ser Asp Thr
            405                 410                 415
```

Asn Ser Thr Ser Glu Thr Leu Ala Ala Thr Pro Lys Ala Val Lys Ala
            420                 425                 430

Ala Tyr Asp Leu Ala Ala Gly Lys Ala Pro Ser Ser His Thr His Pro
        435                 440                 445

Trp Asn Gln Ile Thr Val Val Pro Thr Ala Ser Leu Thr Ala Lys Gly
450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
                485                 490                 495

Tyr Thr Ala Gln Asp Ala Thr Thr Ala Gln Lys Gly Ile Val Gln Leu
            500                 505                 510

Ser Ser Ala Thr Asn Ser Thr Ser Glu Val Leu Ala Ala Thr Pro Lys
        515                 520                 525

Ala Val Lys Ala Ala Tyr Asp Leu Ala Asn Gly Lys Gln Ala Ala Asp
530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
                565                 570                 575

Val Gly Arg Ala Ile Leu Gly Lys Thr Ser Ile Gln Ser Val Leu Asp
            580                 585                 590

Tyr Leu Gly Leu Gly Glu Gly Ser Ala Leu Pro Val Gly Val Pro Val
        595                 600                 605

Pro Trp Pro Leu Glu Thr Pro Pro Thr Gly Trp Leu Lys Cys Asn Gly
610                 615                 620

Ala Ala Phe Ser Ser Glu Met Tyr Pro Lys Leu Ala Lys Ala Tyr Pro
625                 630                 635                 640

Thr Asn Lys Leu Pro Asp Leu Arg Gly Glu Phe Ile Arg Gly Trp Asp
                645                 650                 655

Asp Gly Arg Gly Val Asp Ala Gly Arg Ala Leu Leu Asn Trp Gln Pro
            660                 665                 670

His Thr Ile Leu Asp His Ala His Tyr Met Glu Leu Trp Thr Gly Asp
        675                 680                 685

Gly Leu Ala Ala Gly Ser Ala Arg Glu Gly Val Asn Pro Gly Ile Leu
690                 695                 700

Ala Thr Tyr Gly Asp Gly Gly Ile Val Lys Thr Asp Glu Pro Gly His
705                 710                 715                 720

Lys Val Pro Ser Ser Leu Arg Ala Ile Ser Ser Arg Ser Val Lys Arg
                725                 730                 735

Tyr Gly Glu Ile Ser Gly Asn Val Gly Thr Glu Thr Arg Pro Arg Asn
            740                 745                 750

Val Ala Phe Asn Tyr Ile Val Arg Ala Ala
        755                 760

<210> SEQ ID NO 47
<211> LENGTH: 750
<212> TYPE: PRT
<213> ORGANISM: Artificial Sequence
<220> FEATURE:
<223> OTHER INFORMATION: Indigo Tail Fiber

<400> SEQUENCE: 47

Met Asn Asp Val Thr Val Val Ser Val Thr Tyr Pro Ser Pro Glu
1               5                   10                  15

```
Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln His Arg Lys Asp Ile Ser Leu Ala
                85                  90                  95

Leu Asn Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
            115                 120                 125

Ala Glu Phe Val Ala Arg Thr Tyr Thr Asp Ser Tyr Gln Leu Gly Asp
130                 135                 140

Gly Glu Leu Leu Val Cys Thr Val Asn Ile Pro Ala Gly Val Ser Thr
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Thr Ser Glu Val Leu Ala Ala Thr Pro Lys
225                 230                 235                 240

Ala Val Lys Ala Ala Tyr Asp Leu Ala Asn Gly Lys Tyr Thr Ala Gln
                245                 250                 255

Asp Ala Thr Thr Thr Gln Lys Gly Ile Val Gln Leu Ser Ser Asp Thr
            260                 265                 270

Asn Ser Thr Ser Glu Thr Leu Ala Ala Thr Pro Lys Ala Val Lys Ala
        275                 280                 285

Ala Tyr Asp Leu Ala Ala Gly Lys Ala Pro Ser Ser His Thr His Pro
    290                 295                 300

Trp Asn Gln Ile Thr Gly Val Pro Thr Ala Ser Leu Thr Ala Lys Gly
305                 310                 315                 320

Ile Thr Gln Leu Ser Ser Ala Thr Asn Ser Thr Ser Glu Val Leu Ala
                325                 330                 335

Ala Thr Pro Lys Ala Val Lys Ala Ala Tyr Asp Leu Ala Asn Gly Lys
            340                 345                 350

Tyr Thr Ala Gln Asp Ala Thr Thr Ala Gln Lys Gly Ile Val Gln Leu
        355                 360                 365

Ser Ser Ala Thr Asn Ser Thr Ser Glu Val Leu Ala Ala Thr Pro Lys
    370                 375                 380

Ala Val Lys Ala Ala Tyr Asp Leu Ala Asn Gly Lys Tyr Thr Ala Gln
385                 390                 395                 400

Asp Ala Thr Thr Thr Gln Lys Gly Ile Val Gln Leu Ser Ser Asp Thr
                405                 410                 415

Asn Ser Thr Ser Glu Thr Leu Ala Ala Thr Pro Lys Ala Val Lys Ala
            420                 425                 430
```

```
Ala Tyr Asp Leu Ala Ala Gly Lys Ala Pro Ser Ser His Thr His Pro
            435                 440                 445

Trp Asn Gln Ile Thr Val Val Pro Thr Ala Ser Leu Thr Ala Lys Gly
450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
                485                 490                 495

Tyr Thr Ala Gln Asp Ala Thr Ala Gln Lys Gly Ile Val Gln Leu
            500                 505                 510

Ser Ser Ala Thr Asn Ser Thr Ser Glu Val Leu Ala Thr Pro Lys
            515                 520                 525

Ala Val Lys Ala Ala Tyr Asp Leu Ala Asn Gly Lys Gln Ala Ala Asp
            530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
                565                 570                 575

Val Gly Arg Ala Ile Leu Gly Lys Thr Ser Ile Gln Ser Val Leu Asp
            580                 585                 590

Tyr Leu Gly Leu Gly Glu Gly Ser Ala Leu Pro Val Gly Val Pro Val
            595                 600                 605

Pro Trp Pro Leu Glu Thr Pro Pro Thr Gly Trp Leu Lys Cys Asn Gly
            610                 615                 620

Ala Ala Phe Ser Ser Glu Lys Tyr Pro Asn Leu Ala Lys Ala Tyr Pro
625                 630                 635                 640

Thr Asn Lys Leu Pro Asp Leu Arg Gly Glu Phe Ile Arg Gly Trp Asp
                645                 650                 655

Asp Gly Arg Gly Ile Asp Ser Gly Arg Asn Leu Leu Ser Ala Gln Asn
            660                 665                 670

Asp Ala Ile Gln Asn Ile Val Gly Ser Phe Gly Arg Thr Gln Leu Phe
            675                 680                 685

Arg Asp Val Leu Ser Ser Gly Pro Phe Ser Gln His Gly Gln Val Leu
690                 695                 700

Ser Thr Gly Leu Lys Glu Thr Glu Ile Ile Glu Gly Tyr Gly Ser Tyr
705                 710                 715                 720

Asn Trp Thr Phe Asp Ala Ser Arg Ser Val Arg Thr Ala Ser Glu Thr
                725                 730                 735

Arg Pro Arg Asn Ile Ala Phe Asn Tyr Ile Val Arg Ala Ala
            740                 745                 750
```

<210> SEQ ID NO 48
<211> LENGTH: 1181
<212> TYPE: PRT
<213> ORGANISM: Artificial Sequence
<220> FEATURE:
<223> OTHER INFORMATION: Jazzberry Tail Fiber

<400> SEQUENCE: 48

```
Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
            35                  40                  45
```

```
Ala Gly Phe Leu Pro Lys Pro Gly Gly Met Asn Leu Leu Ile Thr
    50              55                  60

Ser Val Asp Gly Asp Lys Thr Ala Gly Ala Ser Val Asp Ile Gly
65              70              75                      80

Glu Phe Tyr Gln Val Thr Ile Gln Gln Arg Lys Asp Ile Ser Leu Ala
                85              90                  95

Leu Ser Ala Gly Lys Lys Tyr Ala Ile Val Leu Lys Gly Arg Tyr Leu
            100             105             110

Leu Gly Glu Asp Thr Tyr Gln Val Asn Thr Ala Ser His Ile His Ala
        115             120             125

Ala Glu Phe Val Ala Arg Thr Tyr Thr Asp Ser Tyr Gln Leu Gly Asp
    130             135             140

Gly Glu Leu Leu Val Cys Thr Val Asn Ile Pro Ala Ser Val Ser Ala
145             150             155             160

Ile Thr Gln Glu Met Ile Asp Thr Ser Glu Arg Ile Asn Arg Ser Ile
                165             170             175

Gly Ile Asp Ile Ser Asp Ser Val Thr Ser Thr Arg Ser Asp Val Ala
            180             185             190

Ala Ser Ser Leu Ala Val Lys Lys Ala Tyr Asp Leu Ala Lys Ser Lys
    195             200             205

Tyr Thr Ala Gln Asp Ala Ser Thr Thr Gln Lys Gly Leu Val Gln Leu
210             215             220

Ser Ser Ala Thr Asn Ser Asp Ser Glu Thr Met Ala Ala Thr Pro Lys
225             230             235             240

Ala Val Lys Ser Ile Lys Asp Leu Ala Asp Thr Lys Ala Pro Ile Glu
            245             250             255

Ser Pro Ser Leu Thr Gly Thr Pro Thr Ala Pro Thr Ala Ala Gln Gly
            260             265             270

Thr Asn Ser Thr Gln Ile Ala Asn Thr Ala Phe Val Lys Ala Ala Ile
        275             280             285

Thr Ala Leu Ile Asn Gly Ala Pro Gly Thr Leu Asp Thr Leu Lys Glu
    290             295             300

Ile Ala Ala Ala Ile Asn Asn Asp Pro Asn Tyr Ser Thr Thr Ile Asn
305             310             315             320

Asn Ala Leu Ala Leu Lys Ala Pro Leu Ala Ser Pro Ala Leu Thr Gly
            325             330             335

Val Pro Thr Ala Pro Thr Ala Ala Gln Gly Thr Asn Asn Thr Gln Ile
            340             345             350

Ala Thr Thr Ala Tyr Val Arg Ala Ala Ile Ser Ala Leu Val Gly Ser
            355             360             365

Ser Pro Glu Ala Leu Asp Thr Leu Tyr Glu Leu Ala Ala Ala Leu Gly
    370             375             380

Asn Asp Pro Asn Phe Ala Thr Thr Met Thr Asn Ala Leu Ala Gly Lys
385             390             395             400

Gln Pro Leu Asp Ala Thr Leu Thr Ala Leu Ala Gly Leu Ala Thr Gly
            405             410             415

Ala Asn Lys Leu Pro Tyr Phe Thr Gly Thr Asp Thr Val Ser Gln Thr
            420             425             430

Asp Leu Thr Ser Val Gly Arg Asp Ile Leu Ala Lys Thr Ser Ile Leu
        435             440             445

Ala Val Ile Gln Tyr Leu Gly Leu Arg Glu Leu Gly Thr Ser Gly Glu
    450             455             460

Lys Ile Pro Leu Leu Ser Thr Ala Asn Thr Trp Ser Ala Arg Gln Thr
```

```
            465                 470                 475                 480

Phe Asn Gly Gly Ile Thr Gly Ala Leu Thr Gly Asn Ala Asp Thr Ala
                        485                 490                 495

Thr Lys Leu Lys Thr Ala Arg Lys Ile Asn Asn Val Ser Phe Asp Gly
                        500                 505                 510

Ser Ala Asp Ile Thr Leu Thr Pro Glu Asn Leu Gly Val Thr Ser Leu
                        515                 520                 525

Thr Phe Glu Lys Asn Asn Gly Glu Met Pro Ile Asp Ala Asp Leu Asn
                530                 535                 540

Thr Phe Gly Pro Val Glu Ala Tyr Leu Gly Val Trp Ser Lys Ala Thr
        545                 550                 555                 560

Ser Thr Asn Ala Thr Leu Glu Lys Asn Phe Pro Glu Asp Asn Ala Val
                        565                 570                 575

Gly Val Leu Glu Val Phe Ala Ala Gly Asn Phe Ala Gly Thr Gln Arg
                        580                 585                 590

Phe Thr Thr Arg Asp Gly Asn Val Tyr Ile Arg Arg Leu Ala Asn Lys
                        595                 600                 605

Trp Asn Gly Ser Asp Gly Pro Trp Gly Ile Trp Arg His Thr Gln Ser
                        610                 615                 620

Ala Thr Arg Pro Leu Ser Thr Thr Ile Asp Leu Asn Thr Leu Gly Ala
        625                 630                 635                 640

Ala Glu His Leu Gly Leu Trp Arg Asn Ser Ser Ala Ile Ala Ser
                        645                 650                 655

Tyr Glu Arg Asn Tyr Pro Glu Glu Gly Gly Phe Ala Gln Gly Val Leu
                        660                 665                 670

Glu Ile Leu Glu Gly Gly Asn Tyr Gly Arg Thr Gln Arg Tyr Thr Thr
                        675                 680                 685

Arg Arg Gly Asn Met Tyr Val Arg Cys Leu Ala Ala Ser Trp Asp Ala
                        690                 695                 700

Ser Asn Pro Gln Trp Glu Pro Trp Leu Lys Val Gly His Gln Ser Glu
        705                 710                 715                 720

Ser Arg Tyr Tyr Glu Gly Asp Leu Asn Val Leu Thr Asp Pro Gly Ile
                        725                 730                 735

Tyr Ser Val Thr Gly Lys Ala Thr Asn Gly Pro Met Leu Asp Thr Val
                        740                 745                 750

Gly Ala Thr Leu Leu Gly Ile Leu Glu Val Ile Arg Arg Phe Asp Gly
                        755                 760                 765

Val Ser Val Trp Gln Arg Tyr Thr Thr Thr Gly Lys Ser Glu Thr Thr
                        770                 775                 780

Gln Gly Arg Thr Phe Glu Arg Val Tyr Ala Gly Ser Lys Trp Thr Glu
        785                 790                 795                 800

Trp Arg Glu Val Tyr Asn Ser Phe Ser Leu Pro Leu Asn Leu Gly Ile
                        805                 810                 815

Gly Gly Ala Val Ala Lys Leu Ser Ser Leu Asp Trp Gln Thr Tyr Asp
                        820                 825                 830

Phe Val Pro Gly Ser Leu Ile Thr Val Arg Leu Asp Asn Met Thr Asn
                        835                 840                 845

Ile Pro Asp Gly Met Asp Trp Gly Val Ile Asp Gly Asn Leu Ile Asn
                        850                 855                 860

Ile Ala Val Gly Pro Ser Asp Asp Ser Gly Thr Gly Arg Ser Met His
        865                 870                 875                 880

Val Trp Arg Ser Thr Val Ser Lys Ala Asn Tyr Arg Phe Phe Met Val
                        885                 890                 895
```

```
Arg Ile Ser Gly Asn Pro Gly Ser Arg Thr Ile Thr Ala Arg Arg Val
                900                 905                 910

Pro Ile Ile Asp Glu Ala Gln Thr Trp Gly Ala Lys Gln Thr Phe Ser
            915                 920                 925

Ala Gly Leu Ser Gly Glu Leu Ser Gly Asn Ala Ala Thr Ala Thr Lys
        930                 935                 940

Leu Lys Thr Ala Arg Lys Ile Asn Asn Val Ser Phe Asp Gly Ser Gly
945                 950                 955                 960

Asp Ile Glu Val Leu Pro Val Gly Val Pro Leu Pro Trp Pro Ser Asp
                965                 970                 975

Thr Val Pro Ser Gly Tyr Ala Leu Met Gln Gly Gln Thr Phe Asp Lys
            980                 985                 990

Ser Ala Tyr Pro Lys Leu Ala Ala Ala Tyr Pro Ser Gly Val Ile Pro
        995                 1000                1005

Asp Met Arg Gly Trp Thr Ile Lys Gly Lys Pro Ala Ser Gly Arg
    1010                1015                1020

Asp Val Leu Ser Leu Glu Gln Asp Gly Ile Lys Ser His Thr His
    1025                1030                1035

Ser Ala Ser Ala Ser Asn Thr Asp Leu Gly Thr Lys Thr Thr Ser
    1040                1045                1050

Ser Phe Asp Tyr Gly Thr Lys Ser Thr Asn Asn Thr Gly Ala His
    1055                1060                1065

Thr His Asn Val Ser Gly Thr Ala Asn Ser Ala Gly Ala His Thr
    1070                1075                1080

His Thr Val Pro Leu Arg Arg Pro Asn Ser Gly Gly Met Asn Phe
    1085                1090                1095

Asp Trp Leu Asp Gly Ala Ser Ser Gly Thr Val Val Gly Asn Gly
    1100                1105                1110

Thr Val Pro Ser Ser Gly Ala His Thr His Ser Val Ser Gly Thr
    1115                1120                1125

Ala Thr Ser Ala Gly Ala His Ala His Thr Val Gly Ile Gly Ala
    1130                1135                1140

His Thr His Ser Val Ala Ile Gly Ser His Gly His Thr Ile Thr
    1145                1150                1155

Val Asn Ala Ala Gly Asn Ala Glu Asn Thr Val Lys Asn Ile Ala
    1160                1165                1170

Phe Asn Tyr Ile Val Arg Leu Ala
    1175                1180

<210> SEQ ID NO 49
<211> LENGTH: 974
<212> TYPE: PRT
<213> ORGANISM: Artificial Sequence
<220> FEATURE:
<223> OTHER INFORMATION: Jungle Tail Fiber

<400> SEQUENCE: 49

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Gly Met Asn Leu Leu Ile Thr
    50                  55                  60
```

```
Ser Val Asp Gly Asp Lys Thr Ala Gly Ala Ala Ser Val Asp Ile Gly
 65                  70                  75                  80

Glu Phe Tyr Gln Val Thr Ile Gln Gln Arg Lys Asp Ile Ser Leu Ala
                 85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
            115                 120                 125

Ala Glu Phe Val Ala Arg Thr Tyr Thr Asp Ser Tyr Gln Leu Gly Asp
            130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
            195                 200                 205

Tyr Thr Ala Gln Asp Ala Ser Thr Thr Gln Lys Gly Leu Val Gln Leu
210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
            260                 265                 270

Thr Asn Ser Thr Gln Ile Ala Asn Thr Ala Phe Val Lys Ala Ala Ile
            275                 280                 285

Thr Ala Leu Ile Asn Gly Ala Pro Gly Thr Leu Asp Thr Leu Lys Glu
            290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
                325                 330                 335

Val Pro Thr Ala Pro Thr Ala Ala Gln Gly Thr Asn Asn Thr Gln Ile
            340                 345                 350

Ala Thr Thr Ala Tyr Val Arg Ala Ala Ile Ser Ala Leu Val Gly Ser
            355                 360                 365

Ser Pro Glu Ala Leu Asp Thr Leu Tyr Glu Leu Ala Ala Ala Leu Gly
            370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
            420                 425                 430

Asp Leu Thr Ser Val Gly Arg Asp Ile Leu Ala Lys Thr Ser Ile Leu
            435                 440                 445

Ala Val Ile Gln Tyr Leu Gly Leu Arg Glu Leu Gly Thr Ser Gly Glu
            450                 455                 460

Lys Ile Pro Leu Leu Ser Thr Ala Asn Thr Trp Ser Ala Arg Gln Thr
465                 470                 475                 480
```

```
Phe Asn Gly Gly Ile Thr Gly Ala Leu Thr Gly Asn Ala Asp Thr Ala
                485                 490                 495

Thr Lys Leu Lys Thr Ala Arg Asn Ile Asn Gly Val Arg Phe Asp Gly
        500                 505                 510

Ser Gly Asp Ile Asn Ile Asn Thr Leu Val Ser Arg Gly Arg Val Thr
            515                 520                 525

Ala Leu Glu Ala Asn Ala Gln Gly Thr Ser Gly Ile Gln Leu Tyr Glu
        530                 535                 540

Ala Tyr Asn Asn Gly Tyr Pro Ser Pro Tyr Gly Asn Val Leu His Leu
545                 550                 555                 560

Lys Gly Ala Thr Ala Ala Gly Glu Gly Glu Leu Phe Ile Gly Trp Ser
                565                 570                 575

Gly Thr Ser Gly Ala His Ala Pro Val His Ile Arg Ser Arg Arg Asp
            580                 585                 590

Thr Asp Ser Ala Asn Trp Ser Glu Trp Ala Gln Val Tyr Thr Ser Lys
        595                 600                 605

Asp Ser Ile Pro Gly Val Asn Ala Lys Gly Asp Gln Asp Thr Ser Gly
    610                 615                 620

Asn Ala Ala Thr Ala Thr Lys Leu Gln Thr Ala Cys Thr Ile Asn Gly
625                 630                 635                 640

Val Ser Phe Asp Gly Ser Lys Asn Ile Glu Leu Thr Ala Glu Asn Leu
                645                 650                 655

Asn Leu Glu Arg Thr Val Glu Leu Ala Ala Gly Ser Leu Gln Lys Asn
            660                 665                 670

Gln Asn Gly Ala Asp Ile Pro Gly Lys Asp Thr Phe Thr Lys Asn Ile
        675                 680                 685

Gly Ala Cys Arg Ala Tyr Ser Ala Trp Leu Asn Ile Gly Gly Asp Ser
    690                 695                 700

Gln Val Trp Thr Thr Ala Gln Phe Ile Ser Trp Leu Glu Ser Gln Gly
705                 710                 715                 720

Ala Phe Asn His Pro Tyr Trp Met Cys Lys Ser Trp Ala Tyr Ala
                725                 730                 735

Asn Asn Lys Val Ile Thr Asp Thr Gly Cys Gly Asn Ile Cys Leu Ala
            740                 745                 750

Gly Ala Val Val Glu Val Ile Gly Thr Arg Gly Ala Met Thr Ile Arg
        755                 760                 765

Val Thr Thr Pro Ser Thr Ser Ser Gly Gly Ile Thr Asn Ala Gln
    770                 775                 780

Phe Thr Tyr Ile Asn His Gly Asp Ala Tyr Ala Pro Gly Trp Arg Arg
785                 790                 795                 800

Asp Tyr Asn Thr Lys Asn Gln Gln Pro Ala Phe Ala Leu Gly Gln Thr
                805                 810                 815

Gly Ser Thr Val Gly Asn Asp Lys Ala Val Gly Trp Asn Trp Asn Ser
            820                 825                 830

Gly Val Tyr Asn Ala Asn Ile Gly Gly Ala Ser Thr Leu Ile Leu His
        835                 840                 845

Phe Asn Met Asn Thr Gly Ser Cys Pro Ala Val Gln Phe Arg Val Asn
    850                 855                 860

Tyr Arg Asn Gly Gly Ile Phe Tyr Arg Ser Ala Arg Asp Gly Tyr Gly
865                 870                 875                 880

Phe Glu Ala Asp Trp Ser Glu Ile Tyr Thr Thr Thr Arg Lys Pro Ser
                885                 890                 895

Ala Gly Asp Val Gly Ala Tyr Thr Gln Ala Glu Cys Asn Ser Arg Phe
```

-continued

```
                900             905             910
Ile Thr Gly Ile Arg Leu Gly Gly Leu Ser Ser Val Gln Thr Trp Asn
            915                 920                 925

Gly Pro Gly Trp Ser Asp Arg Ser Gly Tyr Val Val Thr Gly Ser Val
        930                 935                 940

Asn Gly Asn Arg Asp Glu Leu Ile Asp Thr Thr Gln Ala Arg Pro Ile
945                 950                 955                 960

Gln Tyr Cys Ile Asn Gly Thr Trp Tyr Asn Ala Gly Ser Ile
                965                 970

<210> SEQ ID NO 50
<211> LENGTH: 765
<212> TYPE: PRT
<213> ORGANISM: Artificial Sequence
<220> FEATURE:
<223> OTHER INFORMATION: Mango Tail Fiber

<400> SEQUENCE: 50

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Gly Ala Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Thr Thr Ala Arg Lys Gly Ile Val Gln Leu
    210                 215                 220

Ser Ser Ala Thr Asp Ser Val Ser Glu Val Leu Ala Thr Pro Lys
225                 230                 235                 240

Ala Val Lys Thr Ala Tyr Asp Leu Ala Asn Ala Lys Tyr Thr Ala Val
                245                 250                 255

Asp Ala Thr Thr Ala Arg Lys Gly Leu Val Gln Leu Ser Ser Ala Ile
            260                 265                 270

Asp Ser Val Ser Glu Met Leu Ala Ala Thr Pro Lys Ala Val Lys Ser
        275                 280                 285

Ala Asn Asp Asn Ala Thr Ala Ala Asn Ile Asn Ala Ser Glu Arg Val
```

```
            290                 295                 300
Ser Lys Ala Gly Asp Ser Met Thr Gly Thr Leu Asn Gln Asp Ala Val
305                 310                 315                 320

Ala Gln Ala Thr Tyr Asn Leu Thr Ala Leu Ser Asn Ala Thr Thr Gly
                325                 330                 335

Asn Lys Asn Tyr Leu Arg Lys Met Arg Gly Gly Ala Thr Asp Thr Ile
                340                 345                 350

Trp His Glu Thr Val Gln Gly Gly Glu Tyr Arg Leu Ala Thr Gly Ser
                355                 360                 365

Thr Asp Ser Gln Glu Glu Leu Ala Ile Ser Thr Asn Thr Gly Leu Arg
                370                 375                 380

Val Arg Gly Asn Leu Thr Ser Gln Leu Gly Gly Phe Tyr Ser Gly Asn
385                 390                 395                 400

Thr Lys Lys Phe Ser Phe Tyr Ser Ser Asn Thr Ser Asp Lys Asn Ala
                405                 410                 415

Ala Leu Arg Leu Trp Gly Asn Val Asp Arg Pro Ser Val Val Glu Leu
                420                 425                 430

Gly Asp Asp Thr Gly Tyr His Phe Tyr Ser Gln Arg Asn Lys Asp Gly
                435                 440                 445

Ser Leu Leu Leu Gln Ala Asn Gly Ala Gly Gln Phe Ser Gly Tyr Leu
450                 455                 460

Arg Ser Asn Gly Glu Val Gln Ser Ile Ser Ala Asn Ser Tyr Arg Ile
465                 470                 475                 480

Ala Tyr Gly Asn Tyr Gly Cys Phe Trp Arg Asn Asp Gly Asn Asn Leu
                485                 490                 495

Tyr Leu Met Leu Thr Asn Lys Gly Asp Ala Tyr Gly Asn Tyr Asn Ser
                500                 505                 510

Leu Arg Pro Leu Arg Val Ser Leu Glu Thr Gly Ala Leu Gln Ser Glu
                515                 520                 525

Thr Pro Phe Thr Val Gly Asn Thr Ile Phe Ala Thr Lys Glu Ile Thr
                530                 535                 540

Ala Gly Tyr Ala Gly Ala Leu Ala Trp Ala Glu Gln Tyr Lys Thr Lys
545                 550                 555                 560

Ala Ala Phe Phe Asn Ser Tyr Ser Thr Thr Gly Ala Ser Glu Tyr His
                565                 570                 575

Pro Ala Leu Lys Gln Gln Ala Ser Ile Ala Gly Val Asn Ser Trp Ala
                580                 585                 590

Phe Ser Met Gly Ser Leu Val Ala Asp Thr Ala Leu Ser Trp His Leu
                595                 600                 605

His Met Lys Gly Ser Gly Gly Gln Asp Val Asn Tyr Lys Trp Asp Thr
                610                 615                 620

Ser Gly Asn Phe Ser Ala Pro Gly Gln Leu Ile Pro Gly Ser Phe Ala
625                 630                 635                 640

Asn Phe Asp Ser Arg Tyr Tyr Thr Lys Gly Gln Ser Asp Ala Gly Tyr
                645                 650                 655

Met Ala Lys Thr Gly Ala Tyr Thr Lys Ala Glu Ser Asp Ala Arg Tyr
                660                 665                 670

Asn Leu Lys Asn Thr Ala Ser Arg Ala Ala Ser Gly Trp Glu Lys Asp
                675                 680                 685

Asn Thr Thr Gly Ile Met Lys Gln Trp Gly Ile Ala Thr Arg Thr Ala
                690                 695                 700

Asp Ser Thr Arg Ile Thr Phe Pro Thr Ala Phe Pro Thr Thr Cys Val
705                 710                 715                 720
```

Ser Val Gln Leu Thr Leu Leu Tyr Thr Asn Gly Phe His Asp Gln Asn
                725                 730                 735

Ile Tyr Val Gln Asn Pro Asp Ala Ser Gly Phe Thr Tyr Ile Ala Gly
            740                 745                 750

Ser Gly Glu Val Lys Val Tyr Phe Glu Ala Arg Gly Tyr
755                 760                 765

<210> SEQ ID NO 51
<211> LENGTH: 753
<212> TYPE: PRT
<213> ORGANISM: Artificial Sequence
<220> FEATURE:
<223> OTHER INFORMATION: Maroon Tail Fiber

<400> SEQUENCE: 51

Met Asn Asp Val Thr Val Val Thr Ser Val Thr Tyr Pro Ser Pro Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
50                  55                  60

Ser Val Asp Gly Asp Lys Thr Ala Gly Ala Ser Val Asp Ile Gly
65                  70                  75                  80

Glu Phe Tyr Gln Val Thr Ile Gln His Arg Lys Asp Ile Ser Leu Ala
                85                  90                  95

Leu Asn Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
130                 135                 140

Gly Glu Leu Leu Val Cys Thr Val Asn Ile Pro Ala Gly Val Ser Thr
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
210                 215                 220

Ser Ser Ala Thr Asn Ser Thr Ser Glu Val Leu Ala Ala Thr Pro Lys
225                 230                 235                 240

Ala Val Lys Ala Ala Tyr Asp Leu Ala Asn Gly Lys Tyr Thr Ala Gln
                245                 250                 255

Asp Ala Thr Thr Thr Gln Lys Gly Ile Val Gln Leu Ser Ser Asp Thr
            260                 265                 270

Asn Ser Thr Ser Glu Thr Leu Ala Ala Thr Pro Lys Ala Val Lys Ala
        275                 280                 285

Ala Tyr Asp Leu Ala Ala Gly Lys Ala Pro Ser Ser His Thr His Pro
290                 295                 300

Trp Asn Gln Ile Thr Gly Val Pro Thr Ala Ser Leu Thr Ala Lys Gly
305                 310                 315                 320

```
Ile Thr Gln Leu Ser Ser Ala Thr Asn Ser Thr Ser Glu Val Leu Ala
                325                 330                 335

Ala Thr Pro Lys Ala Val Lys Ala Ala Tyr Asp Leu Ala Asn Gly Lys
            340                 345                 350

Tyr Thr Ala Gln Asp Ala Thr Thr Ala Gln Lys Gly Ile Val Gln Leu
        355                 360                 365

Ser Ser Ala Thr Asn Ser Thr Ser Glu Val Leu Ala Ala Thr Pro Lys
    370                 375                 380

Ala Val Lys Ala Ala Tyr Asp Leu Ala Asn Gly Lys Tyr Thr Ala Gln
385                 390                 395                 400

Asp Ala Thr Thr Thr Gln Lys Gly Ile Val Gln Leu Ser Ser Asp Thr
                405                 410                 415

Asn Ser Thr Ser Glu Thr Leu Ala Ala Thr Pro Lys Ala Val Lys Ala
            420                 425                 430

Ala Tyr Asp Leu Ala Ala Gly Lys Ala Pro Ser Ser His Thr His Pro
        435                 440                 445

Trp Asn Gln Ile Thr Val Val Pro Thr Ala Ser Leu Thr Ala Lys Gly
    450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
                485                 490                 495

Tyr Thr Ala Gln Asp Ala Thr Thr Ala Gln Lys Gly Ile Val Gln Leu
            500                 505                 510

Ser Ser Ala Thr Asn Ser Thr Ser Glu Val Leu Ala Ala Thr Pro Lys
        515                 520                 525

Ala Val Lys Ala Ala Tyr Asp Leu Ala Asn Gly Lys Gln Ala Ala Asp
    530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
                565                 570                 575

Val Gly Arg Ala Ile Leu Gly Lys Thr Ser Ile Gln Ser Val Leu Asp
            580                 585                 590

Tyr Leu Gly Leu Gly Glu Gly Ser Ala Leu Pro Val Gly Val Pro Val
        595                 600                 605

Pro Trp Pro Ser Ala Thr Pro Pro Thr Gly Trp Leu Lys Cys Asn Gly
    610                 615                 620

Ala Ala Phe Ser Ser Glu Met Tyr Pro Lys Leu Ala Lys Ala Tyr Pro
625                 630                 635                 640

Thr Asn Lys Leu Pro Asp Leu Arg Gly Glu Phe Ile Arg Gly Trp Asp
                645                 650                 655

Asp Gly Arg Gly Val Asp Ala Gly Arg Ala Leu Leu Ser Ile Gln Thr
            660                 665                 670

Gly Met Leu Glu Lys His Arg His Ile Val Val Ala Asn Asp Gly Tyr
        675                 680                 685

Asp Thr Lys Asp Glu Trp Glu Leu Ala Thr Ile Phe Lys Lys Thr Tyr
    690                 695                 700

Thr Gln Gly Arg Gly Leu Asp Ala Ser Asn Thr Gly Gly Asn Leu Ile
705                 710                 715                 720

Pro Ser Pro Thr Leu His Ser Arg Gly Ser Ile Gly Asn Thr Gly Gly
                725                 730                 735
```

-continued

```
Ser Glu Thr Arg Pro Arg Asn Ile Ala Phe Asn Tyr Ile Val Arg Ala
            740                 745                 750
Ala

<210> SEQ ID NO 52
<211> LENGTH: 925
<212> TYPE: PRT
<213> ORGANISM: Artificial Sequence
<220> FEATURE:
<223> OTHER INFORMATION: Mulberry Tail Fiber

<400> SEQUENCE: 52

Met Gly Ala Asp Lys Thr Asn Asn Ile Met Thr Leu Ser Ser Gly Val
1               5                   10                  15

Ser Gln Pro Leu Leu Ala Asp Val Gln Tyr Phe Glu Leu Tyr Ser Ser
            20                  25                  30

Ser Ala Leu Asn Arg Lys Leu Lys Asn Ile Val Leu Pro Gly Phe Tyr
        35                  40                  45

Cys Gly Phe Glu Pro Val Pro Gly Thr Gly Leu Ser Val Arg Ile Thr
50                  55                  60

Ser Glu Asn Ser Glu Gly Lys Gly Ala Ala Ser Val Asp Val Asn Asn
65                  70                  75                  80

Val Gln Ile Ser Val Gln Gln Ile Glu Asp Val Thr Val Ser Val Lys
                85                  90                  95

Ala Gly Ala Thr Asn Ile Ile Val Leu Glu Ala Asn Phe Glu His Gly
            100                 105                 110

Val Lys Thr Thr Gln Val Asp Ser Ala Ser Ser Val Ser Ala Ala Arg
        115                 120                 125

Ile Tyr Ala Arg Thr Asp Asn Thr Ile Gly Gln Asn Gln Ile Glu Leu
130                 135                 140

Cys Arg Val Ile Val Pro Asn Gly Ala Thr Ala Val Thr Lys Glu Met
145                 150                 155                 160

Ile Val Leu Lys Tyr Arg Val Asn Arg Ala Val Gly Val Glu Phe Ser
                165                 170                 175

Asn Glu Ile Ser Ser Thr Glu Glu Arg Lys Ala Ala Thr Pro Leu Ala
            180                 185                 190

Val Lys Thr Leu His Asp Leu Val Asp Thr Lys Ala Pro Leu Asp Ser
        195                 200                 205

Pro His Leu Ser Gly Thr Pro Thr Ser Pro Thr Pro Glu Pro Gly Thr
210                 215                 220

Asn Asn Thr Gln Ile Ala Asn Ala Phe Val Tyr Ala Ala Ile Asn
225                 230                 235                 240

Ala Leu Ile Asn Gly Ala Pro Gly Thr Met Asp Thr Leu Lys Glu Ile
                245                 250                 255

Ala Ala Ala Ile Asn Asn Asp Pro Asn Phe Ser Thr Thr Ile Asn Asn
            260                 265                 270

Ala Leu Ala Leu Lys Ala Pro Leu Ala Ser Pro Ala Leu Thr Gly Ile
        275                 280                 285

Pro Thr Ala Pro Thr Ala Ala Gln Gly Thr Asn Asn Thr Gln Ile Ala
290                 295                 300

Thr Thr Ala Tyr Val Arg Ala Ala Ile Ser Ala Leu Val Gly Ser Ser
305                 310                 315                 320

Pro Glu Ala Leu Asp Thr Leu Asn Glu Leu Ala Ala Ala Leu Gly Asn
                325                 330                 335

Asp Pro Asn Phe Ala Thr Thr Met Thr Asn Ala Leu Ala Gly Lys Gln
```

-continued

```
                340                 345                 350
Pro Leu Asp Ala Thr Leu Thr Ala Leu Ala Gly Leu Ala Thr Gly Ala
            355                 360                 365

Asn Lys Leu Pro Tyr Phe Thr Gly Lys Asp Thr Val Ala Gln Thr Asp
        370                 375                 380

Leu Thr Ser Val Gly Arg Asp Ile Leu Ala Lys Thr Ser Thr Leu Ala
385                 390                 395                 400

Val Ile Gln Tyr Leu Gly Leu Arg Glu Leu Gly Thr Ser Gly Glu Lys
                405                 410                 415

Ile Pro Leu Leu Ser Thr Ala Asn Thr Trp Ser Ala Arg Gln Thr Phe
            420                 425                 430

Asn Gly Gly Ile Thr Gly Ala Leu Ile Gly Asn Ala Asp Thr Ala Thr
        435                 440                 445

Lys Leu Lys Thr Ala Ile Asn Ile Asn Gly Val Arg Phe Asp Gly Ser
    450                 455                 460

Ala Asp Ile Asn Ile Asn Thr Leu Val Ser Arg Gly Arg Val Thr Ala
465                 470                 475                 480

Leu Gly Ala Asn Ala Gln Gly Thr Ser Gly Ile Gln Leu Tyr Glu Ala
                485                 490                 495

Tyr Asn Asn Gly Tyr Pro Ser Pro Tyr Gly Asn Val Leu His Leu Lys
            500                 505                 510

Gly Ala Thr Ala Ala Gly Glu Gly Leu Phe Ile Gly Trp Ser Val
        515                 520                 525

Ser Ser Gly Asp His Ala Pro Val His Ile Arg Ser Arg Arg Asp Ile
    530                 535                 540

Asp Ser Ala Asn Trp Ser Glu Trp Ala Gln Val Tyr Thr Ser Lys Asp
545                 550                 555                 560

Ser Val Pro Gly Val Asn Ala Lys Gly Asn Gln Asp Thr Ser Gly Asn
                565                 570                 575

Ala Ala Thr Ala Thr Lys Leu Gln Thr Ala Cys Thr Ile Asn Gly Val
            580                 585                 590

Ser Phe Asp Gly Ser Lys Asn Ile Glu Leu Thr Ala Glu Asp Leu Asn
        595                 600                 605

Leu Glu Gln Thr Val Glu Leu Ala Ala Gly Ala Leu Gln Lys Asn Gln
    610                 615                 620

Asn Gly Ala Asp Ile Pro Asn Lys Asp Lys Phe Ile Gln Asn Thr Gly
625                 630                 635                 640

Ala Cys Arg Ala Phe Ser Gly Gln Thr Asp Ile Asp Gly Ser Gln Gly
                645                 650                 655

Glu Trp Ser Thr Val Ala Phe Ile Ser Trp Leu Glu Asn Asn Gly Ala
            660                 665                 670

Phe Arg His Pro Tyr Trp Met Cys Lys Gly Ser Trp Ser Tyr Ala Arg
        675                 680                 685

Asn Arg Val Ile Thr Asp Thr Gly Cys Gly Asn Ile Cys Leu Ala Gly
    690                 695                 700

Ala Val Ile Glu Val Met Gly Thr Arg Gly Ala Met Thr Ile Arg Val
705                 710                 715                 720

Thr Thr Pro Ser Thr Ser Ser Gly Gly Ile Thr Asn Ala Gln Phe
                725                 730                 735

Thr Tyr Ile Asn His Gly Asp Ala Tyr Ala Pro Gly Trp Arg Arg Asp
            740                 745                 750

Tyr Asn Thr Lys Asn Gln Gln Pro Ala Phe Ala Leu Gly Gln Thr Gly
        755                 760                 765
```

```
Arg Arg Val Ala Asn Asp Lys Ala Val Gly Trp Asn Trp Asn Ser Gly
        770                 775                 780
Val Tyr Asp Ala Asp Ile Ser Gly Ala Ser Thr Leu Ile Leu His Phe
785                 790                 795                 800
Asn Met Asn Ala Gly Ser Cys Pro Ala Val Gln Phe Arg Val Asn Tyr
            805                 810                 815
Arg Asn Gly Gly Ile Phe Tyr Arg Ser Ala Arg Asp Gly Tyr Gly Phe
                820                 825                 830
Glu Ala Asn Trp Ser Glu Phe Tyr Thr Thr Thr Arg Lys Pro Ser Ala
            835                 840                 845
Gly Asp Val Gly Ala Tyr Thr Gln Ala Glu Cys Asn Ser Arg Phe Ile
        850                 855                 860
Thr Gly Ile Arg Leu Gly Gly Leu Ser Ser Val Gln Thr Trp Asn Gly
865                 870                 875                 880
Pro Gly Trp Ser Asp Arg Ser Gly Tyr Val Val Thr Gly Ser Val Asn
                885                 890                 895
Gly Asn Arg Asp Glu Leu Ile Asp Thr Thr Gln Ala Arg Pro Ile Gln
                900                 905                 910
Tyr Cys Ile Asn Gly Thr Trp Tyr Asn Ala Gly Ser Ile
        915                 920                 925

<210> SEQ ID NO 53
<211> LENGTH: 972
<212> TYPE: PRT
<213> ORGANISM: Bacteriophage P1
<220> FEATURE:
<221> NAME/KEY: MISC_FEATURE
<223> OTHER INFORMATION: P1-S' tail fiber protein

<400> SEQUENCE: 53

Met Asn Asp Val Thr Val Val Thr Ser Val Thr Tyr Pro Ser Ser Glu
1               5                   10                  15
Ser Leu Ala Leu Val Ala Asp Val Gln Tyr His Glu Pro Tyr Leu Ser
            20                  25                  30
Ala Ala Leu Asn Arg Lys Phe Arg Gly Ile Val Asp Pro Gly Phe Tyr
        35                  40                  45
Ala Gly Phe Leu Pro Lys Pro Gly Gly Met Asn Leu Leu Ile Thr
    50                  55                  60
Ser Val Asp Gly Asp Lys Thr Ala Gly Ala Ala Ser Val Asp Ile Gly
65                  70                  75                  80
Glu Phe Tyr Gln Val Thr Ile Gln Gln Arg Lys Asp Ile Ser Leu Ala
                85                  90                  95
Leu Ser Ala Gly Lys Lys Tyr Ala Ile Val Leu Lys Gly Arg Tyr Leu
            100                 105                 110
Leu Gly Glu Asp Thr Tyr Gln Val Asn Thr Ala Ser His Ile His Ala
        115                 120                 125
Ala Glu Phe Val Ala Arg Thr Tyr Thr Asp Ser Tyr Gln Leu Gly Asp
    130                 135                 140
Gly Glu Leu Leu Val Cys Thr Val Asn Ile Pro Ala Ser Val Ser Ala
145                 150                 155                 160
Ile Thr Gln Glu Met Ile Asp Thr Ser Glu Arg Ile Asn Arg Ser Ile
                165                 170                 175
Gly Ile Asp Ile Ser Asp Ser Val Thr Ser Thr Arg Ser Asp Val Ala
            180                 185                 190
Ala Ser Ser Leu Ala Val Lys Lys Ala Tyr Asp Leu Ala Lys Ser Lys
```

```
              195                 200                 205
Tyr Thr Ala Gln Asp Ala Ser Thr Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Gln Gly
                260                 265                 270

Thr Asn Ser Thr Gln Ile Ala Asn Thr Ala Phe Val Lys Ala Ala Ile
                275                 280                 285

Thr Ala Leu Ile Asn Gly Ala Pro Gly Thr Leu Asp Thr Leu Lys Glu
    290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
                325                 330                 335

Val Pro Thr Ala Pro Thr Ala Gln Gly Thr Asn Asn Thr Gln Ile
                340                 345                 350

Ala Thr Thr Ala Tyr Val Arg Ala Ala Ile Ser Ala Leu Val Gly Ser
                355                 360                 365

Ser Pro Glu Ala Leu Asp Thr Leu Tyr Glu Leu Ala Ala Ala Leu Gly
    370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
                420                 425                 430

Asp Leu Thr Ser Val Gly Arg Asp Ile Leu Ala Lys Thr Ser Ile Leu
    435                 440                 445

Ala Val Ile Gln Tyr Leu Gly Leu Arg Glu Leu Gly Thr Ser Gly Glu
    450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
                485                 490                 495

Thr Lys Leu Lys Thr Ala Arg Asn Ile Asn Gly Val Arg Phe Asp Gly
                500                 505                 510

Ser Gly Asp Ile Asn Ile Asn Thr Leu Val Ser Arg Gly Arg Val Thr
    515                 520                 525

Ala Leu Glu Ala Asn Ala Gln Gly Thr Ser Gly Ile Gln Leu Tyr Glu
    530                 535                 540

Ala Tyr Asn Asn Gly Tyr Pro Ser Pro Tyr Gly Asn Val Leu His Leu
545                 550                 555                 560

Lys Gly Ala Thr Ala Ala Gly Glu Gly Glu Leu Phe Ile Gly Trp Ser
                565                 570                 575

Gly Thr Ser Gly Ala His Ala Pro Val His Ile Arg Ser Arg Arg Asp
                580                 585                 590

Thr Asp Ser Ala Asn Trp Ser Glu Trp Ala Gln Val Tyr Thr Ser Lys
                595                 600                 605

Asp Ser Ile Pro Gly Val Asn Ala Lys Gly Asp Gln Asp Thr Ser Gly
    610                 615                 620
```

Asn Ala Ala Thr Ala Thr Lys Leu Gln Thr Ala Cys Thr Ile Asn Gly
625                 630                 635                 640

Val Ser Phe Asp Gly Ser Lys Asn Ile Glu Leu Thr Ala Glu Asn Leu
            645                 650                 655

Asn Leu Glu Arg Thr Val Glu Leu Ala Ala Gly Ser Leu Gln Lys Asn
        660                 665                 670

Gln Asn Gly Ala Asp Ile Pro Gly Lys Asp Thr Phe Thr Lys Asn Ile
    675                 680                 685

Gly Ala Cys Arg Ala Phe His Ser Ser Ile Ser Thr Gly Ala Gly Asn
690                 695                 700

Trp Thr Thr Ala Gln Leu Ile Glu Trp Leu Asp Ser Gly Ala Phe
705                 710                 715                 720

Asn His Pro Tyr Trp Met Cys Lys Cys Ser Trp Ser Tyr Gly Asn Asn
            725                 730                 735

Lys Ile Ile Thr Asp Thr Gly Cys Gly Thr Ile His Leu Ala Gly Cys
        740                 745                 750

Val Ile Glu Val Met Gly Asn Lys Gly Ala Met Thr Ile Arg Val Thr
    755                 760                 765

Thr Pro Ser Thr Ser Ser Gly Gly Ile Thr Asn Ala Gln Phe Thr
770                 775                 780

Tyr Ile Asn His Gly Asp Ala Tyr Ala Pro Gly Trp Arg Arg Asp Tyr
785                 790                 795                 800

Asn Thr Lys Asn Leu Gln Pro Ala Phe Ala Leu Gly Gln Thr Gly Asn
            805                 810                 815

Arg Val Ala Asn Asp Lys Ala Val Gly Trp Asn Trp Asn Ser Gly Val
        820                 825                 830

Tyr Asp Ala Asp Leu Lys Gly Ala Ser Thr Leu Ile Leu His Phe Asn
    835                 840                 845

Met Asn Ala Gly Ser Cys Pro Ala Val Gln Leu Arg Val Asn Tyr Lys
850                 855                 860

Asn Gly Gly Ile Tyr Tyr Arg Ser Ala Arg Asp Gly Tyr Gly Phe Glu
865                 870                 875                 880

Ala Asp Trp Ser Glu Phe Tyr Thr Thr Thr Arg Lys Pro Ser Ala Gly
            885                 890                 895

Asp Val Gly Ala Tyr Thr Gln Ala Glu Cys Asn Ser Arg Phe Ile Thr
        900                 905                 910

Gly Ile Arg Leu Gly Gly Leu Ser Ser Val Gln Thr Trp Asn Gly Pro
    915                 920                 925

Gly Trp Ser Asp Arg Ser Gly Tyr Val Val Thr Gly Ser Val Asn Gly
930                 935                 940

Asn Arg Asp Glu Leu Ile Asp Thr Thr Gln Ala Arg Pro Ile Gln Tyr
945                 950                 955                 960

Cys Ile Asn Gly Thr Trp Tyr Asn Ala Gly Ser Ile
            965                 970

<210> SEQ ID NO 54
<211> LENGTH: 744
<212> TYPE: PRT
<213> ORGANISM: Artificial Sequence
<220> FEATURE:
<223> OTHER INFORMATION: Pine Tail Fiber

<400> SEQUENCE: 54

Met Asn Asp Val Thr Val Val Ser Val Thr Tyr Pro Ser Ser Glu
1               5                   10                  15

```
Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
    290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Asn Ser Pro Ala Leu Thr Gly
                325                 330                 335

Thr Pro Thr Thr Pro Thr Ala Arg Gln Gly Thr Asn Asn Thr Gln Ile
            340                 345                 350

Ala Asn Thr Ala Phe Val Met Ala Ala Ile Ala Ala Leu Val Asp Ser
        355                 360                 365

Ser Pro Asp Ala Leu Asn Thr Leu Asn Glu Leu Ala Ala Ala Leu Gly
    370                 375                 380

Asn Asp Pro Asn Phe Ala Thr Thr Met Thr Asn Ala Leu Ala Gly Lys
385                 390                 395                 400

Gln Pro Lys Asp Ala Thr Leu Thr Ala Leu Ala Gly Leu Ala Thr Ala
                405                 410                 415

Ala Asp Arg Phe Pro Tyr Phe Thr Gly Asn Asp Val Ala Ser Leu Ala
            420                 425                 430
```

Thr Leu Thr Lys Val Gly Arg Asp Ile Leu Ala Lys Ser Thr Val Ala
            435                 440                 445

Ala Val Ile Glu Tyr Leu Gly Leu Gln Glu Thr Val Asn Arg Ala Gly
450                 455                 460

Asn Ala Val Gln Lys Asn Gly Asp Thr Leu Ser Gly Gly Leu Thr Phe
465                 470                 475                 480

Glu Asn Asp Ser Ile Leu Ala Trp Ile Arg Asn Thr Asp Trp Ala Lys
                485                 490                 495

Ile Gly Phe Lys Asn Asp Ala Asp Gly Asp Thr Asp Ser Tyr Met Trp
            500                 505                 510

Phe Glu Thr Gly Asp Asn Gly Asn Glu Tyr Phe Lys Trp Arg Ser Arg
            515                 520                 525

Gln Ser Thr Thr Thr Lys Asp Leu Met Thr Leu Lys Trp Asp Ala Leu
            530                 535                 540

Asn Ile Leu Val Asn Ala Val Ile Asn Gly Cys Phe Gly Val Gly Thr
545                 550                 555                 560

Thr Asn Ala Leu Gly Gly Ser Ser Ile Val Leu Gly Asp Asn Asp Thr
                565                 570                 575

Gly Phe Lys Gln Asn Gly Asp Gly Ile Leu Asp Val Tyr Ala Asn Ser
            580                 585                 590

Gln Arg Val Phe Arg Phe Gln Asn Gly Val Ala Ile Ala Phe Lys Asn
            595                 600                 605

Ile Gln Ala Gly Asp Ser Lys Lys Phe Ser Leu Ser Ser Asn Thr
            610                 615                 620

Ser Thr Lys Asn Ile Thr Phe Asn Leu Trp Gly Ala Ser Thr Arg Pro
625                 630                 635                 640

Val Val Ala Glu Leu Gly Asp Glu Ala Gly Trp His Phe Tyr Ser Gln
                645                 650                 655

Arg Asn Thr Asp Asn Ser Val Ile Phe Ala Val Asn Gly Gln Met Gln
            660                 665                 670

Pro Ser Asn Trp Gly Asn Phe Asp Ser Arg Tyr Val Lys Asp Val Arg
            675                 680                 685

Leu Gly Thr Arg Val Val Gln Leu Met Ala Arg Gly Gly Arg Tyr Glu
690                 695                 700

Lys Ala Gly His Thr Ile Thr Gly Leu Arg Ile Ile Gly Glu Val Asp
705                 710                 715                 720

Gly Asp Asp Glu Ala Ile Phe Arg Pro Ile Gln Lys Tyr Ile Asn Gly
                725                 730                 735

Thr Trp Tyr Asn Val Ala Gln Val
            740

<210> SEQ ID NO 55
<211> LENGTH: 1181
<212> TYPE: PRT
<213> ORGANISM: Artificial Sequence
<220> FEATURE:
<223> OTHER INFORMATION: Plum Tail Fiber

<400> SEQUENCE: 55

Met Asn Asp Val Thr Val Thr Ser Val Thr Tyr Pro Ser Pro Glu
1               5                   10                  15

Ser Leu Ala Leu Val Ala Asp Val Gln Tyr His Glu Pro Tyr Leu Ser
                20                  25                  30

Ala Ala Leu Asn Arg Lys Phe Arg Gly Ile Val Asp Pro Gly Phe Tyr
            35                  40                  45

```
Ala Gly Phe Leu Pro Lys Pro Gly Gly Met Asn Leu Leu Ile Thr
    50              55                  60
Ser Val Asp Gly Asp Lys Thr Ala Gly Ala Ser Val Asp Ile Gly
 65              70                  75                  80
Glu Phe Tyr Gln Val Thr Ile Gln His Arg Lys Asp Ile Ser Leu Ala
             85                  90                  95
Leu Ser Ala Gly Lys Lys Tyr Ala Ile Val Leu Lys Gly Arg Tyr Leu
            100                 105                 110
Leu Gly Glu Asp Thr Tyr Gln Val Asn Thr Ala Ser His Ile His Ala
        115                 120                 125
Ala Glu Phe Val Ala Arg Thr Tyr Thr Asp Ser Tyr Gln Leu Gly Asp
    130                 135                 140
Gly Glu Leu Leu Val Cys Thr Val Asn Ile Pro Ala Gly Val Ser Ala
145                 150                 155                 160
Ile Thr Gln Glu Met Ile Asp Thr Ser Glu Arg Ile Asn Arg Thr Ile
                165                 170                 175
Gly Ile Asp Ile Ser Asp Ser Val Thr Ser Ser Arg Ser Asp Val Ala
            180                 185                 190
Ala Ser Ser Leu Ala Val Lys Lys Ala Tyr Asp Leu Ala Lys Ser Lys
        195                 200                 205
Tyr Thr Ala Gln Asp Ala Ser Thr Thr Gln Lys Gly Leu Val Gln Leu
    210                 215                 220
Ser Ser Glu Thr Asn Ser Asp Ser Glu Thr Met Ala Ala Thr Pro Lys
225                 230                 235                 240
Ala Ile Lys Ser Val Lys Asp Leu Ala Asp Thr Lys Ala Pro Ile Glu
                245                 250                 255
Ser Pro Ser Leu Thr Gly Thr Pro Thr Ala Pro Thr Ala Ala Gln Gly
            260                 265                 270
Thr Asn Ser Thr Gln Ile Ala Asn Thr Ala Phe Val Lys Ala Ala Ile
        275                 280                 285
Thr Ala Leu Ile Asn Gly Ala Pro Gly Thr Leu Asp Thr Leu Lys Glu
    290                 295                 300
Ile Ala Ala Ala Ile Asn Asn Asp Pro Asn Phe Ser Thr Thr Ile Asn
305                 310                 315                 320
Asn Ala Leu Ala Leu Lys Ala Pro Leu Ala Ser Pro Ala Leu Thr Gly
                325                 330                 335
Ile Pro Thr Ala Pro Thr Ala Ala Gln Gly Thr Asn Asn Thr Gln Ile
            340                 345                 350
Ala Thr Thr Ala Tyr Val Arg Ala Ala Ile Ser Ala Leu Val Gly Ser
        355                 360                 365
Ser Pro Glu Ala Leu Asp Thr Leu Asn Glu Leu Ala Ala Ala Leu Gly
    370                 375                 380
Asn Asp Pro Asn Phe Ala Thr Thr Met Thr Asn Ala Leu Ala Gly Lys
385                 390                 395                 400
Gln Pro Leu Asp Ala Thr Leu Thr Ala Leu Ala Gly Leu Ala Thr Gly
                405                 410                 415
Ala Asn Lys Leu Pro Tyr Phe Thr Gly Thr Asp Thr Val Ser Gln Thr
            420                 425                 430
Asp Leu Thr Ser Val Gly Arg Asp Ile Leu Ala Lys Thr Ser Val Leu
        435                 440                 445
Ala Val Ile Gln Tyr Leu Gly Leu Arg Glu Leu Gly Thr Ser Gly Glu
    450                 455                 460
Lys Ile Pro Leu Leu Ser Thr Ala Asn Thr Trp Ser Ala Arg Gln Thr
```

```
            465                 470                 475                 480
        Phe Asn Gly Gly Ile Thr Gly Ala Leu Thr Gly Asn Ala Asp Thr Ala
                        485                 490                 495
        Thr Lys Leu Lys Thr Ala Arg Lys Ile Asn Asn Val Ser Phe Asp Gly
                        500                 505                 510
        Ser Ala Asp Ile Thr Leu Thr Pro Glu Asn Leu Gly Val Thr Ser Leu
                        515                 520                 525
        Thr Phe Glu Lys Asn Asn Gly Glu Met Pro Ile Asp Ala Asp Leu Asn
        530                 535                 540
        Thr Phe Gly Pro Val Glu Ala Tyr Leu Gly Val Trp Ser Lys Ala Thr
        545                 550                 555                 560
        Ser Thr Asn Ala Thr Leu Glu Lys Asn Phe Pro Glu Asp Asn Ala Val
                        565                 570                 575
        Gly Val Leu Glu Val Phe Ala Ala Gly Asn Phe Ala Gly Thr Gln Arg
                        580                 585                 590
        Phe Thr Thr Arg Asp Gly Asn Val Tyr Ile Arg Arg Leu Ala Asn Lys
                        595                 600                 605
        Trp Asn Gly Ser Asp Gly Pro Trp Gly Ile Trp Arg His Thr Gln Ser
                        610                 615                 620
        Ala Thr Arg Pro Leu Ser Thr Thr Ile Asp Leu Asn Thr Leu Gly Ala
        625                 630                 635                 640
        Ala Glu His Leu Gly Leu Trp Arg Asn Ser Ser Ala Ile Ala Ser
                        645                 650                 655
        Tyr Glu Arg Asn Tyr Pro Glu Glu Gly Gly Phe Ala Gln Gly Val Leu
                        660                 665                 670
        Glu Ile Leu Glu Gly Gly Asn Tyr Gly Arg Thr Gln Arg Tyr Thr Thr
                        675                 680                 685
        Arg Arg Gly Asn Met Tyr Val Arg Cys Leu Ala Ala Ser Trp Asp Ala
                        690                 695                 700
        Ser Asn Pro Gln Trp Glu Pro Trp Leu Lys Val Gly His Gln Ser Glu
        705                 710                 715                 720
        Ser Arg Tyr Tyr Glu Gly Asp Leu Asn Val Leu Thr Asp Pro Gly Ile
                        725                 730                 735
        Tyr Ser Val Thr Gly Lys Ala Thr Asn Gly Pro Met Leu Asp Thr Val
                        740                 745                 750
        Gly Ala Thr Leu Leu Gly Ile Leu Glu Val Ile Arg Arg Phe Asp Gly
                        755                 760                 765
        Val Ser Val Trp Gln Arg Tyr Thr Thr Thr Gly Lys Ser Glu Thr Thr
        770                 775                 780
        Gln Gly Arg Thr Phe Glu Arg Val Tyr Ala Gly Ser Lys Trp Thr Glu
        785                 790                 795                 800
        Trp Arg Glu Val Tyr Asn Ser Phe Ser Leu Pro Leu Asn Leu Gly Ile
                        805                 810                 815
        Gly Gly Ala Val Ala Lys Leu Ser Ser Leu Asp Trp Gln Thr Tyr Asp
                        820                 825                 830
        Phe Val Pro Gly Ser Leu Ile Thr Val Arg Leu Asp Asn Met Thr Asn
                        835                 840                 845
        Ile Pro Asp Gly Met Asp Trp Gly Val Ile Asp Gly Asn Leu Ile Asn
                        850                 855                 860
        Ile Ala Val Gly Pro Ser Asp Asp Ser Gly Thr Gly Arg Ser Met His
        865                 870                 875                 880
        Val Trp Arg Ser Thr Val Ser Lys Ala Asn Tyr Arg Phe Phe Met Val
                        885                 890                 895
```

-continued

```
Arg Ile Ser Gly Asn Pro Gly Ser Arg Thr Ile Thr Ala Arg Arg Val
            900                 905                 910

Pro Ile Ile Asp Glu Ala Gln Thr Trp Gly Ala Lys Gln Thr Phe Ser
            915                 920                 925

Ala Gly Leu Ser Gly Glu Leu Ser Gly Asn Ala Ala Thr Ala Thr Lys
            930                 935                 940

Leu Lys Thr Ala Arg Lys Ile Asn Asn Val Ser Phe Asp Gly Ser Gly
945                 950                 955                 960

Asp Ile Glu Val Leu Pro Val Gly Val Pro Leu Pro Trp Pro Ser Asp
                965                 970                 975

Thr Val Pro Ser Gly Tyr Ala Leu Met Gln Gly Gln Thr Phe Asp Lys
            980                 985                 990

Ser Ala Tyr Pro Lys Leu Ala Ala Ala Tyr Pro Ser Gly Val Ile Pro
            995                 1000                1005

Asp Met Arg Gly Trp Thr Ile Lys Gly Lys Pro Ala Ser Gly Arg
        1010                1015                1020

Asp Val Leu Ser Leu Glu Gln Asp Gly Ile Lys Ser His Thr His
        1025                1030                1035

Ser Ala Ser Ala Ser Asn Thr Asp Leu Gly Thr Lys Thr Thr Ser
        1040                1045                1050

Ser Phe Asp Tyr Gly Thr Lys Ser Thr Asn Asn Thr Gly Ala His
        1055                1060                1065

Thr His Asn Val Ser Gly Thr Ala Asn Ser Ala Gly Ala His Thr
        1070                1075                1080

His Thr Val Pro Leu Arg Arg Pro Asn Ser Gly Gly Met Asn Phe
        1085                1090                1095

Asp Trp Leu Asp Gly Ala Ser Ser Gly Thr Val Val Gly Asn Gly
        1100                1105                1110

Thr Val Pro Ser Ser Gly Ala His Thr His Ser Val Ser Gly Thr
        1115                1120                1125

Ala Thr Ser Ala Gly Ala His Ala His Thr Val Gly Ile Gly Ala
        1130                1135                1140

His Thr His Ser Val Ala Ile Gly Ser His Gly His Thr Ile Thr
        1145                1150                1155

Val Asn Ala Ala Gly Asn Ala Glu Asn Thr Val Lys Asn Ile Ala
        1160                1165                1170

Phe Asn Tyr Ile Val Arg Leu Ala
        1175                1180

<210> SEQ ID NO 56
<211> LENGTH: 1250
<212> TYPE: PRT
<213> ORGANISM: Artificial Sequence
<220> FEATURE:
<223> OTHER INFORMATION: Queen Tail Fiber
<220> FEATURE:
<221> NAME/KEY: misc_feature
<222> LOCATION: (642)..(642)
<223> OTHER INFORMATION: Xaa can be any naturally occurring amino acid
<220> FEATURE:
<221> NAME/KEY: misc_feature
<222> LOCATION: (647)..(647)
<223> OTHER INFORMATION: Xaa can be any naturally occurring amino acid
<220> FEATURE:
<221> NAME/KEY: misc_feature
<222> LOCATION: (662)..(662)
<223> OTHER INFORMATION: Xaa can be any naturally occurring amino acid
<220> FEATURE:
<221> NAME/KEY: misc_feature
```

```
<222> LOCATION: (793)..(793)
<223> OTHER INFORMATION: Xaa can be any naturally occurring amino acid
<220> FEATURE:
<221> NAME/KEY: misc_feature
<222> LOCATION: (940)..(940)
<223> OTHER INFORMATION: Xaa can be any naturally occurring amino acid
<220> FEATURE:
<221> NAME/KEY: misc_feature
<222> LOCATION: (943)..(943)
<223> OTHER INFORMATION: Xaa can be any naturally occurring amino acid

<400> SEQUENCE: 56

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
    290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
                325                 330                 335

Val Pro Thr Ala Pro Thr Ala Ala Gln Gly Thr Asn Asn Thr Gln Ile
            340                 345                 350
```

```
Ala Thr Thr Ala Tyr Val Arg Ala Ile Ser Ala Leu Val Gly Ser
            355                 360                 365

Ser Pro Glu Ala Leu Asp Thr Leu Tyr Glu Leu Ala Ala Leu Gly
370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
            420                 425                 430

Asp Leu Thr Ser Val Gly Arg Asp Ile Leu Ala Lys Thr Ser Ile Leu
            435                 440                 445

Ala Val Ile Gln Tyr Leu Gly Leu Arg Glu Leu Gly Thr Ser Gly Glu
            450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
                485                 490                 495

Thr Lys Leu Lys Thr Lys Arg Ser Leu Gln Val Asp Leu Gln Ser Asp
            500                 505                 510

Asn Ala Ile Asp Phe Asp Gly Ser Ser Asn Ala Leu Leu Gly Ile Lys
            515                 520                 525

Gly Ile Leu Pro Ile Thr His Gly Gly Leu Gly Ala Ser Ser Val Ser
            530                 535                 540

Gly Gly Arg Thr Asn Leu Gly Leu Gly Val Ala Asp Ile Pro Gln Phe
545                 550                 555                 560

Lys Gly Ile Asn Leu Val Asn Ser Thr Asp Ser Asp Leu Ala Ala Ser
                565                 570                 575

Gly Ile Val Ser Gly Tyr Leu Asn Asn Ser Ala Gly Val Gln Arg Ser
            580                 585                 590

Arg Phe Arg Ile Tyr Ser Glu Ile Arg Ser Asp Asn Arg Ser Trp Leu
            595                 600                 605

Thr Leu His Leu Gln Ser Asp Thr Asn Thr Asn Lys Tyr Ala Gly Leu
            610                 615                 620

Asp Ile Asp Gly Asn Phe Leu Ile Thr Gly Asp Ser Lys Cys Arg Ala
625                 630                 635                 640

Leu Xaa Pro Thr Asp Val Xaa Leu Thr Arg Lys Asn Ile Asp Val Tyr
                645                 650                 655

Ser Lys Ala Glu Val Xaa Leu Lys Lys Gly Met Lys Phe Thr Arg Val
            660                 665                 670

Asn Ala Pro Ser Gly Ala Glu Glu Gly Lys Phe Tyr Pro Val Val Ile
            675                 680                 685

Lys Arg Ser Ala Thr Ser Asn Gly Glu Leu Ala Ser Arg Val Ile Ile
            690                 695                 700

Ser Thr Ala Pro Arg Gln Ala His Arg Met Asn Asn Cys Glu Phe
705                 710                 715                 720

Asn Gly Phe Val Met Pro Ala Gly Trp Ser Asp Arg Gly Arg Tyr Ala
                725                 730                 735

Tyr Gly Met Phe Trp Gln Tyr Gln Asp Ala Glu Arg Ala Ile His Ser
            740                 745                 750

Ile Ala Met Ser Asn Lys Asp Asp Glu Val Ser Ser Val Phe Tyr Ile
            755                 760                 765

Glu Gly Gly Ala Phe Pro Val Cys Val Leu Val Glu Glu Gly Leu Ser
```

```
                770             775             780
Val Val Val Pro Thr Thr Asp Tyr Xaa Val Gly Gln Thr Thr Tyr Lys
785             790             795             800

Trp Gly Ala Thr Asn Pro Lys Ala Glu Cys Ile Ala Ala Asp Ile Ile
        805             810             815

Ile Asp Phe Ser Asn Gly Arg Gly Phe Tyr Ser Ser Gly Asn Leu Asn
        820             825             830

Gly Asn Ala Ala Thr Ala Thr Lys Leu Gln Thr Ala Arg Thr Ile Asn
        835             840             845

Gly Val Thr Phe Asp Gly Thr Thr Asp Ile Ser Leu Thr Pro Glu Asn
        850             855             860

Ile Gly Ala Leu Ser Leu Ser Gly Gly Thr Leu Leu Gly Gly Leu Thr
865             870             875             880

Ala Pro Leu Leu Thr Thr Lys Ser Asp Leu Ile Phe Ser Ser His Thr
        885             890             895

Ser Arg His Ile Arg Phe Thr Tyr Thr Lys Asn Asp Gly Thr Thr Leu
        900             905             910

Thr Asp Gly Tyr Ile Phe Lys Asp Gly Val Asp Asn Pro Asn Arg Arg
        915             920             925

Pro Gly Ile Arg Ile Asn Cys Ala Ala Pro Asn Xaa Val Leu Xaa Ser
930             935             940

Val Val Asp Asp Ala Lys Met Tyr Leu Arg Arg Phe Arg Ser Ser Thr
945             950             955             960

Gly Ala Ser Ile Trp His Glu Thr Ile Glu Asn Asn Val Tyr Arg Leu
        965             970             975

Cys Thr Gly Thr Thr Asp Ala Gln Glu Glu Leu Val Leu Arg Thr Gly
        980             985             990

Ser Tyr Ala Lys Phe Ala Gly Glu Ile Ile Ser Lys Ser Ala Asn Gly
        995             1000            1005

Leu Arg Ile Ala Tyr Gly Asn Tyr Gly Phe Phe Ile Arg Asn Asp
    1010            1015            1020

Gly Ser Ser Thr Tyr Phe Met Leu Thr Ala Ser Gly Asp Asn Leu
    1025            1030            1035

Gly Thr Trp Asn Ser Leu Arg Pro Leu Thr Ile Asn Asn Ala Asn
    1040            1045            1050

Gly Ala Val Ser Ile Gly Asn Gly Leu Asn Val Thr Gly Asp Ile
    1055            1060            1065

Arg Thr Asn Ala Trp Val Tyr Ala Asn Arg Phe Ser Val Asn Ser
    1070            1075            1080

Ser Ser Gly Ser Trp Ile Ser Met Arg Asp Gln Asn Val Ile Phe
    1085            1090            1095

Gly Leu Asn Lys Val Ser Thr Ser Ser Ala Gln Ala Leu Leu Arg
    1100            1105            1110

Gln Asp His Ala Asp Arg Lys Phe Phe Ile Gly Leu Gly Asn
    1115            1120            1125

Ser Gln Phe Gly Phe Tyr Met Ile Asn Asn Ser Arg Thr Ser Asn
    1130            1135            1140

Gly Thr Asp Gly Gln Ala Phe Leu Asp Ser Ser Gly Asn Phe Gln
    1145            1150            1155

Cys Gly Gly Gln Ile Leu Pro Thr Asn Tyr Ser Asn Phe Asp Ser
    1160            1165            1170

Arg Tyr Thr Leu Lys Thr Ala Cys Val Thr Ser Val Arg Met Gly
    1175            1180            1185
```

Ser Ala Ala Ser Tyr Lys Pro Ser Ser Asn Gly Val Ser Trp Thr
                1190                1195                1200

Gln Asn Leu Gly Ser Gly Leu Val Met Thr Gly Ile Ile Val Gln
        1205                1210                1215

Glu Thr Gly Gly Asn Ser Ala Asp Asn Ile Gly Gly Ile Tyr Tyr
    1220                1225                1230

Arg Pro Val Gln Tyr Cys Ile Asn Gly Thr Trp Tyr Thr Ala Ala
        1235                1240                1245

Ser Val
    1250

<210> SEQ ID NO 57
<211> LENGTH: 975
<212> TYPE: PRT
<213> ORGANISM: Artificial Sequence
<220> FEATURE:
<223> OTHER INFORMATION: Razzmatazz Tail Fiber

<400> SEQUENCE: 57

Met Asn Asp Val Thr Val Val Thr Ser Val Thr Tyr Pro Ser Pro Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Gly Val Ser Ala
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Ile Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Ser Ala Pro Thr Ala Gln Gly
            260                 265                 270

Thr Asn Ser Thr Gln Ile Ala Asn Thr Ala Phe Val Lys Ala Ala Ile
        275                 280                 285

```
Thr Ala Leu Ile Asn Gly Ala Pro Gly Thr Leu Asp Thr Leu Lys Glu
    290                 295                 300

Ile Ala Ala Ala Ile Asn Asn Asp Pro Asn Phe Ser Thr Thr Val Asn
305                 310                 315                 320

Asn Ala Leu Ala Leu Lys Ala Pro Leu Ala Ser Pro Ala Leu Thr Gly
                325                 330                 335

Ile Pro Thr Ala Pro Thr Ala Ala Gln Gly Thr Asn Asn Thr Gln Ile
            340                 345                 350

Ala Thr Thr Ala Tyr Val Arg Ala Ala Ile Ser Ala Leu Val Gly Ser
        355                 360                 365

Ser Pro Glu Ala Leu Asp Thr Leu Asn Glu Leu Ala Ala Ala Leu Gly
    370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Asp
                405                 410                 415

Ala Asn Lys Leu Pro Tyr Phe Thr Gly Thr Asp Thr Val Ser Gln Thr
            420                 425                 430

Asp Leu Thr Ser Val Gly Arg Asp Ile Leu Ala Lys Thr Ser Val Leu
        435                 440                 445

Ala Val Ile Gln Tyr Leu Gly Leu Arg Glu Leu Gly Thr Ser Gly Glu
    450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
                485                 490                 495

Thr Lys Leu Lys Thr Ala Ile Asn Ile Asn Gly Val Arg Phe Asp Gly
            500                 505                 510

Ser Thr Asn Ile Ser Ile Pro Thr Ile Thr Ser Arg Gly Arg Val Thr
        515                 520                 525

Ala Leu Thr Gly Thr Thr Gln Gly Ala Ala Thr Gly Leu Gln Met Tyr
    530                 535                 540

Glu Ala Tyr Asn Asn Gly Tyr Pro Thr Thr Tyr Gly Asn Val Leu His
545                 550                 555                 560

Leu Lys Gly Ala Ala Ser Thr Gly Glu Gly Glu Leu Leu Ile Gly Trp
                565                 570                 575

Ser Gly Thr Asn Gly Ala His Ala Pro Ala Phe Ile Arg Ser Lys Arg
            580                 585                 590

Asp Ser Thr Ala Ala Ala Trp Ser Glu Trp Ala Gln Ile Tyr Thr Ser
        595                 600                 605

Lys Asp Ser Val Pro Gly Val Asn Thr Lys Gly Asn Gln Asp Thr Ser
    610                 615                 620

Gly Asn Ala Ala Thr Ala Thr Lys Leu Gln Thr Ala Cys Thr Ile Asn
625                 630                 635                 640

Gly Val Ser Phe Asp Gly Ser Lys Asn Ile Glu Leu Thr Ala Ala Asp
                645                 650                 655

Leu Asn Leu Glu Gln Thr Val Glu Leu Ala Ala Gly Ala Leu Gln Lys
            660                 665                 670

Asn Gln Asn Gly Ala Asp Ile Pro Gly Lys Asp Thr Phe Thr Lys Asn
        675                 680                 685

Ile Gly Ala Cys Arg Ala Tyr Ser Ala Trp Leu Asn Ile Gly Gly Asp
    690                 695                 700
```

Ser Gln Val Trp Thr Thr Ala Gln Phe Ile Ser Trp Leu Glu Ser Gln
705                 710                 715                 720

Gly Ala Phe Asn His Pro Tyr Trp Met Cys Lys Gly Ser Trp Ala Tyr
            725                 730                 735

Ala Asn Asn Lys Val Ile Thr Asp Thr Gly Cys Gly Asn Ile Cys Leu
        740                 745                 750

Ala Gly Ala Val Val Glu Val Ile Gly Thr Arg Gly Ala Met Thr Ile
    755                 760                 765

Arg Val Thr Thr Pro Ser Thr Ser Ser Gly Gly Ile Thr Asn Ala
770                 775                 780

Gln Phe Thr Tyr Ile Asn His Gly Asp Ala Tyr Ala Pro Gly Trp Arg
785                 790                 795                 800

Arg Asp Tyr Asn Thr Lys Asn Gln Gln Pro Ala Phe Ala Leu Gly Gln
            805                 810                 815

Thr Gly Ser Arg Val Ala Asn Asp Lys Ala Val Gly Trp Asn Trp Asn
        820                 825                 830

Ser Gly Val Tyr Asp Ala Asp Ile Ser Gly Ala Ser Thr Leu Ile Leu
    835                 840                 845

His Phe Asn Met Asn Ala Gly Ser Cys Pro Ala Val Gln Phe Arg Val
850                 855                 860

Asn Tyr Lys Asn Gly Gly Ile Phe Tyr Arg Ser Ala Arg Asp Gly Tyr
865                 870                 875                 880

Gly Phe Glu Ala Asn Trp Ser Glu Phe Tyr Thr Thr Arg Lys Pro
            885                 890                 895

Ser Ala Gly Asp Val Gly Ala Tyr Thr Gln Ala Glu Cys Asn Ser Arg
        900                 905                 910

Phe Ile Thr Gly Ile Arg Leu Gly Gly Leu Ser Ser Val Gln Thr Trp
    915                 920                 925

Asn Gly Pro Gly Trp Ser Asp Arg Ser Gly Tyr Val Val Thr Gly Ser
930                 935                 940

Val Asn Gly Asn Arg Asp Glu Leu Ile Asp Thr Thr Gln Ala Arg Pro
945                 950                 955                 960

Ile Gln Tyr Cys Ile Asn Gly Thr Trp Tyr Asn Ala Gly Ser Ile
            965                 970                 975

<210> SEQ ID NO 58
<211> LENGTH: 901
<212> TYPE: PRT
<213> ORGANISM: Artificial Sequence
<220> FEATURE:
<223> OTHER INFORMATION: Salmon Tail Fiber

<400> SEQUENCE: 58

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln Gln Arg Lys Asp Ile Ser Leu Ala
                85                  90                  95

-continued

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
            115                 120                 125

Ala Glu Phe Val Ala Arg Thr Tyr Thr Asp Ser Tyr Gln Leu Gly Asp
        130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
    290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
                325                 330                 335

Val Pro Thr Ala Pro Thr Ala Ala Gln Gly Thr Asn Asn Thr Gln Ile
            340                 345                 350

Ala Thr Thr Ala Tyr Val Arg Ala Ala Ile Ser Ala Leu Val Gly Ser
        355                 360                 365

Ser Pro Glu Ala Leu Asp Thr Leu Tyr Glu Leu Ala Ala Ala Leu Gly
    370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
            420                 425                 430

Asp Leu Thr Ser Val Gly Arg Asp Ile Leu Ala Lys Thr Ser Ile Leu
        435                 440                 445

Ala Val Ile Gln Tyr Leu Gly Leu Arg Glu Leu Gly Thr Ser Gly Glu
    450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
                485                 490                 495

Thr Lys Leu Lys Thr Ala Arg Thr Ile Gly Gly Val Ala Phe Asp Gly
            500                 505                 510

Thr Ala Asn Ile Asn Leu Pro Gly Val Asn Val Ala Gly Asn Gln Asn

```
                515                 520                 525
Thr Ser Gly Asn Ala Ala Thr Ala Thr Lys Leu Gln Thr Ala Cys Thr
    530                 535                 540
Ile Asn Gly Val Ser Phe Asp Gly Ser Lys Asn Ile Glu Leu Thr Ala
545                 550                 555                 560
Glu Asp Leu Asn Leu Gln Glu Phe Ile Asn Lys Ala Asn Asn Ala Val
                565                 570                 575
Gln Arg Ser Gly Asp Ile Leu Ser Gly Gly Leu Thr Phe Glu Asn Asp
            580                 585                 590
Ser Ile Leu Ala Trp Ile Arg Asn Thr Asp Trp Ala Lys Ile Gly Phe
        595                 600                 605
Lys Asn Asp Ala Asp Ser Asp Thr Asp Ser Tyr Met Trp Phe Glu Thr
    610                 615                 620
Gly Asp Asn Gly Asn Glu Tyr Phe Lys Trp Arg Ser Lys Gln Ser Thr
625                 630                 635                 640
Thr Thr Lys Asp Leu Met Asn Leu Lys Trp Asp Ala Leu Ser Val Leu
                645                 650                 655
Val Lys Ala Leu Phe Ser Ser Glu Val Lys Ile Ser Thr Val Asn Ala
            660                 665                 670
Leu Arg Ile Phe Asn Ser Ser Phe Gly Ala Ile Phe Arg Arg Ser Glu
        675                 680                 685
Glu Cys Leu His Ile Ile Pro Thr Arg Glu Asn Glu Gly Glu Asn Gly
    690                 695                 700
Asp Ile Gly Pro Leu Arg Pro Phe Thr Leu Asn Leu Arg Thr Gly Arg
705                 710                 715                 720
Ile Thr Met Gly His Gly Leu Asp Val Thr Gly Asp Ile Thr Thr Asn
                725                 730                 735
Ala Trp Val Tyr Ala Asn Arg Phe Ala Ile Asn Ser Gly Ser Thr Ser
            740                 745                 750
Trp Ile Asp Met Arg Asn Gln Asn Val Ile Phe Gly Arg Asn Ala Val
        755                 760                 765
Ser Thr Ser Ser Ala Gln Ala Leu Leu Arg Gln Asp His Ala Glu Arg
    770                 775                 780
Lys Phe Phe Val Gly Gly Leu Gly Asn Tyr Gln Phe Gly Phe Tyr Met
785                 790                 795                 800
Ile Asn Asn Ser Arg Thr Ala Asn Gly Thr Asp Gly Gln Ala Tyr Met
                805                 810                 815
Asp Asn Asn Gly Asn Trp Leu Cys Gly Ser Gln Val Ile Pro Gly Asn
            820                 825                 830
Tyr Gly Asn Phe Asp Ser Arg Tyr Val Arg Asp Val Arg Leu Gly Thr
        835                 840                 845
Arg Val Val Gln Leu Met Ala Arg Gly Gly Arg Tyr Glu Lys Ala Gly
    850                 855                 860
His Ala Ile Thr Gly Leu Arg Ile Ile Gly Glu Val Asp Gly Asp Asp
865                 870                 875                 880
Glu Ala Ile Phe Arg Pro Ile Gln Lys Tyr Ile Asn Gly Thr Trp Tyr
                885                 890                 895
Asn Val Ala Gln Val
            900

<210> SEQ ID NO 59
<211> LENGTH: 747
<212> TYPE: PRT
<213> ORGANISM: Artificial Sequence
```

-continued

```
<220> FEATURE:
<223> OTHER INFORMATION: Scarlet Tail Fiber

<400> SEQUENCE: 59
```

| Met | Asn | Asp | Val | Thr | Val | Thr | Ser | Val | Thr | Tyr | Pro | Ser | Pro | Glu |
|---|---|---|---|---|---|---|---|---|---|---|---|---|---|---|
| 1 | | | | 5 | | | | | 10 | | | | | 15 |

| Ser | Leu | Ala | Leu | Val | Ala | Asp | Val | Gln | Tyr | His | Glu | Pro | Tyr | Leu | Ser |
|---|---|---|---|---|---|---|---|---|---|---|---|---|---|---|---|
| | | | 20 | | | | | 25 | | | | | 30 | | |

| Ala | Ala | Leu | Asn | Arg | Lys | Phe | Arg | Gly | Ile | Val | Asp | Pro | Gly | Phe | Tyr |
|---|---|---|---|---|---|---|---|---|---|---|---|---|---|---|---|
| | | 35 | | | | | 40 | | | | | 45 | | | |

| Ala | Gly | Phe | Leu | Pro | Lys | Pro | Gly | Gly | Met | Asn | Leu | Leu | Ile | Thr |
|---|---|---|---|---|---|---|---|---|---|---|---|---|---|---|
| | 50 | | | | | 55 | | | | | 60 | | | |

| Ser | Val | Asp | Gly | Asp | Lys | Thr | Ala | Gly | Ala | Ala | Ser | Val | Asp | Ile | Gly |
|---|---|---|---|---|---|---|---|---|---|---|---|---|---|---|---|
| 65 | | | | | 70 | | | | | 75 | | | | | 80 |

| Glu | Phe | Tyr | Gln | Val | Thr | Ile | Gln | His | Arg | Lys | Asp | Ile | Ser | Leu | Ala |
|---|---|---|---|---|---|---|---|---|---|---|---|---|---|---|---|
| | | | | 85 | | | | | 90 | | | | | 95 | |

| Leu | Asn | Ala | Gly | Lys | Lys | Tyr | Ala | Ile | Val | Leu | Lys | Gly | Arg | Tyr | Leu |
|---|---|---|---|---|---|---|---|---|---|---|---|---|---|---|---|
| | | | 100 | | | | | 105 | | | | | 110 | | |

| Leu | Gly | Glu | Asp | Thr | Tyr | Gln | Val | Asn | Thr | Ala | Ser | His | Ile | His | Ala |
|---|---|---|---|---|---|---|---|---|---|---|---|---|---|---|---|
| | | 115 | | | | | 120 | | | | | 125 | | | |

| Ala | Glu | Phe | Val | Ala | Arg | Thr | Tyr | Thr | Asp | Ser | Tyr | Gln | Leu | Gly | Asp |
|---|---|---|---|---|---|---|---|---|---|---|---|---|---|---|---|
| | 130 | | | | | 135 | | | | | 140 | | | | |

| Gly | Glu | Leu | Leu | Val | Cys | Thr | Val | Asn | Ile | Pro | Ala | Gly | Val | Ser | Thr |
|---|---|---|---|---|---|---|---|---|---|---|---|---|---|---|---|
| 145 | | | | | 150 | | | | | 155 | | | | | 160 |

| Ile | Thr | Gln | Glu | Met | Ile | Asp | Thr | Ser | Glu | Arg | Ile | Asn | Arg | Thr | Ile |
|---|---|---|---|---|---|---|---|---|---|---|---|---|---|---|---|
| | | | | 165 | | | | | 170 | | | | | 175 | |

| Gly | Ile | Asp | Ile | Ser | Asp | Ser | Val | Thr | Ser | Thr | Arg | Ser | Asp | Val | Ala |
|---|---|---|---|---|---|---|---|---|---|---|---|---|---|---|---|
| | | | 180 | | | | | 185 | | | | | 190 | | |

| Ala | Ser | Ser | Leu | Ala | Val | Lys | Lys | Ala | Tyr | Asp | Leu | Ala | Lys | Ser | Lys |
|---|---|---|---|---|---|---|---|---|---|---|---|---|---|---|---|
| | | 195 | | | | | 200 | | | | | 205 | | | |

| Tyr | Thr | Ala | Gln | Asp | Ala | Ser | Thr | Thr | Gln | Lys | Gly | Leu | Val | Gln | Leu |
|---|---|---|---|---|---|---|---|---|---|---|---|---|---|---|---|
| | 210 | | | | | 215 | | | | | 220 | | | | |

| Ser | Ser | Ala | Thr | Asn | Ser | Thr | Ser | Glu | Val | Leu | Ala | Ala | Thr | Pro | Lys |
|---|---|---|---|---|---|---|---|---|---|---|---|---|---|---|---|
| 225 | | | | | 230 | | | | | 235 | | | | | 240 |

| Ala | Val | Lys | Ala | Ala | Tyr | Asp | Leu | Ala | Asn | Gly | Lys | Tyr | Thr | Ala | Gln |
|---|---|---|---|---|---|---|---|---|---|---|---|---|---|---|---|
| | | | | 245 | | | | | 250 | | | | | 255 | |

| Asp | Ala | Thr | Thr | Thr | Gln | Lys | Gly | Ile | Val | Gln | Leu | Ser | Ser | Asp | Thr |
|---|---|---|---|---|---|---|---|---|---|---|---|---|---|---|---|
| | | | 260 | | | | | 265 | | | | | 270 | | |

| Asn | Ser | Thr | Ser | Glu | Thr | Leu | Ala | Ala | Thr | Pro | Lys | Ala | Val | Lys | Ala |
|---|---|---|---|---|---|---|---|---|---|---|---|---|---|---|---|
| | | 275 | | | | | 280 | | | | | 285 | | | |

| Ala | Tyr | Asp | Leu | Ala | Ala | Gly | Lys | Ala | Pro | Ser | Ser | His | Thr | His | Pro |
|---|---|---|---|---|---|---|---|---|---|---|---|---|---|---|---|
| | 290 | | | | | 295 | | | | | 300 | | | | |

| Trp | Asn | Gln | Ile | Thr | Gly | Val | Pro | Thr | Ala | Ser | Leu | Thr | Ala | Lys | Gly |
|---|---|---|---|---|---|---|---|---|---|---|---|---|---|---|---|
| 305 | | | | | 310 | | | | | 315 | | | | | 320 |

| Ile | Thr | Gln | Leu | Ser | Ser | Ala | Thr | Asn | Ser | Thr | Ser | Glu | Val | Leu | Ala |
|---|---|---|---|---|---|---|---|---|---|---|---|---|---|---|---|
| | | | | 325 | | | | | 330 | | | | | 335 | |

| Ala | Thr | Pro | Lys | Ala | Val | Lys | Ala | Ala | Tyr | Asp | Leu | Ala | Asn | Gly | Lys |
|---|---|---|---|---|---|---|---|---|---|---|---|---|---|---|---|
| | | | 340 | | | | | 345 | | | | | 350 | | |

| Tyr | Thr | Ala | Gln | Asp | Ala | Thr | Thr | Ala | Gln | Lys | Gly | Ile | Val | Gln | Leu |
|---|---|---|---|---|---|---|---|---|---|---|---|---|---|---|---|
| | | 355 | | | | | 360 | | | | | 365 | | | |

| Ser | Ser | Ala | Thr | Asn | Ser | Thr | Ser | Glu | Val | Leu | Ala | Ala | Thr | Pro | Lys |
|---|---|---|---|---|---|---|---|---|---|---|---|---|---|---|---|
| | 370 | | | | | 375 | | | | | 380 | | | | |

| Ala | Val | Lys | Ala | Ala | Tyr | Asp | Leu | Ala | Asn | Gly | Lys | Tyr | Thr | Ala | Gln |
|---|---|---|---|---|---|---|---|---|---|---|---|---|---|---|---|
| 385 | | | | | 390 | | | | | 395 | | | | | 400 |

```
Asp Ala Thr Thr Thr Gln Lys Gly Ile Val Gln Leu Ser Ser Asp Thr
            405                 410                 415

Asn Ser Thr Ser Glu Thr Leu Ala Ala Thr Pro Lys Ala Val Lys Ala
        420                 425                 430

Ala Tyr Asp Leu Ala Ala Gly Lys Ala Pro Ser Ser His Thr His Pro
    435                 440                 445

Trp Asn Gln Ile Thr Val Val Pro Thr Ala Ser Leu Thr Ala Lys Gly
450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
                485                 490                 495

Tyr Thr Ala Gln Asp Ala Thr Thr Ala Gln Lys Gly Ile Val Gln Leu
            500                 505                 510

Ser Ser Ala Thr Asn Ser Thr Ser Glu Val Leu Ala Ala Thr Pro Lys
        515                 520                 525

Ala Val Lys Ala Ala Tyr Asp Leu Ala Asn Gly Lys Gln Ala Ala Asp
    530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
                565                 570                 575

Val Gly Arg Ala Ile Leu Gly Lys Thr Ser Ile Gln Ser Val Leu Asp
            580                 585                 590

Tyr Leu Gly Leu Gly Glu Gly Ser Ala Leu Pro Val Gly Val Pro Val
        595                 600                 605

Pro Trp Pro Leu Glu Thr Pro Pro Thr Gly Trp Leu Lys Cys Asn Gly
    610                 615                 620

Ala Ala Phe Ser Ser Glu Met Tyr Pro Lys Leu Ala Lys Ala Tyr Pro
625                 630                 635                 640

Thr Asn Lys Leu Pro Asp Leu Arg Gly Glu Phe Ile Arg Gly Trp Asp
                645                 650                 655

Asp Gly Arg Gly Val Asp Ala Gly Arg Val Ile Leu Ser Ile Gln Gly
            660                 665                 670

Trp Leu Thr Gly Ser His Tyr His Asn Ile Arg Ser Trp Asp Ala Trp
        675                 680                 685

Asp Asn Thr Val Leu Val Pro Asn Asp Arg Gly Gly Asp Ser Leu Leu
    690                 695                 700

Ser Thr Asp Asn Ala Val Arg Gln Gly Ala Ile Asn Gly Lys Phe Thr
705                 710                 715                 720

Ser Gln Tyr Arg Thr Glu Leu Ser Gly Gly Asn Glu Thr Arg Pro Arg
                725                 730                 735

Asn Ile Ala Phe Asn Tyr Ile Val Arg Ala Ala
            740                 745

<210> SEQ ID NO 60
<211> LENGTH: 996
<212> TYPE: PRT
<213> ORGANISM: Artificial Sequence
<220> FEATURE:
<223> OTHER INFORMATION: Shamrock Tail Fiber

<400> SEQUENCE: 60

Met Asn Asp Val Thr Val Val Thr Ser Val Thr Tyr Pro Ser Ser Glu
1               5                   10                  15
```

```
Ser Leu Ala Leu Val Ala Asp Val Gln Tyr His Glu Pro Tyr Leu Ser
             20                  25                  30

Ala Ala Leu Asn Arg Lys Phe Arg Gly Ile Val Asp Pro Gly Phe Tyr
         35                  40                  45

Ala Gly Phe Leu Pro Lys Pro Gly Gly Met Asn Leu Leu Ile Thr
     50                  55                  60

Ser Val Asp Gly Asp Lys Thr Ala Gly Ala Ser Val Asp Ile Gly
 65              70                  75                  80

Glu Phe Tyr Gln Val Thr Ile Gln Gln Arg Lys Asp Ile Ser Leu Ala
                 85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
            115                 120                 125

Ala Glu Phe Val Ala Arg Thr Tyr Thr Asp Ser Tyr Gln Leu Gly Asp
        130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
    290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
                325                 330                 335

Val Pro Thr Ala Pro Thr Ala Ala Gln Gly Thr Asn Asn Thr Gln Ile
            340                 345                 350

Ala Thr Thr Ala Tyr Val Arg Ala Ala Ile Ser Ala Leu Val Gly Ser
        355                 360                 365

Ser Pro Glu Ala Leu Asp Thr Leu Tyr Glu Leu Ala Ala Ala Leu Gly
    370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
            420                 425                 430
```

```
Asp Leu Thr Ser Val Gly Arg Asp Ile Leu Ala Lys Thr Ser Ile Leu
            435                 440                 445
Ala Val Ile Gln Tyr Leu Gly Leu Arg Glu Leu Gly Thr Ser Gly Glu
        450                 455                 460
Lys Ile Pro Leu Leu Ser Thr Ala Asn Thr Trp Ser Ala Arg Gln Thr
465                 470                 475                 480
Phe Asn Gly Gly Ile Thr Gly Ala Leu Thr Gly Asn Ala Asp Thr Ala
                485                 490                 495
Thr Lys Leu Lys Thr Ala Arg Asn Ile Asn Gly Val Arg Phe Asp Gly
            500                 505                 510
Ser Gly Asp Ile Asn Ile Asn Thr Leu Val Ser Arg Gly Arg Val Thr
        515                 520                 525
Ala Leu Glu Ala Asn Ala Gln Gly Thr Ser Gly Ile Gln Leu Tyr Glu
    530                 535                 540
Ala Tyr Asn Asn Gly Tyr Pro Ser Pro Tyr Gly Asn Val Leu His Leu
545                 550                 555                 560
Lys Gly Ala Thr Ala Ala Gly Glu Gly Glu Leu Phe Ile Gly Trp Ser
                565                 570                 575
Gly Thr Ser Gly Ala His Ala Pro Val His Ile Arg Ser Arg Arg Asp
            580                 585                 590
Thr Asp Ser Ala Asn Trp Ser Glu Trp Ala Gln Val Tyr Thr Ser Lys
        595                 600                 605
Asp Ser Ile Pro Gly Val Asn Ala Lys Gly Asp Gln Asp Thr Ser Gly
    610                 615                 620
Asn Ala Ala Thr Ala Thr Lys Leu Gln Thr Ala Cys Thr Ile Asn Gly
625                 630                 635                 640
Val Ser Phe Asp Gly Ser Lys Asn Ile Glu Leu Thr Ala Glu Asp Leu
                645                 650                 655
Asn Leu Gln Glu Thr Val Asn Lys Ala Asp Asn Ala Val Gln Lys Thr
            660                 665                 670
Gly Asp Thr Leu Ser Gly Gly Leu Thr Phe Glu Asn Asp Ser Ile Leu
        675                 680                 685
Ala Trp Ile Arg Asn Thr Asp Trp Ala Lys Ile Gly Phe Lys Asn Asn
    690                 695                 700
Ser Asp Ala Asp Thr Asp Ser Tyr Met Trp Phe Glu Thr Gly Asn Asn
705                 710                 715                 720
Gly Asn Glu Tyr Phe Lys Trp Arg His Arg Ile Ile Gly Thr Arg Pro
                725                 730                 735
Lys Asp Leu Met Asn Leu Lys Trp Asn Ala Leu Ser Val Leu Val Glu
            740                 745                 750
Ala Leu Phe Ser Ser Glu Val Lys Ile Ser Thr Val Asn Ala Leu Arg
        755                 760                 765
Ile Phe Asn Ser Ser Phe Gly Ala Ile Phe Arg Arg Ser Glu Glu Cys
    770                 775                 780
Leu His Ile Ile Pro Thr Arg Glu Asn Glu Gly Glu Asn Gly Asn Ile
785                 790                 795                 800
Gly Pro Leu Arg Pro Phe Thr Leu Asn Leu Arg Thr Gly Arg Ile Ser
                805                 810                 815
Met Gly His Gly Leu Asp Val Thr Gly Asp Ile Phe Ala Asn Arg Phe
            820                 825                 830
Ala Ile Asn Ser Ser Thr Gly Met Trp Ile His Met Arg Asp Gln Asn
        835                 840                 845
Val Ile Leu Gly Arg Asn Ala Val Ser Thr Asp Gly Ala Gln Ala Leu
```

```
                 850                 855                 860
Leu Arg Gln Asp His Ala Asp Arg Lys Phe Met Ile Gly Gly Leu Gly
865                 870                 875                 880

Asn Lys Gln Phe Gly Ile Tyr Met Ile Asn Asn Ser Arg Thr Ala Asn
                885                 890                 895

Gly Thr Asp Gly Gln Ala Tyr Met Asp Asn Asn Gly Asn Trp Leu Cys
                900                 905                 910

Gly Ala Gln Val Ile Pro Gly Asn Tyr Gly Asn Phe Asp Ser Arg Tyr
                915                 920                 925

Val Lys Asp Val Arg Leu Gly Ser Gln Gln Tyr Tyr Gly Val Asn Asn
                930                 935                 940

Trp Gln Thr Trp Asn Phe Gln Cys Pro Ser Gly His Val Leu Ser Gly
945                 950                 955                 960

Ile Asn Val Gln Asp Thr Gly Lys Asn Ser Ala Asp Asn Ile Ala Gly
                965                 970                 975

Val Tyr Tyr Arg Pro Val Gln Lys Tyr Ile Asn Gly Thr Trp Tyr Asn
                980                 985                 990

Val Ala Ser Val
        995

<210> SEQ ID NO 61
<211> LENGTH: 760
<212> TYPE: PRT
<213> ORGANISM: Artificial Sequence
<220> FEATURE:
<223> OTHER INFORMATION: Sunset Tail Fiber

<400> SEQUENCE: 61

Met Asn Asp Val Thr Val Thr Ser Val Thr Tyr Pro Ser Pro Glu
1               5                   10                  15

Ser Leu Ala Leu Val Ala Asp Val Gln Tyr His Glu Pro Tyr Leu Ser
                20                  25                  30

Ala Ala Leu Asn Arg Lys Phe Arg Gly Ile Val Asp Pro Gly Phe Tyr
            35                  40                  45

Ala Gly Phe Leu Pro Lys Pro Gly Gly Met Asn Leu Leu Ile Thr
50                  55                  60

Ser Val Asp Gly Asp Lys Thr Ala Gly Ala Ser Val Asp Ile Gly
65              70                  75                  80

Glu Phe Tyr Gln Val Thr Ile Gln His Arg Lys Asp Ile Ser Leu Ala
                85                  90                  95

Leu Asn Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
            115                 120                 125

Ala Glu Phe Val Ala Arg Thr Tyr Thr Asp Ser Tyr Gln Leu Gly Asp
        130                 135                 140

Gly Glu Leu Leu Val Cys Thr Val Asn Ile Pro Ala Gly Val Ser Thr
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
```

```
              210                 215                 220
Ser Ser Ala Thr Asn Ser Thr Ser Glu Val Leu Ala Ala Thr Pro Lys
225                 230                 235                 240

Ala Val Lys Ala Ala Tyr Asp Leu Ala Asn Gly Lys Tyr Thr Ala Gln
                245                 250                 255

Asp Ala Thr Thr Thr Gln Lys Gly Ile Val Gln Leu Ser Ser Asp Thr
                    260                 265                 270

Asn Ser Thr Ser Glu Thr Leu Ala Ala Thr Pro Lys Ala Val Lys Ala
                275                 280                 285

Ala Tyr Asp Leu Ala Ala Gly Lys Ala Pro Ser Ser His Thr His Pro
        290                 295                 300

Trp Asn Gln Ile Thr Gly Val Pro Thr Ala Ser Leu Thr Ala Lys Gly
305                 310                 315                 320

Ile Thr Gln Leu Ser Ser Ala Thr Asn Ser Thr Ser Glu Val Leu Ala
                325                 330                 335

Ala Thr Pro Lys Ala Val Lys Ala Ala Tyr Asp Leu Ala Asn Gly Lys
                340                 345                 350

Tyr Thr Ala Gln Asp Ala Thr Thr Ala Gln Lys Gly Ile Val Gln Leu
            355                 360                 365

Ser Ser Ala Thr Asn Ser Thr Ser Glu Val Leu Ala Ala Thr Pro Lys
        370                 375                 380

Ala Val Lys Ala Ala Tyr Asp Leu Ala Asn Gly Lys Tyr Thr Ala Gln
385                 390                 395                 400

Asp Ala Thr Thr Thr Gln Lys Gly Ile Val Gln Leu Ser Ser Asp Thr
                    405                 410                 415

Asn Ser Thr Ser Glu Thr Leu Ala Ala Thr Pro Lys Ala Val Lys Ala
                420                 425                 430

Ala Tyr Asp Leu Ala Ala Gly Lys Ala Pro Ser Ser His Thr His Pro
        435                 440                 445

Trp Asn Gln Ile Thr Val Val Pro Thr Ala Ser Leu Thr Ala Lys Gly
450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
                485                 490                 495

Tyr Thr Ala Gln Asp Ala Thr Thr Ala Gln Lys Gly Ile Val Gln Leu
            500                 505                 510

Ser Ser Ala Thr Asn Ser Thr Ser Glu Val Leu Ala Ala Thr Pro Lys
        515                 520                 525

Ala Val Lys Ala Ala Tyr Asp Leu Ala Asn Gly Lys Gln Ala Ala Asp
                530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
                565                 570                 575

Val Gly Arg Ala Ile Leu Gly Lys Thr Ser Ile Gln Ser Val Leu Asp
                580                 585                 590

Tyr Leu Gly Leu Gly Glu Gly Ser Ala Leu Pro Val Gly Val Pro Val
            595                 600                 605

Pro Trp Pro Ser Ala Thr Pro Pro Thr Gly Trp Leu Lys Cys Asn Gly
        610                 615                 620

Ala Ala Phe Ser Ser Glu Lys Tyr Pro Asn Leu Ala Lys Val Tyr Pro
625                 630                 635                 640
```

```
Thr Leu Lys Leu Pro Asp Leu Arg Gly Glu Phe Ile Arg Gly Trp Asp
            645                 650                 655

Asp Gly Arg Gly Ile Asp Ser Gly Arg Ser Ile Leu Ser Glu Gln Gly
        660                 665                 670

Tyr Ala Thr Glu Asp His Ala His Gly Leu Pro Ser Lys Ser Thr Val
        675                 680                 685

Ala Thr Asp Arg Ser Ile Asn Phe Tyr Phe Asp Glu Ala Trp Ala Thr
    690                 695                 700

Ser Gly Asn Thr Gly Val Ile Arg Trp Gly Asn Thr Ser Asp Ala Gly
705                 710                 715                 720

Leu Pro Ala Pro Asn Tyr Gly Thr Phe Lys Thr Tyr Lys Gln Ser Val
                725                 730                 735

Ala Asn Leu Gly Thr Ala Gly Leu Glu Thr Arg Pro Arg Asn Ile Ala
            740                 745                 750

Phe Asn Tyr Ile Val Arg Ala Asp
            755                 760

<210> SEQ ID NO 62
<211> LENGTH: 762
<212> TYPE: PRT
<213> ORGANISM: Artificial Sequence
<220> FEATURE:
<223> OTHER INFORMATION: Tangerine Tail Fiber

<400> SEQUENCE: 62

Met Asn Asp Val Thr Val Val Thr Ser Val Thr Tyr Pro Ser Pro Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln His Arg Lys Asp Ile Ser Leu Ala
                85                  90                  95

Leu Asn Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Gly Val Ser Thr
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Thr Ser Glu Val Leu Ala Ala Thr Pro Lys
225                 230                 235                 240
```

```
Ala Val Lys Ala Ala Tyr Asp Leu Ala Asn Gly Lys Tyr Thr Ala Gln
            245                 250                 255

Asp Ala Thr Thr Thr Gln Lys Gly Ile Val Gln Leu Ser Ser Asp Thr
        260                 265                 270

Asn Ser Thr Ser Glu Thr Leu Ala Ala Thr Pro Lys Ala Val Lys Ala
            275                 280                 285

Ala Tyr Asp Leu Ala Ala Gly Lys Ala Pro Ser Ser His Thr His Pro
        290                 295                 300

Trp Asn Gln Ile Thr Gly Val Pro Thr Ala Ser Leu Thr Ala Lys Gly
305                 310                 315                 320

Ile Thr Gln Leu Ser Ser Ala Thr Asn Ser Thr Ser Glu Val Leu Ala
            325                 330                 335

Ala Thr Pro Lys Ala Val Lys Ala Ala Tyr Asp Leu Ala Asn Gly Lys
        340                 345                 350

Tyr Thr Ala Gln Asp Ala Thr Thr Ala Gln Lys Gly Ile Val Gln Leu
            355                 360                 365

Ser Ser Ala Thr Asn Ser Thr Ser Glu Val Leu Ala Ala Thr Pro Lys
        370                 375                 380

Ala Val Lys Ala Ala Tyr Asp Leu Ala Asn Gly Lys Tyr Thr Ala Gln
385                 390                 395                 400

Asp Ala Thr Thr Thr Gln Lys Gly Ile Val Gln Leu Ser Ser Asp Thr
            405                 410                 415

Asn Ser Thr Ser Glu Thr Leu Ala Ala Thr Pro Lys Ala Val Lys Ala
        420                 425                 430

Ala Tyr Asp Leu Ala Ala Gly Lys Ala Pro Ser Ser His Thr His Pro
            435                 440                 445

Trp Asn Gln Ile Thr Val Val Pro Thr Ala Ser Leu Thr Ala Lys Gly
        450                 455                 460

Ile Thr Gln Leu Ser Ser Ala Thr Asn Ser Thr Ser Glu Val Leu Ala
465                 470                 475                 480

Ala Thr Pro Lys Ala Val Lys Ala Ala Tyr Asp Leu Ala Asn Gly Lys
            485                 490                 495

Tyr Thr Ala Gln Asp Ala Thr Thr Ala Gln Lys Gly Ile Val Gln Leu
        500                 505                 510

Ser Ser Ala Thr Asn Ser Thr Ser Glu Val Leu Ala Ala Thr Pro Lys
            515                 520                 525

Ala Val Lys Ala Ala Tyr Asp Leu Ala Asn Gly Lys Gln Ala Ala Asp
        530                 535                 540

Ala Thr Leu Thr Ala Leu Ala Ala Leu Ala Thr Ala Ala Asp Lys Leu
545                 550                 555                 560

Pro Tyr Phe Thr Gly Val Asp Arg Ala Ala Leu Thr Ala Leu Thr Ser
            565                 570                 575

Val Gly Arg Ala Ile Leu Gly Lys Thr Ser Ile Gln Ser Val Leu Asp
        580                 585                 590

Tyr Leu Gly Leu Gly Glu Gly Ser Ala Leu Pro Val Gly Val Pro Val
            595                 600                 605

Pro Trp Pro Ser Ala Thr Pro Pro Thr Gly Trp Leu Lys Cys Asn Gly
        610                 615                 620

Ala Ala Phe Ser Ser Glu Lys Tyr Pro Asn Leu Ala Lys Val Tyr Pro
625                 630                 635                 640

Thr Leu Lys Leu Pro Asp Leu Arg Gly Glu Phe Ile Arg Gly Trp Asp
            645                 650                 655
```

```
Asp Ser Arg Gly Ile Asp Thr Gly Arg Ser Leu Leu Ser Gly Gln Thr
                660                 665                 670

Ala Thr Phe Ile Arg Thr Ala Leu Gln Asp Tyr Tyr Gly Val Asp Leu
        675                 680                 685

Thr Thr Asn Val Lys Val Gly Ile Ala Tyr Ala Thr Ala Asp Ser Val
    690                 695                 700

Ile Thr Val Gly Asn Pro Ala Asn Pro Lys Ala Gly Asp Asn Ser Asp
705                 710                 715                 720

Tyr Val Pro Ala Ser Ser Asp Asn Ser Ile Thr Gly Thr Gln Arg Thr
                725                 730                 735

Ala Glu Asp Asn Phe Thr Gly Ala Trp Ile Ser Met Arg Pro Arg Asn
        740                 745                 750

Val Ala Phe Asn Tyr Ile Val Arg Ala Thr
    755                 760

<210> SEQ ID NO 63
<211> LENGTH: 1181
<212> TYPE: PRT
<213> ORGANISM: Artificial Sequence
<220> FEATURE:
<223> OTHER INFORMATION: Thistle Tail Fiber

<400> SEQUENCE: 63

Met Asn Asp Val Thr Val Thr Ser Val Thr Tyr Pro Ser Ser Glu
1               5                   10                  15

Ser Leu Ala Leu Val Ala Asp Val Gln Tyr His Glu Pro Tyr Leu Ser
                20                  25                  30

Ala Ala Leu Asn Arg Lys Phe Arg Gly Ile Val Asp Pro Gly Phe Tyr
            35                  40                  45

Ala Gly Phe Leu Pro Lys Pro Gly Gly Met Asn Leu Leu Ile Thr
        50                  55                  60

Ser Val Asp Gly Asp Lys Thr Ala Gly Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255
```

-continued

```
Ser Pro Ser Leu Thr Gly Thr Pro Thr Ala Pro Ala Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
290                 295                 300

Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
                325                 330                 335

Val Pro Thr Ala Pro Thr Ala Ala Gln Gly Thr Asn Asn Thr Gln Ile
            340                 345                 350

Ala Thr Thr Ala Tyr Val Arg Ala Ala Ile Ser Ala Leu Val Gly Ser
        355                 360                 365

Ser Pro Glu Ala Leu Asp Thr Leu Tyr Glu Leu Ala Ala Ala Leu Gly
    370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Thr Asp Thr Val Ser Gln Thr
            420                 425                 430

Asp Leu Thr Ser Val Gly Arg Asp Ile Leu Ala Lys Thr Ser Ile Leu
        435                 440                 445

Ala Val Ile Gln Tyr Leu Gly Leu Arg Glu Leu Gly Thr Ser Gly Glu
    450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
                485                 490                 495

Thr Lys Leu Lys Thr Ala Arg Lys Ile Asn Asn Val Ser Phe Asp Gly
            500                 505                 510

Ser Ala Asp Ile Thr Leu Thr Pro Glu Asn Leu Gly Val Thr Ser Leu
        515                 520                 525

Thr Phe Glu Lys Asn Asn Gly Glu Met Pro Ile Asp Ala Asp Leu Asn
    530                 535                 540

Thr Phe Gly Pro Val Glu Ala Tyr Leu Gly Val Trp Ser Lys Ala Thr
545                 550                 555                 560

Ser Thr Asn Ala Thr Leu Glu Lys Asn Phe Pro Glu Asp Asn Ala Val
                565                 570                 575

Gly Val Leu Glu Val Phe Ala Ala Gly Asn Phe Ala Gly Thr Gln Arg
            580                 585                 590

Phe Thr Thr Arg Asp Gly Asn Val Tyr Ile Arg Arg Leu Ala Asn Lys
        595                 600                 605

Trp Asn Gly Ser Asp Gly Pro Trp Gly Ile Trp Arg His Thr Gln Ser
    610                 615                 620

Ala Thr Arg Pro Leu Ser Thr Thr Ile Asp Leu Asn Thr Leu Gly Ala
625                 630                 635                 640

Ala Glu His Leu Gly Leu Trp Arg Asn Ser Ser Ala Ile Ala Ser
                645                 650                 655

Tyr Glu Arg Asn Tyr Pro Glu Glu Gly Phe Ala Gln Gly Val Leu
            660                 665                 670

Glu Ile Leu Glu Gly Gly Asn Tyr Gly Arg Thr Gln Arg Tyr Thr Thr
```

-continued

```
              675                 680                 685
Arg Arg Gly Asn Met Tyr Val Arg Cys Leu Ala Ala Ser Trp Asp Ala
690                 695                 700
Ser Asn Pro Gln Trp Glu Pro Trp Leu Lys Val Gly His Gln Ser Glu
705                 710                 715                 720
Ser Arg Tyr Tyr Glu Gly Asp Leu Asn Val Leu Thr Asp Pro Gly Ile
                    725                 730                 735
Tyr Ser Val Thr Gly Lys Ala Thr Asn Gly Pro Met Leu Asp Thr Val
                740                 745                 750
Gly Ala Thr Leu Leu Gly Ile Leu Glu Val Ile Arg Arg Phe Asp Gly
                755                 760                 765
Val Ser Val Trp Gln Arg Tyr Thr Thr Thr Gly Lys Ser Glu Thr Thr
770                 775                 780
Gln Gly Arg Thr Phe Glu Arg Val Tyr Ala Gly Ser Lys Trp Thr Glu
785                 790                 795                 800
Trp Arg Glu Val Tyr Asn Ser Phe Ser Leu Pro Leu Asn Leu Gly Ile
                    805                 810                 815
Gly Gly Ala Val Ala Lys Leu Ser Ser Leu Asp Trp Gln Thr Tyr Asp
                820                 825                 830
Phe Val Pro Gly Ser Leu Ile Thr Val Arg Leu Asp Asn Met Thr Asn
                835                 840                 845
Ile Pro Asp Gly Met Asp Trp Gly Val Ile Asp Gly Asn Leu Ile Asn
850                 855                 860
Ile Ala Val Gly Pro Ser Asp Asp Ser Gly Thr Gly Arg Ser Met His
865                 870                 875                 880
Val Trp Arg Ser Thr Val Ser Lys Ala Asn Tyr Arg Phe Phe Met Val
                    885                 890                 895
Arg Ile Ser Gly Asn Pro Gly Ser Arg Thr Ile Thr Ala Arg Arg Val
                900                 905                 910
Pro Ile Ile Asp Glu Ala Gln Thr Trp Gly Ala Lys Gln Thr Phe Ser
                915                 920                 925
Ala Gly Leu Ser Gly Glu Leu Ser Gly Asn Ala Ala Thr Ala Thr Lys
                930                 935                 940
Leu Lys Thr Ala Arg Lys Ile Asn Asn Val Ser Phe Asp Gly Ser Gly
945                 950                 955                 960
Asp Ile Glu Val Leu Pro Val Gly Val Pro Leu Pro Trp Pro Ser Asp
                    965                 970                 975
Thr Val Pro Ser Gly Tyr Ala Leu Met Gln Gly Gln Thr Phe Asp Lys
                980                 985                 990
Ser Ala Tyr Pro Lys Leu Ala Ala Ala Tyr Pro Ser Gly Val Ile Pro
            995                 1000                1005
Asp Met Arg Gly Trp Thr Ile Lys Gly Lys Pro Ala Ser Gly Arg
        1010                1015                1020
Asp Val Leu Ser Leu Glu Gln Asp Gly Ile Lys Ser His Thr His
        1025                1030                1035
Ser Ala Ser Ala Ser Asn Thr Asp Leu Gly Thr Lys Thr Thr Ser
        1040                1045                1050
Ser Phe Asp Tyr Gly Thr Lys Ser Thr Asn Asn Thr Gly Ala His
        1055                1060                1065
Thr His Asn Val Ser Gly Ala Asn Ser Ala Gly Ala His Thr
        1070                1075                1080
His Thr Val Pro Leu Arg Arg Pro Asn Ser Gly Gly Met Asn Phe
        1085                1090                1095
```

-continued

Asp Trp Leu Asp Gly Ala Ser Ser Gly Thr Val Val Gly Asn Gly
    1100                1105                1110

Thr Val Pro Ser Ser Gly Ala His Thr His Ser Val Ser Gly Thr
    1115                1120                1125

Ala Thr Ser Ala Gly Ala His Ala His Thr Val Gly Ile Gly Ala
    1130                1135                1140

His Thr His Ser Val Ala Ile Gly Ser His Gly His Thr Ile Thr
    1145                1150                1155

Val Asn Ala Ala Gly Asn Ala Glu Asn Thr Val Lys Asn Ile Ala
    1160                1165                1170

Phe Asn Tyr Ile Val Arg Leu Ala
    1175                1180

<210> SEQ ID NO 64
<211> LENGTH: 561
<212> TYPE: PRT
<213> ORGANISM: Artificial Sequence
<220> FEATURE:
<223> OTHER INFORMATION: Tropical_pNS88 Tail Fiber

<400> SEQUENCE: 64

Met Asn Asp Val Thr Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
50                  55                  60

Ser Val Asp Gly Asp Lys Thr Gly Ala Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Leu Ile Lys Glu Tyr Asp Glu Asn Ile Gly
    210                 215                 220

Ala Trp Glu Thr Phe Ala Thr Ser Ala Asn Gln Ser Ile Thr Val
225                 230                 235                 240

Thr Ile Asn Gly Thr Pro Val Thr Ile Pro Gly Ile Gly Lys Leu Ala
                245                 250                 255

Gln Lys Gly Thr Asn Gly Ala Leu Pro Ile Asp Gln Gly Gly Thr Gly
            260                 265                 270

```
Ala Thr Asn Ala Ala Asp Val Arg Thr Asn Leu Gly Leu Gly Asp Ser
            275                 280                 285

Val Thr Ala Asn Phe Gly Ser Leu Glu Ile Gly Ala Lys Asn Ala Ser
290                 295                 300

Ser Ala Ser Phe Val Asp Phe His Phe Leu Gly Thr Asn Asp Tyr Asp
305                 310                 315                 320

Ala Arg Ile Leu Cys Gly Gly Asn Ser Asn Gly Gly Met Gly Lys Gly
            325                 330                 335

Asp Phe Thr Phe Tyr Ala Gly Lys Tyr Thr Phe Ile Gly Asp Ser Phe
            340                 345                 350

Glu Phe Arg Asn Pro Ile Thr Cys Gln Asn Ser Ile Thr Ala Ser Gly
            355                 360                 365

Ser Ile Ser Ala Gly Gly Ser Leu Arg Ala Val Thr Ser Ser Asn Val
            370                 375                 380

Trp Ala Ser Ser Asp Thr Gln Asn Ala His Val Trp Phe Tyr Gly Ala
385                 390                 395                 400

Gly Gly Ile Glu Ser Arg Gly Val Ile Tyr Ala Pro Arg Glu Gly Thr
            405                 410                 415

Ile Arg Leu Arg Pro Asp Asn Asn Asp Asn Gly Gly Ala Asn Gly Tyr
            420                 425                 430

Ser Phe Ser Phe Gly Ala Asp Gly Arg Phe Thr Cys Ile Ser Val Asn
            435                 440                 445

Gln Thr Ser Asp Glu Arg Val Lys Phe Asp Lys Glu Pro Val Ser Asn
            450                 455                 460

Ala Leu Glu Lys Ile Cys Ser Leu Thr Gly Tyr Thr Phe Gly Ile Gln
465                 470                 475                 480

Leu Thr Glu Ser Glu Ser Val His Ser Ala Gly Ile Ile Ala Gln Asp
            485                 490                 495

Leu Glu Lys Val Leu Pro Val Ala Val Ser Ser Gly Gly Thr Gly Thr
            500                 505                 510

Thr Pro Thr Gly Glu Glu Ile Asn Asp Leu Lys Thr Val Asp Tyr Ser
            515                 520                 525

Ala Met Ser Ala Leu Tyr Val Glu Ala Met Lys Glu Leu Ala Asn Arg
            530                 535                 540

Val Lys Ser Ile Glu Ser Glu Phe Ala Glu Leu Lys Ala Arg Ser Ala
545                 550                 555                 560

Ile
```

```
<210> SEQ ID NO 65
<211> LENGTH: 556
<212> TYPE: PRT
<213> ORGANISM: Artificial Sequence
<220> FEATURE:
<223> OTHER INFORMATION: Tropical_pNS92 Tail Fiber

<400> SEQUENCE: 65
```

```
Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
            35                  40                  45

Ala Gly Phe Leu Pro Lys Pro Gly Gly Gly Met Asn Leu Leu Ile Thr
            50                  55                  60
```

```
Ser Val Asp Gly Asp Lys Thr Ala Gly Ala Ala Ser Val Asp Ile Gly
 65                  70                  75                  80

Glu Phe Tyr Gln Val Thr Ile Gln Gln Arg Lys Asp Ile Ser Leu Ala
                 85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Asp Glu Asn Ile Gly Ala Trp Glu Thr Phe
    210                 215                 220

Ala Thr Thr Ser Ala Asn Gln Ser Ile Thr Val Thr Ile Asn Gly Thr
225                 230                 235                 240

Pro Val Thr Ile Pro Gly Ile Gly Lys Leu Ala Gln Lys Gly Thr Asn
                245                 250                 255

Gly Ala Leu Pro Ile Asp Gln Gly Gly Thr Gly Ala Thr Asn Ala Ala
            260                 265                 270

Asp Val Arg Thr Asn Leu Gly Leu Gly Asp Ser Val Thr Ala Asn Phe
        275                 280                 285

Gly Ser Leu Glu Ile Gly Ala Lys Asn Ala Ser Ser Ala Ser Phe Val
    290                 295                 300

Asp Phe His Phe Leu Gly Thr Asn Asp Tyr Asp Ala Arg Ile Leu Cys
305                 310                 315                 320

Gly Gly Asn Ser Asn Gly Gly Met Gly Lys Gly Asp Phe Thr Phe Tyr
                325                 330                 335

Ala Gly Lys Tyr Thr Phe Ile Gly Asp Ser Phe Glu Phe Arg Asn Pro
            340                 345                 350

Ile Thr Cys Gln Asn Ser Ile Thr Ala Ser Gly Ser Ile Ser Ala Gly
        355                 360                 365

Gly Ser Leu Arg Ala Val Thr Ser Ser Asn Val Trp Ala Ser Ser Asp
    370                 375                 380

Thr Gln Asn Ala His Val Trp Phe Tyr Gly Ala Gly Gly Ile Glu Ser
385                 390                 395                 400

Arg Gly Val Ile Tyr Ala Pro Arg Glu Gly Thr Ile Arg Leu Arg Pro
                405                 410                 415

Asp Asn Asn Asp Asn Gly Gly Ala Asn Gly Tyr Ser Pro Ser Phe Gly
            420                 425                 430

Ala Asp Gly Arg Phe Thr Cys Ile Ser Val Asn Gln Thr Ser Asp Glu
        435                 440                 445

Arg Val Lys Phe Asp Lys Glu Pro Val Ser Asn Ala Leu Glu Lys Ile
    450                 455                 460

Cys Ser Leu Thr Gly Tyr Thr Phe Gly Ile Gln Leu Thr Glu Ser Glu
465                 470                 475                 480

Ser Val His Ser Ala Gly Ile Ile Ala Gln Asp Leu Glu Lys Val Leu
```

```
                        485                 490                 495
Pro Val Ala Val Ser Ser Gly Gly Thr Gly Thr Thr Pro Thr Gly Glu
                    500                 505                 510

Glu Ile Asn Asp Leu Lys Thr Val Asp Tyr Ser Ala Met Ser Ala Leu
                515                 520                 525

Tyr Val Glu Ala Met Lys Glu Leu Ala Asn Arg Val Lys Ser Ile Glu
            530                 535                 540

Ser Glu Phe Ala Glu Leu Lys Ala Arg Ser Ala Ile
545                 550                 555

<210> SEQ ID NO 66
<211> LENGTH: 975
<212> TYPE: PRT
<213> ORGANISM: Artificial Sequence
<220> FEATURE:
<223> OTHER INFORMATION: Violet Tail Fiber

<400> SEQUENCE: 66

Met Asn Asp Val Thr Val Val Thr Ser Val Thr Tyr Pro Ser Pro Glu
1               5                   10                  15

Ser Leu Ala Leu Val Ala Asp Val Gln Tyr His Glu Pro Tyr Leu Ser
                20                  25                  30

Ala Ala Leu Asn Arg Lys Phe Arg Gly Ile Val Asp Pro Gly Phe Tyr
            35                  40                  45

Ala Gly Phe Leu Pro Lys Pro Gly Gly Met Asn Leu Leu Ile Thr
        50                  55                  60

Ser Val Asp Gly Asp Lys Thr Ala Gly Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Gly Val Ser Ala
145                 150                 155                 160

Ile Thr Gln Glu Met Ile Asp Thr Ser Glu Arg Ile Asn Arg Thr Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Ile Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Ser Ala Pro Thr Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
```

```
            290                 295                 300
Ile Ala Ala Ala Ile Asn Asn Asp Pro Asn Phe Ser Thr Thr Val Asn
305                 310                 315                 320

Asn Ala Leu Ala Leu Lys Ala Pro Leu Ala Ser Pro Ala Leu Thr Gly
                325                 330                 335

Ile Pro Thr Ala Pro Thr Ala Ala Gln Gly Thr Asn Asn Thr Gln Ile
                340                 345                 350

Ala Thr Thr Ala Tyr Val Arg Ala Ala Ile Ser Ala Leu Val Gly Ser
                355                 360                 365

Ser Pro Glu Ala Leu Asp Thr Leu Asn Glu Leu Ala Ala Ala Leu Gly
370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
                405                 410                 415

Ala Asn Lys Leu Pro Tyr Phe Thr Gly Lys Asp Thr Val Ala Gln Thr
                420                 425                 430

Asp Leu Thr Ser Val Gly Arg Asp Ile Leu Ala Lys Thr Ser Val Leu
                435                 440                 445

Ala Val Ile Gln Tyr Leu Gly Leu Arg Glu Leu Gly Thr Ser Gly Glu
                450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
                    485                 490                 495

Thr Lys Leu Lys Thr Ala Ile Asn Ile Asn Gly Val Arg Phe Asp Gly
                500                 505                 510

Ser Thr Asn Ile Ser Ile Pro Thr Ile Thr Ser Arg Gly Arg Val Thr
                515                 520                 525

Ala Leu Thr Gly Thr Thr Gln Gly Ala Ala Thr Gly Leu Gln Met Tyr
                530                 535                 540

Glu Ala Tyr Asn Asn Gly Tyr Pro Thr Thr Tyr Gly Asn Val Leu His
545                 550                 555                 560

Leu Lys Gly Ala Ala Ser Thr Gly Glu Gly Glu Leu Leu Ile Gly Trp
                565                 570                 575

Ser Gly Thr Asn Gly Ala His Ala Pro Ala Phe Ile Arg Ser Lys Arg
                580                 585                 590

Asp Ile Thr Ala Ala Ala Trp Ser Glu Trp Ala Gln Ile Tyr Thr Ser
                595                 600                 605

Lys Asp Ser Val Pro Gly Val Asn Thr Lys Gly Asn Gln Asp Thr Ser
                610                 615                 620

Gly Asn Ala Ala Thr Ala Thr Lys Leu Gln Thr Ala Cys Thr Ile Asn
625                 630                 635                 640

Gly Val Ser Phe Asp Gly Ser Lys Asn Ile Glu Leu Thr Ala Ala Asp
                645                 650                 655

Leu Asn Leu Glu Gln Thr Val Glu Leu Ala Ala Gly Ala Leu Gln Lys
                660                 665                 670

Asn Gln Asn Gly Ala Asp Ile Pro Gly Lys Asp Thr Phe Thr Lys Asn
                675                 680                 685

Ile Gly Ala Cys Arg Ala Tyr Ser Ala Trp Leu Asn Ile Gly Gly Asp
                690                 695                 700

Ser Gln Val Trp Thr Thr Ala Gln Phe Ile Ser Trp Leu Glu Ser Gln
705                 710                 715                 720
```

```
Gly Ala Phe Asn His Pro Tyr Trp Met Cys Lys Gly Ser Trp Ala Tyr
                725                 730                 735

Ala Asn Asn Lys Val Ile Thr Asp Thr Gly Cys Gly Asn Ile Cys Leu
            740                 745                 750

Ala Gly Ala Val Val Glu Val Ile Gly Thr Arg Gly Ala Met Thr Ile
        755                 760                 765

Arg Val Thr Thr Pro Ser Thr Ser Ser Gly Gly Ile Thr Asn Ala
770                 775                 780

Gln Phe Thr Tyr Ile Asn His Gly Asp Ala Tyr Ala Pro Gly Trp Arg
785                 790                 795                 800

Arg Asp Tyr Asn Thr Lys Asn Gln Gln Pro Ala Phe Ala Leu Gly Gln
                805                 810                 815

Thr Gly Ser Arg Val Ala Asn Asp Lys Ala Val Gly Trp Asn Trp Asn
            820                 825                 830

Ser Gly Val Tyr Asp Ala Asp Ile Ser Gly Ala Ser Thr Leu Ile Leu
        835                 840                 845

His Phe Asn Met Asn Ala Gly Ser Cys Pro Ala Val Gln Phe Arg Val
    850                 855                 860

Asn Tyr Lys Asn Gly Gly Ile Phe Tyr Arg Ser Ala Arg Asp Gly Tyr
865                 870                 875                 880

Gly Phe Glu Ala Asn Trp Ser Glu Phe Tyr Thr Thr Thr Arg Lys Pro
                885                 890                 895

Ser Ala Gly Asp Val Gly Ala Tyr Thr Gln Ala Glu Cys Asn Ser Arg
            900                 905                 910

Phe Ile Thr Gly Ile Arg Leu Gly Gly Leu Ser Ser Val Gln Thr Trp
        915                 920                 925

Asn Gly Pro Gly Trp Ser Asp Arg Ser Gly Tyr Val Val Thr Gly Ser
    930                 935                 940

Val Asn Gly Asn Arg Asp Glu Leu Ile Asp Thr Thr Gln Ala Arg Pro
945                 950                 955                 960

Ile Gln Tyr Cys Ile Asn Gly Thr Trp Tyr Asn Ala Gly Ser Ile
                965                 970                 975

<210> SEQ ID NO 67
<211> LENGTH: 175
<212> TYPE: PRT
<213> ORGANISM: Artificial Sequence
<220> FEATURE:
<223> OTHER INFORMATION: Asparagus Chaperone

<400> SEQUENCE: 67

Met Met His Leu Lys Asn Ile Lys Ser Glu Asn Pro Lys Thr Lys Glu
1               5                   10                  15

Gln Tyr Gln Leu Thr Lys Asn Phe Asp Val Ile Trp Leu Trp Ser Glu
            20                  25                  30

Asp Gly Lys Asn Trp Tyr Glu Glu Val Asn Asn Phe Gln Asp Thr
        35                  40                  45

Ile Lys Ile Val Tyr Asp Glu Asn Asn Ile Ile Val Ala Ile Thr Lys
    50                  55                  60

Asp Ala Ser Thr Leu Asn Pro Glu Gly Phe Ser Val Val Glu Ile Pro
65                  70                  75                  80

Asp Ile Thr Ala Asn Arg Arg Ala Asp Ser Gly Lys Trp Met Phe
                85                  90                  95

Lys Asp Gly Ala Val Val Lys Arg Ile Tyr Thr Ala Asp Glu Gln Gln
            100                 105                 110
```

```
Gln Gln Ala Glu Ser Gln Lys Ala Ala Leu Leu Ser Glu Ala Glu Ser
        115                 120                 125

Val Ile Gln Pro Leu Glu Arg Ala Val Arg Leu Asn Met Ala Thr Asp
    130                 135                 140

Glu Glu Arg Ala Arg Leu Glu Ser Trp Glu Arg Tyr Ser Val Leu Val
145                 150                 155                 160

Ser Arg Val Asp Thr Ala Asn Pro Glu Trp Pro Gln Lys Pro Glu
                165                 170                 175
```

<210> SEQ ID NO 68
<211> LENGTH: 140
<212> TYPE: PRT
<213> ORGANISM: Artificial Sequence
<220> FEATURE:
<223> OTHER INFORMATION: Banana Chaperone

<400> SEQUENCE: 68

```
Met Arg Ile Tyr Phe Ser Pro Ser Glu Ile Gly Phe Tyr His Glu Ser
1               5                   10                  15

Asp Lys Gln Ala Tyr Leu Leu Ala Gly Thr Trp Pro Asn Asp Leu Leu
            20                  25                  30

Glu Ile Ser Glu Lys Trp Phe Leu Tyr Leu Leu Glu Gly Gln Gln Lys
        35                  40                  45

Gly Lys Val Ile Thr Val Asn Asp Tyr Asp Gln Pro Val Leu Val Asp
    50                  55                  60

Pro Pro Thr Ala Thr Lys Glu Gln Leu Leu Ala Glu Ala Asp Ala Gln
65                  70                  75                  80

Lys Glu Ala Leu Met Asn Ser Ala Ser Ala Val Ile Glu Pro Leu Lys
                85                  90                  95

Asp Ala Val Glu Leu Gly Met Ser Thr Asp Glu Glu Gly Leu Leu
            100                 105                 110

Leu Ala Trp Gln Gln Tyr Arg Val Leu Leu Met Arg Val Asp Thr Ser
        115                 120                 125

His Ala Pro Asp Ile Glu Trp Pro Val Leu Pro Ala
    130                 135                 140
```

<210> SEQ ID NO 69
<211> LENGTH: 203
<212> TYPE: PRT
<213> ORGANISM: Artificial Sequence
<220> FEATURE:
<223> OTHER INFORMATION: Bittersweet Chaperone

<400> SEQUENCE: 69

```
Met Asp Asn Ala Ile Leu Asn Ser Glu Leu Ile Ala Ile Gln Ala Gly
1               5                   10                  15

Asn Ile Ile Val Tyr Asn Tyr Asp Gly Gly Asn Arg Glu Tyr Ile Ser
            20                  25                  30

Ala Ser Thr Glu Tyr Leu Ala Val Gly Val Gly Ile Pro Ala Asn Ser
        35                  40                  45

Cys Leu Asp Ala Pro Gly Ser His Lys Ala Gly Tyr Ala Ile Leu Arg
    50                  55                  60

Ser Glu Asp Leu Ser Ser Trp Glu Tyr Val Pro Asp His Arg Gly Glu
65                  70                  75                  80

Thr Val Tyr Ser Ile Asp Thr Gly Asn Pro Glu Glu Ile Thr Val Leu
                85                  90                  95

Gly Asp Tyr Pro Glu Asn Thr Thr Thr Ile Ala Pro Leu Thr Pro Tyr
```

```
            100                 105                 110
Asp Lys Trp Asp Gly Glu Lys Trp Val Val Asp Thr Glu Ala Gln His
        115                 120                 125

Ser Ala Val Glu Ala Ala Glu Thr Lys Arg Gln Ser Leu Ile Asp
    130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Thr Ala Pro Asp Leu
            180                 185                 190

Asn Trp Pro Glu Lys Gln Leu Ser Thr Ala Ser
        195                 200

<210> SEQ ID NO 70
<211> LENGTH: 203
<212> TYPE: PRT
<213> ORGANISM: Artificial Sequence
<220> FEATURE:
<223> OTHER INFORMATION: Cobalt Chaperone

<400> SEQUENCE: 70

Met Asp Asn Ala Ile Leu Asn Ser Glu Leu Ile Ala Ile Gln Ala Gly
1               5                   10                  15

Asn Ile Ile Val Tyr Asn Tyr Asp Gly Gly Asn Arg Glu Tyr Ile Ser
            20                  25                  30

Ala Ser Thr Glu Tyr Leu Ala Val Gly Val Gly Ile Pro Ala Asn Ser
        35                  40                  45

Cys Leu Asp Ala Pro Gly Ser His Lys Ala Gly Tyr Ala Ile Leu Arg
    50                  55                  60

Ser Glu Asp Leu Ser Ser Trp Glu Tyr Val Pro Asp His Arg Gly Glu
65                  70                  75                  80

Thr Val Tyr Ser Ile Asp Thr Gly Asn Pro Glu Ile Thr Val Leu
                85                  90                  95

Gly Asp Tyr Pro Glu Asn Thr Thr Thr Ile Ala Pro Leu Thr Pro Tyr
            100                 105                 110

Asp Lys Trp Asp Gly Glu Lys Trp Val Val Asp Thr Glu Ala Gln His
        115                 120                 125

Ser Ala Val Glu Ala Ala Glu Thr Lys Arg Gln Ser Leu Ile Asp
    130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Thr Ala Pro Asp Leu
            180                 185                 190

Asn Trp Pro Glu Lys Gln Leu Ser Thr Ala Ser
        195                 200

<210> SEQ ID NO 71
<211> LENGTH: 203
<212> TYPE: PRT
<213> ORGANISM: Artificial Sequence
<220> FEATURE:
<223> OTHER INFORMATION: Denim Chaperone

<400> SEQUENCE: 71
```

```
Met Asp Asn Ala Ile Leu Asn Ser Glu Leu Ile Ala Ile Gln Ala Gly
1               5                   10                  15

Asn Ile Ile Val Tyr Asn Tyr Asp Gly Gly Asn Arg Glu Tyr Ile Ser
            20                  25                  30

Ala Ser Thr Glu Tyr Leu Ala Val Gly Val Gly Ile Pro Ala Asn Ser
        35                  40                  45

Cys Leu Asp Ala Pro Gly Ser His Lys Ala Gly Tyr Ala Ile Leu Arg
    50                  55                  60

Ser Glu Asp Leu Ser Ser Trp Glu Tyr Val Pro Asp His Arg Gly Glu
65                  70                  75                  80

Thr Val Tyr Ser Ile Asp Thr Gly Asn Pro Glu Glu Ile Thr Val Leu
                85                  90                  95

Gly Asp Tyr Pro Glu Asn Thr Thr Ile Ala Pro Leu Thr Pro Tyr
            100                 105                 110

Asp Lys Trp Asp Gly Glu Lys Trp Val Val Asp Thr Glu Ala Gln His
            115                 120                 125

Ser Ala Ala Val Glu Ala Ala Glu Thr Lys Arg Gln Ser Leu Ile Asp
        130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Ala Pro Asp Leu
            180                 185                 190

Asn Trp Pro Glu Lys Gln Leu Ser Thr Ala Ser
            195                 200

<210> SEQ ID NO 72
<211> LENGTH: 175
<212> TYPE: PRT
<213> ORGANISM: Artificial Sequence
<220> FEATURE:
<223> OTHER INFORMATION: Eggplant Chaperone

<400> SEQUENCE: 72

Met Gln His Leu Lys Asn Ile Arg Ser Gly Asn Pro Lys Thr Lys Glu
1               5                   10                  15

Gln Tyr Gln Leu Thr Lys Asn Phe Asp Val Ile Trp Leu Trp Ser Glu
            20                  25                  30

Asp Gly Lys Asn Trp Tyr Glu Glu Val Lys Asn Phe Gln Pro Asp Thr
        35                  40                  45

Ile Lys Ile Val Tyr Asp Glu Asn Asn Ile Ile Val Ala Ile Thr Lys
    50                  55                  60

Asp Ala Ser Thr Leu Asn Pro Glu Gly Phe Ser Val Val Glu Val Pro
65                  70                  75                  80

Asp Ile Thr Ala Asn Arg Arg Ala Asp Ser Gly Lys Trp Met Phe
                85                  90                  95

Lys Asp Gly Ala Val Val Lys Arg Ile Tyr Thr Ala Asp Glu Gln Gln
            100                 105                 110

Gln Gln Ala Glu Ser Gln Lys Ala Ala Leu Leu Ser Glu Ala Glu Ser
        115                 120                 125

Val Ile Gln Pro Leu Glu Arg Ala Val Arg Leu Asn Met Ala Thr Asp
    130                 135                 140

Glu Glu Arg Thr Arg Leu Glu Ala Trp Glu Arg Tyr Ser Val Leu Val
145                 150                 155                 160
```

-continued

Ser Arg Val Asp Thr Ala Asn Pro Glu Trp Pro Gln Lys Pro Glu
                165                 170                 175

<210> SEQ ID NO 73
<211> LENGTH: 175
<212> TYPE: PRT
<213> ORGANISM: Artificial Sequence
<220> FEATURE:
<223> OTHER INFORMATION: Fern Chaperone

<400> SEQUENCE: 73

Met Gln His Leu Lys Asn Ile Lys Ser Gly Asn Pro Lys Thr Lys Glu
1               5                   10                  15

Gln Tyr Gln Leu Thr Lys Asn Phe Asp Val Ile Trp Leu Trp Ser Glu
                20                  25                  30

Asp Gly Lys Asn Trp Tyr Glu Glu Val Lys Asn Phe Gln Pro Asp Thr
            35                  40                  45

Ile Lys Ile Val Tyr Asp Ala Asn Asn Ile Ile Val Ala Ile Thr Lys
        50                  55                  60

Asp Ala Ser Thr Leu Asn Pro Glu Gly Tyr Ser Val Val Glu Val Pro
65                  70                  75                  80

Asp Ile Thr Ala Asn Arg Arg Ala Asp Asp Ser Gly Lys Trp Met Phe
                85                  90                  95

Lys Asp Gly Ala Val Val Lys Arg Ile Tyr Thr Ala Asp Glu Gln Gln
            100                 105                 110

Gln Gln Ala Glu Ser Gln Lys Ala Ala Leu Leu Ser Glu Ala Glu Asn
        115                 120                 125

Val Ile Gln Pro Leu Glu Arg Ala Val Arg Leu Asn Met Ala Thr Asp
    130                 135                 140

Glu Glu Arg Ala Arg Leu Glu Ser Trp Glu Arg Tyr Ser Val Leu Val
145                 150                 155                 160

Ser Arg Val Asp Thr Ala Asn Pro Glu Trp Pro Gln Lys Pro Glu
                165                 170                 175

<210> SEQ ID NO 74
<211> LENGTH: 177
<212> TYPE: PRT
<213> ORGANISM: Artificial Sequence
<220> FEATURE:
<223> OTHER INFORMATION: Fuchsia Chaperone

<400> SEQUENCE: 74

Met Met His Leu Arg Asn Ile Thr Ala Gly Asn Pro Lys Thr Lys Glu
1               5                   10                  15

Gln Tyr Gln Leu Thr Lys Gln Phe Asn Ile Lys Trp Leu Tyr Thr Glu
                20                  25                  30

Asp Gly Lys Asn Trp Tyr Glu Glu Gln Lys Asn Phe Gln Tyr Asp Thr
            35                  40                  45

Leu Lys Met Ala Tyr Asp His Asn Gly Val Ile Ile Cys Ile Glu Lys
        50                  55                  60

Asp Val Ser Ala Ile Asn Pro Glu Gly Ala Ser Val Val Glu Leu Pro
65                  70                  75                  80

Asp Ile Thr Ala Asn Arg Arg Ala Asp Ile Ser Gly Lys Trp Met Phe
                85                  90                  95

Lys Asp Gly Val Val Val Lys Arg Thr Tyr Thr Glu Glu Gln Arg
            100                 105                 110

Gln Gln Ala Glu Asn Glu Lys Gln Ser Leu Leu Gln Leu Val Arg Asp
        115                 120                 125

```
Lys Thr Gln Leu Trp Asp Ser Gln Leu Arg Leu Gly Ile Ile Ser Ala
            130                 135                 140

Glu Asn Lys Gln Lys Leu Thr Glu Trp Met Leu Phe Ala Gln Lys Val
145                 150                 155                 160

Glu Ser Thr Asp Thr Ser Ser Leu Pro Val Thr Phe Pro Glu Gln Pro
                165                 170                 175

Glu

<210> SEQ ID NO 75
<211> LENGTH: 197
<212> TYPE: PRT
<213> ORGANISM: Artificial Sequence
<220> FEATURE:
<223> OTHER INFORMATION: Fuzzy Chaperone

<400> SEQUENCE: 75

Met Gln Glu Thr Met Thr Arg Ile Glu Leu Ser Gly Val Leu Gly Lys
1               5                   10                  15

Thr Phe Gly Lys Val His Tyr Arg Leu Ile Lys Asn Ile Asn Glu Ala
            20                  25                  30

Gly Glu Ala Leu Ser Ala Thr Ile Pro Gly Phe Glu Arg Phe Met Ile
        35                  40                  45

Ser Ser Glu Glu Arg Gly Leu Thr Tyr Ala Val Phe Lys Gly Asn Lys
50                  55                  60

Asn Ile Gly His Asp Asp Leu Gly Phe Pro Val Ser Gly Glu Ile Ile
65                  70                  75                  80

Arg Ile Val Pro Val Ile Ile Gly Ser Lys Lys Ala Gly Ile Leu Gln
                85                  90                  95

Thr Ile Leu Gly Ala Val Ile Val Ala Ala Ser Val Ala Tyr Gly Phe
            100                 105                 110

Phe Thr Glu Asp Trp Ala Asn Ala Ala Tyr Gly Ile Gln Ala Gly Gly
        115                 120                 125

Ala Met Met Leu Gly Gly Val Val Gln Met Leu Ser Pro Gln Pro Ala
130                 135                 140

Gly Leu Ala Arg Lys Glu Ser Ala Asp Asn Lys Ala Ser Tyr Ala Phe
145                 150                 155                 160

Gly Gly Val Thr Asn Thr Ala Ser Gln Gly Tyr Pro Val Pro Leu Leu
                165                 170                 175

Tyr Gly Lys Arg Arg Ile Gly Gly Ala Ile Ile Ser Ala Gly Ile Tyr
            180                 185                 190

Val Glu Asp Gln Gln
        195

<210> SEQ ID NO 76
<211> LENGTH: 152
<212> TYPE: PRT
<213> ORGANISM: Artificial Sequence
<220> FEATURE:
<223> OTHER INFORMATION: Inchworm Chaperone

<400> SEQUENCE: 76

Met Lys Gly Glu Tyr Tyr Phe Ser Pro Ser Gln Val Ala Phe Tyr Pro
1               5                   10                  15

Ala Ser Leu Arg Glu Val Tyr Glu Tyr Ala Gly Cys Trp Pro Val Asp
            20                  25                  30

Gly Glu Trp Val Ser Ala Glu Leu His Glu Gln Leu Met Asn Glu Gln
        35                  40                  45
```

Ala Ala Gly Arg Ala Ile Ser Ser Asp Val Asn Gly Asn Pro Val Ala
        50                  55                  60

Ile Glu Arg Pro Pro Leu Ser Arg Gln Gln Arg Ser Thr His Glu Arg
 65                  70                  75                  80

Arg Trp Arg Asp Ser Gln Leu Leu Ala Thr Asp Gly Leu Val Val Arg
                 85                  90                  95

His Arg Asp Gln Leu Glu Thr Gly Lys Glu Thr Thr Leu Leu Pro Val
            100                 105                 110

Gln Tyr His Glu Leu Met Ser Tyr Arg Ala Ser Leu Arg Asp Trp Pro
        115                 120                 125

Glu Glu Pro Leu Phe Pro Asp Ser Gly Gly Arg Pro Ser Val Pro Asp
130                 135                 140

Trp Leu Arg Arg Tyr Val Thr Pro
145                 150

<210> SEQ ID NO 77
<211> LENGTH: 203
<212> TYPE: PRT
<213> ORGANISM: Artificial Sequence
<220> FEATURE:
<223> OTHER INFORMATION: Indian Chaperone

<400> SEQUENCE: 77

Met Asp Asn Ala Ile Leu Asn Ser Glu Leu Ala Ile Gln Ala Gly
 1               5                  10                  15

Asn Ile Ile Val Tyr Asn Tyr Asp Gly Gly Asn Arg Glu Tyr Ile Ser
                 20                  25                  30

Ala Ser Thr Glu Tyr Leu Ala Val Gly Val Gly Ile Pro Ala Asn Ser
             35                  40                  45

Cys Leu Asp Ala Pro Gly Ser His Lys Ala Gly Tyr Ala Ile Leu Arg
 50                  55                  60

Ser Glu Asp Leu Ser Ser Trp Glu Tyr Val Pro Asp His Arg Gly Glu
 65                  70                  75                  80

Thr Val Tyr Ser Ile Asp Thr Gly Asn Pro Glu Glu Ile Thr Val Leu
                 85                  90                  95

Gly Asp Tyr Pro Glu Asn Thr Thr Ile Ala Pro Leu Thr Pro Tyr
            100                 105                 110

Asp Lys Trp Asp Gly Glu Lys Trp Val Val Asp Thr Glu Ala Gln His
        115                 120                 125

Ser Ala Ala Val Glu Ala Ala Glu Thr Lys Arg Gln Ser Leu Ile Asp
130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Thr Ala Pro Asp Leu
            180                 185                 190

Asn Trp Pro Glu Lys Gln Leu Ser Thr Ala Ser
        195                 200

<210> SEQ ID NO 78
<211> LENGTH: 203
<212> TYPE: PRT
<213> ORGANISM: Artificial Sequence
<220> FEATURE:
<223> OTHER INFORMATION: Indigo Chaperone

<400> SEQUENCE: 78

```
Met Asp Asn Ala Ile Leu Asn Ser Glu Leu Ile Ala Ile Gln Ala Gly
1               5                   10                  15

Asn Ile Ile Val Tyr Asn Tyr Asp Gly Gly Asn Arg Glu Tyr Ile Ser
                20                  25                  30

Ala Ser Thr Glu Tyr Leu Ala Val Gly Val Gly Ile Pro Ala Asn Ser
            35                  40                  45

Cys Leu Asp Ala Pro Gly Ser His Lys Ala Gly Tyr Ala Ile Leu Arg
        50                  55                  60

Ser Glu Asp Leu Ser Ser Trp Glu Tyr Val Pro Asp His Arg Gly Glu
65                  70                  75                  80

Thr Val Tyr Ser Ile Asp Thr Gly Asn Pro Glu Ile Thr Val Leu
                85                  90                  95

Gly Asp Tyr Pro Glu Asn Thr Thr Thr Ile Ala Pro Leu Thr Pro Tyr
                100                 105                 110

Asp Lys Trp Asp Gly Glu Lys Trp Val Val Asp Thr Glu Ala Gln His
            115                 120                 125

Ser Ala Ala Val Glu Ala Ala Glu Thr Lys Arg Gln Ser Leu Ile Asp
130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Thr Ala Pro Asp Leu
                180                 185                 190

Asn Trp Pro Glu Lys Gln Leu Ser Thr Ala Ser
            195                 200
```

<210> SEQ ID NO 79
<211> LENGTH: 205
<212> TYPE: PRT
<213> ORGANISM: Artificial Sequence
<220> FEATURE:
<223> OTHER INFORMATION: Jazzberry Chaperone

<400> SEQUENCE: 79

```
Met Ala Phe Arg Met Ser Glu Gln Ser Arg Thr Val Lys Ile Tyr Asn
1               5                   10                  15

Leu Leu Ala Gly Thr Asn Glu Phe Ile Gly Glu Gly Asp Ala Tyr Ile
                20                  25                  30

Pro Pro His Thr Gly Leu Pro Ala Asn Ser Thr Asp Ile Ala Pro Pro
            35                  40                  45

Glu Ile Pro Ala Gly Phe Val Ala Val Phe Asn Ser Glu Asn Glu Ser
        50                  55                  60

Trp Asn Ile Val Glu Asp His Arg Gly Lys Thr Val Tyr Asp Val Ala
65                  70                  75                  80

Ser Gly Asp Ala Leu Phe Ile Ser Glu Pro Gly Pro Leu Pro Glu Asn
                85                  90                  95

Val Thr Trp Leu Ser Pro Ala Gly Glu Tyr Gln Lys Trp Asp Gly Val
                100                 105                 110

Ser Trp Val Lys Asp Glu Glu Ala Glu Lys Leu Phe Arg Ile Arg Glu
            115                 120                 125

Ala Glu Glu Lys Lys Ala Arg Leu Ile Gln Glu Ala Thr Asp Asn Ile
130                 135                 140

Ala Ile Leu Gln Asp Ala Val Asn Leu Glu Ile Ala Thr Asn Glu Glu
```

```
                145                 150                 155                 160
Asn Ser Gln Leu Asp Ser Trp Arg Lys Tyr Arg Val Leu Val Ser Arg
                165                 170                 175

Ile Asp Thr Ser Thr Ala Pro Asp Ile Val Trp Pro Glu Leu Met Asn
            180                 185                 190

Gln Gly Tyr Val Arg Glu Asp Glu Gln Ile Thr Ser Asp
        195                 200                 205
```

<210> SEQ ID NO 80
<211> LENGTH: 177
<212> TYPE: PRT
<213> ORGANISM: Artificial Sequence
<220> FEATURE:
<223> OTHER INFORMATION: Jungle Chaperone

<400> SEQUENCE: 80

```
Met Met His Leu Lys Asn Ile Thr Ala Gly Asn Pro Lys Thr Lys Glu
1               5                   10                  15

Gln Tyr Gln Leu Thr Lys Gln Phe Asn Ile Lys Trp Leu Tyr Thr Glu
            20                  25                  30

Asp Gly Lys Asn Trp Tyr Glu Glu Gln Lys Asn Phe Gln Pro Asp Thr
        35                  40                  45

Leu Lys Met Val Tyr Asp His Asn Gly Val Ile Ile Cys Ile Glu Lys
    50                  55                  60

Asp Val Ser Ala Ile Asn Pro Glu Gly Ala Asn Val Val Glu Val Pro
65                  70                  75                  80

Asp Ile Thr Ala Asn Arg Arg Ala Asp Ile Ser Gly Lys Trp Met Phe
                85                  90                  95

Lys Asp Gly Val Val Ile Lys Arg Thr Tyr Thr Glu Glu Gln Arg
            100                 105                 110

Gln Gln Ala Glu Asn Glu Lys Gln Ser Leu Leu Gln Leu Val Arg Asp
        115                 120                 125

Lys Thr Gln Leu Trp Asp Ser Gln Leu Arg Leu Gly Ile Ile Ser Asp
    130                 135                 140

Glu Asn Lys Gln Lys Leu Thr Glu Trp Met Leu Tyr Ala Gln Lys Val
145                 150                 155                 160

Glu Ser Thr Asp Thr Ser Ser Leu Pro Val Thr Phe Pro Glu Gln Pro
                165                 170                 175

Glu
```

<210> SEQ ID NO 81
<211> LENGTH: 140
<212> TYPE: PRT
<213> ORGANISM: Artificial Sequence
<220> FEATURE:
<223> OTHER INFORMATION: Mango Chaperone

<400> SEQUENCE: 81

```
Met Gly Tyr Val Tyr Cys His Ala Thr Gly Ala Phe Tyr Asn Asp Ala
1               5                   10                  15

Leu Val Ala Asp Tyr Arg Ser Ala Gly Ser Trp Pro Asp Asn Tyr Val
            20                  25                  30

Thr Val Leu Asp Asp Tyr Glu Ser Leu Met Ala Gly Gln Ala Val
        35                  40                  45

Gly Lys Met Ile Val Ser Asp Asn Asn Gly Tyr Pro Val Leu Thr Glu
    50                  55                  60

Pro Pro Glu Pro Thr His Glu Glu Gln Val Asn Gln Ala Ser Ser Gln
```

```
              65                  70                  75                  80
Lys Leu Phe Leu Met Lys Thr Ala Asn Glu Ile Ile Thr Pro Leu Glu
                    85                  90                  95

Asp Ala Val Glu Leu Gly Ile Ala Thr Asp Glu Ala Ala Thr Leu
                100                 105                 110

Leu Leu Trp Lys Arg Tyr Arg Val Leu Leu Asn Arg Leu Asp Leu Ser
                115                 120                 125

Lys Ala Pro Asp Ile Gln Trp Pro Glu Arg Pro Ala
            130                 135                 140

<210> SEQ ID NO 82
<211> LENGTH: 203
<212> TYPE: PRT
<213> ORGANISM: Artificial Sequence
<220> FEATURE:
<223> OTHER INFORMATION: Maroon Chaperone

<400> SEQUENCE: 82

Met Asp Asn Ala Ile Leu Asn Ser Glu Leu Ile Ala Ile Gln Ala Gly
1               5                   10                  15

Asn Ile Ile Val Tyr Asn Tyr Asp Gly Gly Asn Arg Glu Tyr Ile Ser
                20                  25                  30

Ala Ser Thr Glu Tyr Leu Ala Val Gly Val Gly Ile Pro Ala Asn Ser
            35                  40                  45

Cys Leu Asp Ala Pro Gly Ser His Lys Ala Gly Tyr Ala Ile Leu Arg
        50                  55                  60

Ser Glu Asp Leu Ser Ser Trp Glu Tyr Val Pro Asp His Arg Gly Glu
65                  70                  75                  80

Thr Val Tyr Ser Ile Asp Thr Gly Asn Pro Glu Glu Ile Thr Val Leu
                85                  90                  95

Gly Asp Tyr Pro Glu Asn Thr Thr Ile Ala Pro Leu Thr Pro Tyr
                100                 105                 110

Asp Lys Trp Asp Gly Glu Lys Trp Val Val Asp Thr Glu Ala Gln His
            115                 120                 125

Ser Ala Ala Val Glu Ala Ala Glu Thr Lys Arg Gln Ser Leu Ile Asp
        130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Thr Ala Pro Asp Leu
            180                 185                 190

Asn Trp Pro Glu Lys Gln Leu Ser Thr Ala Ser
        195                 200

<210> SEQ ID NO 83
<211> LENGTH: 177
<212> TYPE: PRT
<213> ORGANISM: Artificial Sequence
<220> FEATURE:
<223> OTHER INFORMATION: Mulberry Chaperone

<400> SEQUENCE: 83

Met Met His Leu Arg Asn Ile Thr Ala Gly Asn Pro Lys Thr Lys Glu
1               5                   10                  15

Gln Tyr Gln Leu Thr Lys Gln Phe Asn Ile Lys Trp Leu Tyr Thr Glu
                20                  25                  30
```

```
Asp Gly Lys Asn Trp Tyr Glu Glu Gln Lys Asn Phe Gln Tyr Asp Thr
            35                  40                  45

Leu Lys Met Ala Tyr Asp His Asn Gly Val Ile Ile Cys Ile Glu Lys
 50                  55                  60

Asp Val Ser Ala Ile Asn Pro Glu Gly Ala Ser Val Val Glu Leu Pro
 65                  70                  75                  80

Asp Ile Thr Ala Asn Arg Arg Ala Asp Ile Ser Gly Lys Trp Met Phe
                 85                  90                  95

Lys Asp Gly Val Val Lys Arg Thr Tyr Thr Glu Glu Glu Gln Arg
                100                 105                 110

Gln Gln Ala Glu Asn Glu Lys Gln Ser Leu Leu Gln Leu Val Arg Asp
            115                 120                 125

Lys Thr Gln Leu Trp Asp Ser Gln Leu Arg Leu Gly Ile Ile Ser Ala
130                 135                 140

Glu Asn Lys Gln Lys Leu Thr Glu Trp Met Leu Phe Ala Gln Lys Val
145                 150                 155                 160

Glu Ser Thr Asp Thr Ser Ser Leu Pro Val Thr Phe Pro Glu Gln Pro
                165                 170                 175

Glu

<210> SEQ ID NO 84
<211> LENGTH: 177
<212> TYPE: PRT
<213> ORGANISM: Bacteriophage P1
<220> FEATURE:
<221> NAME/KEY: MISC_FEATURE
<223> OTHER INFORMATION: P1_U' Chaperone

<400> SEQUENCE: 84

Met Met His Leu Arg Asn Ile Thr Ala Gly Asn Pro Lys Thr Lys Glu
  1               5                  10                  15

Gln Tyr Gln Leu Thr Lys Gln Phe Asn Ile Lys Trp Leu Tyr Thr Glu
                 20                  25                  30

Asp Gly Lys Asn Trp Tyr Glu Glu Gln Lys Asn Phe Gln Tyr Asp Thr
             35                  40                  45

Leu Lys Met Ala Tyr Asp His Asn Gly Val Ile Ile Cys Ile Glu Lys
 50                  55                  60

Asp Val Ser Ala Ile Asn Pro Glu Gly Ala Ser Val Val Glu Leu Pro
 65                  70                  75                  80

Asp Ile Thr Ala Asn Arg Arg Ala Asp Ile Ser Gly Lys Trp Met Phe
                 85                  90                  95

Lys Asp Gly Val Val Lys Arg Thr Tyr Thr Glu Glu Glu Gln Arg
                100                 105                 110

Gln Gln Ala Glu Asn Glu Lys Gln Ser Leu Leu Gln Leu Val Arg Asp
            115                 120                 125

Lys Thr Gln Leu Trp Asp Ser Gln Leu Arg Leu Gly Ile Ile Ser Ala
130                 135                 140

Glu Asn Lys Gln Lys Leu Thr Glu Trp Met Leu Phe Ala Gln Lys Val
145                 150                 155                 160

Glu Ser Thr Asp Thr Ser Ser Leu Pro Val Thr Phe Pro Glu Gln Pro
                165                 170                 175

Glu

<210> SEQ ID NO 85
<211> LENGTH: 175
<212> TYPE: PRT
```

<213> ORGANISM: Artificial Sequence
<220> FEATURE:
<223> OTHER INFORMATION: Pine Chaperone

<400> SEQUENCE: 85

Met Gln His Leu Lys Asn Ile Lys Ser Gly Asn Pro Lys Thr Lys Glu
1               5                   10                  15

Gln Tyr Gln Leu Thr Lys Asn Phe Asp Val Ile Trp Leu Trp Ser Glu
            20                  25                  30

Asp Gly Lys Asn Trp Tyr Glu Val Lys Asn Phe Gln Pro Asp Thr
        35                  40                  45

Ile Lys Ile Val Tyr Asp Glu Asn Asn Ile Ile Val Ala Ile Thr Arg
50                  55                  60

Asp Ala Ser Thr Leu Asn Pro Glu Gly Phe Ser Val Val Glu Val Pro
65                  70                  75                  80

Asp Ile Thr Ser Asn Arg Arg Ala Asp Ser Gly Lys Trp Met Phe
                85                  90                  95

Lys Asp Gly Ala Val Val Lys Arg Ile Tyr Thr Ala Asp Glu Gln Gln
                100                 105                 110

Gln Gln Ala Glu Ser Gln Lys Ala Ala Leu Leu Ser Glu Ala Glu Asn
            115                 120                 125

Val Ile Gln Pro Leu Glu Arg Ala Val Arg Leu Asn Met Ala Thr Asp
130                 135                 140

Glu Glu Arg Ala Arg Leu Glu Ser Trp Glu Arg Tyr Ser Val Leu Val
145                 150                 155                 160

Ser Arg Val Asp Pro Ala Asn Pro Glu Trp Pro Glu Met Pro Gln
                165                 170                 175

<210> SEQ ID NO 86
<211> LENGTH: 205
<212> TYPE: PRT
<213> ORGANISM: Artificial Sequence
<220> FEATURE:
<223> OTHER INFORMATION: Plum Chaperone

<400> SEQUENCE: 86

Met Ala Phe Arg Met Ser Glu Gln Ser Arg Thr Val Lys Ile Tyr Asn
1               5                   10                  15

Leu Leu Ala Gly Thr Asn Glu Phe Ile Gly Glu Gly Asp Ala Tyr Ile
            20                  25                  30

Pro Pro His Thr Gly Leu Pro Ala Asn Ser Thr Asp Ile Ala Pro Pro
        35                  40                  45

Glu Ile Pro Ala Gly Phe Val Ala Val Phe Asn Ser Glu Asn Glu Ser
50                  55                  60

Trp Asn Ile Val Glu Asp His Arg Gly Lys Thr Val Tyr Asp Val Ala
65                  70                  75                  80

Ser Gly Asp Ala Leu Phe Ile Ser Glu Pro Gly Pro Leu Pro Glu Asn
                85                  90                  95

Val Thr Trp Leu Ser Pro Ala Gly Glu Tyr Gln Lys Trp Asp Gly Val
                100                 105                 110

Ser Trp Val Lys Asp Glu Glu Ala Glu Lys Leu Phe Arg Ile Arg Glu
            115                 120                 125

Ala Glu Glu Lys Lys Ala Arg Leu Ile Gln Glu Ala Thr Asp Asn Ile
130                 135                 140

Ala Ile Leu Gln Asp Ala Val Asn Leu Glu Ile Ala Thr Asn Glu Glu
145                 150                 155                 160

```
Asn Ser Gln Leu Asp Ser Trp Arg Lys Tyr Arg Val Leu Val Ser Arg
                165                 170                 175

Ile Asp Thr Ser Thr Ala Pro Asp Ile Val Trp Pro Glu Leu Met Asn
            180                 185                 190

Gln Gly Tyr Val Arg Glu Asp Glu Gln Ile Thr Ser Asp
        195                 200                 205

<210> SEQ ID NO 87
<211> LENGTH: 170
<212> TYPE: PRT
<213> ORGANISM: Artificial Sequence
<220> FEATURE:
<223> OTHER INFORMATION: Queen Chaperone

<400> SEQUENCE: 87

Met Asn Asn Phe Lys Asn Phe Ala Pro Tyr Thr Pro Gly Glu Asp Lys
1               5                   10                  15

Arg Glu Leu Val Asp Ala Gly Val Leu Phe Leu Leu Asp Glu Asn Gly
            20                  25                  30

Asn Asp Trp Tyr Glu Cys Gln Lys Leu Phe Ser Glu Cys Thr Lys Val
        35                  40                  45

Ile Ala Tyr Asp Ser Asn Asn Ile Val Val Ser Ile Thr Asp Asp Ala
50                  55                  60

Ser Thr Leu Trp Pro Ile Gly Leu Ser Val Ala Glu Val Asp Ser Leu
65                  70                  75                  80

Pro Glu Asp Val Asp Ile Asn Gly Gly Trp Val Phe Arg Asp Asn Ser
                85                  90                  95

Val Val Lys Arg Ile Tyr Ser Asp Thr Glu Leu Gln Gln Gln Ala Glu
            100                 105                 110

Ser Lys Lys Ala Ala Leu Leu Ser His Ala Glu Ser Val Ile Val Thr
        115                 120                 125

Leu Glu Arg Ala Val Lys Leu Asn Met Ala Thr Asp Glu Glu Arg Ala
130                 135                 140

Lys Leu Glu Ala Trp Glu Arg Tyr Ser Val Leu Val Tyr Arg Val Asp
145                 150                 155                 160

Thr Ala Lys Pro Glu Trp Pro Glu Pro
                165                 170

<210> SEQ ID NO 88
<211> LENGTH: 93
<212> TYPE: PRT
<213> ORGANISM: Artificial Sequence
<220> FEATURE:
<223> OTHER INFORMATION: Razzmatazz Chaperone A

<400> SEQUENCE: 88

Met Met His Leu Lys Asn Ile Thr Ala Gly Asn Pro Lys Thr Lys Glu
1               5                   10                  15

Gln Tyr Gln Leu Thr Lys Gln Phe Asn Ile Lys Trp Leu Tyr Thr Glu
            20                  25                  30

Asp Gly Lys Asn Trp Tyr Glu Glu Gln Lys Asn Phe Gln Pro Asp Thr
        35                  40                  45

Leu Lys Met Val Tyr Asp His Asn Asp Val Ile Cys Ile Glu Lys
50                  55                  60

Asp Val Ser Ala Ile Asn Pro Glu Gly Ala Ser Val Val Glu Val Pro
65                  70                  75                  80

Asp Ile Thr Ala Asn Arg Arg Ala Asp Ile Ser Gly Lys
                85                  90
```

```
<210> SEQ ID NO 89
<211> LENGTH: 83
<212> TYPE: PRT
<213> ORGANISM: Artificial Sequence
<220> FEATURE:
<223> OTHER INFORMATION: Razzmatazz Chaperone B

<400> SEQUENCE: 89
```

Met Phe Lys Asp Gly Val Val Ile Lys Arg Thr Tyr Thr Glu Glu
1               5                   10                  15

Gln Arg Gln Gln Ala Glu Asn Glu Lys Gln Ser Leu Leu Gln Leu Val
            20                  25                  30

Arg Asp Lys Thr Gln Leu Trp Asp Ser Gln Leu Arg Leu Gly Ile Ile
            35                  40                  45

Ser Asp Glu Asn Lys Gln Lys Leu Thr Glu Trp Met Leu Tyr Ala Gln
50                  55                  60

Lys Val Glu Ser Thr Asp Thr Ser Ser Leu Pro Val Thr Phe Pro Glu
65                  70                  75                  80

Gln Pro Glu

```
<210> SEQ ID NO 90
<211> LENGTH: 176
<212> TYPE: PRT
<213> ORGANISM: Artificial Sequence
<220> FEATURE:
<223> OTHER INFORMATION: Salmon Chaperone

<400> SEQUENCE: 90
```

Met Met Gln His Leu Lys Asn Ile Lys Ser Gly Asn Pro Lys Thr Lys
1               5                   10                  15

Glu Gln Tyr Gln Leu Thr Lys Asn Phe Asp Val Ile Trp Leu Trp Ser
            20                  25                  30

Glu Asp Asp Lys Asn Trp Tyr Glu Glu Val Lys Asn Phe Gln Pro Asp
            35                  40                  45

Thr Ile Lys Ile Val Tyr Asp Ala Asn Asn Ile Ile Val Ala Ile Thr
50                  55                  60

Lys Asp Ala Ser Thr Leu Asn Pro Glu Gly Phe Ser Val Val Glu Val
65                  70                  75                  80

Pro Asp Ile Thr Ala Asn Arg Arg Ala Asp Ser Gly Lys Trp Met
            85                  90                  95

Phe Lys Asp Gly Ala Val Val Lys Arg Ile Tyr Thr Ala Asp Glu Gln
            100                 105                 110

Gln Gln Gln Ala Glu Ser Gln Lys Ala Ala Leu Leu Ser Glu Ala Glu
            115                 120                 125

Ser Val Ile Gln Pro Leu Glu Arg Ala Val Arg Leu Asn Met Ala Thr
            130                 135                 140

Asp Glu Glu Arg Thr Arg Leu Glu Ala Trp Glu Arg Tyr Ser Val Leu
145                 150                 155                 160

Val Ser Arg Val Asp Thr Ala Asn Pro Glu Trp Pro Gln Lys Pro Glu
                165                 170                 175

```
<210> SEQ ID NO 91
<211> LENGTH: 203
<212> TYPE: PRT
<213> ORGANISM: Artificial Sequence
<220> FEATURE:
<223> OTHER INFORMATION: Scarlet Chaperone
```

-continued

<400> SEQUENCE: 91

```
Met Asp Asn Ala Ile Leu Asn Ser Glu Leu Ile Ala Ile Gln Ala Gly
1               5                   10                  15

Asn Ile Ile Val Tyr Asn Tyr Asp Gly Gly Asn Arg Glu Tyr Ile Ser
            20                  25                  30

Ala Ser Thr Glu Tyr Leu Ala Val Gly Val Gly Ile Pro Ala Asn Ser
        35                  40                  45

Cys Leu Asp Ala Pro Gly Ser His Lys Ala Gly Tyr Ala Ile Leu Arg
    50                  55                  60

Ser Glu Asp Leu Ser Ser Trp Glu Tyr Val Pro Asp His Arg Gly Glu
65                  70                  75                  80

Thr Val Tyr Ser Ile Asp Thr Gly Asn Pro Glu Ile Thr Val Leu
                85                  90                  95

Gly Asp Tyr Pro Glu Asn Thr Thr Thr Ile Ala Pro Leu Thr Pro Tyr
            100                 105                 110

Asp Lys Trp Asp Gly Glu Lys Trp Val Val Asp Thr Glu Ala Gln His
        115                 120                 125

Ser Ala Ala Val Glu Ala Ala Glu Thr Lys Arg Gln Ser Leu Ile Asp
130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Thr Ala Pro Asp Leu
            180                 185                 190

Asn Trp Pro Glu Lys Gln Leu Ser Thr Ala Ser
        195                 200
```

<210> SEQ ID NO 92
<211> LENGTH: 175
<212> TYPE: PRT
<213> ORGANISM: Artificial Sequence
<220> FEATURE:
<223> OTHER INFORMATION: Shamrock Chaperone

<400> SEQUENCE: 92

```
Met Met His Leu Lys Asn Ile Lys Ala Gly Asn Ala Lys Thr Leu Glu
1               5                   10                  15

Gln Tyr Glu Leu Thr Lys Lys His Gly Val Ile Trp Leu Tyr Ala Glu
            20                  25                  30

Asp Gly Lys Asn Trp Tyr Glu Glu Val Lys Asn Phe Gln Pro Asp Thr
        35                  40                  45

Ile Lys Ile Val Tyr Asp Glu Asn Asn Ile Ile Val Ala Val Thr Lys
    50                  55                  60

Asp Ala Ser Thr Leu Asn Pro Glu Gly Phe Ser Val Val Glu Ile Pro
65                  70                  75                  80

Asp Ile Thr Ala Asn Arg Arg Ala Asp Ser Gly Lys Trp Met Phe
                85                  90                  95

Lys Asp Gly Ala Val Val Arg Arg Thr Tyr Thr Ala Asp Glu Gln Gln
            100                 105                 110

Gln Gln Ala Glu Ser Gln Lys Ala Leu Leu Ser Glu Ala Glu Ser
        115                 120                 125

Val Ile Gln Pro Leu Glu Arg Ala Val Arg Leu Asn Met Ala Thr Asp
130                 135                 140

Glu Glu His Ala Arg Leu Glu Ser Trp Glu Arg Tyr Ser Val Leu Val
```

```
145                 150                 155                 160
Ser Arg Val Asp Thr Ala Asn Pro Glu Trp Pro Gln Lys Pro Glu
                165                 170                 175

<210> SEQ ID NO 93
<211> LENGTH: 203
<212> TYPE: PRT
<213> ORGANISM: Artificial Sequence
<220> FEATURE:
<223> OTHER INFORMATION: Sunset Chaperone

<400> SEQUENCE: 93

Met Asp Asn Ala Ile Leu Asn Ser Glu Leu Ile Ala Ile Gln Ala Gly
1               5                   10                  15

Asn Ile Ile Val Tyr Asn Tyr Asp Gly Gly Asn Arg Glu Tyr Ile Ser
                20                  25                  30

Ala Ser Thr Glu Tyr Leu Ala Val Gly Val Gly Ile Pro Ala Asn Ser
            35                  40                  45

Cys Leu Asp Ala Pro Gly Ser His Lys Ala Gly Tyr Ala Ile Leu Arg
    50                  55                  60

Ser Glu Asp Leu Ser Ser Trp Glu Tyr Val Pro Asp His Arg Gly Glu
65                  70                  75                  80

Thr Val Tyr Ser Ile Asp Thr Gly Asn Pro Glu Glu Ile Thr Val Leu
                85                  90                  95

Gly Asp Tyr Pro Glu Asn Thr Thr Ile Ala Pro Leu Thr Pro Tyr
            100                 105                 110

Asp Lys Trp Asp Gly Glu Lys Trp Val Val Asp Thr Glu Ala Gln His
    115                 120                 125

Ser Ala Ala Val Glu Ala Ala Glu Thr Lys Arg Gln Ser Leu Ile Asp
130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Thr Ala Pro Asp Leu
            180                 185                 190

Asn Trp Pro Glu Lys Gln Leu Ser Thr Ala Ser
        195                 200

<210> SEQ ID NO 94
<211> LENGTH: 203
<212> TYPE: PRT
<213> ORGANISM: Artificial Sequence
<220> FEATURE:
<223> OTHER INFORMATION: Tangerine Chaperone

<400> SEQUENCE: 94

Met Asp Asn Ala Ile Leu Asn Ser Glu Leu Ile Ala Ile Gln Ala Gly
1               5                   10                  15

Asn Ile Ile Val Tyr Asn Tyr Asp Gly Gly Asn Arg Glu Tyr Ile Ser
                20                  25                  30

Ala Ser Thr Glu Tyr Leu Ala Val Gly Val Gly Ile Pro Ala Asn Ser
            35                  40                  45

Cys Leu Asp Ala Pro Gly Ser His Lys Ala Gly Tyr Ala Ile Leu Arg
    50                  55                  60

Ser Glu Asp Leu Ser Ser Trp Glu Tyr Val Pro Asp His Arg Gly Glu
65                  70                  75                  80
```

```
Thr Val Tyr Ser Ile Asp Thr Gly Asn Pro Glu Glu Ile Thr Val Leu
                85                  90                  95

Gly Asp Tyr Pro Glu Asn Thr Thr Ile Ala Pro Leu Thr Pro Tyr
            100                 105                 110

Asp Lys Trp Asp Gly Glu Lys Trp Val Val Asp Thr Glu Ala Gln His
            115                 120                 125

Ser Ala Val Glu Ala Ala Glu Thr Lys Arg Gln Ser Leu Ile Asp
130                 135                 140

Thr Ala Met Asp Ser Ile Ser Leu Ile Gln Leu Lys Leu Arg Ala Gly
145                 150                 155                 160

Arg Lys Leu Thr Gln Ala Glu Thr Thr Gln Leu Asn Ser Val Leu Asp
                165                 170                 175

Tyr Ile Asp Glu Leu Asn Ala Met Asp Leu Thr Thr Ala Pro Asp Leu
                180                 185                 190

Asn Trp Pro Glu Lys Gln Leu Ser Thr Ala Ser
            195                 200
```

<210> SEQ ID NO 95
<211> LENGTH: 175
<212> TYPE: PRT
<213> ORGANISM: Artificial Sequence
<220> FEATURE:
<223> OTHER INFORMATION: Thistle Chaperone

<400> SEQUENCE: 95

```
Met Gln His Leu Lys Asn Ile Arg Ser Gly Asn Pro Lys Thr Lys Glu
1               5                   10                  15

Gln Tyr Gln Leu Thr Lys Asn Phe Asp Val Ile Trp Leu Trp Ser Glu
            20                  25                  30

Asp Gly Lys Asn Trp Tyr Glu Glu Val Lys Asn Phe Gln Pro Asp Thr
        35                  40                  45

Ile Lys Ile Val Tyr Asp Glu Asn Asn Ile Ile Val Ala Ile Thr Lys
    50                  55                  60

Asp Ala Ser Thr Leu Asn Pro Glu Gly Phe Ser Val Val Glu Val Pro
65                  70                  75                  80

Asp Ile Thr Ala Asn Arg Arg Ala Asp Asp Ser Gly Lys Trp Met Phe
                85                  90                  95

Lys Asp Gly Ala Val Val Lys Arg Ile Tyr Thr Ala Asp Glu Gln Gln
            100                 105                 110

Gln Gln Ala Glu Ser Gln Lys Ala Ala Leu Leu Ser Glu Ala Glu Ser
        115                 120                 125

Val Ile Gln Pro Leu Glu Arg Ala Val Arg Leu Asn Met Ala Thr Asp
    130                 135                 140

Glu Glu Arg Thr Arg Leu Glu Ala Trp Glu Arg Tyr Ser Val Leu Val
145                 150                 155                 160

Ser Arg Val Asp Thr Ala Asn Pro Glu Trp Pro Gln Lys Pro Glu
                165                 170                 175
```

<210> SEQ ID NO 96
<211> LENGTH: 177
<212> TYPE: PRT
<213> ORGANISM: Artificial Sequence
<220> FEATURE:
<223> OTHER INFORMATION: Violet Chaperone

<400> SEQUENCE: 96

```
Met Met His Leu Lys Asn Ile Thr Ala Gly Asn Pro Lys Thr Lys Glu
1               5                   10                  15
```

Gln Tyr Gln Leu Thr Lys Gln Phe Asn Ile Lys Trp Leu Tyr Thr Glu
            20                  25                  30

Asp Gly Lys Asn Trp Tyr Glu Glu Lys Asn Phe Gln Pro Asp Thr
        35                  40                  45

Leu Lys Met Val Tyr Asp His Asn Asp Val Ile Cys Ile Glu Lys
50                  55                  60

Asp Val Ser Ala Ile Asn Pro Glu Gly Ala Ser Val Val Glu Val Pro
65                  70                  75                  80

Asp Ile Thr Ala Asn Arg Arg Ala Asp Ile Ser Gly Lys Trp Met Phe
                85                  90                  95

Lys Asp Gly Val Val Ile Lys Arg Thr Tyr Thr Glu Glu Gln Arg
            100                 105                 110

Gln Gln Ala Glu Asn Glu Lys Gln Ser Leu Leu Gln Leu Val Arg Asp
        115                 120                 125

Lys Thr Gln Leu Trp Asp Ser Gln Leu Arg Leu Gly Ile Ile Ser Asp
130                 135                 140

Glu Asn Lys Gln Lys Leu Thr Glu Trp Met Leu Tyr Ala Gln Lys Val
145                 150                 155                 160

Glu Ser Thr Asp Thr Ser Ser Leu Pro Val Thr Phe Pro Glu Gln Pro
                165                 170                 175

Glu

<210> SEQ ID NO 97
<211> LENGTH: 4494
<212> TYPE: DNA
<213> ORGANISM: Artificial Sequence
<220> FEATURE:
<223> OTHER INFORMATION: P1 Bald Chassis Tail Fiber Region

<400> SEQUENCE: 97

```
taatcacccc gtccgcaggg cggggtgaca agttacttat cttacaatga ggcttcacaa      60
cattgattag ggaaaatcat gtctgacgtc tcaacaaacc tctataagag tcagttgttg     120
gactattact atcagcggcg cgctgaatcg tccattaaca aaggctctcg atttttaatc     180
agcaaggccg ttttcggtac cagttcgctg gttactaaga aaggagatgg cacttatgag     240
attggagaac tgccaaaggc tttcgaactg gcagaactga ccagtcaatt ttgcaccatc     300
aacctcgtcc caacctactc aggcgggata attactgtcc gaatgaccct tgatcaaagc     360
cagttgcagg aagggaaaaa ctacccattc aacactctgg ttgttctgga taacgagaac     420
aagccaatcg ccattatttg tgtccaggaa gactcgctgt atgtgggcaa acatatacc      480 gcagttatgg ccataaacac gactacagca taaggatatg cttgcggaat ctgtgggtaa     540
ctttgtatgt gtccgcagcg cccgccgcag tctcacgccc ggagcgtagc gaccgagtga     600
gctagctatt tgtttatttt tctaaataca ttcaaatatg tatccgctca tgagacaata     660
accctgataa atgcttcaat aatattgaaa aaggaagagt atgagggaag cggtgatcgc     720
cgaagtatcg actcaactat cagaggtagt tggcgtcatc gagcgccatc tcgaaccgac     780
gttgctggcc gtacatttgt acggctccgc agtggatggc ggcctgaagc cacacagtga     840
tattgatttg ctggttacgg tgaccgtaag gcttgatgaa caacgcggc gagctttgat     900 caacgacctt ttggaaactt cggcttcccc tggagagagc gagattctcc gcgctgtaga     960
agtcaccatt gttgtgcacg acgacatcat tccgtggcgt tatccagcta agcgcgaact    1020
gcaatttgga gaatggcagc gcaatgacat tcttgcaggt atcttcgagc cagccacgat    1080
```

```
cgacattgat ctggctatct tgctgacaaa agcaagagaa catagcgttg ccttggtagg    1140
tccagcggcg gaggaactct tgatccggt tcctgaacag gatctatttg aggcgctaaa    1200 tgaaaccta acgctatgga actcgccgcc cgactgggct ggcgatgagc gaaatgtagt    1260
gcttacgttg tcccgcattt ggtacagcgc agtaaccggc aaaatcgcgc cgaaggatgt    1320
cgctgccgac tgggcaatgg agcgcctgcc ggcccagtat cagcccgtca tacttgaagc    1380
tagacaggct tatcttggac aagaagaaga tcgcttggcc tcgcgcgcag atcagttgga    1440
agaatttgtc cactacgtga aaggcgagat caccaaggta gtcggcaaat aatgtctaac    1500
aattcgttca agccgagtat ggcaacagac gaggaacgca cacgactgga agcatgggaa    1560
cgctacagtg ttctggtcag ccgtgtggat acggcaaatc ctgaatggcc acaaaagcct    1620
gaataaaaat taaggcccgc tatcgggcct tgtctcattc aggttgttcg ggaaatgtta    1680
ctggtaggct ggaggtgtct gtggattcga ctttctgcgc aaagagcatc cactcggtta    1740
atttctgctt attctcggcg gaaatgatac ccagccgtag ctgtgagtcc catagctggg    1800 tttatccct gacgagctgt agcagacttt gcttttcatt ttccgcttgt tgcctctgct    1860
cttcctcggt ataagttcgc tttaccacta cgccatcttt gaacatccat ttaccagaaa    1920
tatcagcccg gcgatttgct gtaatatcag gtaattcaac gacgcttgcg ccttctggat    1980
taattgctga acatcctt tcaatacaaa taataacgcc gttgtggtca taggccattt    2040
tcaacgtatc atactggaaa ttcttttgtt cctcatacca gttttttcca tcctctgtat    2100
aaagccattt gatgttaaat tgtttcgtta gctggtattg ctcttttgtt ttagggttgc    2160
cagctgtaat atttcttaag tgcatcataa ttaaatactc cccgcgttat accacgtccc    2220
attaatgcaa tactgaattg gccttgcctg tgttgtatca attaattcat cacggttccc    2280
gttaactgaa cccgtaacga cataacctga cctgtcagac cagccgggc cattccatgt    2340 ctggacagat gacagaccgc ccaggcgaat acctgtaata aaccttgagt tacattctgc    2400
ctgcgtatat gcaccaacat cccccgcaga ggtttgcgg gttgtggtgt aaaactctga    2460
ccagtcagcc tcaaatccat aaccatcacg cgctgaacga taataaatac cgccgttctt    2520
ataattcacg cgtaattgta cagccgggca gctacccgcg ttcatattga aatgaagaat    2580
taatgttgat gcgcctttta ggtctgcatc ataaacaccg ctattccagt tccagccaac    2640
agctttatca tttgcaaccc tgtttcctgt ctgccctaaa gcaaatgcag gttgcaggtt    2700
tttcgtgttg tagtctcgtc gccagccagg agcgtaagca tcaccatgat taatataagt    2760
gaattgagcg ttagtgattc cgccaccgct ggaagtgctt ggtgttgtta cacgatggt    2820 catggcacct ttattaccca taacctcaat aacgcaacct gcaagatgaa tagttccaca    2880
gccagtatcg gttataattt tattattgcc gtacgaccat gaacatttgc acatccagta    2940
tgggtgattg aatgccccctt gagaatccag ccattcaatc aattgtgccg ttgtccagtt    3000
ccctgcacct gtactaatag aactgtgaaa agcgcgacat gcaccaatat ttttgtgaa    3060 ggtatctttt ccaggaatat ccgcgccgtt ctgatttttc tgcaatgacc cagcggctaa    3120
ttctactgtt cgctcaagat ttaaatttc agccgttagc tcaatatttt tagaaccatc    3180
aaacgagaca ccgttgatag tacatgctgt ctgcaacttg gtcgctgtag ccgcattacc    3240
agaggtatcc tgatcccctt tggcattgac gccgggaatt gaatcttttg acgtatagac    3300
ctgcgcccat tcagaccagt tggcagaatc agtatcccgc cgcgaacgga tatgtacggg    3360
cgcatgggca ccgctcgtgc cactccagcc aatgaataac tcaccttcgc cagcagcggt    3420 ggcacccttta aggtgaagca cattgccata gggggaaggg tagccattgt tgtatgcctc    3480
```

```
atacagctga atcccggatg ttccctgtgc attcgcctcc agggccgtta cgcgaccgcg    3540
cgataccaga gtattgatat taatgtcacc agaaccatcg aacctgacgc cattaatgtt    3600
tctggctgtt ttcaatttcg ttgcggtatc ggcgttccct gtcagcgccc cggtgatccc    3660
gccgttgaaa gtctggcgtg cactccatgt gttagccgtg ctcaacaggg ggatcttttc    3720
accgctggta ccgagttctc ttaaaccaag gtttaggatt gaaatgatga cgccggaaac    3780
ttcttataaa gcgtggaaac agccacatca tagatgattg caacctgctt acggggatg     3840 cccttctcca gcaatcgccg catttgctgc catgtttctt cttggtattt aggccgacgc    3900
ccacctatac gaccttctgc gcgagctgca tcaagtccag cgcgtgtacg ttcaacgata    3960
agctcacgtt ccatttctgc cagcgccccc attacgtgaa agaaaaagcg ccccattggt    4020
gtactggtgt cgatggagtc agtgagactc cggaagttaa tgcctctgtc acgcagctct    4080
tccaccagca caactaagtg acgcatgctg cgcccaagac ggtctaactt ccatacgacc    4140
agggtatcac ctctggaaag catacggagt accttttta  acccagggcg ctcagccttt    4200
ttgccgctcg ccttgtcctc aaaaattagc tcacatcctg cgctttcaag agcgtttcgt    4260
tgtaaagcag tgttttgttc atttgttgat acgcgtacat agcctattag catattttct    4320
gctcactatc gttatttata gcaagctgcg gattttaatt aacaaaaacc agtatgtgtg    4380
gaaatcacaa agtacatacc gtttcccaat gatatttaat tcactattaa ggaaatagtt    4440
atgtgtgatt tcacaataat gctcctctcc atccttggcg gggtgcattc gttt          4494
```

<210> SEQ ID NO 98
<211> LENGTH: 1950
<212> TYPE: DNA
<213> ORGANISM: Artificial Sequence
<220> FEATURE:
<223> OTHER INFORMATION: Rio Tail Fiber S gene

<400> SEQUENCE: 98

```
atgaatgacg ttacagttgt tacatcggtt acttacccat catccgagtc gttggctctg      60
gtggccgatg tgcaataccc cgaaccatat ctgtcagccg cgctaaaccg aaaaattcagg    120 gggattgttg acccgggatt ttatgccggt ttcttaccta gcctggcgg  tgggatgaac     180 ctgttaatta cctcagtgga tggtgataaa accgcaggcg cggcgtcggt ggatattggt    240
gaattttacc agtaactat  tcagcaacgt aaggatattt ctcttgcact tagtgcaggc    300
aagaaatatg caattgtgct gaagggaaga tacctccttg agaagatac  ctaccaggtg    360 aataccgcgt cacatattca tgcggctgaa tttgttgcca gaacctatac cgattcatat    420
cagttaggag atggggagct gcttgtttgt acggtgaata tccctgctag tgtatctgcc    480 attcccagg  agatgattga tacatccgag cgtatcaacc gctcgatcgg cattgatatt    540
tcagactctg taaccagtac cagaagtgat gttgctgcaa gttcgctggc agttaaaaaa    600
gcctacgatc tggcgaaaag caagtatacg gcacaggatg caacaacaac agtaaaaggc    660
tttacaaagt taaataatca ggtgggtgac agtgaaaata ccgcattaac tccttacggc    720
gctaaaaaag aattgaaaaa ctatcaaccc aaaggcaatt atcaaccggc tggtaattat    780
gtcactactg cgacatttaa tttagaaatc aataaaaaaa tagataaagc aagtctctca    840
cagcaacttg gtaatgatgt aaataaagta cctagtttag atttggtgac taaagagcta    900
gggaataaac aacctaaagg tgattatgca ttaaaaacat gggttgataa tatttattat    960
aaacgagatg acagtccttc atttaatgaa attagtgcta cagctattcg agtgaatagt    1020
```

| | | |
|---|---|---|
| gttaacgtcg cgctaaaagg ggattgctat acaaaatcag aatctgataa taaatattct | 1080 | |
| ccgaaattac cctttgtata ctcttcgggt gaggagtcaa aaatcatatc accaaacaat | 1140 | |
| aaaatcctta tttttgttaa tgataatgga acaacaggag ggtatgacag ggatactcaa | 1200 | |
| gcaacagtct gggggtttga taaacgtgga tttatgacaa gaggcactgt gcattttgac | 1260 | |
| agaatgtcag gtgtttattc acaatcacag gtagatgcta agttaaaaga gtgcctaaat | 1320 | |
| ttaaaaacat catcaaaaca atttattgca agtgatatat atgcacccac tttcattaca | 1380 | |
| ggctcgcagt atggagaacg ttcctattta gaacataaaa gtgatgagct tactattact | 1440 | |
| cacatatcgc caaaatcagg ggcaacaaat attacttgta gaaataaaag tggtacctta | 1500 | |
| gcactattgg gtgatctcga agatgttaat aatatccctg ttggttcccc tattccgtgg | 1560 | |
| tcattagcta cagcaccctc tggttatcta atctgtaatg gtcaaacatt taataaatca | 1620 | |
| acatacccaa aacttgccgt tgcttatcca tcaggaaaac tacctgattt gcgcggtgag | 1680 | |
| tttattcgtg gtttggacag cgggcgcggt attgatgcgg ggcgttcggt attatcagtt | 1740 | |
| caaaaggta atagcttgtt atccagtaat attttttggtg gattgagttc atcggaatca | 1800 | |
| aacaaatggc ataaagcaat taattatatc ggtattacag gtactgataa tgacggtggt | 1860 | |
| tatggagttc accagcaaat agaaggcgct aatggaaatg aaactcgccc acgtaatatc | 1920 | |
| gccttttttat atatagtgag agcagcataa | 1950 | |

<210> SEQ ID NO 99
<211> LENGTH: 621
<212> TYPE: DNA
<213> ORGANISM: Artificial Sequence
<220> FEATURE:
<223> OTHER INFORMATION: Rio Tail Fiber U gene

<400> SEQUENCE: 99

| | | |
|---|---|---|
| atgagcaaat atagtttaga tatccagaaa ggaaaaatcg gtgataatgg tttggcagaa | 60 | |
| atcgcaggtt gggttaagtg ttatttagct catccaatta cgcatgaata tatgggcgca | 120 | |
| accatggaaa atgtcatgtt tgatgtttca ttatctgcgg gtgcttattt agatgaacca | 180 | |
| ccattacccc aaaagaaaa tcaagccgtt agacgtagag aagatggtag tgcatgggag | 240 | |
| attgttgacg attgccgagg tttaaccgcc tacaatacgc aaacaaagca acctatcatc | 300 | |
| attgatttta tggggccatt gcctgaatct ctcacattgt taaaaccgaa tagtgagttt | 360 | |
| gataaatggg atggtaagaa ctggattgtt gacacagaag cccaaaaagc ggcactcatt | 420 | |
| acacagatta acaggagaa atcacgacgc ttagatgaag cagataatat aatcacatat | 480 | |
| ttgcaagaag ctgttgatgt tgacttagcc acagaagaag aggctacagc actgcaaaaa | 540 | |
| tggaaaaaat accgagttct gttaaatcgt gttgatattt caacggcgcc agatatcgaa | 600 | |
| tggccggaga aaccgcaatg a | 621 | |

<210> SEQ ID NO 100
<211> LENGTH: 1746
<212> TYPE: DNA
<213> ORGANISM: Artificial Sequence
<220> FEATURE:
<223> OTHER INFORMATION: Limon Tail Fiber S gene

<400> SEQUENCE: 100

| | | |
|---|---|---|
| atgaatgacg ttacagttgt tacatcggtt acttacccat catccgagtc gttggctctg | 60 | |
| gtggccgatg tgcaatacca cgaaccatat ctgtcagccg cgctaaaccg aaaattcagg | 120 | |
| gggattgttg acccgggatt ttatgccggt ttcttaccta agcctggcgg tgggatgaac | 180 | |

```
ctgttaatta cctcagtgga tggtgataaa accgcaggcg cggcgtcggt ggatattggt      240
gaattttacc aggtaactat tcagcaacgt aaggatattt ctcttgcact tagtgcaggc      300
aagaaatatg caattgtgct gaagggaaga tacctccttg gagaagatac ctaccaggtg      360
aataccgcgt cacatattca tgcggctgaa tttgttgcca gaacctatac cgattcatat      420
cagttaggag atggggagct gcttgtttgt acggtgaata tccctgctag tgtatctgcc      480
attacccagg agatgattga tacatccgag cgtatcaacc gctcgatcgg cattgatatt      540
tcagactctg taaccagtac cagaagtgat gttgctgcaa gttcgctggc agttaaaaaa      600
gcctacgatc tggcgaaaag caagtatacg gcacaggatg caaccacagc aagaaaaggt      660
atcgtccagt taagcagtgc aacggacagc accagcgaag aactggctgc tacattgaaa      720
gcggttaaaa tcgcgatgga taacgccaac gcgcgtcttg caaagagcg taacggtgga       780 gacgttccga ataaacctct gtttattcaa acattggtt tgcaggaaac agttaacaaa       840
gcagccggag cagtgcagcg aagtgaggtc cagacttctc aggatgatat tactgccgga      900
aaattgctgg ttaatggtag cgctattgct gttcgtggca tccgcgcaat caatggagga      960
caggtagacg atgctaataa ccttccggtt aacgcagtat cgtttgtcta tggtgatgcc     1020
aaaaactcac cgagtggaaa tacagggact atcctggatg tttccgggct tggtagtggt     1080
tatagcatcc agctattcgc taactactcg acaggcgaaa tactggcgtt tcgtgcgcgt     1140
aatggtgata acagaacatg gaataaatgg aattatgtgt tcacacggg aaataaacca      1200 acctctacag atgtggggc gctaccaata acaggtggtg atttaaaggg gcaacttccc      1260
ttttcgttct cgcaacccag aaatggcgct aaccacttaa tatacaacgg cgatgataac     1320
ggagtactgg cttgcggata tggttattat caggacagat ttgatattca tttttatgac     1380
attaaaggtg cgtgggaatc aaatccatta accataggac gcaatggaaa tacgacagtt     1440
agtggtaatt tgtcaggtcg tgctgtttat gaaggtaaca ctcgcgttta ttcacccaac     1500
aacccgcagc ccgttagctt tgaaggttat gcaacgcaaa gctgggtgtt gcagaacttt     1560
gtccaaaata ttgacctgac agcacctgct gaagttggat ttcgtgatgg gtggggtat      1620 ccacgaggga cagatggcgc agccatgtac aactttaata tggttggtgg tagcagtaac     1680
gttggtaatt ttatcattcg ttatatgcgg aaacaggtga ataacacctg gtatgtgatt     1740
aattaa                                                                1746
```

<210> SEQ ID NO 101
<211> LENGTH: 534
<212> TYPE: DNA
<213> ORGANISM: Artificial Sequence
<220> FEATURE:
<223> OTHER INFORMATION: Limon Tail Fiber U gene

<400> SEQUENCE: 101

```
atgcaacgct ttggcaaatt caccccatat acaccagaca ctactgacag gccaagaatt       60
attgatggtc agaatgttat gttttttgcag gatgataaag gtaatgactg gtatgacgtt     120
attgaattat ttgatgaatc aaaaacgctg aaaattggat atgacgatga tggtcgtgta      180
agaacgttca cgacaaatat tcatgcgctt ttcccggtca atctgagtgt tgtcgagctt      240
ccggccacaa aagctaattt gcgcgtcacg ctgggtgatg actggtttta taaagacggc      300
aaattacagc aaatccgcaa ttacctggct gacgctgaag cggaacgtgg caaccgtatg      360
gcggaggtta caacgcgtat tgactggctg gaggatgcgc aaaaagacgg tgatatttca     420
```

```
tcctatgagg aaacagaact ggcaacacta cgcgcttacc gcactgcttt gcgccgtctg    480
gatctgagca cagcgccaga tattaactgg ccggaggtgc ctgatgtggc gtga          534
```

<210> SEQ ID NO 102
<211> LENGTH: 3210
<212> TYPE: DNA
<213> ORGANISM: Artificial Sequence
<220> FEATURE:
<223> OTHER INFORMATION: Orchid Tail Fiber S gene

<400> SEQUENCE: 102

```
atgaatgacg ttacagttgt tacatcggtt acttacccat catccgagtc gttggctctg     60
gtggccgatg tgcaatacca cgaaccatat ctgtcagccg cgctaaaccg aaaattcagg    120
gggattgttg acccgggatt ttatgccggt ttcttaccta agcctggcgg tgggatgaac    180
ctgttaatta cctcagtgga tggtgataaa accgcaggcg cggcgtcggt ggatattggt    240
gaattttacc aggtaactat tcagcaacgt aaggatattt ctcttgcact tagtgcaggc    300
aagaaatatg caattgtgct gaagggaaga tacctccttg agaagatac  ctaccaggtg    360 aataccgcgt cacatattca tgcggctgaa tttgttgcca gaacctatac cgattcatat    420
cagttaggag atggggagct gcttgtttgt acggtaata tccctgctag tgtatctgcc     480
attacccagg agatgattga tacatccgag cgtatcaacc gctcgatcgg cattgatatt    540
tcagactctg taaccagtac cagaagtgat gttgctgcaa gttcgctggc agttaaaaaa    600
gcctacgatc tggcgaaaag caagtatacg gcacaggatg caagcacaac gcaaaaggga    660
ttagttcagc tcagtagcgc aactaacagc gacagcgaaa caatggcggc taccccctaaa   720 gctgttaagt ctataaaaga tctggctgat accaaagcgc aatagaaag  cccgagtctg    780 acaggaacgc caaccgcgcc gacggcagcg caaggtacaa acagcacgca gatcgcaaat    840
acagcctttg ttaaggcagc tataactgca cttatcaacg gtgcgcctgg cacactggat    900
acgctgaaag aaatagcggc tgcgatcaat aacgacccga attacagcac aactatcaac    960
aatgccttgg ctctcaaagc gcctttggca agccctgcat taacgggtgt ccctactgcg   1020
cctacggctg cacagggcac aaacaatacg cagatcgcta cgactgctta cgtacgggct   1080
gctatctctg cattggtcgg ctcatcacct gaagctcttg ataccctgta tgagcttgca   1140
gcagcactgg gcaatgaccc gaactttgcg acaacaatga caaatgcgct ggcagggaaa   1200
cagccacttg atgcaacttt aaccgcgctt gctggtcttg cgacaggcgc aaataaattg   1260 ccgtactttta ccggtacaga cactgtttct cagactgact taacgtcagt tggtcgcgat   1320
attctggcca aaacaagcat tcttgctgtt atccaatacc ttggtttaag agaactcggt   1380
accagcggtg aaaagatccc cctgttgagc acggctaaca catggagtgc acgccagact   1440
ttcaacggcg ggatcaccgg ggcgctgaca gggaacgccg ataccgcaac gaaattgaaa   1500
acagccgcac gctcgattgg cggtgtggca tttgatggct cggccaatat caatcttcca   1560
ggtgtaaata caacaggtaa ccagaacacc acggggaatg ctgctaccgc gacgaaactt   1620
gcgacggcaa gaaacatcaa cggtgttaaa tttgatggtt ctgtggacat ttcgatacca   1680
acaattacgt ccagagggcg tgttactgcg ctcaccggta caacacaagg tgctgctact   1740
ggattgcaaa tgtatgaggc gtacaacaac ggctatcctt ctgcttacgg gaatgtgctt   1800
catcttaagg gcgcaacggc agttggtgaa ggtgagttgt tcataggttg gagcggtaca   1860
agtggcgctc atgcacctgt acatgtacgt tcgcgacgag atactgatac agccagttgg   1920
tcagagtggg cgcaggtcta cacatcgaag gattccatcc ctggtgtaaa taccacgggc   1980
```

```
aaccagaaca caaccggaaa cgcggcgtct gcaacgaaat tacaaacggc aagaactatt    2040
ggtggtgttt catttaatgg caccgcaaac atcgacctgc cgggcgtgaa taaaacaggt    2100
aatcagaaca caaccggtaa tgcagcgaca gcgaccaagt tacaaaccgc tcgaactata    2160 aatgggtct cgtttgatgg ttctaaaaat attgagctaa cggcggaaga tttaaatcta     2220
caggaattta ttaataaagc aaataatgcc gttcagcgtt caggcgatac tttgtccggt    2280
gggcttactt ttaaaaatga ctcaatcctt gcctggattc gaaatactga ctgggcgaag    2340
attggattta aaaatgatgc tgatggtgac actgattcat acatgtggtt tgaaacaggc    2400
gacaacggca tgaatattt caaatggaga agcaaacaaa gcaccacaac aaaagacctg     2460
atgaatctta aatgggatgc tttgtatgtt cttgtcaatg ccattgtaaa tggcgaagtc    2520
atatcaaaat cagcaaacgg cctacgtatt gcttatggta attacggatt ctttattcgt    2580
aatgatggtt cagatacata cttcatgttg accaactccg gtgacaacat ggggacttat    2640
aacggattaa ggccattatg gattaataac gctactggcg ctgtttcgat ggggcgtggc    2700
cttaatgttt caggggagac actttcagac cgttttgcta ttaacagcag tacaggcatg    2760
tggattaata tgcgtgacca gaacgttatt atgggacgta atgcggtatc cactgatggt    2820
gctcaggcct tgctccgtca ggaccatgcc gaccgcaaat ttatgattgg cggtctggga    2880
aataagcaat ttggcatcta catgattaat aactcaagga cagccaatgg caccgatggt    2940
caggcgtaca tggacaataa cggtaactgg ctttgcggtg cgcaaattat tcccggaaat    3000
tatggcaatt ttgactcacg ctatgtgaaa gatgttcgcc tgggtacgcg tgttgttcaa    3060
ttgatggcgc gtggtggtcg ttatgaaaaa gccggacacg caattaccgg attaagaatc    3120
attggtgaag tagatggcga tgatgaagcc atcttcagac caatacaaaa atacatcaat    3180
ggcacatggt ataacgtagc acaggtgtaa                                     3210
```

<210> SEQ ID NO 103
<211> LENGTH: 528
<212> TYPE: DNA
<213> ORGANISM: Artificial Sequence
<220> FEATURE:
<223> OTHER INFORMATION: Orchid Tail Fiber U gene

<400> SEQUENCE: 103

```
atgcagcatt taaaaaatat taagtctgga atcctaaaa cgaaagaaca atatcagcta      60
acaaagaatt ttgatgttat ctggttatgg tccgaagacg gtaaaaactg gtatgaggaa    120
gtaaataact ttcaggacga caccataaag attgtatacg acgaaaataa tattattgtt    180
gccataacca agatgcctc aacgcttaat cccgaaggct ttagtgtcgt tgagattcca     240
gatataacag ccaatcgtcg tgccgatgat tcagggaagt ggatgtttaa ggatggatct    300
gtagttaaac ggatttatac ggcagacgaa cagcaacaac aagccgaatc acaaaaggcc    360
gcattgcttt ccgaagctga atcagtcatc cagccgctgg aacgcgctgt caggttgaat    420
atggcaacag acgaggaacg cacacgactg gaagcatggg aacgctacag tgttctggtc    480
agccgtgtgg atacggcaaa tcctgaatgg ccacaaaagc ctgaataa                 528
```

<210> SEQ ID NO 104
<211> LENGTH: 2016
<212> TYPE: DNA
<213> ORGANISM: Artificial Sequence
<220> FEATURE:
<223> OTHER INFORMATION: Gold Tail Fiber S gene

<400> SEQUENCE: 104

```
atgaatgacg ttacagttgt tacatcggtt acttacccat catccgagtc gttggctctg      60
gtggccgatg tgcaatacca cgaaccatat ctgtcagccg cgctaaaccg aaaattcagg     120
gggattgttg acccgggatt ttatgccggt ttcttaccta agcctggcgg tgggatgaac     180
ctgttaatta cctcagtgga tggtgataaa accgcaggcg cggcgtcggt ggatattggt     240
gaattttacc aggtaactat tcagcaacgt aaggatattt ctcttgcact tagtgcaggc     300
aagaaatatg caattgtgct gaagggaaga tacctccttg gagaagatac ctaccaggtg     360
aataccgcgt cacatattca tgcggctgaa tttgttgcca gaacctatac cgattcatat     420
cagttaggag atggggagct gcttgttttgt acggtgaata tccctgctag tgtatctgcc     480
attacccagg agatgattga tacatccgag cgtatcaacc gctcgatcgg cattgatatt     540
tcagactctg taaccagtac cagaagtgat gttgctgcaa gttcgctggc agttaaaaaa     600
gcctacgatc tggcgaaaag caagtatacg gcacaggatg caaccttgct ggcaaagggt     660
ttcactcaat tgagcaacga cagcaatagc ggtagcgaaa cgctggccgc taccccgaaa     720
gccgtcaaag cggttaacga tgcctcgctg aaaatcgcgg cgaacctgaa agacctgcca     780
aacaagtccg tcgcgcgcgg caacctggag ctgggtactg ccgccacacg caacgtcggc     840
gcgcaaaaaa ccaacctgat ggaggtgggc gcgttcggtt tggggggggg cccgatacat     900
cgcgaagacg ctctgagcaa ccgtggcgaa atctatcggg ttacgggtgc atcgaaaaat     960
gcgccgggcg gcggtgttta tggcgtcttg aacctgccgt gtgacggcgg cccttccagc    1020
ggctatctgg cgatccagcc taatggatca tcttacatcg gcacgtccac gacccctgac    1080
aaaccgctga actggtaccg aatttacact accggcttta aaccgacggc cacagacgtc    1140
gacgcctaca gcaaggcgga agccgacggg aagttcgtca acagagcgg cgataccatt    1200
accggcgctt taacggtcaa tggagcgatt gagagtaaat ccggcctcac tacaccctct    1260
ttagccgtaa atggcagcgt aaccatcgcc ggagcgttga ccacaaaagc cggtgtcgag    1320
ctgttcggta ccaccccccta tctggatttt cattacggca atagcaacgg tgacttcgat    1380
gtcagactca tcaatgacaa caaaggcacc ttagccttt c acggcaatga atattacgtc    1440
aatggcaagc tgagcgcgac gggtgatgcc tggataggcg gaaaggccaa tatcaacggt    1500
atggccgctt tttatagttc tgattttat actaaacaag gaaatcttac tcatcccgac    1560
ggcaatcgcc aaacaaacgg tatgcgtcta caggggcaag gtaatctgct cgtcgatctt    1620
taccactatg agaaggtcgg gagccaccat gagttcggta tccatgttgc caacggcggg    1680
gccgatggct ggttcagctt ccgtaataac ggtgaactcc gcgcgaacgg cacccttattt    1740
gctgcaggtg ccgcttatca aacagacggc aatattaacg gcggcatttg gggaggctat    1800
ttaagcaact atctcaatca aactttgtg cgggatgttc gcctgggtaa tgtggaaagt    1860
atcgctacct ggcgaggccc cggctattcg gatagcgcgg ttatgtcct gaccggcgca    1920
gcaaacaaca acgtggatga atacatcgac gtaattttcc gtcgtccgct gcaaaaacac    1980
attggtggca attgggttac cgtctggagc gtataa                              2016
```

<210> SEQ ID NO 105
<211> LENGTH: 558
<212> TYPE: DNA
<213> ORGANISM: Artificial Sequence
<220> FEATURE:
<223> OTHER INFORMATION: Gold Tail Fiber U gene

<400> SEQUENCE: 105

```
atgatgaata acatgaaaaa ctttaccctc gccgcgccgg aaacggtaga acagaaacag      60
ctggccgcct cgcacggtgt tttgttttta aaatccgatg ccggggaaga ctggtatgaa     120
tgtcaaaaaa gcttccgtcc tgagacggta aaactgatgt atgacaagga cgggatcatt     180
cgttcaatca ccgcgaaacc gaatgccgaa ggccattatg acgtttccgg atttttccca     240
gaaaatatga gtgtggcgga ggtcgaaaac ttgccggaag cgctgatat caacggccgc      300 tggattttg atggagaaaa catcatacca agatcgtatt caactcagga gctacggcaa      360
caggccgcca ataaaaaaca agagttgatt aagcaaagtt cgctgcagat agaaacgctt     420
aacgacgcta ctgacctggg aatggcaagc gaagaggaac tgcggctgct gacccgctgg     480
aaaacctacc gcgtattgct taatcgggtc gatcccgaag cggccccgga tatcgactgg     540
ccgcaaccac cgcaataa                                                   558
```

<210> SEQ ID NO 106
<211> LENGTH: 2760
<212> TYPE: DNA
<213> ORGANISM: Artificial Sequence
<220> FEATURE:
<223> OTHER INFORMATION: Bluetiful Tail Fiber S gene

<400> SEQUENCE: 106

```
atgaatgacg ttacagttgt tacatcggtt acttacccat catccgagtc gttggctctg      60
gtggccgatg tgcaatacca cgaaccatat ctgtcagccg cgctaaaccg aaaattcagg     120
gggattgttg acccgggatt ttatgccggt ttcttaccta agcctggcgg tgggatgaac     180
ctgttaatta cctcagtgga tggtgataaa accgcaggcc cggcgtcggt ggatattggt     240
gaattttacc aggtaactat tcagcaacgt aaggatattt ctcttgcact tagtgcaggc     300
aagaaatatg caattgtgct gaagggaaga tacctccttg gagaagatac ctaccaggtg     360
aataccgcgt cacatattca tgcggctgaa tttgttgcca gaacctatac cgattcatat     420
cagttaggag atggggagct gcttgtttgt acggtgaata tccctgctag tgtatctgcc     480
attacccagg agatgattga tacatccgag cgtatcaacc gctcgatcgg cattgatatt     540
tcagactctg taaccagtac cagaagtgat gttgctgcaa gttcgctggc agttaaaaaa     600
gcctacgatc tggcgaaaag caagtatacg gcacaggatg caagcaccac ggcgaaaggg     660
ctggtgcagc tgagtagcgc gacgaccagc acagacgaaa cgaaagccag cacgcctaag     720
gcgcttaaaa ctgtcagtga tgccagcatg aaaaaggccg ccaatctgtc cgacgtggcc     780
gacaaggccg ccgcgcgtgg caatttagca ctgggtacgg ccgcgacgaa aaacgtcggg     840
gtggatggcg ggcagttgat ggaggtcggc gcctttggat tgggaagcgg ctcacgtcat     900
cgagaggatg cttattgcaa tcaggggaa atctatcggg ttaatggctc atcaaagaat     960
gcaccgggcg gcgatgttta tggcgtgctg agtttacctt gtgacggcgg cccgtcgggt    1020
gcgtatcttg cggtacaaaa cagcggtaac gcattttttg gccgttcaaa tatcgcggaa    1080
aacggtgtga cttggtttca ggcttacacg acgaagttta aaccgactgc ggcagacgtc    1140
ggggcatgga gcaaagcaga agccgatggc cgttttctga tgctttccgg cggcacagta    1200
aaaaaactgg cgattaagcc cggcaacgcg gaaacagagg gtagcacact caatattgag    1260
ggaaatcagc atacgccctt agtgatgagc cgtctctctg ctcaaggaaa tctctctatc    1320
ggattccaag tcgccggaaa ggcgttaatg gccgttggtt ttgggctga tgacgagttg    1380 cattggggga cagaagctaa tcaggcgtcg aatccgcgca tttatacgac ggctaagccg    1440
```

```
cctacagcac aagaaaccgg ggcgttgacg gatgcgcagg ccgtaaagaa atacgcgctg   1500
cgctctatca aagtcaacgg taagccgttg agcggcgatg tcaatctgtt ggcagggat    1560 gtcaacgcat ggaacaaaac cgaagcggat ggccgctatg taaaacagag cggcgacacg   1620
atgaaagggg cattaactct gccgcgtatc gtattcccga acgaaaatac cgccaatgct   1680
gacgatgact taaatcgcga aaatggcttt accgttgagt cattggttgc cactaccaat   1740
aagggctatc ccgtgccggg cggcatgggg gtgttgttta ccgggaaagt gaacgagttc   1800
cgcaatgtgc aatttgccgt aggctccggc gatatggcgt tttatttgcg ctcgatgcga   1860
aaagacaact cggcttcgct ccgctgggcg cgagtttata cgacggacta caaaccgacg   1920
gcggctgacg ttggcgcgct gacggatgcg caagccgcgc agaaatacgc gctgcgctct   1980
atcaaggtga acgtaagcc gctgtccgct gatgtgaatt tgttggccgg tgacgttaac    2040
gcgtggaata agacagaagc ggatggccgc tatttggcta aaaccggcgg caatattacg   2100
ggcggggtat cgtcaagctc ctgggtatct gctgcggcgt tgacatcgga ttatcacggc   2160
accggcgata acacgaataa agccccggaa ggcgccggag cgtacagcaa tcagcttgcc   2220
acgcgcgcgc cttttttacca gactgatttt cagtgggaag caaacagcgg cgcgatttat   2280
gtgccactgg tgaaaggtaa atcgacgcgt aagggcaagg gctggccgac cgcagttagc   2340
tacggctatt tgatgccggg cgagaatatg catgctcatc ccgttattca tgcgcttggt   2400 gatgagtgg aaagtatttg gcagtttaat acccaaactg gcggcattat tagtgggaaa    2460
atgggcgagt cgcgagtca ggcatgggtt aacaatgggt tgaatggtcg ggttgactgg    2520
ccctccttta atcagcatgt gggcgccaga gcgacaattg actgggttaa tcagaacttt   2580
attcaaaatg tcagatacag cgcggaaatg catgtcggcg cgaccgggat ttatacctat   2640
cacgataata ccgtactaac cggtttcaat aacaaagacg gcgattactc tgctgaggaa   2700 ctgtttttgga gctacatcca aatttataaa aatggtcagt ggatcacagt aggacgataa   2760
```

<210> SEQ ID NO 107
<211> LENGTH: 546
<212> TYPE: DNA
<213> ORGANISM: Artificial Sequence
<220> FEATURE:
<223> OTHER INFORMATION: Bluetiful Tail Fiber U gene

<400> SEQUENCE: 107

```
gtgaagaata ttaaaaactt tcagctcggc gagccaaaaa caccggagca attaaaatta     60
cgcaatcagc ataatgccat gttccttttc tctgacgatg gtaaggagtg gtatcactgc    120
cagaaagatt ttgcggccga tacgataaaa gttgcctacg atgaaaaagg tattatccgc    180
agcattgccg ccaacaacga tatttctacg ttgtggcctg tcgggctaag cgtcgcggaa    240
gtggcaaaca caaccgccaa tcgccgggcc gatatttcag gcggttgggt atttgatggg    300
aaagccattg ttaaacgcag ttattcgcct gacgaatatc aggaacaagc gaaaaaggaa    360
caggttgccc gcattgcggc ggtggcgcgg catatcgcgc cattacagga tgctgttgat    420
ttggacatgg cgaccgagga agaaaaagcg ctgttggcgg actggaaaaa ataccgtgtg    480
atgctgaatc gtctggatat gtcgtcggcc ccggatattg actggccagt ggcgcccagt    540
gcctaa                                                              546
```

<210> SEQ ID NO 108
<211> LENGTH: 649
<212> TYPE: PRT
<213> ORGANISM: Artificial Sequence
<220> FEATURE:
<223> OTHER INFORMATION: Rio Tail Fiber (S)

<400> SEQUENCE: 108

```
Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Thr Thr Val Lys Gly Phe Thr Lys Leu
    210                 215                 220

Asn Asn Gln Val Gly Asp Ser Glu Asn Thr Ala Leu Thr Pro Tyr Gly
225                 230                 235                 240

Ala Lys Lys Glu Leu Glu Asn Tyr Gln Pro Lys Gly Asn Tyr Gln Pro
                245                 250                 255

Ala Gly Asn Tyr Val Thr Thr Ala Thr Phe Asn Leu Glu Ile Asn Lys
            260                 265                 270

Lys Ile Asp Lys Ala Ser Leu Ser Gln Gln Leu Gly Asn Asp Val Asn
        275                 280                 285

Lys Val Pro Ser Leu Asp Leu Val Thr Lys Glu Leu Gly Asn Lys Gln
    290                 295                 300

Pro Lys Gly Asp Tyr Ala Leu Lys Thr Trp Val Asp Asn Ile Tyr Tyr
305                 310                 315                 320

Lys Arg Asp Asp Ser Pro Ser Phe Asn Glu Ile Ser Ala Thr Ala Ile
                325                 330                 335

Arg Val Asn Ser Val Asn Val Ala Leu Lys Gly Asp Cys Tyr Thr Lys
            340                 345                 350

Ser Glu Ser Asp Asn Lys Tyr Ser Pro Lys Leu Pro Phe Val Tyr Ser
        355                 360                 365

Ser Gly Glu Glu Ser Lys Ile Ile Ser Pro Asn Asn Lys Ile Leu Ile
    370                 375                 380

Phe Val Asn Asp Asn Gly Thr Thr Gly Gly Tyr Asp Arg Asp Thr Gln
385                 390                 395                 400
```

Ala Thr Val Trp Gly Phe Asp Lys Arg Gly Phe Met Thr Arg Gly Thr
                405                 410                 415

Val His Phe Asp Arg Met Ser Gly Val Tyr Ser Gln Ser Gln Val Asp
            420                 425                 430

Ala Lys Leu Lys Glu Cys Leu Asn Leu Lys Thr Ser Ser Lys Gln Phe
        435                 440                 445

Ile Ala Ser Asp Ile Tyr Ala Pro Thr Phe Ile Thr Gly Ser Gln Tyr
    450                 455                 460

Gly Glu Arg Ser Tyr Leu Glu His Lys Ser Asp Glu Leu Thr Ile Thr
465                 470                 475                 480

His Ile Ser Pro Lys Ser Gly Ala Thr Asn Ile Thr Cys Arg Asn Lys
                485                 490                 495

Ser Gly Thr Leu Ala Leu Leu Gly Asp Leu Glu Asp Val Asn Asn Ile
            500                 505                 510

Pro Val Gly Ser Pro Ile Pro Trp Ser Leu Ala Thr Ala Pro Ser Gly
        515                 520                 525

Tyr Leu Ile Cys Asn Gly Gln Thr Phe Asn Lys Ser Thr Tyr Pro Lys
    530                 535                 540

Leu Ala Val Ala Tyr Pro Ser Gly Lys Leu Pro Asp Leu Arg Gly Glu
545                 550                 555                 560

Phe Ile Arg Gly Leu Asp Ser Gly Arg Gly Ile Asp Ala Gly Arg Ser
                565                 570                 575

Val Leu Ser Val Gln Lys Gly Asn Ser Leu Leu Ser Ser Asn Ile Phe
            580                 585                 590

Gly Gly Leu Ser Ser Glu Ser Asn Lys Trp His Lys Ala Ile Asn
        595                 600                 605

Tyr Ile Gly Ile Thr Gly Thr Asp Asn Asp Gly Tyr Gly Val His
    610                 615                 620

Gln Gln Ile Glu Gly Ala Asn Gly Asn Glu Thr Arg Pro Arg Asn Ile
625                 630                 635                 640

Ala Phe Leu Tyr Ile Val Arg Ala Ala
                645

<210> SEQ ID NO 109
<211> LENGTH: 581
<212> TYPE: PRT
<213> ORGANISM: Artificial Sequence
<220> FEATURE:
<223> OTHER INFORMATION: Limon Tail Fiber (S)

<400> SEQUENCE: 109

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

```
Leu Gly Glu Asp Thr Tyr Gln Val Asn Thr Ala Ser His Ile His Ala
            115                 120                 125

Ala Glu Phe Val Ala Arg Thr Tyr Thr Asp Ser Tyr Gln Leu Gly Asp
        130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Thr Thr Ala Arg Lys Gly Ile Val Gln Leu
    210                 215                 220

Ser Ser Ala Thr Asp Ser Thr Ser Glu Glu Leu Ala Ala Thr Leu Lys
225                 230                 235                 240

Ala Val Lys Ile Ala Met Asp Asn Ala Asn Ala Arg Leu Ala Lys Glu
                245                 250                 255

Arg Asn Gly Gly Asp Val Pro Asn Lys Pro Leu Phe Ile Gln Asn Ile
            260                 265                 270

Gly Leu Gln Glu Thr Val Asn Lys Ala Ala Gly Ala Val Gln Arg Ser
        275                 280                 285

Glu Val Gln Thr Ser Gln Asp Asp Ile Thr Ala Gly Lys Leu Leu Val
    290                 295                 300

Asn Gly Ser Ala Ile Ala Val Arg Gly Ile Arg Ala Ile Asn Gly Gly
305                 310                 315                 320

Gln Val Asp Asp Ala Asn Asn Leu Pro Val Asn Ala Val Ser Phe Val
                325                 330                 335

Tyr Gly Asp Ala Lys Asn Ser Pro Ser Gly Asn Thr Gly Thr Ile Leu
            340                 345                 350

Asp Val Ser Gly Leu Gly Ser Gly Tyr Ser Ile Gln Leu Phe Ala Asn
        355                 360                 365

Tyr Ser Thr Gly Glu Ile Leu Ala Phe Arg Ala Arg Asn Gly Asp Asn
    370                 375                 380

Arg Thr Trp Asn Lys Trp Asn Tyr Val Phe His Thr Gly Asn Lys Pro
385                 390                 395                 400

Thr Ser Thr Asp Val Gly Ala Leu Pro Ile Thr Gly Gly Asp Leu Lys
                405                 410                 415

Gly Gln Leu Ser Phe Ser Phe Ser Gln Pro Arg Asn Gly Ala Asn His
            420                 425                 430

Leu Ile Tyr Asn Gly Asp Asp Asn Gly Val Leu Ala Cys Gly Tyr Gly
        435                 440                 445

Tyr Tyr Gln Asp Arg Phe Asp Ile His Phe Tyr Asp Ile Lys Gly Ala
    450                 455                 460

Trp Glu Ser Asn Pro Leu Thr Ile Gly Arg Asn Gly Asn Thr Thr Val
465                 470                 475                 480

Ser Gly Asn Leu Ser Gly Arg Ala Val Tyr Glu Gly Asn Thr Arg Val
                485                 490                 495

Tyr Ser Pro Asn Asn Pro Gln Pro Val Ser Phe Glu Gly Tyr Ala Thr
            500                 505                 510

Gln Ser Trp Val Leu Gln Asn Phe Val Gln Asn Ile Asp Leu Thr Ala
        515                 520                 525
```

```
Pro Ala Glu Val Gly Phe Arg Asp Gly Trp Gly Tyr Pro Arg Gly Thr
            530                 535                 540

Asp Gly Ala Ala Met Tyr Asn Phe Asn Met Val Gly Gly Ser Ser Asn
545                 550                 555                 560

Val Gly Asn Phe Ile Ile Arg Tyr Met Arg Lys Gln Val Asn Asn Thr
            565                 570                 575

Trp Tyr Val Ile Asn
            580

<210> SEQ ID NO 110
<211> LENGTH: 1069
<212> TYPE: PRT
<213> ORGANISM: Artificial Sequence
<220> FEATURE:
<223> OTHER INFORMATION: Orchid Tail Fiber (S)

<400> SEQUENCE: 110

Met Asn Asp Val Thr Val Val Thr Ser Val Thr Tyr Pro Ser Ser Glu
1               5                   10                  15

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
    50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
    130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Ser Thr Thr Gln Lys Gly Leu Val Gln Leu
    210                 215                 220

Ser Ser Ala Thr Asn Ser Asp Ser Glu Thr Met Ala Ala Thr Pro Lys
225                 230                 235                 240

Ala Val Lys Ser Ile Lys Asp Leu Ala Asp Thr Lys Ala Pro Ile Glu
                245                 250                 255

Ser Pro Ser Leu Thr Gly Thr Pro Thr Ala Pro Thr Ala Ala Gln Gly
            260                 265                 270

Thr Asn Ser Thr Gln Ile Ala Asn Thr Ala Phe Val Lys Ala Ala Ile
        275                 280                 285

Thr Ala Leu Ile Asn Gly Ala Pro Gly Thr Leu Asp Thr Leu Lys Glu
    290                 295                 300
```

```
Ile Ala Ala Ala Ile Asn Asn Asp Pro Asn Tyr Ser Thr Thr Ile Asn
305                 310                 315                 320

Asn Ala Leu Ala Leu Lys Ala Pro Leu Ala Ser Pro Ala Leu Thr Gly
            325                 330                 335

Val Pro Thr Ala Pro Thr Ala Ala Gln Gly Thr Asn Asn Thr Gln Ile
            340                 345                 350

Ala Thr Thr Ala Tyr Val Arg Ala Ala Ile Ser Ala Leu Val Gly Ser
            355                 360                 365

Ser Pro Glu Ala Leu Asp Thr Leu Tyr Glu Leu Ala Ala Leu Gly
370                 375                 380

Asn Asp Pro Asn Phe Ala Thr Thr Met Thr Asn Ala Leu Ala Gly Lys
385                 390                 395                 400

Gln Pro Leu Asp Ala Thr Leu Thr Ala Leu Ala Gly Leu Ala Thr Gly
            405                 410                 415

Ala Asn Lys Leu Pro Tyr Phe Thr Gly Thr Asp Thr Val Ser Gln Thr
            420                 425                 430

Asp Leu Thr Ser Val Gly Arg Asp Ile Leu Ala Lys Thr Ser Ile Leu
            435                 440                 445

Ala Val Ile Gln Tyr Leu Gly Leu Arg Glu Leu Gly Thr Ser Gly Glu
            450                 455                 460

Lys Ile Pro Leu Leu Ser Thr Ala Asn Thr Trp Ser Ala Arg Gln Thr
465                 470                 475                 480

Phe Asn Gly Gly Ile Thr Gly Ala Leu Thr Gly Asn Ala Asp Thr Ala
            485                 490                 495

Thr Lys Leu Lys Thr Ala Ala Arg Ser Ile Gly Gly Val Ala Phe Asp
            500                 505                 510

Gly Ser Ala Asn Ile Asn Leu Pro Gly Val Asn Thr Thr Gly Asn Gln
            515                 520                 525

Asn Thr Thr Gly Asn Ala Ala Thr Ala Thr Lys Leu Ala Thr Ala Arg
            530                 535                 540

Asn Ile Asn Gly Val Lys Phe Asp Gly Ser Val Asp Ile Ser Ile Pro
545                 550                 555                 560

Thr Ile Thr Ser Arg Gly Arg Val Thr Ala Leu Thr Gly Thr Thr Gln
            565                 570                 575

Gly Ala Ala Thr Gly Leu Gln Met Tyr Glu Ala Tyr Asn Asn Gly Tyr
            580                 585                 590

Pro Ser Ala Tyr Gly Asn Val Leu His Leu Lys Gly Ala Thr Ala Val
            595                 600                 605

Gly Glu Gly Glu Leu Phe Ile Gly Trp Ser Gly Thr Ser Gly Ala His
610                 615                 620

Ala Pro Val His Val Arg Ser Arg Arg Asp Thr Asp Thr Ala Ser Trp
625                 630                 635                 640

Ser Glu Trp Ala Gln Val Tyr Thr Ser Lys Asp Ser Ile Pro Gly Val
            645                 650                 655

Asn Thr Thr Gly Asn Gln Asn Thr Thr Gly Asn Ala Ala Ser Ala Thr
            660                 665                 670

Lys Leu Gln Thr Ala Arg Thr Ile Gly Gly Val Ser Phe Asn Gly Thr
            675                 680                 685

Ala Asn Ile Asp Leu Pro Gly Val Asn Lys Thr Gly Asn Gln Asn Thr
            690                 695                 700

Thr Gly Asn Ala Ala Thr Ala Thr Lys Leu Gln Thr Ala Arg Thr Ile
705                 710                 715                 720

Asn Gly Val Ser Phe Asp Gly Ser Lys Asn Ile Glu Leu Thr Ala Glu
```

```
                    725                 730                 735
Asp Leu Asn Leu Gln Glu Phe Ile Asn Lys Ala Asn Ala Val Gln
                740                 745                 750

Arg Ser Gly Asp Thr Leu Ser Gly Gly Leu Thr Phe Lys Asn Asp Ser
            755                 760                 765

Ile Leu Ala Trp Ile Arg Asn Thr Asp Trp Ala Lys Ile Gly Phe Lys
        770                 775                 780

Asn Asp Ala Asp Gly Asp Thr Asp Ser Tyr Met Trp Phe Glu Thr Gly
785                 790                 795                 800

Asp Asn Gly Asn Glu Tyr Phe Lys Trp Arg Ser Lys Gln Ser Thr Thr
                805                 810                 815

Thr Lys Asp Leu Met Asn Leu Lys Trp Asp Ala Leu Tyr Val Leu Val
            820                 825                 830

Asn Ala Ile Val Asn Gly Glu Val Ile Ser Lys Ser Ala Asn Gly Leu
        835                 840                 845

Arg Ile Ala Tyr Gly Asn Tyr Gly Phe Phe Ile Arg Asn Asp Gly Ser
    850                 855                 860

Asp Thr Tyr Phe Met Leu Thr Asn Ser Gly Asp Asn Met Gly Thr Tyr
865                 870                 875                 880

Asn Gly Leu Arg Pro Leu Trp Ile Asn Asn Ala Thr Gly Ala Val Ser
                885                 890                 895

Met Gly Arg Gly Leu Asn Val Ser Gly Glu Thr Leu Ser Asp Arg Phe
            900                 905                 910

Ala Ile Asn Ser Ser Thr Gly Met Trp Ile Asn Met Arg Asp Gln Asn
        915                 920                 925

Val Ile Met Gly Arg Asn Ala Val Ser Thr Asp Gly Ala Gln Ala Leu
    930                 935                 940

Leu Arg Gln Asp His Ala Asp Arg Lys Phe Met Ile Gly Gly Leu Gly
945                 950                 955                 960

Asn Lys Gln Phe Gly Ile Tyr Met Ile Asn Asn Ser Arg Thr Ala Asn
                965                 970                 975

Gly Thr Asp Gly Gln Ala Tyr Met Asp Asn Asn Gly Asn Trp Leu Cys
            980                 985                 990

Gly Ala Gln Ile Ile Pro Gly Asn Tyr Gly Asn Phe Asp Ser Arg Tyr
        995                 1000                1005

Val Lys Asp Val Arg Leu Gly Thr Arg Val Val Gln Leu Met Ala
    1010                1015                1020

Arg Gly Gly Arg Tyr Glu Lys Ala Gly His Ala Ile Thr Gly Leu
    1025                1030                1035

Arg Ile Ile Gly Glu Val Asp Gly Asp Glu Ala Ile Phe Arg
    1040                1045                1050

Pro Ile Gln Lys Tyr Ile Asn Gly Thr Trp Tyr Asn Val Ala Gln
    1055                1060                1065

Val

<210> SEQ ID NO 111
<211> LENGTH: 671
<212> TYPE: PRT
<213> ORGANISM: Artificial Sequence
<220> FEATURE:
<223> OTHER INFORMATION: Gold Tail Fiber (S)

<400> SEQUENCE: 111

Met Asn Asp Val Thr Val Val Thr Ser Val Thr Tyr Pro Ser Ser Glu
1               5                   10                  15
```

-continued

Ser Leu Ala Leu Val Ala Asp Val Gln Tyr His Glu Pro Tyr Leu Ser
            20                  25                  30

Ala Ala Leu Asn Arg Lys Phe Arg Gly Ile Val Asp Pro Gly Phe Tyr
        35                  40                  45

Ala Gly Phe Leu Pro Lys Pro Gly Gly Met Asn Leu Leu Ile Thr
50                  55                  60

Ser Val Asp Gly Asp Lys Thr Ala Gly Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125

Ala Glu Phe Val Ala Arg Thr Tyr Thr Asp Ser Tyr Gln Leu Gly Asp
130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
            180                 185                 190

Ala Ser Ser Leu Ala Val Lys Lys Ala Tyr Asp Leu Ala Lys Ser Lys
        195                 200                 205

Tyr Thr Ala Gln Asp Ala Thr Leu Leu Ala Lys Gly Phe Thr Gln Leu
210                 215                 220

Ser Asn Asp Ser Asn Ser Gly Ser Glu Thr Leu Ala Ala Thr Pro Lys
225                 230                 235                 240

Ala Val Lys Ala Val Asn Asp Ala Ser Leu Lys Ile Ala Ala Asn Leu
                245                 250                 255

Lys Asp Leu Pro Asn Lys Ser Val Ala Arg Gly Asn Leu Glu Leu Gly
            260                 265                 270

Thr Ala Ala Thr Arg Asn Val Gly Ala Gln Lys Thr Asn Leu Met Glu
        275                 280                 285

Val Gly Ala Phe Gly Leu Gly Gly Pro Ile His Arg Glu Asp Ala
290                 295                 300

Leu Ser Asn Arg Gly Glu Ile Tyr Arg Val Thr Gly Ala Ser Lys Asn
305                 310                 315                 320

Ala Pro Gly Gly Gly Val Tyr Gly Val Leu Asn Leu Pro Cys Asp Gly
                325                 330                 335

Gly Pro Ser Ser Gly Tyr Leu Ala Ile Gln Pro Asn Gly Ser Ser Tyr
            340                 345                 350

Ile Gly Thr Ser Thr Thr Pro Asp Lys Pro Leu Asn Trp Tyr Arg Ile
        355                 360                 365

Tyr Thr Thr Gly Phe Lys Pro Thr Ala Thr Asp Val Asp Ala Tyr Ser
370                 375                 380

Lys Ala Glu Ala Asp Gly Lys Phe Val Lys Gln Ser Gly Asp Thr Ile
385                 390                 395                 400

Thr Gly Ala Leu Thr Val Asn Gly Ala Ile Glu Ser Lys Ser Gly Leu
                405                 410                 415

Thr Thr Pro Ser Leu Ala Val Asn Gly Ser Val Thr Ile Ala Gly Ala
            420                 425                 430

-continued

```
Leu Thr Thr Lys Ala Gly Val Glu Leu Phe Gly Thr Pro Tyr Leu
        435                 440                 445

Asp Phe His Tyr Gly Asn Ser Asn Gly Asp Phe Asp Val Arg Leu Ile
450                 455                 460

Asn Asp Asn Lys Gly Thr Leu Ala Phe His Gly Asn Glu Tyr Tyr Val
465                 470                 475                 480

Asn Gly Lys Leu Ser Ala Thr Gly Asp Ala Trp Ile Gly Gly Lys Ala
            485                 490                 495

Asn Ile Asn Gly Met Ala Ala Phe Tyr Ser Ser Asp Phe Ile Thr Lys
                500                 505                 510

Gln Gly Asn Leu Thr His Pro Asp Gly Asn Arg Gln Thr Asn Gly Met
            515                 520                 525

Arg Leu Gln Gly Gln Gly Asn Leu Leu Val Asp Leu Tyr His Tyr Glu
        530                 535                 540

Lys Val Gly Ser His His Glu Phe Gly Ile His Val Ala Asn Gly Gly
545                 550                 555                 560

Ala Asp Gly Trp Phe Ser Phe Arg Asn Asn Gly Glu Leu Arg Ala Asn
                565                 570                 575

Gly Thr Leu Phe Ala Ala Gly Ala Ala Tyr Gln Thr Asp Gly Asn Ile
            580                 585                 590

Asn Gly Gly Ile Trp Gly Gly Tyr Leu Ser Asn Tyr Leu Asn His Asn
        595                 600                 605

Phe Val Arg Asp Val Arg Leu Gly Asn Val Glu Ser Ile Ala Thr Trp
610                 615                 620

Arg Gly Pro Gly Tyr Ser Asp Ser Ala Gly Tyr Val Leu Thr Gly Ala
625                 630                 635                 640

Ala Asn Asn Asn Val Asp Glu Tyr Ile Asp Val Ile Phe Arg Arg Pro
                645                 650                 655

Leu Gln Lys His Ile Gly Gly Asn Trp Val Thr Val Trp Ser Val
            660                 665                 670

<210> SEQ ID NO 112
<211> LENGTH: 919
<212> TYPE: PRT
<213> ORGANISM: Artificial Sequence
<220> FEATURE:
<223> OTHER INFORMATION: Bluetiful Tail Fiber (S)

<400> SEQUENCE: 112

Met Asn Asp Val Thr Val Val Ser Val Thr Tyr Pro Ser Ser Glu
1               5                   10                  15

Ser Leu Ala Leu Val Ala Asp Val Gln Tyr His Glu Pro Tyr Leu Ser
                20                  25                  30

Ala Ala Leu Asn Arg Lys Phe Arg Gly Ile Val Asp Pro Gly Phe Tyr
            35                  40                  45

Ala Gly Phe Leu Pro Lys Pro Gly Gly Met Asn Leu Leu Ile Thr
        50                  55                  60

Ser Val Asp Gly Asp Lys Thr Ala Gly Ala Ala Ser Val Asp Ile Gly
65                  70                  75                  80

Glu Phe Tyr Gln Val Thr Ile Gln Gln Arg Lys Asp Ile Ser Leu Ala
                85                  90                  95

Leu Ser Ala Gly Lys Lys Tyr Ala Ile Val Leu Lys Gly Arg Tyr Leu
            100                 105                 110

Leu Gly Glu Asp Thr Tyr Gln Val Asn Thr Ala Ser His Ile His Ala
        115                 120                 125
```

```
Ala Glu Phe Val Ala Arg Thr Tyr Thr Asp Ser Tyr Gln Leu Gly Asp
            130                 135                 140

Gly Glu Leu Leu Val Cys Thr Val Asn Ile Pro Ala Ser Val Ser Ala
145                 150                 155                 160

Ile Thr Gln Glu Met Ile Asp Thr Ser Glu Arg Ile Asn Arg Ser Ile
                165                 170                 175

Gly Ile Asp Ile Ser Asp Ser Val Thr Ser Thr Arg Ser Asp Val Ala
                180                 185                 190

Ala Ser Ser Leu Ala Val Lys Lys Ala Tyr Asp Leu Ala Lys Ser Lys
            195                 200                 205

Tyr Thr Ala Gln Asp Ala Ser Thr Thr Ala Lys Gly Leu Val Gln Leu
    210                 215                 220

Ser Ser Ala Thr Thr Ser Thr Asp Glu Thr Lys Ala Ser Thr Pro Lys
225                 230                 235                 240

Ala Leu Lys Thr Val Ser Asp Ala Ser Met Lys Lys Ala Ala Asn Leu
                245                 250                 255

Ser Asp Val Ala Asp Lys Ala Ala Arg Gly Asn Leu Ala Leu Gly
            260                 265                 270

Thr Ala Ala Thr Lys Asn Val Gly Val Asp Gly Gly Gln Leu Met Glu
    275                 280                 285

Val Gly Ala Phe Gly Leu Gly Ser Gly Ser Arg His Arg Glu Asp Ala
290                 295                 300

Tyr Cys Asn Gln Gly Glu Ile Tyr Arg Val Asn Gly Ser Ser Lys Asn
305                 310                 315                 320

Ala Pro Gly Gly Asp Val Tyr Gly Val Leu Ser Leu Pro Cys Asp Gly
                325                 330                 335

Gly Pro Ser Gly Ala Tyr Leu Ala Val Gln Asn Ser Gly Asn Ala Phe
            340                 345                 350

Phe Gly Arg Ser Asn Ile Ala Glu Asn Gly Val Thr Trp Phe Gln Ala
            355                 360                 365

Tyr Thr Thr Lys Phe Lys Pro Thr Ala Ala Asp Val Gly Ala Trp Ser
    370                 375                 380

Lys Ala Glu Ala Asp Gly Arg Phe Leu Met Leu Ser Gly Gly Thr Val
385                 390                 395                 400

Lys Lys Leu Ala Ile Lys Pro Gly Asn Ala Glu Thr Glu Gly Ser Thr
                405                 410                 415

Leu Asn Ile Glu Gly Asn Gln His Thr Pro Leu Val Met Ser Arg Leu
                420                 425                 430

Ser Ala Gln Gly Asn Leu Ser Ile Gly Phe Gln Val Ala Gly Lys Ala
            435                 440                 445

Leu Met Arg Leu Gly Phe Gly Ala Asp Asp Glu Leu His Trp Gly Thr
    450                 455                 460

Glu Ala Asn Gln Ala Ser Asn Pro Arg Ile Tyr Thr Thr Ala Lys Pro
465                 470                 475                 480

Pro Thr Ala Gln Glu Thr Gly Ala Leu Thr Asp Ala Gln Ala Val Lys
                485                 490                 495

Lys Tyr Ala Leu Arg Ser Ile Lys Val Asn Gly Lys Pro Leu Ser Gly
                500                 505                 510

Asp Val Asn Leu Leu Ala Gly Asp Val Asn Ala Trp Asn Lys Thr Glu
            515                 520                 525

Ala Asp Gly Arg Tyr Val Lys Gln Ser Gly Asp Thr Met Lys Gly Ala
    530                 535                 540

Leu Thr Leu Pro Arg Ile Val Phe Pro Asn Glu Asn Thr Ala Asn Ala
```

```
            545                 550                 555                 560
Asp Asp Asp Leu Asn Arg Glu Asn Gly Phe Thr Val Glu Ser Leu Val
                565                 570                 575
Ala Thr Thr Asn Lys Gly Tyr Pro Val Pro Gly Gly Met Gly Val Leu
                580                 585                 590
Phe Thr Gly Lys Val Asn Glu Phe Arg Asn Val Gln Phe Ala Val Gly
                595                 600                 605
Ser Gly Asp Met Ala Phe Tyr Leu Arg Ser Met Arg Lys Asp Asn Ser
            610                 615                 620
Ala Ser Leu Arg Trp Ala Arg Val Tyr Thr Thr Asp Tyr Lys Pro Thr
625                 630                 635                 640
Ala Ala Asp Val Gly Ala Leu Thr Asp Ala Gln Ala Ala Gln Lys Tyr
                645                 650                 655
Ala Leu Arg Ser Ile Lys Val Asn Gly Lys Pro Leu Ser Ala Asp Val
                660                 665                 670
Asn Leu Leu Ala Gly Asp Val Asn Ala Trp Asn Lys Thr Glu Ala Asp
            675                 680                 685
Gly Arg Tyr Leu Ala Lys Thr Gly Gly Asn Ile Thr Gly Gly Val Ser
            690                 695                 700
Ser Ser Ser Trp Val Ser Ala Ala Leu Thr Ser Asp Tyr His Gly
705                 710                 715                 720
Thr Gly Asp Asn Thr Asn Lys Ala Pro Glu Gly Ala Gly Ala Tyr Ser
                725                 730                 735
Asn Gln Leu Ala Thr Arg Ala Pro Phe Tyr Gln Thr Asp Phe Gln Trp
            740                 745                 750
Glu Ala Asn Ser Gly Ala Ile Tyr Val Pro Leu Val Lys Gly Lys Ser
            755                 760                 765
Thr Arg Lys Gly Lys Gly Trp Pro Thr Ala Val Ser Tyr Gly Tyr Leu
            770                 775                 780
Met Pro Gly Glu Asn Met His Ala His Pro Val Ile His Ala Leu Gly
785                 790                 795                 800
Asp Gly Val Glu Ser Ile Trp Gln Phe Asn Thr Gln Thr Gly Gly Ile
                805                 810                 815
Ile Ser Gly Lys Met Gly Glu Phe Ala Ser Gln Ala Trp Val Asn Asn
                820                 825                 830
Gly Leu Asn Gly Arg Val Asp Trp Pro Ser Phe Asn Gln His Val Gly
            835                 840                 845
Ala Arg Ala Thr Ile Asp Trp Val Asn Gln Asn Phe Ile Gln Asn Val
850                 855                 860
Arg Tyr Ser Ala Glu Met His Val Gly Ala Thr Gly Ile Tyr Thr Tyr
865                 870                 875                 880
His Asp Asn Thr Val Leu Thr Gly Phe Asn Asn Lys Asp Gly Asp Tyr
                885                 890                 895
Ser Ala Glu Glu Leu Phe Trp Ser Tyr Ile Gln Ile Tyr Lys Asn Gly
                900                 905                 910
Gln Trp Ile Thr Val Gly Arg
            915

<210> SEQ ID NO 113
<211> LENGTH: 206
<212> TYPE: PRT
<213> ORGANISM: Artificial Sequence
<220> FEATURE:
<223> OTHER INFORMATION: Rio Chaperone (U)
```

-continued

<400> SEQUENCE: 113

Met Ser Lys Tyr Ser Leu Asp Ile Gln Lys Gly Lys Ile Gly Asp Asn
1               5                   10                  15

Gly Leu Ala Glu Ile Ala Gly Trp Val Lys Cys Tyr Leu Ala His Pro
            20                  25                  30

Ile Thr His Glu Tyr Met Gly Ala Thr Met Glu Asn Val Met Phe Asp
        35                  40                  45

Val Ser Leu Ser Ala Gly Ala Tyr Leu Asp Glu Pro Pro Leu Pro Gln
    50                  55                  60

Lys Glu Asn Gln Ala Val Arg Arg Glu Asp Gly Ser Ala Trp Glu
65                  70                  75                  80

Ile Val Asp Asp Cys Arg Gly Leu Thr Ala Tyr Asn Thr Gln Thr Lys
                85                  90                  95

Gln Pro Ile Ile Ile Asp Phe Met Gly Pro Leu Pro Glu Ser Leu Thr
            100                 105                 110

Leu Leu Lys Pro Asn Ser Glu Phe Asp Lys Trp Asp Gly Lys Asn Trp
        115                 120                 125

Ile Val Asp Thr Glu Ala Gln Lys Ala Ala Leu Ile Thr Gln Ile Lys
130                 135                 140

Gln Glu Lys Ser Arg Arg Leu Asp Glu Ala Asp Asn Ile Ile Thr Tyr
145                 150                 155                 160

Leu Gln Glu Ala Val Asp Val Asp Leu Ala Thr Glu Glu Ala Thr
                165                 170                 175

Ala Leu Gln Lys Trp Lys Lys Tyr Arg Val Leu Leu Asn Arg Val Asp
            180                 185                 190

Ile Ser Thr Ala Pro Asp Ile Glu Trp Pro Glu Lys Pro Gln
        195                 200                 205

<210> SEQ ID NO 114
<211> LENGTH: 177
<212> TYPE: PRT
<213> ORGANISM: Artificial Sequence
<220> FEATURE:
<223> OTHER INFORMATION: Limon Chaperone (U)

<400> SEQUENCE: 114

Met Gln Arg Phe Gly Lys Phe Thr Pro Tyr Thr Pro Asp Thr Thr Asp
1               5                   10                  15

Arg Pro Arg Ile Ile Asp Gly Gln Asn Val Met Phe Leu Gln Asp Asp
            20                  25                  30

Lys Gly Asn Asp Trp Tyr Asp Val Ile Glu Leu Phe Asp Glu Ser Lys
        35                  40                  45

Thr Leu Lys Ile Gly Tyr Asp Asp Asp Gly Arg Val Arg Thr Phe Thr
    50                  55                  60

Thr Asn Ile His Ala Leu Phe Pro Val Asn Leu Ser Val Val Glu Leu
65                  70                  75                  80

Pro Ala Thr Lys Ala Asn Leu Arg Val Thr Leu Gly Asp Asp Trp Phe
                85                  90                  95

Tyr Lys Asp Gly Lys Leu Gln Gln Ile Arg Asn Tyr Leu Ala Asp Ala
            100                 105                 110

Glu Ala Glu Arg Gly Asn Arg Met Ala Glu Val Thr Thr Arg Ile Asp
        115                 120                 125

Trp Leu Glu Asp Ala Gln Lys Asp Gly Asp Ile Ser Ser Tyr Glu Glu
    130                 135                 140

Thr Glu Leu Ala Thr Leu Arg Ala Tyr Arg Thr Ala Leu Arg Arg Leu

```
                145                 150                 155                 160
Asp Leu Ser Thr Ala Pro Asp Ile Asn Trp Pro Glu Val Pro Asp Val
                165                 170                 175

Ala

<210> SEQ ID NO 115
<211> LENGTH: 175
<212> TYPE: PRT
<213> ORGANISM: Artificial Sequence
<220> FEATURE:
<223> OTHER INFORMATION: Orchid Chaperone (U)

<400> SEQUENCE: 115

Met Gln His Leu Lys Asn Ile Lys Ser Gly Asn Pro Lys Thr Lys Glu
1               5                   10                  15

Gln Tyr Gln Leu Thr Lys Asn Phe Asp Val Ile Trp Leu Trp Ser Glu
                20                  25                  30

Asp Gly Lys Asn Trp Tyr Glu Glu Val Asn Asn Phe Gln Asp Asp Thr
            35                  40                  45

Ile Lys Ile Val Tyr Asp Glu Asn Asn Ile Ile Val Ala Ile Thr Lys
        50                  55                  60

Asp Ala Ser Thr Leu Asn Pro Glu Gly Phe Ser Val Val Glu Ile Pro
65                  70                  75                  80

Asp Ile Thr Ala Asn Arg Arg Ala Asp Ser Gly Lys Trp Met Phe
                85                  90                  95

Lys Asp Gly Ser Val Val Lys Arg Ile Tyr Thr Ala Asp Glu Gln Gln
                100                 105                 110

Gln Gln Ala Glu Ser Gln Lys Ala Ala Leu Leu Ser Glu Ala Glu Ser
            115                 120                 125

Val Ile Gln Pro Leu Glu Arg Ala Val Arg Leu Asn Met Ala Thr Asp
        130                 135                 140

Glu Glu Arg Thr Arg Leu Glu Ala Trp Glu Arg Tyr Ser Val Leu Val
145                 150                 155                 160

Ser Arg Val Asp Thr Ala Asn Pro Glu Trp Pro Gln Lys Pro Glu
                165                 170                 175

<210> SEQ ID NO 116
<211> LENGTH: 185
<212> TYPE: PRT
<213> ORGANISM: Artificial Sequence
<220> FEATURE:
<223> OTHER INFORMATION: Gold Chaperone (U)

<400> SEQUENCE: 116

Met Met Asn Asn Met Lys Asn Phe Thr Leu Ala Ala Pro Glu Thr Val
1               5                   10                  15

Glu Gln Lys Gln Leu Ala Ala Ser His Gly Val Leu Phe Leu Lys Ser
                20                  25                  30

Asp Ala Gly Glu Asp Trp Tyr Glu Cys Gln Lys Ser Phe Arg Pro Glu
            35                  40                  45

Thr Val Lys Leu Met Tyr Asp Lys Asp Gly Ile Ile Arg Ser Ile Thr
        50                  55                  60

Ala Lys Pro Asn Ala Glu Gly His Tyr Asp Val Ser Gly Phe Phe Pro
65                  70                  75                  80

Glu Asn Met Ser Val Ala Glu Val Glu Asn Leu Pro Glu Gly Ala Asp
                85                  90                  95

Ile Asn Gly Arg Trp Ile Phe Asp Gly Glu Asn Ile Ile Pro Arg Ser
```

```
                    100                 105                 110
Tyr Ser Thr Gln Glu Leu Arg Gln Gln Ala Ala Asn Lys Lys Gln Glu
        115                 120                 125

Leu Ile Lys Gln Ser Ser Leu Gln Ile Glu Thr Leu Asn Asp Ala Thr
    130                 135                 140

Asp Leu Gly Met Ala Ser Glu Glu Glu Leu Arg Leu Leu Thr Arg Trp
145                 150                 155                 160

Lys Thr Tyr Arg Val Leu Leu Asn Arg Val Asp Pro Glu Ala Ala Pro
                165                 170                 175

Asp Ile Asp Trp Pro Gln Pro Pro Gln
            180                 185

<210> SEQ ID NO 117
<211> LENGTH: 181
<212> TYPE: PRT
<213> ORGANISM: Artificial Sequence
<220> FEATURE:
<223> OTHER INFORMATION: Bluetiful Chaperone (U)

<400> SEQUENCE: 117

Val Lys Asn Ile Lys Asn Phe Gln Leu Gly Glu Pro Lys Thr Pro Glu
1               5                   10                  15

Gln Leu Lys Leu Arg Asn Gln His Asn Ala Met Phe Leu Phe Ser Asp
            20                  25                  30

Asp Gly Lys Glu Trp Tyr His Cys Gln Lys Asp Phe Ala Ala Asp Thr
        35                  40                  45

Ile Lys Val Ala Tyr Asp Glu Lys Gly Ile Ile Arg Ser Ile Ala Ala
    50                  55                  60

Asn Asn Asp Ile Ser Thr Leu Trp Pro Val Gly Leu Ser Val Ala Glu
65                  70                  75                  80

Val Ala Asn Thr Thr Ala Asn Arg Arg Ala Asp Ile Ser Gly Gly Trp
                85                  90                  95

Val Phe Asp Gly Lys Ala Ile Val Lys Arg Ser Tyr Ser Pro Asp Glu
            100                 105                 110

Tyr Gln Glu Gln Ala Lys Lys Glu Gln Val Ala Arg Ile Ala Ala Val
        115                 120                 125

Ala Arg His Ile Ala Pro Leu Gln Asp Ala Val Asp Leu Asp Met Ala
    130                 135                 140

Thr Glu Glu Glu Lys Ala Leu Leu Ala Asp Trp Lys Lys Tyr Arg Val
145                 150                 155                 160

Met Leu Asn Arg Leu Asp Met Ser Ser Ala Pro Asp Ile Asp Trp Pro
                165                 170                 175

Val Ala Pro Ser Ala
            180
```

NON-REPLICATIVE TRANSDUCTION PARTICLES WITH ONE OR MORE NON-NATIVE TAIL FIBERS AND TRANSDUCTION PARTICLE-BASED REPORTER SYSTEMS

CROSS REFERENCE TO RELATED APPLICATIONS

This application claims the benefit of priority to U.S. Provisional Patent Application No. 62/787,151, filed on Dec. 31, 2018, and to U.S. Provisional Patent Application No. 62/926,989 filed on Oct. 28, 2019, each of which is hereby incorporated in its entirety by reference.

REFERENCE TO SEQUENCE LISTING

This application contains a Sequence Listing submitted as an electronic text file named "34922 US2.txt", having a size in bytes of 515 kb, and created on Nov. 27, 2019.

BACKGROUND OF THE INVENTION

Field of the Invention

The invention relates to methods and compositions for packaging and delivery of non-replicative transduction particles derived from bacteriophages with non-native tail fibers that contain reporter molecules for detecting target organisms.

Description of the Related Art

A transduction particle refers to a virus capable of delivering a non-viral nucleic acid into a cell. Viral-based reporter systems have been used to detect the presence of cells and rely on the lysogenic phase of the virus to allow expression of a reporter molecule from the cell. These viral-based reporter systems use replication-competent transduction particles that express reporter molecules and cause a target cell to emit a detectable signal.

However, the lytic cycle of the virus has been shown to be deleterious to viral-based reporter assays. Carrière, C. et al., *Conditionally replicating luciferase reporter phages: Improved sensitivity for rapid detection and assessment of drug susceptibility of Mycobacterium tuberculosis*. Journal of Clinical Microbiology, 1997. 35(12): p. 3232-3239. Carrière et al. developed *M. tuberculosis*/bacillus Calmette-Guérin (BCG) luciferase reporter phages that have their lytic cycles suppressed at 30° C., but active at 37° C. Using this system, Carrière et al. have demonstrated the detection of BCG using phage reporters with a suppressed lytic cycle.

There are disadvantages, however, associated with suppressing but not eliminating the replication functions of the bacteriophage in bacteriophage-based reporter assays. First, controlling replication functions of the bacteriophage imposes limiting assay conditions. For example, the lytic cycle of the reporter phage phAE40 used by Carrière et al. was repressed when the phage was used to infect cells at the non-permissive temperature of 30° C. This temperature requirement imposed limiting conditions on the reporter assay in that the optimum temperature for the target bacteria was 37° C. These limiting conditions hinder optimum assay performance.

Moreover, the replication functions of the virus are difficult to control. The replication of the virus should be suppressed during the use of the transduction particles as a reporter system. For example, the lytic activity of the reporter phage phAE40 reported by Carrière et al. was reduced but was not eliminated, resulting in a drop in luciferase signal in the assay. Carrière et al. highlighted possible causes for the resulting drop in reporter signal, such as intact phage-expressed genes and temperature limitations of the assay, all stemming from the fact that the lytic cycle of the phage reporter was not eliminated.

Reporter assays relying on the natural lysogenic cycle of phages can be expected to exhibit lytic activity sporadically. In addition, assays that rely on the lysogenic cycle of the phage can be prone to superinfection immunity from target cells already lysogenized with a similar phage, as well as naturally occurring host restriction systems that target incoming virus nucleic acid, thus limiting the host range of these reporter phages.

In other examples, transduction particle production systems are designed to package exogenous nucleic acid molecules, but the transduction particle often contains a combination of exogenous nucleic acid molecules and native progeny virus nucleic acid molecules. The native virus can exhibit lytic activity that is a hindrance to assay performance, and the lytic activity of the virus must be eliminated to purify transduction particles. However, this purification is generally not possible. In U.S. 2009/0155768 A, entitled Reporter Plasmid Packaging System for Detection of Bacteria, Scholl et al. describes the development of such a transduction particle system. The product of the system is a combination of reporter transduction particles and native bacteriophage (FIG. 8 in the reference). Although the authors indicate that the transduction particle and native bacteriophage can be separated by ultracentrifugation, this separation is only possible in a system where the transduction particle and the native virus exhibit different densities that would allow separation by ultracentrifugation. While this characteristic is exhibited by the bacteriophage T7-based packaging system described in the reference, this is not a characteristic that is generally applicable for other virus systems. It is common for viral packaging machinery to exhibit headful packaging that would result in native virus and transduction particles to exhibit indistinguishable densities that cannot be separated by ultracentrifugation. Virus packaging systems also rely on a minimum amount of packaging as a requirement for proper virus structural assembly that results in native virus and transduction particles with indistinguishable densities.

Recently, methods and systems for packaging reporter nucleic acid molecules into non-replicative transduction particles (NRTPs), also referred herein as Smarticles, have been described in U.S. Pat. No. 9,388,453 and in U.S. Patent Application Publication No. 2017/0166907 (both of which are incorporated herein by reference in their entireties) in which the production of replication-competent native progeny virus nucleic acid molecules were greatly reduced due to the disruption of the packaging initiation site in the bacteriophage genome Currently NRTPs are produced from naturally occurring lysogenic bacteriophages found in nature, e.g. φ80α bacteriophage or P1 bacteriophage. It is a time consuming process to find, characterize, and modify new bacteriophages into NRTPs that are able to transduce cells with the desired host range specificity.

Several recent studies (Ando et al., Cell Systems 2015, 1: 187-196; Yosef et al., Molecular Cell 2017, 66: 721-728) have shown that T3 and T7 bacteriophages and bacteriophage/transduction particle mixtures can be re-programmed to recognize desired hosts by swapping tail/tail fibers from T3/T7-like viral sources that would enable the phage to recognize different hosts. To this end, different tail/tail fibers were constructed on the T3/T7 chassis and tested for their ability to inject DNA into different hosts. While these experiments paved the way for producing hybrid particles with novel host ranges, these effects were shown only with phages/tail/tail fibers found in T3- and T7-like bacteriophages. Particularly, these studies do not enable a phage-genome engineering platform that is based on the chassis from other bacteriophage families, such as the Myroviridae family which, unlike the T3/T7 bacteriophages, have long and contractile tails and involve completely different tail fiber genes.

One of the most well characterized Myoviridae phage is the P1 bacteriophage that infects *Escherichia coli* (*E. coli*) and other bacteria in the Enterobacteriaceae family. Host-range specificity of P1 is controlled within the tail-fiber operon that is approximately 6 kb in length (FIG. 2) and includes an invertible C-segment region where either of two alternate 3' ends of the tail fiber gene ($s_v$ or $s_v'$) can be fused to a constant 5' end ($s_c$) located outside of the invertible region. Two alternate genes u and u' are located outside of the S gene and encode alternate forms of a chaperone protein that is involved in tail fiber assembly. Two other genes in the tail-fiber operon are the r gene, whose gene product R is believed to be involved in tail fiber assembly and the gene cin which encodes a sequence specific recombinase enzyme which can "flip" the nucleic acid between the Cin recombination sites, known as cix sites, that modifies host specificity, and are described in Guidolin et al., 1989 Gene, 76: 239-243, and in Sandmeier et al., 1992, Journal of Bacteriology, 174(12): 3936-3944, both incorporated by reference herein in their entireties.

Accordingly, there is a need in the art for a quick, reliable, and scalable method to generate new NRTPs derived from the tail fibers of many types of phages. Therefore, the present invention relates to a tail fiber replacement platform (or chassis) derived from P1 bacteriophage that can be altered in only the tail fibers in order to change or extend their host specificity, and that this platform can utilize tail fibers from many viral families. Additionally, the present invention relates to methods to improve the yield of NRTPs from an engineered production line and methods of producing multiple natural or engineered tail fibers-endowed NRTPs in a single fermentation. This approach can be used for other diverse bacteriophages to develop new NRTPs with desired inclusivity and exclusivity profiles with respect to host-range specificities.

SUMMARY OF THE INVENTION

The present invention contemplates a bacteriophage lysogen genetically disrupted to the expression of one or more factors critical to native tail fiber production (examples—genes s, u, u', r and s'). This could be accomplished through any mutagenesis approach known to one skilled in the art, or through isolation of a tail fiber deficient phage remnant from natural sources. This genetically disrupted phage lysogen that lacks the ability to express functional tail fibers of its own without complementation is referred as a chassis or a "Bald" chassis. In one embodiment, the disrupted lysogen has a mutation or a deletion in one or more of the genes selected from a gene that encodes a tail fiber structural protein responsible for binding a bacteria cell receptor, a gene that encodes a chaperone protein needed for folding of one or more regions of a tail fiber structural protein, a gene that encodes a protein required for attaching the tail fiber structural protein to a tail, or any combination of these genes In another embodiment, the disrupted lysogen contains a gene coding for a selectable marker that disrupts the expression of one or more of the genesr. In yet another embodiment, the disrupted lysogen comprises a nucleotide sequence of SEQ ID NO: 97.

One aspect of the invention relates to methods involving the expression of native, new tail fiber genes, or hybrid tail fibers in a lysogen genetically disrupted for native tail fiber expression. This could be accomplished using a packaging plasmid, secondary expression plasmid, genomic expression (phage lysogen or bacterial genome), or any other method known to one skilled in the art.

Therefore, the present invention relates to a bacteriophage tail fiber replacement platform comprising a bacteriophage lysogen from the family Myoviridae (Myoviridae lysogen) that contains a genetic disruption that prevents the expression of one or more genes that are critical for the production of tail fibers native to the Myoviridae lysogen, wherein said one or more genes are selected from a gene that encodes a tail fiber structural protein responsible for binding a bacteria cell receptor, a gene that encodes a chaperone protein needed for folding of one or more regions of a tail fiber structural protein, a gene that encodes a protein required for attaching the tail fiber structural protein to a tail, or any combination of these genes; and a complementary nucleic acid molecule comprising one or more genes selected from a gene that encodes a tail fiber structural protein responsible for binding a bacteria cell receptor, a gene that encodes a chaperone protein needed for folding of one or more regions of a tail fiber structural protein, a gene that encodes a protein required for attaching the tail fiber structural protein to a tail, or any combination of these genes wherein the complementary nucleic acid complements the genetic disruption of the Myoviridae lysogen whereby functional tail fibers are produced.

In one embodiment, the Myoviridae lysogen is derived from a genus selected from: Bcep781 likevirus, Bcepmulikevirus, FelixO11likevirus, Hapunalikevirus, I3likevirus, Mulikevirus, Punalikevirus, Pbunalikevirus, PhiCD119likevirus, Phihlikevirus, Phikzlikevirus, Viunalikevirus, Eucampyvirinae, Cp220likevirus, Cp8unalikevirus, Peduovirinae, Hpunalikevirus, P2likevirus, Spounavirinae, Spounalikevirus, Twortlikevirus, Tevenvirinae, Schizot4likevirus, or T4likevirus. In one embodiment, the Myoviridae lysogen is from the Punalikevirus genus. In another embodiment, the Myoviridae lysogen is Enterobacteria bacteriophage phage P1 (P1 bacteriophage).

In one embodiment, the one or more genes or the combination of genes on the complementary nucleic acid molecule contain regions that are not derived from the one or more genes that are critical for the production of tail fibers native to the Myoviridae lysogen such that the functional tail fibers that are produced are not native tail fibers. In another embodiment, the one or more genes or the combination of genes contain regions that are not derived from P1 bacteriophage such that the functional tail fibers that are produced are not native P1 bacteriophage tail fibers.

In yet another embodiment, the genetic disruption on the Myoviridae lysogen comprises one or more mutation in any of the one or more genes. In one embodiment, the one or more mutation is in any one of the P1 bacteriophage genes s, s', u, u' and r, in any combination of genes s, s', u, u' and r, or homologs, orthologs, or analogs of genes s, s', u, u' and r.

In one embodiment, the genetic disruption on the Myoviridae lysogen comprises one or more deletion in any one of the one or more genes. In one embodiment, the one or more deletion is in any one of the P1 bacteriophage genes s, s', u, u' and r, in any combination of genes s, s', u, u' and r, or homologs, orthologs, or analogs of genes s, s', u, u' and r. In another embodiment, the genetic disruption on the Myoviridae lysogen further comprises the insertion of a gene coding for a selectable marker that disrupts the expression of any one of the P1 bacteriophage genes. In one embodiment, the Myoviridae lysogen comprises a nucleic acid sequence of SEQ ID NO: 97.

In one embodiment, the complementary nucleic acid molecule is contained in a plasmid molecule. In another embodiment, the complementary nucleic acid molecule is integrated into the Myoviridae lysogen at the site of the genetic disruption. In yet another embodiment, the complementary nucleic acid molecule is integrated into the Myoviridae lysogen at a site other than the site of the genetic disruption. In yet another embodiment, the complementary nucleic acid molecule is integrated into a genome of a host bacteria cell that contains the Myoviridae lysogen.

In one embodiment, the Myoviridae lysogen contains a further disruption in one or more packaging genes that are involved in packaging the genome of the Myoviridae lysogen. In one embodiment, one or more packaging genes that complement the disruption in the one or more packaging genes in the Myoviridae lysogen are contained a plasmid molecule that also contains the complementary nucleic acid molecule. In another embodiment, one or more packaging genes that complement the disruption in the one or more packaging genes in the Myoviridae lysogen are contained in a reporter or therapeutic expression plasmid that is different from the plasmid molecule that contains the complementary nucleic acid molecule.

The present invention also relates to a bacterial cell line comprising a P1 bacteriophage lysogen that comprises a nucleic acid sequence of SEQ ID NO: 97.

The present invention further relates to a method for producing bacteriophage particles or non-replicating transduction particles (NRTPs) with non-native tail fibers comprising, providing a bacteria cell containing the bacteriophage tail fiber replacement platform of the present invention, wherein the complementary nucleic acid molecule comprises a gene that encodes a tail fiber structural protein with one or more regions that are not derived from the one or more genes that are critical for the production of tail fibers native to the Myoviridae lysogen, and providing conditions to the bacterial cell that induces a lytic phase of the Myoviridae lysogen to produce bacteriophage particles with non-native tail fibers.

In one embodiment, the one or more regions that are not derived from the one or more genes native to the Myoviridae lysogen comprises a variable region of the tail fiber structural protein (tail fiber variable region) obtained from bacteriophages within the order Caudovirales. In one embodiment, the tail fiber variable region is obtained from bacteriophages within the family Myoviridae. In another embodiment, the tail fiber variable region is obtained from bacteriophages within a genus selected from: Bcep781likevirus, Bcepmulikevirus, FelixO1likevirus, Hapunalikevirus, I3likevirus, Mulikevirus, Punalikevirus, Pbunalikevirus, PhiCD119likevirus, Phihlikevirus, Phikzlikevirus, Viunalikevirus, Eucampyvirinae, Cp220likevirus, Cp8unalikevirus, Peduovirinae, Hpunalikevirus, P2likevirus, Spounavirinae, Spounalikevirus, Twortlikevirus, Tevenvirinae, Schizot4likevirus, or T4likevirus. In one embodiment, the genus is Punalikevirus.

In one embodiment, the complementary nucleic acid molecule further comprises a gene that encodes a chaperone protein. In one embodiment, the gene that encodes the chaperone protein is obtained from bacteriophages within the order Caudovirales. In another embodiment, the gene that encodes the chaperone protein is obtained from bacteriophages within the family Myoviridae. In yet another embodiment, the gene that encodes the chaperone protein is obtained from bacteriophages from a genus selected from: Bcep781likevirus, Bcepmulikevirus, FelixO1likevirus, Hapunalikevirus, I3likevirus, Mulikevirus, Punalikevirus, Pbunalikevirus, PhiCD119likevirus, Phihlikevirus, Phikzlikevirus, Viunalikevirus, Eucampyvirinae, Cp220likevirus, Cp8unalikevirus, Peduovirinae, Hpunalikevirus, P2likevirus, Spounavirinae, Spounalikevirus, Twortlikevirus, Tevenvirinae, Schizot4likevirus, or T4likevirus. In one embodiment, the genus is Punalikevirus.

In one embodiment, the chaperone protein is obtained from bacterial genomes encoding non-replicative virus derived structures or from nucleic acid delivery particles. In one embodiment, the gene that encodes the chaperone protein comprises an amino acid sequence selected from the group consisting of SEQ ID Nos: 67-96 and 113-117.

In one embodiment, the one or more regions that are not derived from the one or more genes native to the Myoviridae lysogen comprises a variable region of the tail fiber structural protein (tail fiber variable region) obtained from bacterial genomes encoding phage tail-like particles or structures or from nucleic acid delivery particles. In one embodiment, the gene that encodes the tail fiber structural protein comprises of an amino acid sequence selected from the group consisting of SEQ ID Nos: 35-66, and 108-112. In another embodiment, the gene that encodes the tail fiber structural protein comprises a nucleotide sequence selected from the group consisting of SEQ ID Nos: 1-34, 98, 100, 102, 104 and 106.

In another aspect, the present invention contemplates expressing chimeric tail fiber genes that generate a bacteriophage and/or a NRTP displaying a host-range specificity and/or reactivity that differs from the host-range specificity and/or reactivity of the native bacteriophage chassis. Therefore, the present invention relates to a method of generating an engineered bacteriophage or a NRTP that displays a bacteria host cell specificity that differs from the bacteria host cell specificity displayed by a native bacteriophage comprising, fusing a first nucleotide sequence from one tail fiber structural protein encoding gene with a second nucleotide sequence from a second tail fiber structural protein encoding gene from a different source to generate a chimeric tail fiber structural protein encoding gene; and expressing the chimeric tail fiber structural protein gene in a bacteria cell that contains the bacteriophage tail fiber replacement platform of the present invention; and providing conditions to the bacteria cell that induces a lytic phase of the Myoviridae lysogen to generate the engineered bacteriophage or NRTP.

In one embodiment, the first nucleotide sequence is derived from the Myoviridae lysogen that contains the genetic disruption. In another embodiment, the first nucleotide sequence comprises the $s_c$ region of tail fiber gene s from P1 bacteriophage. In yet another embodiment, the first nucleotide sequence comprises a sequence with at least 90% sequence identity with the nucleotide sequence that encodes amino acid sequence 1-250 of SEQ ID NO: 53. In yet another embodiment, the first nucleotide sequence comprises a sequence with at least 90% sequence identity with the nucleotide sequence that encodes amino acid sequence 1-500 of SEQ ID NO: 53.

In one embodiment, the first nucleotide sequences comprises the $S_c$ region derived from plasmid p15B (as described in Ikeda et al., J. Mol. Biol., 1970, 50: 457-470) or from a P1-like type 11 bacteriophage in *Klebsiella pneumoniae* (Kpn).

In another aspect, the present invention relates to a method of generating engineered bacteriophages or NRTPs having multiple types of tail fibers from a single bacteria cell line wherein at least one of the tail fiber type is a non-native tail fiber comprising, providing a bacteria cell containing the bacteriophage tail fiber replacement platform of the present invention, wherein the complementary nucleic acid molecule comprises at least two receptor binding regions from tail fiber structural protein encoding genes that are fused to one or more tail interacting regions from tail fiber structural protein encoding genes, wherein at least one of the receptor binding regions is derived from a different source than the source of one of the tail interacting region; and providing conditions to the bacterial cell that induces a lytic phase of the Myoviridae lysogen to produce bacteriophages or NRTPs having multiple types of tail fibers.

In one embodiment, the complementary nucleic acid molecule is integrated into the Myoviridae lysogen at the site of the genetic disruption. In another embodiment, the complementary nucleic acid molecule is integrated into the Myoviridae lysogen at a site other than the site of the genetic disruption. In yet another embodiment, the complementary nucleic acid molecule is integrated into the genome of the bacteria cell. In yet another embodiment, the complementary nucleic acid molecule is contained in a plasmid molecule.

In one embodiment, fusing the two or more receptor binding regions to the tail interacting region is performed by a cin recombinase and in the presence of multiple cix recombination sites. In one embodiment, fusing the two or more receptor binding regions to the tail interacting region is performed by a cin recombinase or a homolog, ortholog, or paralog of the cin recombinase and in the presence of multiple associated recombination sites. In one embodiment, the two or more distinct tail fiber structural protein encoding genes are expressed in an operon. In another embodiment, the two or more distinct tail fiber structural protein encoding genes are expressed from independent promoters. In yet another embodiment, the two or more distinct tail fiber structural protein encoding genes are expressed from independent genomic locations.

In another aspect, the present invention relates to a bacterial cell packaging system for packaging a reporter or therapeutic nucleic acid molecule into a non-replicative transduction particle (NRTP) for introduction into a cell, the packaging system comprising, a host bacteria cell; a bacteriophage lysogen that contains a genetic disruption that prevents the expression of one or more genes that are critical for the production of native tail fibers, wherein said one or more genes encode a tail fiber structural protein responsible for binding a receptor, a chaperone needed for folding of one or more regions of a tail fiber structural protein, a protein required for attaching the tail fiber structural protein to the tail structure, or any combination of these genes; and also comprising a first bacteriophage gene that contains a non-functional packaging initiation site sequence, wherein the non-functional packaging initiation site sequence prevents preferential packaging of the bacteriophage genome into the NRTP; one or more complementary nucleic acid molecules comprising one or more genes selected from genes encoding a tail fiber structural protein responsible for binding a receptor, a chaperone needed for folding of one or more regions of a tail fiber structural protein, a protein required for attaching the tail fiber structural protein to the tail structure, or any combination of these genes that complements the genetic disruption of the bacteriophage lysogen whereby functional tail fibers are produced; and a reporter or therapeutic nucleic acid molecule and a second bacteriophage gene that contains a functional packaging initiation site sequence for facilitating packaging of a replicon of the reporter nucleic acid molecule into the NRTP, wherein the functional packaging initiation site sequence on the reporter nucleic acid molecule complements the non-functional packaging initiation site sequence in the bacteriophage lysogen.

In one embodiment, the reporter gene is luxAB. In another embodiment, the reporter gene is a fluorescent reporter protein which includes but is not limited to Green Fluorescent Protein (GFP), Yellow Fluorescent Protein (YFP), Cyan Fluorescent Protein (CFP), and Red Fluorescent Protein (RFP). In one embodiment, the first bacteriophage gene and the second bacteriophage gene is a pacA terminase gene. In another embodiment, the first bacteriophage gene and the second bacteriophage gene is a terS terminase gene.

In another aspect, the present invention relates to a method of generating Myoviridae-family bacteriophages or Myoviridae-family derived NRTPs that are able to recognize and transduce bacteria cells for diagnostic or therapeutic use comprising, providing a bacteria cell containing the bacteriophage tail fiber replacement platform of the present invention, wherein the complementary nucleic acid molecule comprises tail fiber genes non-native to the Myovridae lysogen and derived partially or entirely from either Myoviridae, Siphoviridae (as represented in SEQ ID Nos: 5, 10, 32, 33), or Podoviridae tail fiber sequences; and providing conditions to the bacterial cell that induces a lytic phase of the bacteriophage lysogen to produce Myoviridae-family bacteriophages or Myoviridae-family derived NRTPs capable of recognizing and transducing bacteria previously refractory to a native Myoviridae bacteriophage or Myoviridae-family derived NRTP particles for diagnostic or therapeutic use.

BRIEF DESCRIPTION OF THE DRAWINGS

These and other features, aspects, and advantages of the present invention will become better understood with regard to the following description, and accompanying drawings, where.

DETAILED DESCRIPTION OF THE INVENTION

Definitions

Figure 1:
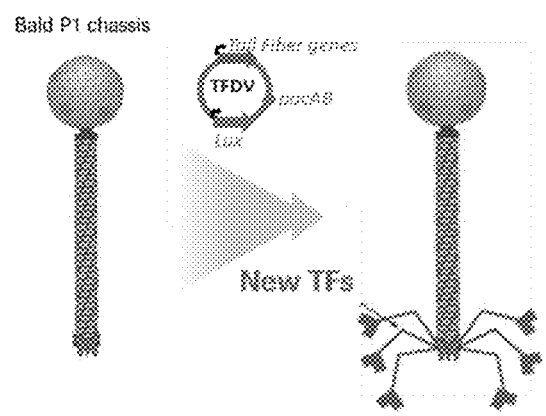
FIG. 1 is a diagram showing the tail-fiber swapping platform.

Terms used in the claims and specification are defined as set forth below unless otherwise specified.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

As used herein, "therapeutic nucleic acid molecule" refers to a nucleotide sequence that has a therapeutic effect to treat diseases, either by sequence-specific recognition of target nucleic acid that causes the disease (e.g. antisense nucleic acids) or by encoding a gene product that possesses therapeutic activity (e.g. antimicrobial proteins). In some embodiments, the therapeutic nucleic molecule can be introduced into a host cell as part of an exogenous nucleic acid molecule, such as a plasmid. As used herein, a "therapeutic expression plasmid" refers to a plasmid that contains a therapeutic nucleic acid molecule that encodes a gene product having therapeutic activity.

A "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be a nucleic acid, such as an aptamer or ribozyme.

In some aspects of the invention, the reporter nucleic acid molecule is operatively linked to a promoter. In other aspects of the invention, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross-reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

As used herein, a "target transcript" refers to a portion of a nucleotide sequence of a DNA sequence or an mRNA molecule that is naturally formed by a target cell including that formed during the transcription of a target gene and mRNA that is a product of RNA processing of a primary transcription product. The target transcript can also be referred to as a cellular transcript or naturally occurring transcript.

As used herein, the term "transcript" refers to a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be protein coding or non-coding. The transcript can also be transcribed from an engineered nucleic acid construct.

A transcript derived from a reporter nucleic acid molecule can be referred to as a "reporter transcript." The reporter transcript can include a reporter sequence and a cis-repressing sequence. The reporter transcript can have sequences that form regions of complementarity, such that the transcript includes two regions that form a duplex (e.g., an intermolecular duplex region). One region can be referred to as a "cis-repressing sequence" and has complementarity to a portion or all of a target transcript and/or a reporter sequence. A second region of the transcript is called a "reporter sequence" and can have complementarity to the cis-repressing sequence. Complementarity can be full complementarity or substantial complementarity. The presence and/or binding of the cis-repressing sequence with the reporter sequence can form a conformation in the reporter transcript, which can block further expression of the reporter molecule. The reporter transcript can form secondary structures, such as a hairpin structure, such that regions within the reporter transcript that are complementary to each other can hybridize to each other.

"Introducing into a cell," when referring to a nucleic acid molecule or exogenous sequence (e.g., plasmid, vector, construct), means facilitating uptake or absorption into the cell, as is understood by those skilled in the art. Absorption or uptake of nucleic acid constructs or transcripts can occur through unaided diffusive or active cellular processes, or by auxiliary agents or devices including via the use of bacteriophage, virus, and transduction particles. The meaning of this term is not limited to cells in vitro; a nucleic acid molecule may also be "introduced into a cell," wherein the cell is part of a living organism. In such instance, introduction into the cell will include the delivery to the organism. For example, for in vivo delivery, nucleic acid molecules, constructs or vectors of the invention can be injected into a tissue site or administered systemically. In vitro introduction into a cell includes methods known in the art, such as electroporation and lipofection. Further approaches are described herein or known in the art.

A "transduction particle" refers to a virus capable of delivering a non-viral nucleic acid molecule into a cell. The virus can be a bacteriophage, adenovirus, etc.

A "phage tail-like particle" or "phage tail-like structures" refers to a bacterially produced high-molecular-weight phage tail-like protein complexe that resemble bacteriophage tails in form, however, do not encode or deliver replicative viral genomes and therefore are not viruses. Non-limiting examples of phage tail-like particles or structures include Type 6 Secretion Systems (T6SS) and R-type tailocins (also known as pyocins) which are found in diverse bacteria types. Further descriptions of these particles are found in Williams et al., Applied and Environmental Microbiology, 2008, 74:12, 3868-3876, and in Scholl et al., Antimicrobial Agents and Chemotherapy, 2009, 53:7, 3074-3080, both incorporated by reference herein in their entireties. While these example structures do not encode viral capsid heads, they are able to mediate binding and tail injection into target cells resulting in either killing target cells or delivering protein effectors. Phage tail-like particles or structures can harbor and utilize specificity determining elements such as tail fibers and therefore their genetic sequences can be mined to re-target cell binding specificity. One example of a pyocin-derived tail fiber is shown in the nucleotide sequence of SEQ ID NO: 11.

A "non-replicative transduction particle" or "NRTP" refers to a virus capable of delivering a non-viral nucleic acid molecule into a cell, but is incapable of packaging its own replicated viral genome into the transduction particle. The virus can be a bacteriophage, adenovirus, etc.

A "plasmid" is a small DNA molecule that is physically separate from, and can replicate independently of, chromosomal DNA within a cell. Most commonly found as small circular, double-stranded DNA molecules in bacteria, plasmids are sometimes present in archaea and eukaryotic organisms. Plasmids are considered replicons, capable of replicating autonomously within a suitable host. As used herein, the term "packaging plasmid" refers to a plasmid encoding both the elements required for being packaged into a given viral capsid (i.e. packaging genes) and an expressible reporter gene. As used herein, the term "tail fiber display vector" and abbreviated as "TFDV" refers to a plasmid encoding the elements required for being packaged into a given viral capsid, an expressible reporter gene, and a tail fiber encoded sequence that produces a binding protein able to attach to the given capsid. As used herein, the term "secondary tail fiber expression plasmid" refers to a plasmid which encodes a functional tail fiber that can be attached to a given capsid, but does not necessarily harbor a reporter molecule or packaging site/machinery.

A "vector" is a nucleic acid molecule used as a vehicle to artificially carry foreign genetic material into another cell, where it can be replicated and/or expressed.

A "virus" is a small infectious agent that replicates only inside the living cells of other organisms. Virus particles (known as virions) include two or three parts: i) the genetic material made from either DNA or RNA molecules that carry genetic information; ii) a protein coat that protects these genes; and in some cases, iii) an envelope of lipids that 9388

As used herein, the term "complement" refers to a non-disrupted sequence that is in the presence of an identical sequence that has been disrupted, or to the relationship of the non-disrupted sequence to the disrupted sequence. In one embodiment, the complement comprises a gene encoded on a polynucleotide in a cell that is functional and capable of expression, and expresses a protein with the same function as a disrupted gene on a bacteriophage prior to disruption. In some embodiments, the complement gene has greater than 80%, 85%, 90%, 91%, 92%, 93%, 94%, 95%, 96%, 97%, 98%, or 99% sequence identity to the disrupted bacteriophage gene prior to disruption, i.e., the native bacteriophage gene. In some embodiments, the complement gene is identical to the disrupted bacteriophage gene prior to disruption, i.e., the native bacteriophage gene. In some embodiments, the complement gene comprises a polynucleotide sequence that has been deleted from the bacteriophage. In some embodiments, the complement gene refers to a gene encoding packaging machinery of a bacteriophage on a plasmid, where the same gene has been disrupted in a bacteriophage. Thus, the plasmid is required to be in the presence of a bacteriophage with a mutated packaging machinery gene to provide the necessary packaging machinery necessary for packaging a polynucleotide into a transduction particle.

As used herein, the term "packaging-related enzymatic activity" refers to one or more polypeptides crucial for the interaction with a packaging initiation site sequence to package a polynucleotide into a transduction particle. In some embodiments, a pair of terminase genes is required for such an interaction, wherein each terminase encodes a packaging-related enzymatic activity. In some embodiments, the enzymatic activity is encoded by a terS and/or terL gene from a S. aureus bacteriophage φ11 or φ80α, a terA and terB gene from an E. faecalis bacteriophage φEf11, or a pacA and pacB gene of Enterobacteriaceae bacteriophage P1. In these embodiments, each of the pair of terminase genes express a packaging-related enzymatic activity, and a functional version of both are required for packaging of a polynucleotide with the packaging initiation site. In some embodiments, disruption of one of the genes of a plurality of genes associated with a packaging-related enzymatic activity eliminates the packaging-related enzymatic activity. In some embodiments, both of a pair of terminase genes are disrupted on the bacteriophage, thus disrupting the entire set of packaging-related enzymatic activity encoding genes on the bacteriophage.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Complementary sequences are also described as binding to each other and characterized by binding affinities.

For example, a first nucleotide sequence can be described as complementary to a second nucleotide sequence when the two sequences hybridize (e.g., anneal) under stringent hybridization conditions. Hybridization conditions include temperature, ionic strength, pH, and organic solvent concentration for the annealing and/or washing steps. The term "stringent hybridization conditions" refers to conditions under which a first nucleotide sequence will hybridize preferentially to its target sequence, e.g., a second nucleotide sequence, and to a lesser extent to, or not at all to, other sequences. Stringent hybridization conditions are sequence dependent, and are different under different environmental parameters. Generally, stringent hybridization conditions are selected to be about 5° C. lower than the thermal melting point ($T_m$) for the nucleotide sequence at a defined ionic strength and pH. The $T_m$ is the temperature (under defined ionic strength and pH) at which 50% of the first nucleotide sequences hybridize to a perfectly matched target sequence. An extensive guide to the hybridization of nucleic acids is found in, e.g., Tijssen (1993) Laboratory Techniques in Biochemistry and Molecular Biology—Hybridization with Nucleic Acid Probes part I, chap. 2, "Overview of principles of hybridization and the strategy of nucleic acid probe assays," Elsevier, N.Y. ("Tijssen"). Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, provided the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between two strands of a dsRNA, or between the antisense strand of a dsRNA and a target sequence, between complementary strands of a single stranded RNA sequence or a single stranded DNA sequence, as will be understood from the context of their use.

As used herein, a "duplex structure" comprises two antiparallel and substantially complementary nucleic acid sequences. Complementary sequences in a nucleic acid construct, between two transcripts, between two regions within a transcript, or between a transcript and a target sequence can form a "duplex structure." In general, the majority of nucleotides of each strand are ribonucleotides, but as described in detail herein, each or both strands can also include at least one non-ribonucleotide, e.g., a deoxyribonucleotide and/or a modified nucleotide. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the duplex minus any overhangs that are present in the duplex. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect, e.g., an amount sufficient to produce a detectable signal from a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Lysogenic and Lytic Cycle of Viruses

Viruses undergo lysogenic and lytic cycles in a host cell. If the lysogenic cycle is adopted, the phage chromosome can be integrated into the bacterial chromosome, or it can establish itself as a stable plasmid in the host, where it can remain dormant for long periods of time. If the lysogen is induced, the phage genome is excised from the bacterial chromosome and initiates the lytic cycle, which culminates in lysis of the cell and the release of phage particles. The lytic cycle leads to the production of new phage particles which are released by lysis of the host.

In addition, virus-based reporter assays, such as phage-based reporters, can suffer from limited reactivity (i.e., analytical inclusivity) due to limits in the phage host range caused by host-based and prophage-derived phage resistance mechanisms. These resistance mechanisms target native phage nucleic acid that can result in the degradation or otherwise inhibition of the phage DNA and functions. Such resistance mechanisms include restriction systems that cleave phage DNA and CRISPR systems that inhibit phage-derived transcripts.

Both lytic activity and phage resistance can be inhibitory to assays based on reporter phages. Lytic activity can inhibit signal by destroying or otherwise inhibiting the cell in its ability to generate a detectable signal and thus affecting limits of detection by reducing the amount of detectable signal or preventing the generation of a detectable signal. Phage resistance mechanisms can limit the host range of the phage and limit the inclusivity of the phage-based reporter, similarly affecting limits of detection by reducing the amount of detectable signal or preventing the generation of a detectable signal. Both lytic activity and phage resistance caused by the incorporation of phage DNA in a reporter phage can lead to false-negative results in assays that incorporate these phage reporters.

III. Methods for Producing Non-Replicative Transduction Particles (NRTP)

Disruption/Complementation-Based Methods for Producing Non-Replicative Transduction Particles.

Disclosed herein are non-replicative transduction particle packaging systems based on disruption of a component of the genome of a virus that is recognized by the viral packaging machinery as the element from which genomic packaging is initiated during viral production. In an embodiment, this disruption disrupts a packaging initiation site from a bacteriophage, and also disrupts a terminase function. Examples of the disrupted elements include the pac-site sequence of pac-type bacteriophages and the cos-site sequence of cos-type bacteriophages. When the packaging initiation site sequence within the phage is disrupted, the phage cannot produce functional terminases. In an example, the pac-site is encoded within a pacA gene sequence, and terminase functions require both a functional PacA and PacB. Plasmid DNA is packaged into a phage capsid by complementing said disrupted terminases and including a recognizable packaging initiation site on the plasmid DNA. The bacteriophage can be any bacteriophage, such as an Enterobacteriaceae bacteriophage P1 or φEF11, or an S. aureus bacteriophage φ80α or a bacteriophage φ11.

Packaging initiation sites are often found within coding regions of genes that are essential to virus production. A region of the bacteriophage genome can be disrupted by an insertion, replacement, deletion, or mutation that disrupts the packaging initiation site. Examples of disruptions that accomplish this include, but are not limited to, an allelic exchange event that replaces a sequence on the bacteriophage genome that contains the packaging initiation site sequence with another sequence such as that of an antibiotic resistance gene, or the complete deletion of the small and large terminase genes. In an example employing the terminase genes pacA and pacB, pacA can be disrupted in a manner that causes polar effects that also disrupt pacB expression and/or overall terminase function mediated by PacA and PacB. Other examples can include terminase genes can also include terS and terL genes from S. aureus bacteriophage φ11 or φ80α, or the terS and terL genes from E. faecalis bacteriophage φEf11

In one example, a cell's genome is lysogenized with a viral genome where the packaging initiation site has been disrupted. In some embodiments, the cell can be an E. coli cell, an S. aureus cell, or an E. faecalis cell. The cell can be Gram-negative or Gram-positive. A complementing plasmid (or reporter nucleic acid molecule) is introduced into the cell, and the plasmid DNA includes at least the gene that has been disrupted in the bacteriophage, as well as the packaging initiation site sequence, and optionally additional bacteriophage genes and a reporter gene, which can encode a detectable and/or a selectable marker. The plasmid can be constructed using methods found in U.S. Pat. No. 9,388,453, and in U.S Patent Application Publication No. 2017/0166907, hereby incorporated by reference in their entireties. One or more genes of the plasmid can be operatively linked to a promoter, such as an inducible promoter (which can be induced when packaging is initiated by inducing the bacteriophage). In some embodiments, the promoter can be a native promoter of a small terminase gene or a large terminase gene. The native promoter can be controlled by the bacteriophage, and thus effectively acts as a conditional promoter induced during packaging.

In some examples, it is preferable that the disruption/complementation is designed such that there is no homology between the mutated virus DNA and the complementing exogenous DNA. This is because lack of homology between the mutated virus DNA and the complementing exogenous DNA avoids the possibility of homologous recombination between the two DNA molecules that can result in re-introduction of a packaging sequence into the virus genome. To accomplish a lack of homology, one strategy is to delete the entire gene (or genes) that contains the packaging initiation site sequence from the virus genome and then complement this gene with an exogenous DNA molecule that preferably contains no more than exactly the DNA sequence that was deleted from virus. In this strategy, the complementing DNA molecule is designed to express the gene that was deleted from the virus. Another example of such a system is provided using the bacteriophage φ80α, a pac-type phage. The phage genome is lysogenized in a host bacterial cell, and the phage genome includes a small terminase gene where the pac-site of a pac-type prophage φ80α has been deleted. A plasmid including a complementary small terminase gene with a native pac-site is transformed into the cell. When the lytic cycle of the lysogenized prophage is induced, the bacteriophage packaging system packages plasmid DNA into progeny bacteriophage structural components, rather than packaging the native bacteriophage DNA. The packaging system thus produces non-replicative transduction particles carrying plasmid DNA.

The reporter gene encodes a detectable marker or a selectable marker. In an example, the reporter gene is selected from the group consisting of enzymes mediating luminescence reactions (luxA, luxB, luxAB, luc, ruc, nluc), enzymes mediating colorimetric reactions (lacZ, HRP), fluorescent proteins (GFP, eGFP, YFP, RFP, CFP, BFP, mCherry, near-infrared fluorescent proteins), affinity peptides (His-tag, 3X-FLAG), and selectable markers (ampC, tet(M), CAT, erm). In an embodiment, the reporter gene is luxA. In some embodiments, the resistance marker comprises an antibiotic resistance gene. In some embodiments, the resistance marker is a kanamycin resistance gene (kan). In some embodiments, the constitutive promoter comprises Pblast. In some embodiments, the bacteriophage genome disruption is accomplished by an allelic exchange event that replaces or disrupts a sequence on the bacteriophage genome that contains the packaging initiation site sequence.

In an example, a pair of terminase genes on a bacteriophage genome, e.g., pacA and pacB, terA and terB, or terS and terL, can be disrupted in a manner that causes polar effects that also disrupt expression of one of the terminase genes and/or overall terminase function mediated by the terminase genes. The disrupted bacteriophage can be complemented with a plasmid comprising terminase genes, e.g., pacA and pacB, terA and terB, or terS and terL, of the bacteriophage genome. When the mutated virus is undergoing a lytic cycle, the viral packaging proteins, produced either from the bacteriophage genome or (if disrupted) the complementing plasmid, package a replicon of the plasmid DNA into the packaging unit because it contains a packaging initiation site, and non-replicative transduction particles are produced carrying the replicated plasmid DNA.

Reporters

In some embodiments, the NRTPs and constructs of the invention comprise a reporter nucleic acid molecule including a reporter gene. The reporter gene can encode a reporter molecule, and the reporter molecule can be a detectable or selectable marker. In certain embodiments, the reporter gene encodes a reporter molecule that produces a detectable signal when expressed in a cell.

In certain embodiments, the reporter molecule can be a fluorescent reporter molecule, such as, but not limited to, a green fluorescent protein (GFP), enhanced GFP, yellow fluorescent protein (YFP), cyan fluorescent protein (CFP), blue fluorescent protein (BFP), red fluorescent protein (RFP) or mCherry, as well as near-infrared fluorescent proteins.

In other embodiments, the reporter molecule can be an enzyme mediating luminescence reactions (LuxA, LuxB, LuxAB, Luc, Ruc, nLuc, etc.). Reporter molecules can include a bacterial luciferase, a eukaryotic luciferase, an enzyme suitable for colorimetric detection (LacZ, HRP), a protein suitable for immunodetection, such as affinity peptides (His-tag, 3X-FLAG), a nucleic acid that function as an aptamer or that exhibits enzymatic activity (ribozyme), or a selectable marker, such as an antibiotic resistance gene (ampC, tet(M), CAT, erm). Other reporter molecules known in the art can be used for producing signals to detect target nucleic acids or cells.

In other aspects, the reporter molecule comprises a nucleic acid molecule. In some aspects, the reporter molecule is an aptamer with specific binding activity or that exhibits enzymatic activity (e.g., aptazyme, DNAzyme, ribozyme).

Reporters and reporter assays are described further in Section V herein.

V. NRTPs and Reporter Assays

Inducer Reporter Assay

In some embodiments, the invention comprises methods for the use of NRTPs as reporter molecules for use with endogenous or native inducers that target gene promoters within viable cells. The NRTPs of the invention can be engineered using the methods described in Section III and below in Examples 1-2.

In some embodiments, the method comprises employing a NRTP as a reporter, wherein the NRTP comprises a reporter gene that is operably linked to an inducible promoter that controls the expression of a target gene within a target cell. When the NRTP that includes the reporter gene is introduced into the target cell, expression of the reporter gene is possible via induction of the target gene promoter in the reporter nucleic acid molecule.

Transcripts

As described above, a transcript is a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be transcribed from an engineered nucleic acid construct. The transcript can have regions of complementarity within itself, such that the transcript includes two regions that can form an intra-molecular duplex. One region can be referred to as a "cis-repressing sequence" that binds to and blocks translation of a reporter sequence. A second region of the transcript is called a "reporter sequence" that encodes a reporter molecule, such as a detectable or selectable marker.

The transcripts of the invention can be a transcript sequence that can be 5, 6, 7, 8, 9, 10, 11, 12, 13, 14, 15, 16, 17, 18, 19, 20, 21, 22, 23, 24, or 25 nucleotides in length. In other embodiments, the transcript can be at least 25, 30, 40, 50, 60, 70, 80, 90, 100, 500, 1000, 1500, 2000, 3000, 4000, 5000 or more nucleotides in length. The cis-repressing sequence and the reporter sequence can be the same length or of different lengths.

In some embodiments, the cis-repressing sequence is separated from the reporter sequence by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, or more spacer nucleotides.

Vectors

In another aspect, the transcripts (including antisense and sense sequences) of the invention are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These sequences can be introduced as a linear construct, a circular plasmid, or a viral vector, including bacteriophage-based vectors, which can be incorporated and inherited as a transgene integrated into the host genome. The transcript can also be constructed to permit it to be inherited as an extrachromosomal plasmid (Gassmann, et al., *Proc. Natl. Acad. Sci. USA* (1995) 92:1292).

The transcript sequences can be transcribed by a promoter located on the expression plasmid. In one embodiment, the cis-repressing and reporter sequences are expressed as an inverted repeat joined by a linker polynucleotide sequence such that the transcript has a stem and loop structure.

Recombinant expression vectors can be used to express the transcripts of the invention. Recombinant expression vectors are generally DNA plasmids or viral vectors. Viral vectors expressing the transcripts can be constructed based on, but not limited to, adeno-associated virus (for a review, see Muzyczka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), Cell 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl.

Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the transcript(s) to be expressed can be used, for example, vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the transcripts into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. A suitable AV vector for expressing the transcripts featured in the invention, a method for constructing the recombinant AV vector, and a method for delivering the vector into target cells, are described in Xia H et al. (2002), Nat. Biotech. 20: 1006-1010. Suitable AAV vectors for expressing the transcripts featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

The promoter driving transcript expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transcript can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D-1-thiogalactopyranoside (IPTG). A person skilled in the art would be able to choose the appropriate regulatory/promoter sequence based on the intended use of the dsRNA transgene.

Generally, recombinant vectors capable of expressing transcript molecules are delivered as described below, and persist in target cells. Alternatively, viral vectors can be used that provide for transient expression of transcript molecules. Such vectors can be repeatedly administered as necessary. Once expressed, the transcript binds to target RNA and modulates its function or expression. Delivery of transcript expressing vectors can be systemic, such as by intravenous or intramuscular administration, by administration to target cells ex-planted from the patient followed by reintroduction into the patient, or by any other means that allows for introduction into a desired target cell.

Transcript expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single PROC gene or multiple PROC genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

The delivery of the vector containing the recombinant DNA can by performed by abiologic or biologic systems. Including but not limited to liposomes, virus-like particles, transduction particles derived from phage or viruses, and conjugation.

Reporters for Transcript Assay

In some embodiments, the nucleic acid construct comprises a reporter sequence (e.g., a reporter gene sequence). The reporter gene encodes a reporter molecule that produces a signal when expressed in a cell. In some embodiments, the reporter molecule can be a detectable or selectable marker. In certain embodiments, the reporter molecule can be a fluorescent reporter molecule, such as a green fluorescent protein (GFP), yellow fluorescent protein (YFP), cyan fluorescent protein (CFP), blue fluorescent protein (BFP), or red fluorescent protein (RFP). In other embodiments, the reporter molecule can be a chemiluminescent protein.

Reporter molecules can be a bacterial luciferase, an eukaryotic luciferase, a fluorescent protein, an enzyme suitable for colorimetric detection, a protein suitable for immunodetection, a peptide suitable for immunodetection or a nucleic acid that function as an aptamer or that exhibits enzymatic activity.

Selectable markers can also be used as a reporter. The selectable marker can be an antibiotic resistance gene, for example.

EXAMPLES

Example 1: Disruption/Complementation-Based Methods for Producing Non-Replicative Transdcution Particles with Non-Native Tail Fibers A diagram of the tail-fiber replacement platform is shown in FIG. 1. The attachment of NTRPs to their target bacteria cell is mediated by bacteriophage tail fibers. By removing the native P1 NRTP tail fiber genes, a "bald" chassis was created to test the functionality of heterologous tail fibers. New tail fibers were then expressed in the "bald" background using a Tail Fiber Display Vector (TFDV). The P1 based Smarticles genome was modified using the λ-RED Recombineering method from Murphy et al. (1998) to create a deletion in the genes encoding the S structural tail fiber protein and the U tail fiber assembly chaperone protein. This disruption created a platform to express any desired tail fibers in trans. Bacterial strains were grown on Luria-Bertani (LB) broth and LB agar with the following antibiotic concentrations Gentamicin 15 µg/mL, Cabinicillin 100 µg/mL, Spectinomycin 50 µg/mL, Zeocin 100 µg/mL and Hygromycin 150 µg/mL. New England Biolabs (NEB) cloning strain NEB5α was used to propagate and archive plasmids. Assembly of DNA for plasmids as well as linear DNA products for Recombineering were produced using NEB Gibson Assembly Master Mix. EMD Millipore KOD Xtreme Hot Start Polymerase was used for amplification of DNA in all PCR reactions.

Example 2: Construction of a "Bald" P1 Chassis

The λ-RED encoding Recombineering plasmid pKM208 was first transformed into the bacterial strain BAA-1001 (with the pacAB genes replaced with a hygromycin cassette) to facilitate the Recombineering reaction. The strain was made electrocompetent and induced with 1 mM IPTG for expression of recombination proteins. Linear DNA containing the antibiotic resistance marker spectinomycin was then transformed into the strain, this DNA contains homology to the surrounding regions of the s and u genes of P1. After recovery at 30° C., transformants were plated onto LB agar containing spectinomycin, then patched. Colony PCR for the removal of the s and u genes followed by Sanger sequencing were used to ensure the desired modification was made. During construction the u' and $s_v$' regions were left intact, but because the $s_v$' does not code for the full structural protein, the S' tail fiber cannot be produced. This bacterial lysogen represented the "Bald" P1 chassis that lacks the ability to express functional tail fibers of its own without complementation. The resulting bacterial strain containing the Bald P1 chassis was designated as SEG_170 cell line. Functional tests of the chassis consisted of packaging plasmids with and without coding sequences for the native S and U proteins. Loss of Smarticles functionality was seen from lysate derived from the packaging line with no tail fibers on the packaging plasmid. Activity was recovered from lysate derived from the packaging line with tail fibers on the packaging plasmid, achieving successful complementation in trans.

Example 3: Construction of Tail Fiber Display Vectors (TFDV)

Tail Fiber Display Vectors (TFDV) were utilized to express native and/or novel tail fibers in the bald bacteriophage P1 chassis. These display vectors utilized either Gentamicin or Zeocin resistance cassettes, pUC/RO1600 origins of replication, and tail fiber genes under the control of the pTac IPTG inducible promoter. All vectors also contained the pacAB genes/packaging site together with the P23-luxAB-TT (luciferase) cassette for transduction and light assays. Tail fiber candidates were de novo synthesized at IDT or PCR amplified from bacterial gDNA, Gibson Assembled into PCR amplified vectors, transformed into NEBa cells, patched, colony PCR verified, and sequence verified. Sequence verified plasmids were transformed into the well characterized SEG_170 bald packaging line (competent cells purchased from Lucigen). Transformants were patched onto selective media and screened in small volume lysates to determine the best Smarticles producing clones. Top clones were handed off for large volume lysate production, QC, and reactivity analysis on bacterial panels.

Example 4: Construction of Genomic Expression of Tail Fibers

Figure 2:
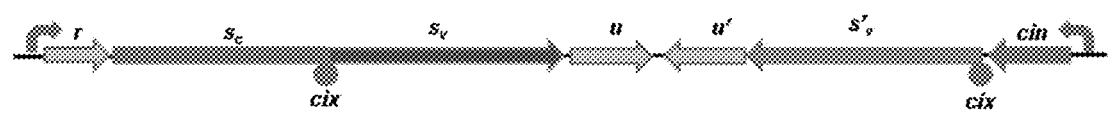
FIG. 2 Diagram of natural P1 tail fiber genomic region. Gene r encodes a tail fiber accessory protein putatively involved in attaching tail fibers to the tail structure. The cin gene encodes a sequence specific recombinase which flips the DNA between the Cin recombination sites (called cix sites) enabling expression of two distinct tail fibers from a single piece of DNA, sites are denoted as circles in diagram. Genes u and u' encode distinct tail fiber accessory proteins which are thought to act as chaperones to fold the binding domain of the S and S' tail fiber proteins, respectively (binding domains encoded by $s_v$ and $s_v'$ coding sequences, respectively). The conserved region of both S and S' tail fibers proteins are encoded by the $s_c$ coding sequence which is transcriptionally and translationally fused to either the $s_v$ or $s_v'$ depending on activity of the Cin recombinase.

To facilitate optimal Smarticles production with native and/or novel tail fibers, tail fiber and chaperone genes were integrated into the P1 Smarticles genome at the s and u genes native locations. This expression from the genome instead of in trans ensured the proper expression and timing with the rest of the P1 based genome, reducing the burden from in trans expression. Tail fibers were first amplified by PCR with primers containing homology to the hygromycin cassette on the C-terminal portion of the tail fiber structural gene (s gene) or tail fiber chaperone gene (u gene). PCR was also used to amplify the hygromycin cassette. These two fragments were assembled with Gibson Assembly and further amplified with primers that contain homology to the P1 genome where s was previously found and homology in the recombinase cin which lies just downstream of the native s and u genes (see FIG. 2). This Recombineering event performed the dual functions of inserting the tail fiber on the P1 genome as well as disrupting the cin recombinase responsible for switching the variable regions of the s tail fiber gene. This linear DNA product of tail fiber and hygromycin cassette was transformed into BAA-1001 containing the spectinomycin resistance cassette. Recovery at 30° C. and plating followed transformation. Cells were plated onto LB agar containing hygromycin and patched for spectinomycin sensitivity. Promising colonies were checked with colony PCR and Sanger sequencing.

Positive colonies containing the non-native tail fiber and hygromycin resistance were then transformed with a packaging plasmid. Cells were grown overnight in media containing antibiotic. Lysates were generated using a 90 minute 42° C. heat induction to inactivate the P1 master repressor and facilitate Smarticles production. Lysates were then spun down to pellet the bacterial cell debris and then filter sterilized through a 2 µm filter. Lysates were checked for proper Smarticles functionality on the new hosts similar to the process for the TFDV packaging lines described above.

Figure 6:
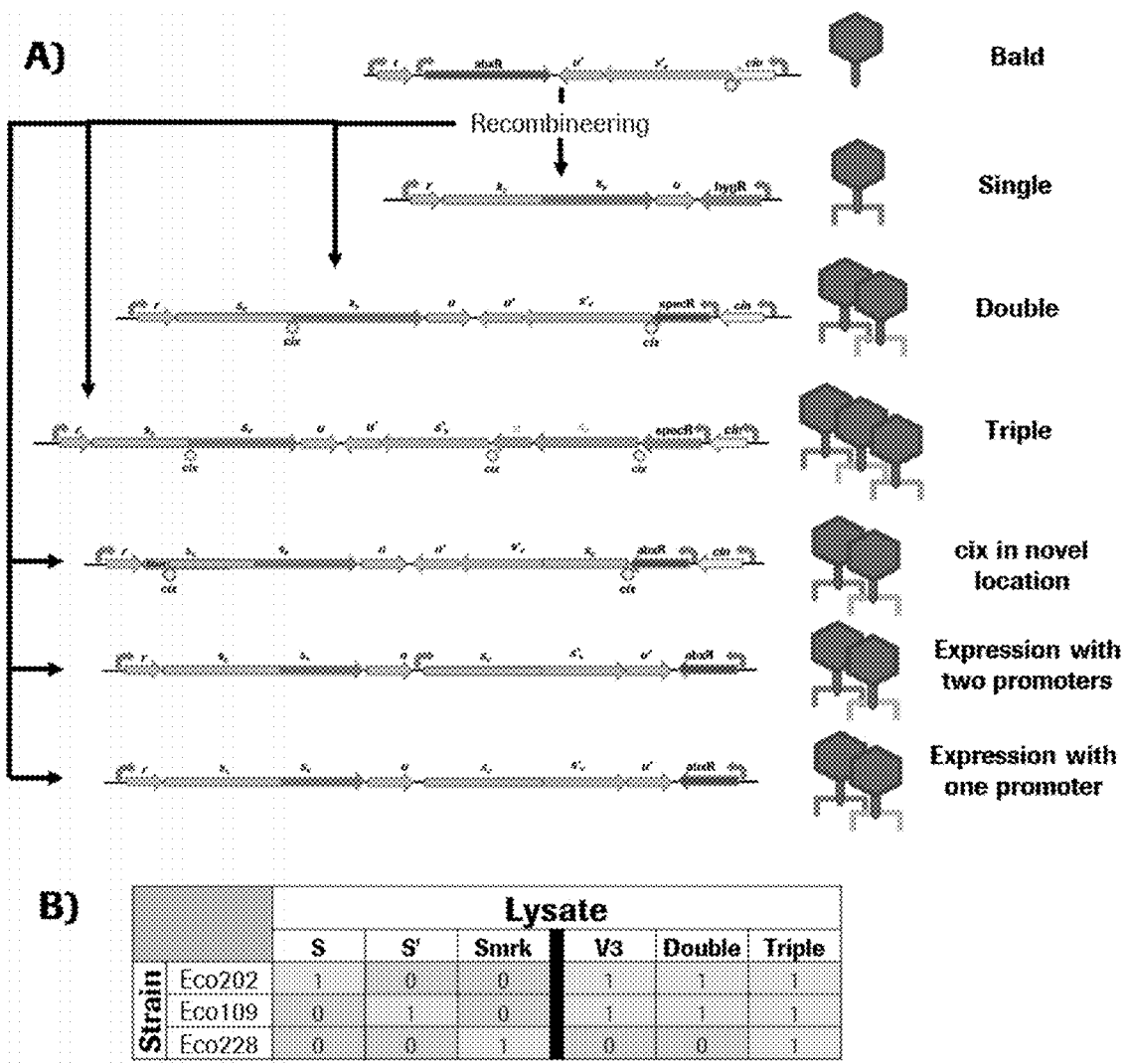
FIG. 6 Production of one, two, or more tail fibers in a single production line A) a single bacterial packaging lines that expresses one, two, three, or more functional tail fibers. S, S', and Shamrock tail fibers were added to a packaging line along with an antibiotic marker. Tail fiber genes can be arranged with cix crossover site in a novel location. Genes can also be arranged for expression not dependent on recombination in large or small operons. B) Lysates were generated from packaging lines expressing single tail fibers (indicated as S, S', Smrk) as well as engineered double and triple tail fiber strains (indicated as V3, Double, Triple). E. coli strains that have specific reactivity to a single tail fiber were used to demonstrate multiple functional tail fibers were expressed from a single host.

To construct a packaging line that expresses two or more tail fibers from a single Smarticles genome, a similar Recombineering approach was used as described above. The first tail fiber was similarly placed on the P1 genome, but instead of the tail fiber being linked to hygromycin resistance, it was attached to an alternative antibiotic, such as kanamycin or gentamicin. The cin recombinase was also left intact to facilitate switching of the multiple tail fibers. A second recombineering reaction was performed to place the second variable portion of the tail fiber attached to the hygromycin casstte to replacement of the kanamycin (or gentamicin) cassette already on the genome. This could be repeated to add three, four, five, etc. . . . tail fibers to the genome (see FIG. 6).

Example 5: NRTP Assay Conditions

The assay involved an initial 2.5 hour pre-treatment of bacterial cells at a concentration of 5.0E+05 CFU/mL in assay media (10 g/L Tryptone+5 g/L Yeast Extract+5% PEG8000). Following the pre-treatment step, both NRTPs and transduction salts (1M MgCl2+0.5M CaCl2) were added to the reaction and incubated for 2 hours—which allowed for transduction of the reporter molecule that contained the luciferase gene, luxAB. Light production from bacteria was measured by Relative Luminometer Units (RLU) output using a luminometer.

Example 6: Performance of NRTPs with Engineered Tail Fibers

The improved reactivity of engineered NRTPs against various species and strains can be seen on Table 1. These data clearly show 1) the diversity of tail fibers analyzed, 2) the robust alterations reactivity observed by different tail fiber protein binding domains, 3) that some tail fibers are highly specific for certain species, and 4) some tail fibers are highly reactive against many diverse species of bacteria. Both nucleotide and amino acid sequences of the tail fibers from these engineered NRTPs (e.g. "Sunset", "Indian", "Tangerine" etc.) are listed in the SEQUENCE LISTING which is submitted herewith as a text document, 34922 US2.txt.

TABLE 1

| Lysate* | Test Panels | | | | | |
| --- | --- | --- | --- | --- | --- | --- |
| | Abi (n = 73) | Cfi (N = 88) | Cko (N = 88) | Eae (N = 88) | Ecl (N = 68) | Eco (N = 87) |
| 5X V3 | 45.9%*** | 56.8%* | 63.6%* | 61.4%* | 95.6%* | 88.5%* |
| S | 40.3%** | NA | NA | NA | 67.6%** | 71.3%** |
| S' | 41.6%** | NA | NA | NA | 89.7%** | 60.9%** |
| Sunset TFDV | 0%** | 5.7%* | 0%* | 2.3%* | 7.4%** | 12.6%** |
| Indian TFDV | 1.3%** | 10.2%* | 0%* | 4.5%* | 14.7%** | 2.3%** |
| Tangerine Genomic | 1.4%*** | NA | NA | NA | 1.5%* | 13.8%* |
| Tangerine TFDV | NA | 3.4%* | 0%* | 0%* | NA | NA |
| Maroon TFDV | 0%** | 0%* | 0%* | 0%* | 4.4%** | 14.9%** |
| Scarlett Genomic | 0%** | 6.8%* | 6.8%* | 45.5%* | 8.8%** | 14.9%** |
| Bittersweet Genomic | 1.4%*** | NA | NA | NA | 0%* | 4.6%* |
| Bittersweet TFDV | 2.7%*** | 4.5%* | 0%* | 0%* | 0%* | 3.4%* |
| Indigo Genomic | 0%*** | NA | NA | NA | 16.2%* | 1.1%* |
| 5x Indigo TFDV | 1.4%*** | NA | NA | NA | 14.7%* | 1.1%* |
| DenimTFDV | 4.1%*** | NA | NA | NA | 4.4%* | 12.6%* |
| Cobalt TFDV | 5.5%*** | NA | NA | NA | 5.9%* | 16.1%* |
| Pine TFDV | 35.1% | 23.9%* | 63.6%* | 47.7%* | 83.8% | 79.3%** |
| Jungle TFDV | 50.6%** | 42%* | 12.5%* | 48.9%* | 88.2%** | 65.5%** |
| Shamrock | 6.8%*** | 34.1%* | 1.1%* | 1.1%* | 22.1%* | 73.6%* |
| Violet TFDV | 56.8%*** | 23.9%* | 1.1%* | 35.2%* | 80.9%* | 66.7%* |
| Plum TFDV | 2.7%*** | 0%* | 0%* | 0%* | 1.5%* | 43.7%* |
| Salmon TFDV | 40.5%*** | 28.4%* | 76.1%* | 34.1%* | 33.8%* | 55.2%* |
| Jazzberry TFDV | 2.7%*** | 1.1%* | 0%* | 0%* | 1.5%* | 42.5%* |
| Razzmatazz TFDV | 52.1%*** | NA | NA | NA | 85.3%* | 62.1%* |
| ShamJazz genomic | 4.1%*** | NA | NA | NA | 14.7%* | 72.4%* |
| 5x Fuzzy + Chaperone TFDV | 0%*** | NA | NA | NA | 0%* | 2.3%* |
| Banana TFDV | 0%*** | NA | NA | NA | 1.1%* | 82.4%* | 0%* |
| Mango TFDV | 13.7%*** | NA | NA | NA | 97.1%* | 26.4%* |
| 10x Queen TFDV (Eco0229) | 6.8%*** | NA | NA | NA | 25%* | 80.5%* |
| Tropical TFDV | 0%*** | NA | NA | NA | 2.9%* | 0%* |
| Gold TFDV | 2.7%** | 5.7%** | NA | 37.5%** | 22.1%** | 32.2%** |
| Bluetiful TFDV | 0%** | 1.1%** | NA | 22.7%** | NA | 0.0%** |
| Rio TFDV | 0%** | 3.4%** | NA | 3.4%** | 92%** | 0%** |
| Orchid TFDV | 8.2%** | 17.0%** | NA | 22.7%** | 42.6%** | 79.3%** |
| Limon TFDV | 1.4%** | 56.8%** | 34.1%** | NA | NA | 0%** |

| Lysate* | Test Panels | | | | |
| --- | --- | --- | --- | --- | --- |
| | Kox (N = 88) | Kpn (N = 89) | Pae (N = 87) | Pms (N = 88) | Sms (N = 88) |
| 5X V3 | 94.3%* | 82%* | 23%*** | 17%* | 89.8%* |
| S | NA | 75.3%** | 10.3%** | 20.5%** | NA |
| S' | NA | 73.0%** | 3.4%** | 29.5%** | NA |
| Sunset TFDV | 1.1%* | 1.1%** | 0%** | 0%* | 1.1%* |
| Indian TFDV | 40.9%* | 14.6%** | 1.1%** | 5.7%* | 6.8%* |
| Tangerine Genomic | NA | 0%* | 9.2%*** | NA | NA |
| Tangerine TFDV | 0%* | NA | NA | 0%* | 6.8%* |
| Maroon TFDV | 0%* | 0%** | 0%** | 0%* | 4.5%* |
| Scarlett Genomic | 47.7%* | 11.2%** | 0%** | 6.8%* | 11.4%* |
| Bittersweet Genomic | NA | 0%* | 0%*** | NA | NA |
| Bittersweet TFDV | 0%* | 0%* | 0%** | 1.1%* | 0%* |
| Indigo Genomic | NA | 0%* | 0%*** | NA | NA |
| 5x Indigo TFDV | NA | 0%* | 0%*** | NA | NA |
| DenimTFDV | NA | 22.5%* | 0%*** | NA | NA |
| Cobalt TFDV | NA | 29.2%* | 0%*** | NA | NA |
| Pine TFDV | 78.4%* | 80.9%* | 9.2%** | 6.8%* | 38.6%* |
| Jungle TFDV | 90.9%* | 79.8%* | 1.1%** | 26.1%* | 97.7%* |

TABLE 1-continued

| | | | | | |
|---|---|---|---|---|---|
| Shamrock | 0%* | 0%* | 8%*** | 9.3%* | 17.1%* |
| Violet TFDV | 71.6%* | 65.2%* | 20.7%*** | 2.3%* | 79.6%* |
| Plum TFDV | 0%* | 0%* | 8%*** | 0%* | 0%* |
| Salmon TFDV | 77.3%* | 46.1%* | 20.7%*** | 9.1%* | 73.6%* |
| Jazzberry TFDV | 0%* | 0%* | 8%*** | 0%* | 0%* |
| Razzmatazz TFDV | NA | 60.7%* | 16.1%*** | NA | NA |
| ShamJazz genomic | NA | *0%** | *0%**** | NA | NA |
| 5x Fuzzy + Chaperone TFDV | NA | 20.2%* | 0%*** | NA | NA |
| Banana TFDV | NA | *1.1%** | *0%**** | NA | NA |
| Mango TFDV | NA | *47.2%** | 2.3%*** | NA | NA |
| 10x Queen TFDV (Eco0229) | NA | *0%** | *0.0%**** | NA | NA |
| Tropical TFDV | NA | *0%** | *0%**** | NA | NA |
| Gold TFDV | 87.5%** | 62.9%** | 0%** | 22.7%** | 68.2%** |
| Bluetiful TFDV | *30.7%*** | NA | 0%** | *4.5%*** | *76.1%*** |
| Rio TFDV | *84%*** | *53.9%*** | 0%** | *86.4%*** | *80.7%** |
| Orchid TFDV | NA | *55.1%*** | 0%** | *5.7%*** | *63.6%*** |
| Limon TFDV | NA | NA | 0%** | NA | NA |

Figure 3:
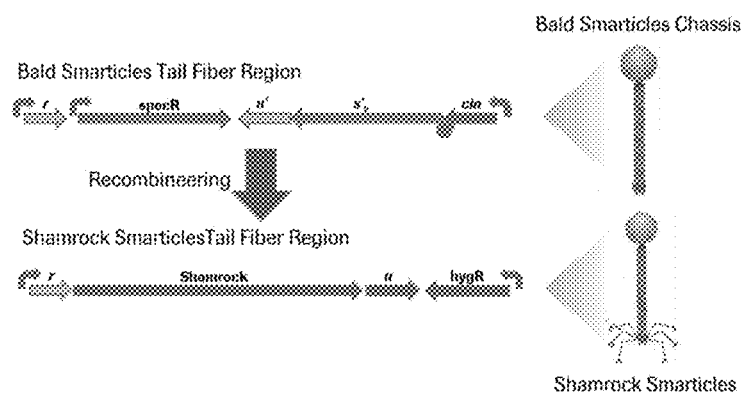
FIG. 3 Diagram of Tail Fiber Replacement Platform. A tail fiber deficient (bald) packaging line harboring a spectinomycin resistance cassette in place of the s and u genes is induced to express recombineering machinery (SEQ ID NO: 97) and comprises an operon promoter, the r gene, the spectinomycin resistance promoter, the spectinomycin resistance gene, the u' gene, the $s_v$' coding region, the cin gene, and the cin promoter. PCR fragments harboring a new tail fiber, hygromycin resistance cassette, and flanking homology arms is then transformed into the induced strain (in this case "Shamrock" and "Shamrock" u). The recombineering machinery integrates the new tail fiber operon in place of the spectinomycin resistance cassette-u'-$s_v$' region to generate the new chromosomal packaging line able to produce tail fiber endowed Smarticles.
Figure 4:
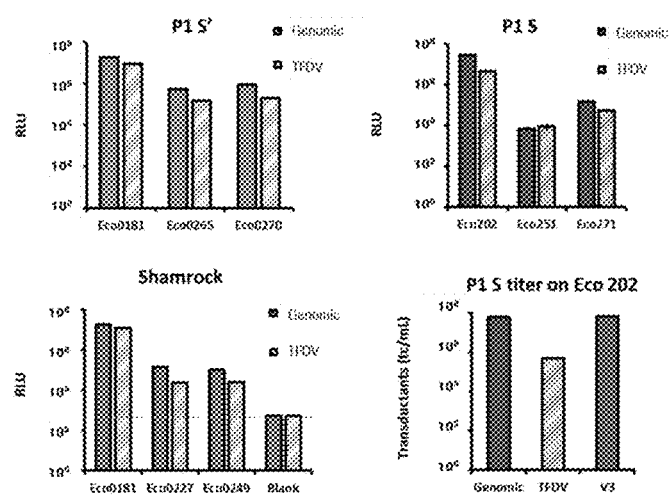
FIG. 4 Improved Smarticles performance following chromosomal integration of tail fibers. Graphs comparing performance of Smarticles endowed with tail fibers expressed from either plasmids (TFDV) or chromosomally. Reactivity of Smarticles harboring only S' (top left), S (top right), or "Shamrock" (bottom left) tail fibers on various E. coli strains is shown. Bottom right, improved Smarticles yield obtained from a S tail fiber packaging line genomically integrated vs. plasmid expressed. V3 Smarticles (native tail fibers region) are supplied as a positive control.

A. baumannii   Abi
C. freundii   Cfi
C. koseri   Cko
E. aerogenes   Eae
E. cloacae   Ecl
E. coli   Eco
K. oxytoca   Kox
K. pneumoniae   Kpn
P. aeruginosa   Pae
P. mirabilis   Pms
S. marcescens   Sms
*Detection observed at 1E4 CFU/mL
**Detection observed at 5E5 CFU/mL
***Detection observed at 1E7 CFU/mL
Bold denotes lysate concentration of 1x utilized in diagnostic assay
Normal font denotes concentration of 5x utilized in diagnostic assay
Italics denote lysate concentration of 10x utilized in diagnostic assay FIG. 3 graphically depicts how a bald (tail fiber deficient) P1 lysogen can be altered to express a new tail fiber from the genome. FIG. 4 depicts how genomic integration of a given tail fiber can improve performance compared to trans expression from a TFDV. Light activity is shown for 3 distinct tail fibers on 3 indicator strains for both the TFDV and genomically expressed versions. Additionally, transduction efficiency of the TFDV and genomic S tail fiber NRTPs were also compared to the WT P1 NRTP control (V3).

Figure 5:
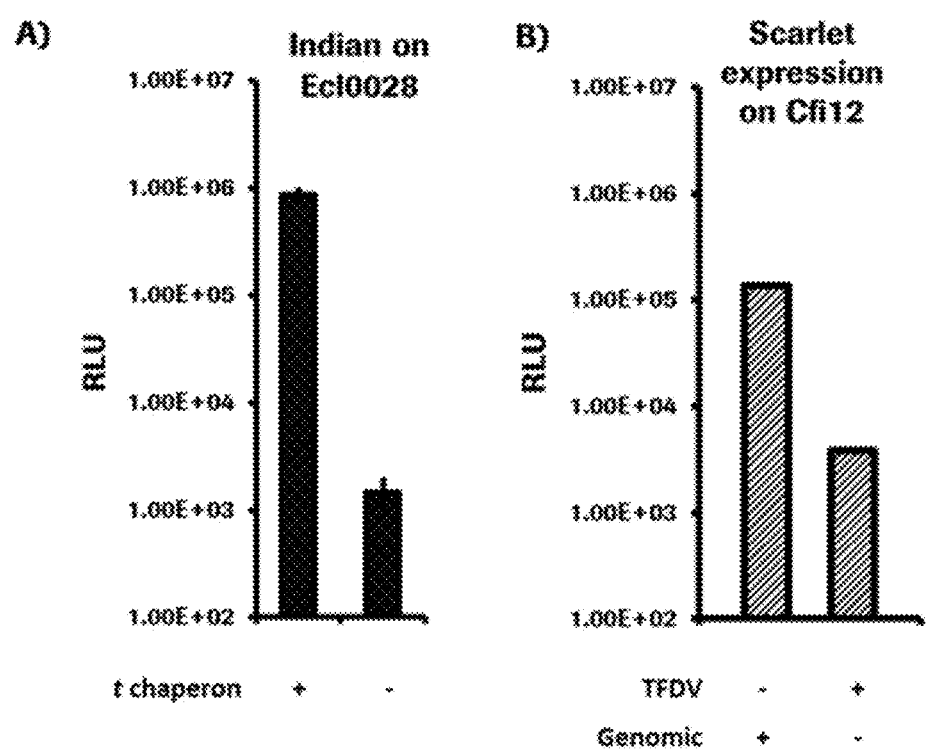
FIG. 5 Shows improved tail fiber activity with expression of native U protein homolog or from bacteriophage genome. A) Performance of "Indian" NRTP produced in packaging line expressing or not expressing plasmid p15B U protein homolog T; B) Performance of "Scarlet" NRTPs produced either from bacteriophage genome or from separate packaging plasmid.

FIG. 5A depicts a graph that show improved tail fiber activity of the engineered "Indian" NRTP as light production (RLU) comparing a packaging line that expresses the plasmid p15B U protein "t chaperon" compared to packaging line not expressing this protein. FIG. 5B depicts a graph that shows improved performance of "Scarlet" NRTPs that are produced from a bacteriophage genome compared to "Scarlet" NRTPs produced from a separate packaging plasmid (TFDV).

FIG. 6A displays the genomic arrangement of production lines harboring 0, 1, 2, or 3 distinct tail fiber genes and demonstrates how lysogens can be engineered to produce multiple NRTPs from a single fermentation. Tail fiber genes can be arranged with cix crossover site in a novel location. Genes can also be arranged for expression not dependent on recombination in large or small operons. FIG. 6B depicts indicator strains specifically detected by given NRTPs endowed individual tail fibers (left). While the right panel shows that packaging lines expressing multiple tail fibers can detect multiple indicator stains, demonstrating that multiple functional NRTPs with varying specificities can be produced at once.

Figure 7:
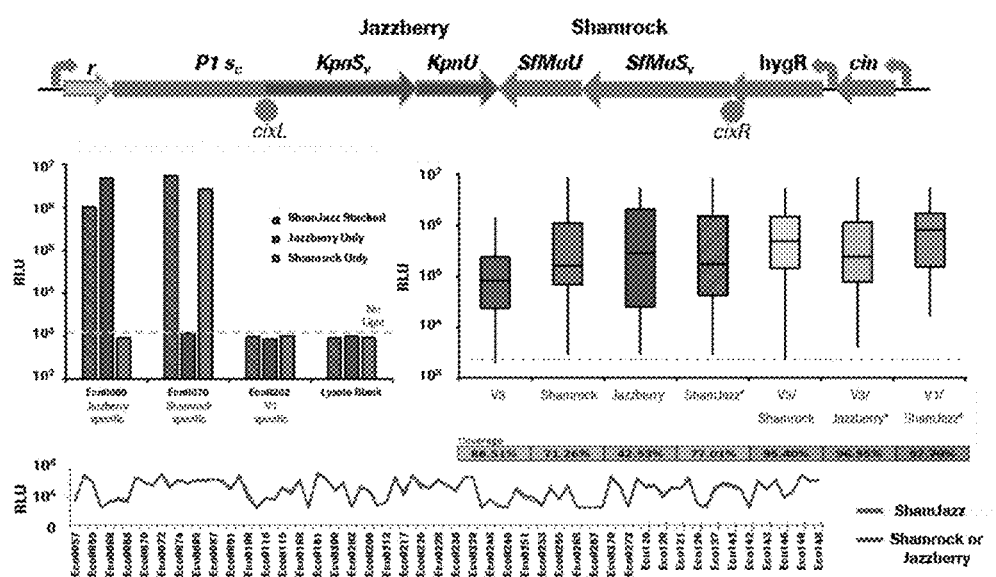
FIG. 7 Analysis of Bi-functional Smarticles packaging line. Bi-functional P1 derived Smarticles were created endowed with both "Jazzberry" and "Shamrock" tail-fibers. A) Cartoon depiction of the genetic arrangement of genome integrated "ShamJazz" dual expression system. B) Confirmation of bi-functional activity on strains that are specific for the "Jazzberry", "Shamrock", or "V3" (S and S') tail fibers. C) Predicted and/or observed activity of select individual and combined Smarticles on a collection of E. coli strains (EcoAD panel). Percent coverage depicted below, with stem and whisker plot depicting light distribution on the panel. D) Comparison of predicted activity of the bi-functional Smarticles and observed activity (purple) which are indistinguishable. * denotes cumulative predicted coverage vs. actual experimentally observed coverage.

FIG. 7 compares the performance of NRTPs derived from a bi-functional (two tail fiber) expression strain relative to individual NRTPs produced in separate production runs. Top image shows genomic arrangement of bi-functional tail fiber region from the Jazzberry and Shamrock tail fibers. Left middle, compares individually produced and bi-functional NRTPs on indicator strains specific for the different tail fibers. Right middle, shows how detection and light production were improved on a large panel of E. coli strains by making bi-functional production lines in addition to mixing into a cocktail with other NRTPs (such as the native P1 NRTP, called V3). The bottom part of FIG. 7 directly compares the performance of bi-functionally produced NRTPs to the cumulative performance of the individual tail fibers produced separately.

Figure 8:
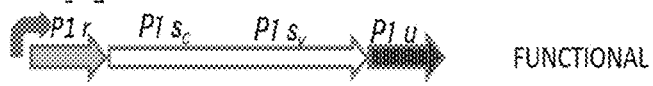
FIG. 8 Establishment of Elements Required for Functional Tail Fibers A) 3 distinct tail fiber Sc regions (see Native P1, "Plum", and "Tangerine") were functionalized on a P1 chassis, expanding the understanding of the determinants required for functional tail fibers. All constructs harbored the P1 r gene encoding the R protein. Each tail fiber variable region ($S_v$) was most functional when expressed with its cognate U accessory protein. B) Protein alignments of the 3 functional $S_c$ regions demonstrate that the N-terminal 250 amino acids are important.
Figure 8:
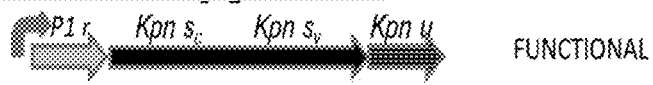
Figure 8:
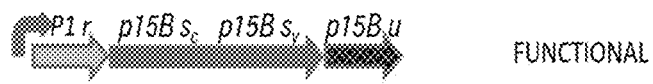
Figure 8:
Figure 8:
Figure 8:
Figure 8:
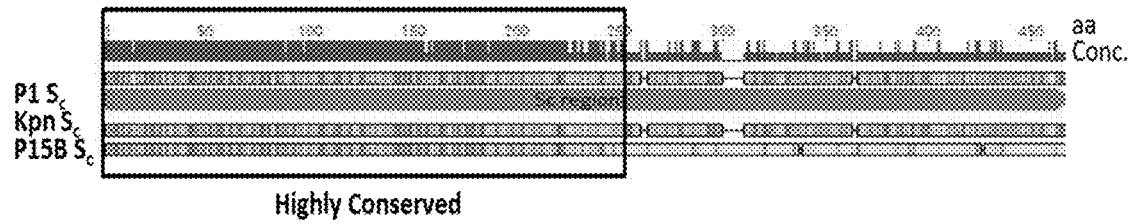

FIG. 8 shows the results of experiments performed that identified the elements that are required for functionalizing new tail fibers on a viral chassis. Panel A illustrates that the P1 r gene is required and that the tail fiber variable region ($S_v$) should be pared with its cognate u homolog accessory protein for maximal activity. Additionally, panel A shows that 3 distinct tail fiber conserved regions could allow functionalization of non-native tail fibers on a new chassis. Panel B shows the alignment of the amino acid sequence of the 3 $S_c$ regions from P1 bacteriophage, type 11 Kpn bacteriophage, and p15B plasmid (related to P1), highlighting a highly conserved N-terminal 150 amino acid sequence motif.

Figure 9:
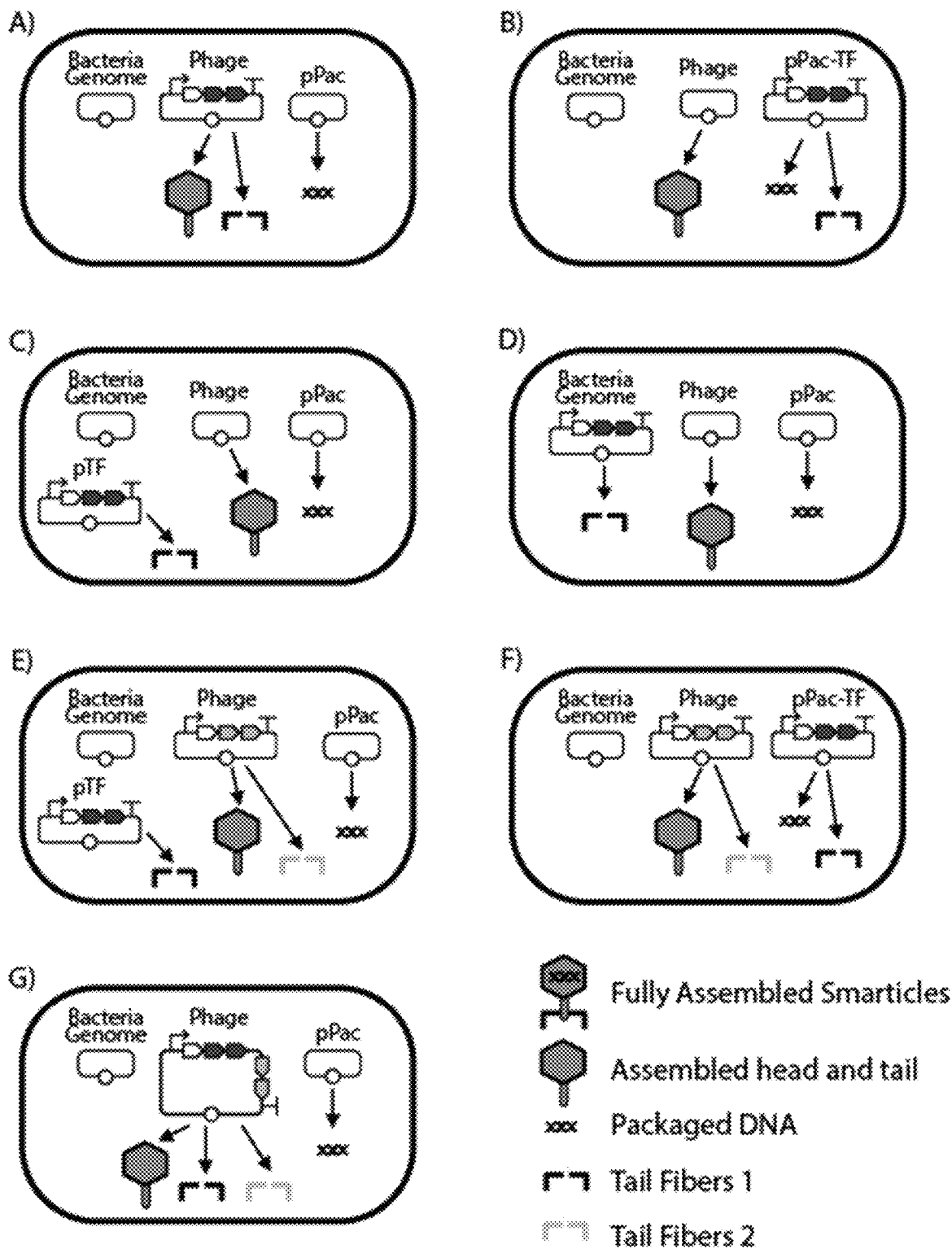
FIG. 9 Displays the various arrangements for expression of tail fiber genes from fermentation strain. A) shows expression of tail fibers and viral chassis from phage genome. B) Shows viral chassis expression from phage genome and tail fibers genes from packaging plasmid. C) Shows viral chassis from phage genome and tail fibers from independent plasmid. D) Shows viral chassis from phage genome and tail fibers from bacterial genome. E) Shows viral chassis and one set of tail fibers from phage genome. A second, unique set of tail fibers is expressed from an independent plasmid. F) Shows viral chassis and tail fibers from phage genome. A second, unique set of tail fibers is expressed from the packaging plasmid. G) Shows viral chassis and two, unique sets of tail fibers from phage genome.

FIG. 9 Displays the various arrangements for expression of tail fiber genes from fermentation strain. A) shows expression of tail fibers and viral chassis from phage genome. B) Shows viral chassis expression from phage genome and tail fibers genes from packaging plasmid. C) Shows viral chassis from phage genome and tail fibers from independent plasmid. D) Shows viral chassis from phage genome and tail fibers from bacterial genome. E) Shows viral chassis and one set of tail fibers from phage genome. A second, unique set of tail fibers is expressed from an independent plasmid. F) Shows viral chassis and tail fibers from phage genome. A second, unique set of tail fibers is expressed from the packaging plasmid. G) Shows viral chassis and two, unique sets of tail fibers from phage genome.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference, in their entirety, for all purposes.

Description of Sequences Listed in Sequence Listing:

| Nucleotide sequences of tail fibers functionally expressed on a P1 chassis. | |
| --- | --- |
| Asparagus Tail Fiber Nucleotide Sequence | SEQ ID NO: 1 |
| Banana Tail Fiber Nucleotide Sequence | SEQ ID NO: 2 |
| Bittersweet Tail Fiber Nucleotide Sequence | SEQ ID NO: 3 |
| Cobalt Tail Fiber Nucleotide Sequence | SEQ ID NO: 4 |
| Cornflower Tail Fiber Nucleotide Sequence | SEQ ID NO: 5 |
| Denim Tail Fiber Nucleotide Sequence | SEQ ID NO: 6 |
| Eggplant Tail Fiber Nucleotide Sequence | SEQ ID NO: 7 |
| Fern Tail Fiber Nucleotide Sequence | SEQ ID NO: 8 |
| Fuchsia Tail Fiber Nucleotide Sequence | SEQ ID NO: 9 |
| Fuzzy Tail Fiber Nucleotide Sequence | SEQ ID NO: 10 |
| Inchworm Tail Fiber Nucleotide Sequence | SEQ ID NO: 11 |
| Indian Tail Fiber Nucleotide Sequence | SEQ ID NO: 12 |
| Indigo Tail Fiber Nucleotide Sequence | SEQ ID NO: 13 |
| Jazzberry Tail Fiber Nucleotide Sequence | SEQ ID NO: 14 |
| Jazzberry-ShamrocK Dual Tail Fiber Nucleotide Seq. | SEQ ID NO: 15 |
| Jungle Tail Fiber Nucleotide Sequence | SEQ ID NO: 16 |
| Mango Tail Fiber Nucleotide Sequence | SEQ ID NO: 17 |
| Maroon Tail Fiber Nucleotide Sequence | SEQ ID NO: 18 |
| Mulberry Tail Fiber Nucleotide Sequence | SEQ ID NO: 19 |
| P1_S'gene Nucleotide Sequence | SEQ ID NO: 20 |
| P1S-P1S'-Shamrock Dual Tail Fiber Nucleotide Seq. | SEQ ID NO: 21 |
| Pine Tail Fiber Nucleotide Sequence | SEQ ID NO: 22 |
| Plum Tail Fiber Nucleotide Sequence | SEQ ID NO: 23 |
| Queen Tail Fiber Nucleotide Sequence | SEQ ID NO: 24 |
| Razzmatazz Tail Fiber Nucleotide Sequence | SEQ ID NO: 25 |
| Salmon Tail Fiber Nucleotide Sequence | SEQ ID NO: 26 |
| Scarlet Tail Fiber Nucleotide Sequence | SEQ ID NO: 27 |
| Shamrock Tail Fiber Nucleotide Sequence | SEQ ID NO: 28 |
| Sunset Tail Fiber Nucleotide Sequence | SEQ ID NO: 29 |
| Tangerine Tail Fiber Nucleotide Sequence | SEQ ID NO: 30 |
| Thistle Tail Fiber Nucleotide Sequence | SEQ ID NO: 31 |
| Tropical_pNS88 Tail Fiber Nucleotide Sequence | SEQ ID NO: 32 |
| Tropical_pNS92 Tail Fiber Nucleotide Sequence | SEQ ID NO: 33 |
| Violet Tail Fiber Nucleotide Sequence | SEQ ID NO: 34 |
| Amino Acid sequences of tail fibers functionally expressed on a P1 chassis. | |
| Asparagus_-_P1Sc-(P1Sv-MuS_hybrid)_translation | SEQ ID NO: 35 |
| Banana_-_P1Sc(aa1-114)-Ecl112(aa218-end)_translation | SEQ ID NO: 36 |
| Bittersweet_-_p15b_Sc-p15b_SvQ_translation | SEQ ID NO: 37 |
| Cobalt_-_ p15bSc-Kpn_SCKP_TF4_translation | SEQ ID NO: 38 |
| Cornflower_-_P1Sc(aa1-208)-Kpn478_tail_fiber(aa131-499)_translation | SEQ ID NO: 39 |
| Denim_-_ p15bSc-Kpn_SCKP_TF1_translation | SEQ ID NO: 40 |
| Eggplant_-_D6Sc-D6Sv'_translation | SEQ ID NO: 41 |
| Fern_-_P1Sc-(P1Sv-D108S_hybrid)_translation | SEQ ID NO: 42 |
| Fuchsia_-_P1Sc-D6Sv_translation | SEQ ID NO: 43 |
| Fuzzy_-_P1Sc(aa1-208)-Kpn051_TF(aa40-382)_translation | SEQ ID NO: 44 |
| Inchworm_-_P1Sc-R2_pyocin_translation | SEQ ID NO: 45 |
| Indian_-_ p15bSc-p15bSvN_translation | SEQ ID NO: 46 |
| Indigo_-_p15bSc-Kpn_SCKP_TF3_translation | SEQ ID NO: 47 |
| Jazzberry_-_P1Sc-KpnSv_translation | SEQ ID NO: 48 |
| Jungle_-_P1Sc-(P1Sv'-MuS'_hybrid)_translation | SEQ ID NO: 49 |
| Mango_-_P1Sc(aa1-214)-Ecl117B(aa214-764)_translation | SEQ ID NO: 50 |
| Maroon_-_ p15bSc-p15bSvP_translation | SEQ ID NO: 51 |
| Mulberry_-_D6Sc-D6Sv_translation | SEQ ID NO: 52 |
| P1_S'_-_p1Sc-P1Sv'_translation | SEQ ID NO: 53 |
| Pine_-_P1Sc(nt1-987)-P2H_translation | SEQ ID NO: 54 |
| Plum_-_KpnSc-KpnSv_translation | SEQ ID NO: 55 |
| Queen_-_S-Queen_Sv_translation | SEQ ID NO: 56 |
| Razzmatazz_-_P1Sc-P7Sv_translation | SEQ ID NO: 57 |
| Salmon_-_P1Sc-P7Sv'_translation | SEQ ID NO: 58 |
| Scarlet_-_p15bSc-p15bSvI_translation | SEQ ID NO: 59 |
| Shamrock_-_P1Sc-(P1S-SfMuS'_hybrid)_translation | SEQ ID NO: 60 |
| Sunset_-_p15bSc-p15bSvR_translation | SEQ ID NO: 61 |
| Tangerine_-_ p15bSc-p15bSv0_translation | SEQ ID NO: 62 |
| Thistle_-_P1Sc-KpnSv_translation | SEQ ID NO: 63 |
| Tropical_pNS88_-_P1Sc(aa1-214)-Ecl117A(aa91-437)_translation | SEQ ID NO: 64 |
| Tropical_pNS92_-_P1Sc(aa1-214)-Ecl117A(aa96-437)_translation | SEQ ID NO: 65 |
| Violet_-_RCS47Sc-RCS47Sv_translation | SEQ ID NO: 66 |

| Amino Acid sequences of chaperone proteins | |
|---|---|
| Asparagus_-_MuU_translation | SEQ ID NO: 67 |
| Banana_-_Ecl112_U_chaperone_translation | SEQ ID NO: 68 |
| Bittersweet_-_p15b_T_translation | SEQ ID NO: 69 |
| Cobalt_-_p15b_T_translation | SEQ ID NO: 70 |
| Denim_-_p15b_T_translation | SEQ ID NO: 71 |
| Eggplant_-_P1_U_translation | SEQ ID NO: 72 |
| Fern_-_D108_U_translation | SEQ ID NO: 73 |
| Fuchsia_-_P1_U'_translation | SEQ ID NO: 74 |
| Fuzzy_-_PROKKA_00043_(Kpn478_chaperone)_translation | SEQ ID NO: 75 |
| Inchworm_-_PA0621_translation | SEQ ID NO: 76 |
| Indian_-_p15b_T_translation | SEQ ID NO: 77 |
| Indigo_-_p15b_T_translation | SEQ ID NO: 78 |
| Jazzberry_-_Kpn_U_translation | SEQ ID NO: 79 |
| Jungle_-_Mu_U'_translation | SEQ ID NO: 80 |
| Mango_-_Ecl117B_U_chaperone_translation | SEQ ID NO: 81 |
| Maroon_-_p15_T_translation | SEQ ID NO: 82 |
| Mulberry_-_P1_U'_translation | SEQ ID NO: 83 |
| P1_S'_-_p1_U'_translation | SEQ ID NO: 84 |
| Pine_-_P2_G_translation | SEQ ID NO: 85 |
| Plum_-_Kpn_U_translation | SEQ ID NO: 86 |
| Queen_-_Queen_U_chaperone_translation | SEQ ID NO: 87 |
| Razzmatazz_-_P7_Ua_translation | SEQ ID NO: 88 |
| Razzmatazz_-_P7_Ub_translation | SEQ ID NO: 89 |
| Salmon_-_P7_U'_translation | SEQ ID NO: 90 |
| Scarlet_-_p15b_T_translation | SEQ ID NO: 91 |
| Shamrock_-_SfMuU'_translation | SEQ ID NO: 92 |
| Sunset_-_p15b_T_translation | SEQ ID NO: 93 |
| Tangerine_-_p15_T_translation | SEQ ID NO: 94 |
| Thistle_-_KpnU_translation | SEQ ID NO: 95 |
| Violet_-_RCS47_U_translation | SEQ ID NO: 96 |
| Other Sequences | |
| Bald_Chassis_tail_fiber_region_P1_s-u::aadA | SEQ ID NO: 97 |
| Rio Tail Fiber_s_hybrid_nucleotide sequence | SEQ ID NO: 98 |
| Rio Chaperone_u_nucleotide_sequence | SEQ ID NO: 99 |
| Limon Tail Fiber_s_hybrid_nucleotide sequence | SEQ ID NO: 100 |
| Limon Chaperone_u_nucleotide_sequence | SEQ ID NO: 101 |
| Orchid Tail Fiber_s_hybrid_nucleotide sequence | SEQ ID NO: 102 |
| Orchid Chaperone_u_nucleotide sequence | SEQ ID NO: 103 |
| Gold Tail Fiber_s_hybrid_nucleotide sequence | SEQ ID NO: 104 |
| Gold Chaperone_u_nucleotide sequence | SEQ ID NO: 105 |
| Bluetiful Tail Fiber_s_hybrid_nucleotide sequence | SEQ ID NO: 106 |
| Bluetiful Chaperone_u_nucleotide sequence | SEQ ID NO: 107 |
| Rio Tail Fiber_S_hybrid_amino acid sequence | SEQ ID NO: 108 |
| Limon Tail Fiber_S_hybrid_amino acid sequence | SEQ ID NO: 109 |
| Orchid Tail Fiber_S_hybrid_amino acid sequence | SEQ ID NO: 110 |
| Gold Tail Fiber_S_hybrid_amino acid sequence | SEQ ID NO: 111 |
| Bluetiful Tail Fiber_S_hybrid_amino acid sequence | SEQ ID NO: 112 |
| Rio Chaperone_U_amino acid sequence | SEQ ID NO: 113 |
| Limon Chaperone_U_amino acid sequence | SEQ ID NO: 114 |
| Orchid Chaperone_U_amino acid sequence | SEQ ID NO: 115 |
| Gold Chaperone_U_amino acid sequence | SEQ ID NO: 116 |
| Bluetiful Chaperone_U_amino acid sequence | SEQ ID NO: 117 |

The invention claimed is:

1. A bacteriophage tail fiber replacement platform comprising: a bacteriophage lysogen from the family Myoviridae (Myoviridae lysogen) that contains a genetic disruption that prevents the expression of one or more genes that are critical for the production of tail fibers native to the Myoviridae lysogen, wherein the Myoviridae lysogen comprises a nucleic acid sequence of SEQ ID NO: 97, and a complementary nucleic acid molecule that complements the genetic disruption of the Myoviridae lysogen whereby functional tail fibers are produced, wherein the complementary nucleic acid molecule comprises a sequence selected from SEQ ID NOs: 1-34 or a pair of sequences consisting of SEQ ID NOs: 98 and 99, 100 and 101, 102 and 103, 104 and 105, or 106 and 107.

2. A bacterial cell line comprising a P1 bacteriophage lysogen that comprises a nucleic acid sequence of SEQ ID NO: 97.

* * * * *